US011827682B2

(12) United States Patent
Bosques et al.

(10) Patent No.: US 11,827,682 B2
(45) Date of Patent: Nov. 28, 2023

(54) ENGINEERED FC CONSTRUCTS

(71) Applicant: MOMENTA PHARMACEUTICALS, INC., Titusville, NJ (US)

(72) Inventors: Carlos J. Bosques, Arlington, MA (US); Jonathan C. Lansing, Reading, MA (US); Daniel Ortiz, Stoneham, MA (US)

(73) Assignee: Momenta Pharmaceuticals, Inc., Titusville, NJ (US)

( * ) Notice: Subject to any disclaimer, the term of this patent is extended or adjusted under 35 U.S.C. 154(b) by 0 days.

(21) Appl. No.: 17/527,741

(22) Filed: Nov. 16, 2021

(65) Prior Publication Data

US 2022/0267388 A1 Aug. 25, 2022

Related U.S. Application Data

(63) Continuation of application No. 16/474,640, filed as application No. PCT/US2018/012488 on Jan. 5, 2018, now Pat. No. 11,220,531.

(60) Provisional application No. 62/589,473, filed on Nov. 21, 2017, provisional application No. 62/510,228, filed on May 23, 2017, provisional application No. 62/443,495, filed on Jan. 6, 2017.

(51) Int. Cl.

| | |
|---|---|
| ***C07K 16/00*** | (2006.01) |
| ***A61K 39/395*** | (2006.01) |
| ***C07K 14/47*** | (2006.01) |
| ***A61P 37/06*** | (2006.01) |
| ***A61P 19/02*** | (2006.01) |
| ***A61K 39/00*** | (2006.01) |
| *C07K 1/00* | (2006.01) |

(52) U.S. Cl.

CPC .......... *C07K 14/47* (2013.01); *A61K 39/0008* (2013.01); *A61P 19/02* (2018.01); *A61P 37/06* (2018.01); *A61K 2039/577* (2013.01); *C07K 2319/30* (2013.01)

(58) Field of Classification Search

None

See application file for complete search history.

(56) References Cited

U.S. PATENT DOCUMENTS

| | | | |
|---|---|---|---|
| 4,719,107 | A | 1/1988 | Carosella et al. |
| 5,426,641 | A | 6/1995 | Afrashteh et al. |
| 5,731,168 | A | 3/1998 | Carter et al. |
| 6,737,056 | B1 | 5/2004 | Presta |
| 7,183,076 | B2 | 2/2007 | Arathoon et al. |
| 7,803,769 | B2 | 9/2010 | Sullivan et al. |
| 7,951,917 | B1 | 5/2011 | Arathoon et al. |
| 8,216,805 | B2 | 7/2012 | Carter et al. |
| 8,592,562 | B2 | 11/2013 | Kannan et al. |
| 8,680,237 | B2 | 3/2014 | Strome et al. |
| 9,238,080 | B2 | 1/2016 | Nielsen et al. |
| 10,239,944 | B2 | 3/2019 | Bosques et al. |
| 11,124,573 | B2 | 9/2021 | Bosques et al. |
| 11,155,640 | B2 | 10/2021 | Bosques et al. |
| 11,220,531 | B2 | 1/2022 | Bosques et al. |
| 2003/0078385 | A1 | 4/2003 | Arathoon |
| 2009/0074839 | A1 | 3/2009 | Milankovits |
| 2009/0304696 | A1 | 12/2009 | Lawson et al. |
| 2010/0093979 | A1 | 4/2010 | Lazar |
| 2010/0143353 | A1 | 6/2010 | Mosser et al. |
| 2010/0216663 | A1 | 8/2010 | Kolkman et al. |
| 2010/0239633 | A1 | 9/2010 | Strome et al. |
| 2010/0286374 | A1 | 11/2010 | Kannan |
| 2011/0262477 | A1 | 10/2011 | Cheng et al. |
| 2011/0311535 | A1 | 12/2011 | Dranoff et al. |
| 2012/0149876 | A1 | 6/2012 | Von Kreudenstein et al. |
| 2012/0219551 | A1 | 8/2012 | Johnson et al. |
| 2012/0244578 | A1 | 9/2012 | Kannan et al. |
| 2013/0156765 | A1 | 6/2013 | Block et al. |
| 2013/0177555 | A1 | 7/2013 | Wilkinson et al. |
| 2014/0024111 | A1 | 1/2014 | Kannan et al. |
| 2014/0051834 | A1 | 2/2014 | Hoffman et al. |
| 2014/0066599 | A2 | 3/2014 | Blein et al. |
| 2014/0105913 | A1 | 4/2014 | Strome et al. |
| 2014/0187753 | A1 | 7/2014 | Blein et al. |
| 2014/0294817 | A1 | 10/2014 | Mosser et al. |
| 2014/0335075 | A1 | 11/2014 | Strome et al. |
| 2015/0056185 | A1 | 2/2015 | Strome et al. |
| 2015/0184142 | A1 | 7/2015 | Hong et al. |
| 2015/0218236 | A1 | 8/2015 | Pleass |
| 2016/0229913 | A1 | 8/2016 | Bosques et al. |
| 2017/0029505 | A1 | 2/2017 | Griffin et al. |
| 2019/0225688 | A1 | 7/2019 | Bosques et al. |
| 2019/0284305 | A1 | 9/2019 | Bosques et al. |
| 2019/0345206 | A1 | 11/2019 | Bosques et al. |
| 2021/0221917 | A1 | 7/2021 | Lansing et al. |
| 2022/0033499 | A1 | 2/2022 | Bosques et al. |
| 2022/0049019 | A1 | 2/2022 | Bosques et al. |

FOREIGN PATENT DOCUMENTS

| | | |
|---|---|---|
| BR | PI0620639-5 | 11/2011 |
| CN | 101835802 | 9/2010 |
| CN | 102549016 | 7/2012 |

(Continued)

OTHER PUBLICATIONS

Anthony, "Identification of a receptor required for the anti-inflammatory activity of IVIG," Proc. Natl. Acad. Sci. U.S.A., Dec. 16, 2008, 105(50):19571-19578.

Atwell et al., "Stable heterodimers from remodeling the domain interface of a homodimer using a phage display library," Biol., Jul. 4, 1997, 270(1):26-35.

Boruchov AM et al., "Activating and inhibitory IgG Fc receptors on human DCs mediate opposing functions," J Clin Invest., Oct. 2005 115(10):2914-2923.

Carter "Bispecific human IgG by design," J of Immunol Methods., Feb. 1, 2001, 248(1-2):7-15.

Chamow et al., "A humanized, bispecific immunoadhesin-antibody that retargets CD3+ effectors to kill HIV-1-infected cells," J. Immunol., 1994, 153:4268-4280 (Abstract Only).

(Continued)

*Primary Examiner* — Chun W Dahle

(74) *Attorney, Agent, or Firm* — Fish & Richardson P.C.

(57) ABSTRACT

The present disclosure relates to engineered IgG Fc constructs and uses thereof.

9 Claims, 55 Drawing Sheets

Specification includes a Sequence Listing.

(56) References Cited

FOREIGN PATENT DOCUMENTS

| | | |
|---|---|---|
| JP | 2007-289200 | 11/2007 |
| JP | 2010-529043 | 8/2010 |
| JP | 2011-508604 | 3/2011 |
| JP | 2011-517456 | 6/2011 |
| JP | 2014-510084 | 4/2014 |
| JP | 2015-527366 | 9/2015 |
| JP | 2015-536317 | 12/2015 |
| KR | 2010-0028599 | 3/2010 |
| RU | 2583298 | 5/2016 |
| WO | WO 1997/047732 | 12/1997 |
| WO | WO 01/45746 | 6/2001 |
| WO | WO 2005/077981 | 8/2005 |
| WO | WO 2006/106905 | 10/2006 |
| WO | WO 2008/012543 | 1/2008 |
| WO | WO 2008/131242 | 10/2008 |
| WO | WO 2008/143954 | 11/2008 |
| WO | WO 2008/151088 | 12/2008 |
| WO | WO 2009/089004 | 7/2009 |
| WO | WO 2010/085682 | 7/2010 |
| WO | WO 2010/135521 | 11/2010 |
| WO | WO 2010/135534 | 11/2010 |
| WO | WO 2011/034605 | 3/2011 |
| WO | WO 2011/073692 | 6/2011 |
| WO | WO 2012/006635 | 1/2012 |
| WO | WO 2012/123949 | 9/2012 |
| WO | WO 2014/031646 | 2/2014 |
| WO | WO 2014/060712 | 4/2014 |
| WO | WO 2015/054958 | 4/2015 |
| WO | WO 2015/095684 | 6/2015 |
| WO | WO 2015/107025 | 7/2015 |
| WO | WO 2015/107026 | 7/2015 |
| WO | WO 2015/132364 | 9/2015 |
| WO | WO 2015/132365 | 9/2015 |
| WO | WO 2015/168643 | 11/2015 |
| WO | WO 2015/184207 | 12/2015 |
| WO | WO 2017/151971 | 9/2017 |
| WO | WO 2017/205434 | 11/2017 |
| WO | WO 2017/205436 | 11/2017 |

OTHER PUBLICATIONS

Chu et al., "Inhibition of B cell receptor-mediated activation of primary human B cells by coengagement of CD19 and FcgammaRIIb with Fc-engineered antibodies," Mol Immunol., Sep. 2008, 45(15):3926-3933.

Crick et al., "A tracer study of the metabolism of p-iodophenyl urethane; the selective localization of radioactive material," Br J Pharmacol Chemother., Mar. 1952, 7(1):142-151.

Dall'Acqua et al., "Modulation of the Effector Functions of a Human IgG 1 through Engineering of Its Hinge Region," J. Immunol, 2006, 177:1129-1138.

Davis et al., "SEEDbodies: fusion proteins based on strand-exchange engineered domain (SEED) CH3 heterodimers in an Fc analogue platform for asymmetric binders or immunofusions and bispecific antibodies," *Protein Eng Des Sel.*, Apr. 2010, 2(4)3:195-202.

Dick Jr et al., "C-terminal lysine variants in fully human monoclonal antibodies: investigation of test methods and possible causes," Biotechnology and Bioengineering 2008, 100(6):1132-1143.

European Search Report in Application No. 15785583.4, dated Nov. 7, 2017, 12 pages.

European Search Report in Application No. 17760849.4, dated Sep. 24, 2019, 12 pages.

European Search Report in Application No. 17803465.8, dated Feb. 17, 2020, 12 pages.

European Search Report in Application No. 17803463.3, dated Jul. 15, 2020, 11 pages.

European Office Action in Application No. 15785583.4, dated Oct. 12, 2020, 4 pages.

European Search Report in Application No. 18736414.6, dated Nov. 16, 2020, 16 pages.

European Search Report in Application No. 17760849.4, dated Jan. 11, 2021, 4 pages.

European Office Action in Application No. 17803465.8, dated Jan. 20, 2021, 8 pages.

Gunadekaran et al., "Enhancing antibody Fc heterodimer formation through electrostatic steering effects: applications to bispecific molecules and monovalent IgG.," J Biol Chem, Jun. 18, 2010, 285(25):19637-19646.

Grevys et al., "Open Access Fc Engineering of Human IgG1 for Altered Binding to the Neonatal Fc Receptor Affects Fc Effector Functions," The Journal of Immunology, 194(11):5497-5508.

International Preliminary Report on Patentability in International Patent Application No. PCT/US2017/020519, dated Sep. 4, 2018 (2 pages).

International Preliminary Report on Patentability in International Patent Application No. PCT/US2015/028926, dated Nov. 8, 2016, 10 pages.

International Preliminary Report on Patentability in International Patent Application No. PCT/US2017/034087, dated Nov. 27, 2018, 11 pages.

International Preliminary Report on Patentability in International Patent Application No. PCT/US2017/034084, dated Nov. 27, 2018, 10 pages.

International Preliminary Report on Patentability in International Application No. PCT/US2018/012488, dated Jul. 9, 2019, 10 pages.

International Search Report and Written Opinion in International Application No. PCT/US17/20519, dated Aug. 24, 2017, 17 pages.

International Search Report and Written Opinion in International Application No. PCT/US17/34084, dated Sep. 14, 2017, 19 pages.

International Search Report and Written Opinion in International Application No. PCT/US17/34087, dated Oct. 18, 2017, 20 pages.

International Search Report and Written Opinion in International Application No. PCT/US2015/028926, dated Oct. 28, 2015, 16 pages.

International Search Report and Written Opinion in International Application No. PCT/US2018/012488, dated May 25, 2018, 26 pages.

Jain et al., "Fully recombinant IgG2a Fc multimers (stradomers) effectively treat collagen-induced arthritis and prevent idiopathic thrombocytopenia purpura in mice," Arthritis Res Ther., Aug. 20, 2012, 14(4):R192.

Kacskovics et al., "Fc receptors in livestock species," Veterinary Immunology and Immunopathology, 2004, 102:351-362.

Kinder et al., "Engineered protease-resistant antibodies with selectable cell-killing functions," J of Biol Chem., Oct. 25, 2013, 288(43):30843-30854.

Lund et al., "Multiple Interactions of Ig with Its Core Oligosacchadde Can Modulate Recognition by Cornplernent and Human Fcy Receptor I and Influence the Synthesis of Its Oligosaccharide Chains," The Journal of Immunology, 1996, 157:4963-4969.

Martens et al., "A novel one-armed anti-c-Met antibody inhibits glioblastoma growth in vivo," Clin Cancer Res., 2006, 12(20):6144-6152.

Mekhaiel et al., "Polymeric human Fc-fusion proteins with modified effector functions," Scientific Reports, Aug. 2011, 1: 124 (11 pages).

Merchant et al., "An efficient route to human bispecific IgG," *Nat Biotechnol*, Jul. 1998, 16(7):677-681.

Mestas et al., "Of Mice and Not Men: Differences between Mouse and Human Immunology," J Immunology., 2004, 172(5):2731-2738.

Mimoto et al., "Novel asymmetrically engineered antibody Fc variant with superior FcyR binding affinity and specificity compared with afucosylated Fc variant," mAbs, Feb. 2013, 5: 229-236.

Office Action in Israeli Application No. 247442, dated Jun. 3, 2018, 7 pages.

Ortiz et al., "Elucidating the interplay between IgG-Fc valency and FcgR actication for the design of immune complex inhibitors," Science Translational Medicine, Nov. 16, 2016, 8(365):1-13.

Rajpal et al., "Introduction: Antibody Structure and Function," Therapeutic Fc-Fusion Proteins, 2014, Chapter 1, 43 pages.

Ridgway et al., "'Knobs-into-holes' engineering of antibody CH3 domains for heavy chain heterodimerization," *Protein Eng.*, Jul. 1996, 9(7):617-612.

(56) References Cited

OTHER PUBLICATIONS

Salfeld, "Isotype selection in antibody engineering," Nature Biotech, 2007, 25(12): 1369-1372.
Shields et al., "High Resolution Mapping of the Binding Site on Human IgG1 for FcγRI, FcγRII, FcγRIII, and FcRn and Design of IgG1 Variants with Improved Binding to the FcγR," J. Biol. Chem., 2001, 276(9):6591-6604.
Sowdhamini et al., "Stereochemical modeling of disulfide bridges. Criteria for introduction into proteins by site-directed mutagenesis," Protein Eng., Nov. 1989, 3(2):95-103.
Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res, 2007, 67: 8882-8890.
Van Den Bremer et al., "Human IgG is produced in a pro-form that requires clipping of C-terminal lysines for maximal complement activation," mAbs., 2015, 7(4):672-680.
Wilson et al., "The structure of an antigenic determinant in a protein," Cell, Jul. 1984, 37(3):767-778.
Zeidler et al., "Simultaneous activation of T cells and accessory cells by a new class of intact bispecific antibody results in efficient tumor cell killing," J Immunol., Aug. 1999, 163(3):1246-1252.
Armour et al., "Differential binding to human FcyRIIa and FcyRIIb receptors by human IgG wildtype and mutant antibodies," Molecular immunology, 2003, 40(9):585-593.
Radaev et al., "Recognition of IgG by Fcy receptor: the role of Fc glycosylation and the binding of peptide inhibitors," Journal of Biological Chemistry, 2001, 276(19):16478-16483.
Cai et al., "C-terminal lysine processing of human immunoglobulin G2 heavy chain in vivo," Biotechnol Bioeng., Feb. 2011, 108(2):404-412.
Mimoto et al., "Engineered antibody Fc variant with selectively enhanced FcγRIIb binding over both FcγRIIa(R131) and FcγRIIa(H131)," Protein Eng Des Sel., Oct. 2013, 26(10):589-598.
Nicolaou et al., "Calicheamicin: A Rationally Designed Molecule with Extremely Potent and Selective DNA Cleaving Properties and Apoptosis Inducing Activity," Angew Chem Intl Ed Engl., 1994, 33:183-186.

(Fc constructs 1, 2, and 3)

(Fc construct 4)

| Construct | Isoform | Band % |
|---|---|---|
| F construct 4 | Fc3 | 88.2 |
| | Fc2 | 5.0 |
| | Fc1 | 6.8 |
| Fc construct 2 | Fc3 | 78.1 |
| | Fc2 | 17.1 |
| | Fc1 | 4.8 |

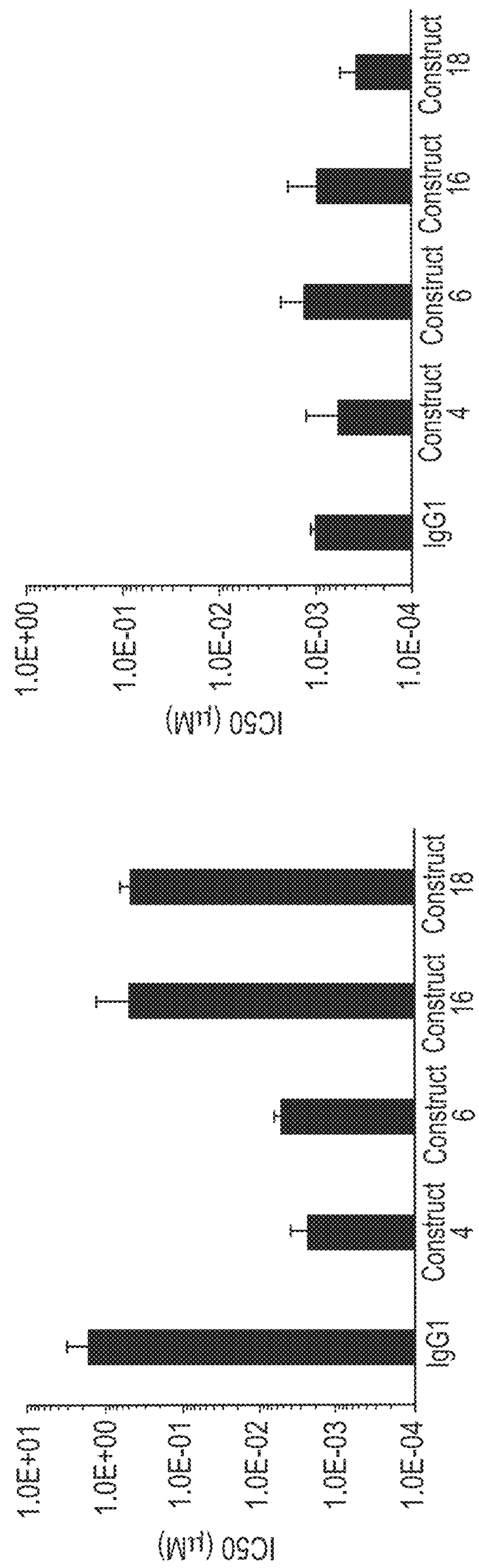
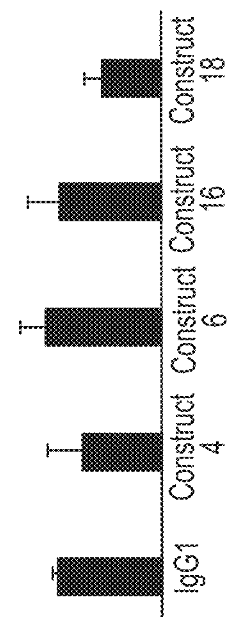
FIG. 19A
FIG. 19B
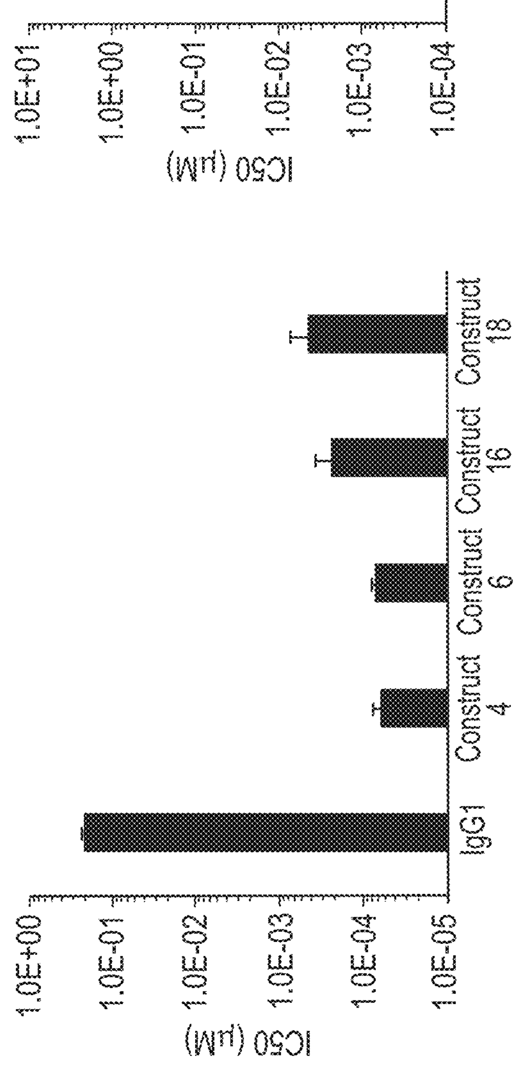
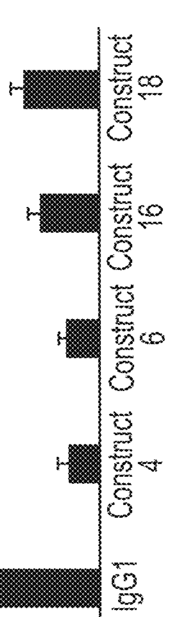
FIG. 19C
FIG. 19D

35

SEQUENCE LISTING

```
<160> NUMBER OF SEQ ID NOS: 80

<210> SEQ ID NO 1
<211> LENGTH: 5
<212> TYPE: PRT
<213> ORGANISM: Artificial Sequence
<220> FEATURE:
<223> OTHER INFORMATION: Linker sequence

<400> SEQUENCE: 1

Gly Gly Gly Gly Ser
1               5


<210> SEQ ID NO 2
<211> LENGTH: 4
<212> TYPE: PRT
<213> ORGANISM: Artificial Sequence
<220> FEATURE:
<223> OTHER INFORMATION: Linker sequence

<400> SEQUENCE: 2

Gly Gly Ser Gly
1


<210> SEQ ID NO 3
<211> LENGTH: 4
<212> TYPE: PRT
<213> ORGANISM: Artificial Sequence
<220> FEATURE:
<223> OTHER INFORMATION: Linker sequence

<400> SEQUENCE: 3

Ser Gly Gly Gly
1


<210> SEQ ID NO 4
<211> LENGTH: 4
<212> TYPE: PRT
<213> ORGANISM: Artificial Sequence
<220> FEATURE:
<223> OTHER INFORMATION: Linker sequence

<400> SEQUENCE: 4

Gly Ser Gly Ser
1


<210> SEQ ID NO 5
<211> LENGTH: 6
```

<212> TYPE: PRT
<213> ORGANISM: Artificial Sequence
<220> FEATURE:
<223> OTHER INFORMATION: Linker sequence

<400> SEQUENCE: 5

Gly Ser Gly Ser Gly Ser
1               5

<210> SEQ ID NO 6
<211> LENGTH: 8
<212> TYPE: PRT
<213> ORGANISM: Artificial Sequence
<220> FEATURE:
<223> OTHER INFORMATION: Linker sequence

<400> SEQUENCE: 6

Gly Ser Gly Ser Gly Ser Gly Ser
1               5

<210> SEQ ID NO 7
<211> LENGTH: 10
<212> TYPE: PRT
<213> ORGANISM: Artificial Sequence
<220> FEATURE:
<223> OTHER INFORMATION: Linker sequence

<400> SEQUENCE: 7

Gly Ser Gly Ser Gly Ser Gly Ser Gly Ser
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Linker sequence

<400> SEQUENCE: 8

Gly Ser Gly Ser Gly Ser Gly Ser Gly Ser Gly Ser
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Linker sequence

<400> SEQUENCE: 9

Gly Gly Ser Gly Gly Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Linker sequence

<400> SEQUENCE: 10

Gly Gly Ser Gly Gly Ser Gly Gly Ser
1               5

<210> SEQ ID NO 11
<211> LENGTH: 12
<212> TYPE: PRT

```
<213> ORGANISM: Artificial Sequence
<220> FEATURE:
<223> OTHER INFORMATION: Linker sequence

<400> SEQUENCE: 11

Gly Gly Ser Gly Gly Ser Gly Gly Ser Gly Gly Ser
1               5                   10


<210> SEQ ID NO 12
<211> LENGTH: 8
<212> TYPE: PRT
<213> ORGANISM: Artificial Sequence
<220> FEATURE:
<223> OTHER INFORMATION: Linker sequence

<400> SEQUENCE: 12

Gly Gly Ser Gly Gly Gly Ser Gly
1               5


<210> SEQ ID NO 13
<211> LENGTH: 12
<212> TYPE: PRT
<213> ORGANISM: Artificial Sequence
<220> FEATURE:
<223> OTHER INFORMATION: Linker sequence

<400> SEQUENCE: 13

Gly Gly Ser Gly Gly Gly Ser Gly Gly Gly Ser Gly
1               5                   10


<210> SEQ ID NO 14
<211> LENGTH: 16
<212> TYPE: PRT
<213> ORGANISM: Artificial Sequence
<220> FEATURE:
<223> OTHER INFORMATION: Linker sequence

<400> SEQUENCE: 14

Gly Gly Ser Gly Gly Gly Ser Gly Gly Gly Ser Gly Gly Gly Ser Gly
1               5                   10                  15


<210> SEQ ID NO 15
<211> LENGTH: 20
<212> TYPE: PRT
<213> ORGANISM: Artificial Sequence
<220> FEATURE:
<223> OTHER INFORMATION: Linker sequence

<400> SEQUENCE: 15

Gly Gly Ser Gly Gly Gly Ser Gly Gly Gly Ser Gly Gly Gly Ser Gly
1               5                   10                  15

Gly Gly Ser Gly
            20


<210> SEQ ID NO 16
<211> LENGTH: 10
<212> TYPE: PRT
<213> ORGANISM: Artificial Sequence
<220> FEATURE:
<223> OTHER INFORMATION: Linker sequence

<400> SEQUENCE: 16

Gly Gly Gly Gly Ser Gly Gly Gly Gly Ser
1               5                   10


<210> SEQ ID NO 17
```

<211> LENGTH: 15
<212> TYPE: PRT
<213> ORGANISM: Artificial Sequence
<220> FEATURE:
<223> OTHER INFORMATION: Linker sequence

<400> SEQUENCE: 17

Gly Gly Gly Gly Ser Gly Gly Gly Gly Ser Gly Gly Gly Gly Ser
1 5 10 15

<210> SEQ ID NO 18
<211> LENGTH: 20
<212> TYPE: PRT
<213> ORGANISM: Artificial Sequence
<220> FEATURE:
<223> OTHER INFORMATION: Linker sequence

<400> SEQUENCE: 18

Ser Gly Gly Gly Ser Gly Gly Gly Ser Gly Gly Gly Ser Gly Gly Gly
1 5 10 15

Ser Gly Gly Gly
20

<210> SEQ ID NO 19
<211> LENGTH: 4
<212> TYPE: PRT
<213> ORGANISM: Artificial Sequence
<220> FEATURE:
<223> OTHER INFORMATION: Linker sequence

<400> SEQUENCE: 19

Gly Gly Gly Gly
1

<210> SEQ ID NO 20
<211> LENGTH: 8
<212> TYPE: PRT
<213> ORGANISM: Artificial Sequence
<220> FEATURE:
<223> OTHER INFORMATION: Linker sequence

<400> SEQUENCE: 20

Gly Gly Gly Gly Gly Gly Gly Gly
1 5

<210> SEQ ID NO 21
<211> LENGTH: 12
<212> TYPE: PRT
<213> ORGANISM: Artificial Sequence
<220> FEATURE:
<223> OTHER INFORMATION: Linker sequence

<400> SEQUENCE: 21

Gly Gly Gly Gly Gly Gly Gly Gly Gly Gly Gly Gly
1 5 10

<210> SEQ ID NO 22
<211> LENGTH: 16
<212> TYPE: PRT
<213> ORGANISM: Artificial Sequence
<220> FEATURE:
<223> OTHER INFORMATION: Linker sequence

<400> SEQUENCE: 22

Gly Gly Gly Gly Gly Gly Gly Gly Gly Gly Gly Gly Gly Gly Gly Gly
1 5 10 15

<210> SEQ ID NO 23
<211> LENGTH: 20
<212> TYPE: PRT
<213> ORGANISM: Artificial Sequence
<220> FEATURE:
<223> OTHER INFORMATION: Linker sequence

<400> SEQUENCE: 23

```
Gly Gly Gly Gly Gly Gly Gly Gly Gly Gly Gly Gly Gly Gly Gly Gly
1               5                   10                  15

Gly Gly Gly Gly
            20
```

<210> SEQ ID NO 24
<211> LENGTH: 5
<212> TYPE: PRT
<213> ORGANISM: Artificial Sequence
<220> FEATURE:
<223> OTHER INFORMATION: Linker sequence

<400> SEQUENCE: 24

```
Gly Gly Gly Gly Gly
1               5
```

<210> SEQ ID NO 25
<211> LENGTH: 10
<212> TYPE: PRT
<213> ORGANISM: Artificial Sequence
<220> FEATURE:
<223> OTHER INFORMATION: Linker sequence

<400> SEQUENCE: 25

```
Gly Gly Gly Gly Gly Gly Gly Gly Gly Gly
1               5                   10
```

<210> SEQ ID NO 26
<211> LENGTH: 15
<212> TYPE: PRT
<213> ORGANISM: Artificial Sequence
<220> FEATURE:
<223> OTHER INFORMATION: Linker sequence

<400> SEQUENCE: 26

```
Gly Gly Gly Gly Gly Gly Gly Gly Gly Gly Gly Gly Gly Gly Gly
1               5                   10                  15
```

<210> SEQ ID NO 27
<211> LENGTH: 20
<212> TYPE: PRT
<213> ORGANISM: Artificial Sequence
<220> FEATURE:
<223> OTHER INFORMATION: Linker sequence

<400> SEQUENCE: 27

```
Gly Gly Gly Gly Gly Gly Gly Gly Gly Gly Gly Gly Gly Gly Gly Gly
1               5                   10                  15

Gly Gly Gly Gly
            20
```

<210> SEQ ID NO 28
<211> LENGTH: 10
<212> TYPE: PRT
<213> ORGANISM: Artificial Sequence
<220> FEATURE:
<223> OTHER INFORMATION: Linker sequence

```
<400> SEQUENCE: 28

Gly Glu Asn Leu Tyr Phe Gln Ser Gly Gly
1               5                   10


<210> SEQ ID NO 29
<211> LENGTH: 8
<212> TYPE: PRT
<213> ORGANISM: Artificial Sequence
<220> FEATURE:
<223> OTHER INFORMATION: Linker sequence

<400> SEQUENCE: 29

Ser Ala Cys Tyr Cys Glu Leu Ser
1               5


<210> SEQ ID NO 30
<211> LENGTH: 5
<212> TYPE: PRT
<213> ORGANISM: Artificial Sequence
<220> FEATURE:
<223> OTHER INFORMATION: Linker sequence

<400> SEQUENCE: 30

Arg Ser Ile Ala Thr
1               5


<210> SEQ ID NO 31
<211> LENGTH: 17
<212> TYPE: PRT
<213> ORGANISM: Artificial Sequence
<220> FEATURE:
<223> OTHER INFORMATION: Linker sequence

<400> SEQUENCE: 31

Arg Pro Ala Cys Lys Ile Pro Asn Asp Leu Lys Gln Lys Val Met Asn
1               5                   10                  15

His


<210> SEQ ID NO 32
<211> LENGTH: 36
<212> TYPE: PRT
<213> ORGANISM: Artificial Sequence
<220> FEATURE:
<223> OTHER INFORMATION: Linker sequence

<400> SEQUENCE: 32

Gly Gly Ser Ala Gly Gly Ser Gly Ser Gly Ser Ser Gly Gly Ser Ser
1               5                   10                  15

Gly Ala Ser Gly Thr Gly Thr Ala Gly Gly Thr Gly Ser Gly Ser Gly
            20                  25                  30

Thr Gly Ser Gly
        35


<210> SEQ ID NO 33
<211> LENGTH: 17
<212> TYPE: PRT
<213> ORGANISM: Artificial Sequence
<220> FEATURE:
<223> OTHER INFORMATION: Linker sequence

<400> SEQUENCE: 33

Ala Ala Ala Asn Ser Ser Ile Asp Leu Ile Ser Val Pro Val Asp Ser
1               5                   10                  15

Arg
```

```
<210> SEQ ID NO 34
<211> LENGTH: 36
<212> TYPE: PRT
<213> ORGANISM: Artificial Sequence
<220> FEATURE:
<223> OTHER INFORMATION: Linker sequence

<400> SEQUENCE: 34

Gly Gly Ser Gly Gly Gly Ser Glu Gly Gly Gly Ser Glu Gly Gly Gly
1               5                   10                  15

Ser Glu Gly Gly Gly Ser Glu Gly Gly Gly Ser Glu Gly Gly Gly Ser
            20                  25                  30

Gly Gly Gly Ser
        35


<210> SEQ ID NO 35
<211> LENGTH: 12
<212> TYPE: PRT
<213> ORGANISM: Artificial Sequence
<220> FEATURE:
<223> OTHER INFORMATION: Linker sequence

<400> SEQUENCE: 35

Gly Gly Gly Ser Gly Gly Gly Ser Gly Gly Gly Ser
1               5                   10


<210> SEQ ID NO 36
<211> LENGTH: 18
<212> TYPE: PRT
<213> ORGANISM: Artificial Sequence
<220> FEATURE:
<223> OTHER INFORMATION: Linker sequence

<400> SEQUENCE: 36

Gly Gly Ser Gly Gly Gly Ser Gly Gly Gly Ser Gly Gly Gly Ser Gly
1               5                   10                  15

Gly Ser


<210> SEQ ID NO 37
<211> LENGTH: 11
<212> TYPE: PRT
<213> ORGANISM: Artificial Sequence
<220> FEATURE:
<223> OTHER INFORMATION: Albumin binding peptide

<400> SEQUENCE: 37

Asp Ile Cys Leu Pro Arg Trp Gly Cys Leu Trp
1               5                   10


<210> SEQ ID NO 38
<211> LENGTH: 6
<212> TYPE: PRT
<213> ORGANISM: Artificial Sequence
<220> FEATURE:
<223> OTHER INFORMATION: Hexa-histidine peptide

<400> SEQUENCE: 38

His His His His His His
1               5


<210> SEQ ID NO 39
<211> LENGTH: 8
<212> TYPE: PRT
<213> ORGANISM: Artificial Sequence
```

```
<220> FEATURE:
<223> OTHER INFORMATION: FLAG peptide

<400> SEQUENCE: 39

Asp Tyr Lys Asp Asp Asp Asp Lys
1               5


<210> SEQ ID NO 40
<211> LENGTH: 10
<212> TYPE: PRT
<213> ORGANISM: Artificial Sequence
<220> FEATURE:
<223> OTHER INFORMATION: Myc peptide

<400> SEQUENCE: 40

Glu Gln Lys Leu Ile Ser Glu Glu Asp Leu
1               5                   10


<210> SEQ ID NO 41
<211> LENGTH: 9
<212> TYPE: PRT
<213> ORGANISM: Artificial Sequence
<220> FEATURE:
<223> OTHER INFORMATION: HA peptide

<400> SEQUENCE: 41

Tyr Pro Tyr Asp Val Pro Asp Tyr Ala
1               5


<210> SEQ ID NO 42
<211> LENGTH: 227
<212> TYPE: PRT
<213> ORGANISM: Homo sapiens

<400> SEQUENCE: 42

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
```

```
        195                 200                 205

His Glu Ala Leu His Asn His Tyr Thr Gln Lys Ser Leu Ser Leu Ser
    210                 215                 220

Pro Gly Lys
225


<210> SEQ ID NO 43
<211> LENGTH: 474
<212> TYPE: PRT
<213> ORGANISM: Artificial Sequence
<220> FEATURE:
<223> OTHER INFORMATION: Long chain polypeptide

<400> SEQUENCE: 43

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ser Gly Gly Gly Ser Gly Gly Gly Ser Gly Gly Gly Ser
225                 230                 235                 240

Gly Gly Gly Ser Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
```

```
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470


<210> SEQ ID NO 44
<211> LENGTH: 227
<212> TYPE: PRT
<213> ORGANISM: Artificial Sequence
<220> FEATURE:
<223> OTHER INFORMATION: Fc domain monomer, short chain polypeptide

<400> SEQUENCE: 44

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

```
    210                 215                 220

Pro Gly Lys
225


<210> SEQ ID NO 45
<211> LENGTH: 473
<212> TYPE: PRT
<213> ORGANISM: Artificial Sequence
<220> FEATURE:
<223> OTHER INFORMATION: Long chain polypeptide

<400> SEQUENCE: 45

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ser Gly Gly Gly Ser Gly Gly Gly Ser Gly Gly Gly Ser
225                 230                 235                 240

Gly Gly Gly Ser Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
```

```
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 46
<211> LENGTH: 226
<212> TYPE: PRT
<213> ORGANISM: Artificial Sequence
<220> FEATURE:
<223> OTHER INFORMATION: Fc domain monomer, short chain polypeptide

<400> SEQUENCE: 46

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
```

225

<210> SEQ ID NO 47
<211> LENGTH: 468
<212> TYPE: PRT
<213> ORGANISM: Artificial Sequence
<220> FEATURE:
<223> OTHER INFORMATION: Long chain polypeptide

<400> SEQUENCE: 47

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
```

```
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Lys Ser Asp Gly Ser Phe Phe Leu Tyr Ser Asp Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465


<210> SEQ ID NO 48
<211> LENGTH: 226
<212> TYPE: PRT
<213> ORGANISM: Artificial Sequence
<220> FEATURE:
<223> OTHER INFORMATION: Fc domain monomer, short chain polypeptide

<400> SEQUENCE: 48

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 49
<211> LENGTH: 473
<212> TYPE: PRT
<213> ORGANISM: Artificial Sequence
<220> FEATURE:
<223> OTHER INFORMATION: Long polypeptide, construct 4/AA

<400> SEQUENCE: 49

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
```

```
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 50
<211> LENGTH: 227
<212> TYPE: PRT
<213> ORGANISM: Artificial Sequence
<220> FEATURE:
<223> OTHER INFORMATION: Fc domain monomer, short chain polypeptide

<400> SEQUENCE: 50

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 51
<211> LENGTH: 227
<212> TYPE: PRT
```

```
<213> ORGANISM: Artificial Sequence
<220> FEATURE:
<223> OTHER INFORMATION: Fc domain monomer, short chain polypeptide

<400> SEQUENCE: 51

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 52
<211> LENGTH: 225
<212> TYPE: PRT
<213> ORGANISM: Artificial Sequence
<220> FEATURE:
<223> OTHER INFORMATION: Fc domain monomer, short chain polypeptide

<400> SEQUENCE: 52

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95
```

```
Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Asp Glu Leu Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Lys Ser Asp Gly Ser Phe Phe Leu Tyr Ser Asp Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225


<210> SEQ ID NO 53
<211> LENGTH: 227
<212> TYPE: PRT
<213> ORGANISM: Artificial Sequence
<220> FEATURE:
<223> OTHER INFORMATION: Fc domain monomer, short chain polypeptide

<400> SEQUENCE: 53

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220
```

```
Pro Gly Lys
225


<210> SEQ ID NO 54
<211> LENGTH: 474
<212> TYPE: PRT
<213> ORGANISM: Artificial Sequence
<220> FEATURE:
<223> OTHER INFORMATION: Fc construct long polypeptide with N-terminal
      Asp to Gln

<400> SEQUENCE: 54

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Ser Gly Gly Gly Ser Gly Gly Gly Ser Gly Gly Gly Ser
225                 230                 235                 240

Gly Gly Gly Ser Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350
```

```
Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly Lys
465                 470


<210> SEQ ID NO 55
<211> LENGTH: 227
<212> TYPE: PRT
<213> ORGANISM: Artificial Sequence
<220> FEATURE:
<223> OTHER INFORMATION: Fc construct short polypeptide with N-terminal
      Asp to Gln

<400> SEQUENCE: 55

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
```

225

<210> SEQ ID NO 56
<211> LENGTH: 473
<212> TYPE: PRT
<213> ORGANISM: Artificial Sequence
<220> FEATURE:
<223> OTHER INFORMATION: Fc construct long polypeptide with N-terminal Asp to Gln

<400> SEQUENCE: 56

Gln Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Cys Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro Gly Lys Ser Gly Gly Gly Ser Gly Gly Gly Ser Gly Gly Gly Ser
225 230 235 240

Gly Gly Gly Ser Gly Gly Gly Asp Lys Thr His Thr Cys Pro Pro Cys
245 250 255

Pro Ala Pro Glu Leu Leu Gly Gly Pro Ser Val Phe Leu Phe Pro Pro
260 265 270

Lys Pro Lys Asp Thr Leu Met Ile Ser Arg Thr Pro Glu Val Thr Cys
275 280 285

Val Val Val Asp Val Ser His Glu Asp Pro Glu Val Lys Phe Asn Trp
290 295 300

Tyr Val Asp Gly Val Glu Val His Asn Ala Lys Thr Lys Pro Arg Glu
305 310 315 320

Glu Gln Tyr Asn Ser Thr Tyr Arg Val Val Ser Val Leu Thr Val Leu
325 330 335

His Gln Asp Trp Leu Asn Gly Lys Glu Tyr Lys Cys Lys Val Ser Asn
340 345 350

```
Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 57
<211> LENGTH: 226
<212> TYPE: PRT
<213> ORGANISM: Artificial Sequence
<220> FEATURE:
<223> OTHER INFORMATION: Fc construct short polypeptide with N-terminal
      Asp to Gln

<400> SEQUENCE: 57

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

<210> SEQ ID NO 58
<211> LENGTH: 468
<212> TYPE: PRT
<213> ORGANISM: Artificial Sequence
<220> FEATURE:
<223> OTHER INFORMATION: Fc construct long polypeptide with N-terminal
      Asp to Gln

<400> SEQUENCE: 58

```
Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
```

```
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Lys Ser Asp Gly Ser Phe Phe Leu Tyr Ser Asp Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465


<210> SEQ ID NO 59
<211> LENGTH: 226
<212> TYPE: PRT
<213> ORGANISM: Artificial Sequence
<220> FEATURE:
<223> OTHER INFORMATION: Fc construct short polypeptide with N-terminal
      Asp to Gln

<400> SEQUENCE: 59

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225
```

```
<210> SEQ ID NO 60
<211> LENGTH: 473
<212> TYPE: PRT
<213> ORGANISM: Artificial Sequence
<220> FEATURE:
<223> OTHER INFORMATION: Fc construct long polypeptide with N-terminal
      Asp to Gln

<400> SEQUENCE: 60

Gln Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365
```

```
Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 61
<211> LENGTH: 226
<212> TYPE: PRT
<213> ORGANISM: Artificial Sequence
<220> FEATURE:
<223> OTHER INFORMATION: Short polypeptide

<400> SEQUENCE: 61

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225


<210> SEQ ID NO 62
```

```
<211> LENGTH: 473
<212> TYPE: PRT
<213> ORGANISM: Artificial Sequence
<220> FEATURE:
<223> OTHER INFORMATION: Long polypeptide

<400> SEQUENCE: 62

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ala Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380
```

```
Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 63
<211> LENGTH: 226
<212> TYPE: PRT
<213> ORGANISM: Artificial Sequence
<220> FEATURE:
<223> OTHER INFORMATION: Short polypeptide construct 6/A1

<400> SEQUENCE: 63

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225


<210> SEQ ID NO 64
<211> LENGTH: 473
<212> TYPE: PRT
<213> ORGANISM: Artificial Sequence
```

<220> FEATURE:
<223> OTHER INFORMATION: Long peptide construct 6/A1

<400> SEQUENCE: 64

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400
```

```
Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 65
<211> LENGTH: 473
<212> TYPE: PRT
<213> ORGANISM: Artificial Sequence
<220> FEATURE:
<223> OTHER INFORMATION: Long polypeptide

<400> SEQUENCE: 65

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ala Ser Arg Thr Pro Glu Val Thr Cys
        275                 280                 285
```

```
Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470
```

<210> SEQ ID NO 66
<211> LENGTH: 473
<212> TYPE: PRT
<213> ORGANISM: Artificial Sequence
<220> FEATURE:
<223> OTHER INFORMATION: Long polypeptide

<400> SEQUENCE: 66

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Pro Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 67
<211> LENGTH: 473
<212> TYPE: PRT
<213> ORGANISM: Artificial Sequence
<220> FEATURE:
<223> OTHER INFORMATION: Long polypeptide

<400> SEQUENCE: 67

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

```
His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ala Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Pro Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470
```

```
<210> SEQ ID NO 68
<211> LENGTH: 473
<212> TYPE: PRT
<213> ORGANISM: Artificial Sequence
<220> FEATURE:
<223> OTHER INFORMATION: Long protein

<400> SEQUENCE: 68

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Pro Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365
```

```
Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 69
<211> LENGTH: 473
<212> TYPE: PRT
<213> ORGANISM: Artificial Sequence
<220> FEATURE:
<223> OTHER INFORMATION: Long polypeptide

<400> SEQUENCE: 69

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255
```

```
Pro Ala Pro Glu Leu Leu Gly Gly Pro Ser Val Phe Leu Phe Pro Pro
            260                 265                 270

Lys Pro Lys Asp Thr Leu Met Ala Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Pro Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 70
<211> LENGTH: 226
<212> TYPE: PRT
<213> ORGANISM: Artificial Sequence
<220> FEATURE:
<223> OTHER INFORMATION: Short polypeptide construct 16/CC

<400> SEQUENCE: 70

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140
```

```
Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225


<210> SEQ ID NO 71
<211> LENGTH: 473
<212> TYPE: PRT
<213> ORGANISM: Artificial Sequence
<220> FEATURE:
<223> OTHER INFORMATION: Long protein

<400> SEQUENCE: 71

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270
```

```
Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470
```

<210> SEQ ID NO 72
<211> LENGTH: 473
<212> TYPE: PRT
<213> ORGANISM: Artificial Sequence
<220> FEATURE:
<223> OTHER INFORMATION: Long protein

<400> SEQUENCE: 72

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ala Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 73
<211> LENGTH: 226
<212> TYPE: PRT
<213> ORGANISM: Artificial Sequence
<220> FEATURE:
<223> OTHER INFORMATION: Short polypeptide construct 18/Q1

<400> SEQUENCE: 73

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45
```

```
Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Asp Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225


<210> SEQ ID NO 74
<211> LENGTH: 473
<212> TYPE: PRT
<213> ORGANISM: Artificial Sequence
<220> FEATURE:
<223> OTHER INFORMATION: Long polypeptide

<400> SEQUENCE: 74

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175
```

```
Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470
```

<210> SEQ ID NO 75
<211> LENGTH: 473
<212> TYPE: PRT
<213> ORGANISM: Artificial Sequence
<220> FEATURE:
<223> OTHER INFORMATION: Long polypeptide

<400> SEQUENCE: 75

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

```
His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ala Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Arg Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470
```

<210> SEQ ID NO 76
<211> LENGTH: 473
<212> TYPE: PRT
<213> ORGANISM: Artificial Sequence
<220> FEATURE:
<223> OTHER INFORMATION: Long polypeptide

<400> SEQUENCE: 76

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Pro Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
```

```
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 77
<211> LENGTH: 473
<212> TYPE: PRT
<213> ORGANISM: Artificial Sequence
<220> FEATURE:
<223> OTHER INFORMATION: Long polypeptide

<400> SEQUENCE: 77

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
```

```
            260                 265                 270

Lys Pro Lys Asp Thr Leu Met Ala Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Pro Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 78
<211> LENGTH: 473
<212> TYPE: PRT
<213> ORGANISM: Artificial Sequence
<220> FEATURE:
<223> OTHER INFORMATION: Long polypeptide Construct 18/Q1

<400> SEQUENCE: 78

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
```

```
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ile Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Pro Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400

Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470
```

<210> SEQ ID NO 79
<211> LENGTH: 473
<212> TYPE: PRT
<213> ORGANISM: Artificial Sequence
<220> FEATURE:

<223> OTHER INFORMATION: Long polypeptide construct 19/Q2

<400> SEQUENCE: 79

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ala Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Pro Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Lys Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys Gly Gly Gly Gly Gly Gly Gly Gly Gly Gly Gly Gly Gly
225                 230                 235                 240

Gly Gly Gly Gly Gly Gly Gly Asp Lys Thr His Thr Cys Pro Pro Cys
                245                 250                 255

Pro Ala Pro Glu Leu Leu Gly Gly Pro Ser Val Phe Leu Phe Pro Pro
            260                 265                 270

Lys Pro Lys Asp Thr Leu Met Ala Ser Arg Thr Pro Glu Val Thr Cys
        275                 280                 285

Val Val Val Asp Val Ser His Glu Asp Pro Glu Val Lys Phe Asn Trp
    290                 295                 300

Tyr Val Asp Gly Val Glu Val His Asn Ala Lys Thr Lys Pro Pro Glu
305                 310                 315                 320

Glu Gln Tyr Asn Ser Thr Tyr Arg Val Val Ser Val Leu Thr Val Leu
                325                 330                 335

His Gln Asp Trp Leu Asn Gly Lys Glu Tyr Lys Cys Lys Val Ser Asn
            340                 345                 350

Lys Ala Leu Pro Ala Pro Ile Glu Lys Thr Ile Ser Lys Ala Lys Gly
        355                 360                 365

Gln Pro Arg Glu Pro Gln Val Tyr Thr Leu Pro Pro Ser Arg Asp Glu
    370                 375                 380

Leu Thr Lys Asn Gln Val Ser Leu Thr Cys Leu Val Lys Gly Phe Tyr
385                 390                 395                 400
```

-continued

```
Pro Ser Asp Ile Ala Val Glu Trp Glu Ser Asn Gly Gln Pro Glu Asn
                405                 410                 415

Asn Tyr Lys Thr Thr Pro Pro Val Leu Lys Ser Asp Gly Ser Phe Phe
            420                 425                 430

Leu Tyr Ser Asp Leu Thr Val Asp Lys Ser Arg Trp Gln Gln Gly Asn
        435                 440                 445

Val Phe Ser Cys Ser Val Met His Glu Ala Leu His Asn His Tyr Thr
    450                 455                 460

Gln Lys Ser Leu Ser Leu Ser Pro Gly
465                 470


<210> SEQ ID NO 80
<211> LENGTH: 32
<212> TYPE: PRT
<213> ORGANISM: Artificial Sequence
<220> FEATURE:
<223> OTHER INFORMATION: Linker sequence

<400> SEQUENCE: 80

Gly Gly Ser Gly Gly Gly Ser Gly Gly Gly Ser Gly Gly Gly Gly Gly
1               5                   10                  15

Ser Gly Gly Gly Gly Ser Gly Gly Gly Gly Ser Gly Gly Gly Gly Ser
            20                  25                  30
```

ENGINEERED FC CONSTRUCTS

CROSS-REFERENCE TO RELATED APPLICATIONS

This application is a Continuation application of U.S. application Ser. No. 16/474,640, filed on Jun. 28, 2019, which is a National Phase application under 35 U.S.C. § 371 of PCT International Application No. PCT/US2018/012488 filed Jan. 5, 2018, which claims the benefit of the filing dates of U.S. Provisional Application No. 62/443,495, filed Jan. 6, 2017, U.S. Provisional Application No. 62/510,228, filed on May 23, 2017 and U.S. Provisional Application No. 62/589,473, filed on Nov. 21, 2017. The contents of each of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Nov. 3, 2021, is named 14131_0150002_Seq_Listing.txt and is 139,264 bytes.

BACKGROUND

Therapeutic proteins, e.g., therapeutic antibodies and Fc-fusion proteins, have rapidly become a clinically important drug class for patients with immunological and inflammatory diseases, cancers, and infections.

SUMMARY

The present disclosure features biologically active Fc domain-containing therapeutic constructs. Such constructs may have desirable serum half-life and/or binding affinity and/or avidity for Fc receptors.

In general, the disclosure features Fc constructs having 2-10 Fc domains, e.g., Fc constructs having 2, 3, 4, 5, 6, 7, 8, 9, or 10 Fc domains. In some embodiments, the Fc construct includes 2-10 Fc domains, 2-5 Fc domains, 2-4 Fc domains, 2-3 Fc domains, 3-5 Fc domains, 2-8 Fc domains, or 2-6 Fc domains. In some embodiments, the Fc construct includes 2-4 Fc domains. In some embodiments, the Fc construct includes 5-10 Fc domains (e.g., 5-6, 5-7, 5-8, 5-9, or 5-10 Fc domains).

In some embodiments, constructs (e.g., Fc constructs having 2-4 Fc domains, e.g., 2, 3, or 4 Fc domains) and homogenous pharmaceutical compositions (e.g., those containing Fc constructs having 2-4 Fc domains, e.g., 2, 3, or 4 Fc domains) of the disclosure are useful, e.g., to reduce inflammation in a subject, to promote clearance of autoantibodies in a subject, to suppress antigen presentation in a subject, to block an immune response, e.g., block an immune complex-based activation of the immune response in a subject, and to treat immunological and inflammatory diseases (e.g., autoimmune diseases) in a subject. The Fc constructs described herein can be used to treat patients having immunological and inflammatory diseases without significant stimulation of immune cells. In some embodiments, constructs (e.g., Fc constructs having 5-10 Fc domains, e.g., 5, 6, 7, 8, 9, or 10 Fc domains) and homogenous pharmaceutical compositions (e.g., those containing Fc constructs having 5-10 Fc domains, e.g., 5, 6, 7, 8, 9, or 10 Fc domains) of the disclosure are useful, e.g., to induce immune cell activation of the immune response in a subject, to increase phagocytosis of a target cell (i.e., a cancer cell or an infected cell) in a subject, and to treat diseases such as cancers and infections in a subject.

The properties of these constructs allow for the efficient generation of substantially homogenous compositions. The degree of homogeneity of a composition influences the pharmacokinetics and in vivo performance of the composition. Such homogeneity in a composition is desirable in order to ensure the safety, efficacy, uniformity, and reliability of the composition. An Fc construct of the disclosure can be in a composition or population that is substantially homogenous (e.g., at least 85%, 90%, 95%, 98%, or 99% homogeneous).

As described in further detail herein, the disclosure features substantially homogenous compositions containing Fc constructs that all have the same number of Fc domains, as well as methods of preparing such substantially homogenous compositions.

In a first aspect, the disclosure features an Fc construct including a) a first polypeptide including i) a first Fc domain monomer; ii) a second Fc domain monomer; and iii) a linker joining the first Fc domain monomer to the second Fc domain monomer; b) a second polypeptide including i) a third Fc domain monomer; ii) a fourth Fc domain monomer; and iii) a linker joining the third Fc domain monomer to the fourth Fc domain monomer; c) a third polypeptide includes a fifth Fc domain monomer; and d) a fourth polypeptide includes a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein each of the first and second polypeptides comprises the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPPC-PAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVF-SCSVMHEALHNHYTQKSLSLSPG (SEQ ID NO: 76), and each of the third and fourth polypeptides comprises the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDS-DGSFFLVSKLTVDKSRWQQGNVFSCSV MHEALHN-HYTQKSLSLSPG (SEQ ID NO: 70).

In another aspect, the disclosure features an Fc construct including a) a first polypeptide including i) a first Fc domain monomer; ii) a second Fc domain monomer; and iii) a linker joining the first Fc domain monomer to the second Fc domain monomer; b) a second polypeptide including i) a third Fc domain monomer; ii) a fourth Fc domain monomer; and iii) a linker joining the third Fc domain monomer to the fourth Fc domain monomer; c) a third polypeptide includes a fifth Fc domain monomer; and d) a fourth polypeptide includes a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein at least one Fc domain includes an amino acid modification at position I253 (e.g., a single amino acid modification at position I253). In another aspect, the disclosure features an Fc construct including a) a first polypeptide including i) a first Fc domain monomer; ii) a second Fc domain monomer; and iii) a linker joining the first Fc domain monomer to the second Fc domain monomer; b) a second polypeptide including i) a third Fc domain monomer; ii) a fourth Fc domain monomer; and iii) a linker joining the third Fc domain monomer to the fourth Fc domain monomer; c) a third polypeptide includes a fifth Fc domain monomer; and d) a fourth polypeptide includes a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein at least one Fc domain monomer includes an amino acid substitution at position I253.

In some cases the first and second polypeptides are identical to each other and the third and fourth polypeptides are identical to each other. In some embodiments, the first Fc domain includes an amino acid modification at position I253. In some cases, one or both of the first and fifth Fc domain monomers comprises an amino acid substitution at position I253. In some embodiments, the second Fc domain includes an amino acid modification at position I253. In some embodiments, one or both of the second and fourth Fc domain monomers comprises an amino acid substitution at position I253. In some embodiments, the third Fc domain includes an amino acid modification at position I253. In some embodiments, one or both of the third and sixth Fc domain monomers comprises an amino acid substitution at position I253. In some embodiments, each amino acid modification (e.g., substitution) at position I253 is independently selected from the group consisting of I253A, I253C, I253D, I253E, I253F, I253G, I253H, I253I, I253K, I253L, I253M, I253N, I253P, I253Q, I253R, I253S, I253T, I253V, I253W, and I253Y. In some embodiments, each amino acid modification (e.g., substitution) at position I253 is I253A. In some embodiments, the Fc construct (e.g., at least one Fc domain monomer) includes at least one amino acid modification at position R292. In some embodiments, at least one Fc domain monomer includes an amino acid substitution at position R292. In some embodiments, the first Fc domain includes an amino acid modification at position R292. In some embodiments, the first Fc domain (e.g., one or both of the first Fc domain monomer and the fifth Fc domain monomer) includes an amino acid substitution at position R292. In some embodiments, the second Fc domain includes an amino acid modification at position R292. In some embodiments, the second Fc domain (e.g., one or both of the second Fc domain monomer and the fourth Fc domain monomer) includes an amino acid substitution at position R292. In some embodiments, the third Fc domain includes an amino acid modification at position R292. In some embodiments, the third Fc domain (e.g., one or both of the third Fc domain monomer and the sixth Fc domain monomer) includes an amino acid substitution at position R292. In some embodiments, each of the first, second, and third Fc domain includes an amino acid modification (e.g., substitution) at position R292. In some cases, one or both of the first and fifth Fc domain monomers comprises an amino acid substitution at position R292, one or both of the second and fourth Fc domain monomers comprises an amino acid substitution at position R292, and one or more of the third and sixth Fc domain monomers comprises an amino acid substitution at position R292. In some embodiments, each of the first, second, and third Fc domain includes the amino acid modification (e.g., substitution) R292P. In some embodiments, each amino acid modification (e.g., substitution) at position R292 is independently selected from the group consisting of R292D, R292E, R292L, R292P, R292Q, R292R, R292T, and R292Y. In some embodiments, each amino acid modification (e.g., substitution) at position R292 is R292P.

In some embodiments of all aspects, each of the Fc domains is based on a human IgG1 Fc sequence and includes the modifications described herein (i.e., is a variant of a human IgG Fc sequence). In some embodiments, the base IgG1 Fc sequence is SEQ ID NO: 42 and includes up to 10 single amino acid modifications. In some embodiments, each of the Fc domains of the Fc constructs described herein are an IgG1 Fc sequence (e.g., SEQ ID NO: 42) with up to 10 single amino acid modifications. In some embodiments, the IgG1 Fc sequence is SEQ ID NO: 42 and includes the modifications of an engineered cavity, engineered protuberance, and/or electrostatic steering modifications to control assembly of the polypeptides; and/or the modifications of binding-related mutations to modify the pharmacokinetics of the construct, as described herein. Thus, the up to 10 single amino acid modifications can include a modification (e.g., substitution) at one or both of I253 (e.g., I253A) and R292 (e.g., R292P) and modifications (e.g., substitutions) to provide: an engineered cavity, and engineered protuberance, and/or electrostatic steering modifications to control assembly of the polypeptides. In some cases, each Fc domain monomer comprises up to 10, 9, 8, 7, 6, 5, 4, 3, 2, or 1 single amino acid modifications in addition to a substitution at one or both of I253 and R292. The modifications to provide an engineered cavity, engineered protuberance, and/or electrostatic steering modifications to control assembly of the polypeptides are preferably in the CH3 domain(s) of an Fc domain.

In another aspect, the disclosure features an Fc construct including: a) a first polypeptide including: i). a first Fc domain monomer; ii). a second Fc domain monomer; and iii). a linker joining the first Fc domain monomer to the second Fc domain monomer; b). a second polypeptide including i). a third Fc domain monomer; ii). a fourth Fc domain monomer; and iii). a linker joining the third Fc domain monomer to the fourth Fc domain monomer; c). a third polypeptide includes a fifth Fc domain monomer; and d). a fourth polypeptide includes a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein at least one Fc domain comprises an amino acid modification at position R292 (e.g., a single amino acid modification). In another aspect, the disclosure features an Fc construct including: a) a first polypeptide including: i). a first Fc domain monomer; ii). a second Fc domain monomer; and iii). a linker joining the first Fc domain monomer to the second Fc domain monomer; b). a second polypeptide including i). a third Fc domain monomer; ii). a fourth Fc domain monomer; and iii). a linker joining the third Fc domain monomer to the fourth Fc domain monomer; c). a third polypeptide includes a fifth Fc domain monomer; and d). a fourth polypeptide includes a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein at least one Fc domain monomer comprises an amino acid substitution at position R292.

In some embodiments, the first Fc domain includes an amino acid modification at position R292. In some embodiments, one or both of the first and the fifth Fc domain monomers comprises an amino acid substitution at position R292. In some embodiments, the second Fc domain includes an amino acid modification at position R292. In some embodiments, one or both of the second and the fourth Fc domain monomers comprises an amino acid substitution at position R292. In some embodiments, the third Fc domain includes an amino acid modification at position R292. In some embodiments, one or both of the third and the sixth Fc domain monomers comprises an amino acid substitution at position R292. In some embodiments, each of the first, second, and third Fc domain includes an amino acid modification (e.g., substitution) at position R292. In some embodiments, each of the first, second, and third Fc domain includes the amino acid modification (e.g., substitution) R292P (i.e., each Fc monomer has R292P modification, e.g., compared to SEQ ID NO:42). In some embodiments, one or both of the first and fifth Fc domain monomers includes the amino acid substitution R292P, one or both of the second and fourth Fc domain monomers includes amino acid substitution R292P, and one or both of the third and sixth Fc domain monomers includes the amino acid substitution R292P.

In some embodiments, each amino acid modification (e.g., substitution) at position R292 is independently selected from R292D, R292E, R292L, R292P, R292Q, R292R, R292T, or R292Y. In some embodiments, each amino acid modification (e.g., substitution) at position R292 is R292P. In some embodiments, each of the first and third Fc domain includes the amino acid modification (e.g., substitution) I253A, and each of the first, second, and third Fc domain includes the amino acid modification (e.g., substitution) R292P. In some embodiments, one or both of the first and fifth Fc domain monomers includes the amino acid substitution I253A, one or both of the third and sixth Fc domain monomers includes the amino acid substitution I253A, one or both of the first and fifth Fc domain monomers includes the amino acid substitution R292P, one or both of the second and fourth Fc domain monomers includes amino acid substitution R292P, and one or both of the third and sixth Fc domain monomers includes the amino acid substitution R292P. In some embodiments, each of the first, second, and third Fc domain includes the amino acid modification (e.g., substitution) I253A and R292P. In some embodiments, one or both of the first and fifth Fc domain monomers includes the amino acid substitution I253A, one or both of the second and fourth Fc domain monomers includes amino acid substitution I253A, and one or both of the third and sixth Fc domain monomers includes the amino acid substitution I253A, one or both of the first and fifth Fc domain monomers includes the amino acid substitution R292P, one or both of the second and fourth Fc domain monomers includes amino acid substitution R292P, and one or both of the third and sixth Fc domain monomers includes the amino acid substitution R292P.

In some embodiments, the sequence of each Fc domain is based on a human IgG1 Fc domain sequence with no more than ten single amino acid modifications. In some embodiments, the sequence of each Fc domain is based on SEQ ID NO: 42 with no more than ten single amino acid modifications.

In some embodiments, each of the first Fc domain and third Fc domain include the amino acid substitutions I253A and R292P, and the second Fc domain includes the amino acid substitution R292P.

In some cases, one or both of the first and fifth Fc domain monomers comprises the amino acid substitution I253A; one or both of the first and fifth Fc domain monomers comprises the amino acid substitution R292P; one or both of the third and sixth Fc domain monomers comprises the amino acid substitution I253A; one or both of the third and sixth Fc domain monomers comprises the amino acid substitution R292P; and one or both of the second and fourth Fc domain monomers comprises the amino acid substitution R292P.

In some embodiments, the second Fc domain includes the amino acid substitution I253A. In some embodiments, one or both of the second and fourth Fc domain monomers comprises the amino acid substitution I253A. In some embodiments, each of the first Fc domain and third Fc domain include the amino acid substitution I253A. In some embodiments, one or both of the first and fifth Fc domain monomers comprises the amino acid substitution I253A and one or both of the third and sixth Fc domain monomers comprises the amino acid substitution I253A. In some embodiments, each of the first Fc domain, second Fc domain, and third Fc domain include the amino acid substitution I253A. In some embodiments, one or both of the first and fifth Fc domain monomers comprises the amino acid substitution I253A, one or both of the second and fourth Fc domain monomers comprises the amino acid substitution I253A, and one or both of the third and sixth Fc domain monomers comprises the amino acid substitution I253A.

In some embodiments, the second Fc domain includes the amino acid substitution R292P. In some embodiments, one or both of the second and fourth Fc domain monomers comprises the amino acid substitution R292P. In some embodiments, the second Fc domain includes the amino acid substitutions I253A and R292P. In some embodiments, one or both of the second and fourth Fc domain monomers comprises the amino acid substitution I253A, and one or both of the second and fourth Fc domain monomers comprises the amino acid substitution R292P. In some embodiments, each of the first Fc domain and third Fc domain include the amino acid substitution I253A, and the second Fc domain includes the amino acid substitution R292P. In some embodiments, one or both of the first and fifth Fc domain monomers comprises the amino acid substitution I253A; one or both of the third and sixth Fc domain monomers comprises the amino acid substitution I253A; and one or both of the second and fourth Fc domain monomers comprises the amino acid substitution R292P.

In some embodiments, each of the first Fc domain and third Fc domain include the amino acid substitution I253A, and the second Fc domain includes the amino acid substitution I253A and R292P. In some embodiments, one or both of the first and fifth Fc domain monomers comprises the amino acid substitution I253A; one or both of the third and sixth Fc domain monomers comprises the amino acid substitution I253A; one or both of the second and fourth Fc domain monomers comprises the amino acid substitution I253A; and one or both of the second and fourth Fc domain monomers comprises the amino acid substitution R292P. In some embodiments, each of the first Fc domain and third Fc domain include the amino acid substitution R292P. In some embodiments, one or both of the first and fifth Fc domain monomers comprises the amino acid substitution R292P and one or both of the third and sixth Fc domain monomers comprises the amino acid substitution R292P.

In some embodiments, the first Fc domain and third Fc domain include the amino acid substitution R292P, and the second Fc domain includes the amino acid substitution I253A. In some embodiments, one or both of the first and fifth Fc domain monomers comprises the amino acid substitution R292P; one or both of the third and sixth Fc domain monomers comprises the amino acid substitution R292P; and one or both of the second and fourth Fc domain monomers comprises the amino acid substitution I253A. In some embodiments, each of the first Fc domain and third Fc domain include I253A and R292P (e.g., include the amino acid substitutions I253A and R292P). In some embodiments, one or both of the first and fifth Fc domain monomers comprises the amino acid substitution I253A; one or both of the first and fifth Fc domain monomers comprises the amino acid substitution R292P; one or both of the third and sixth Fc domain monomers comprises the amino acid substitution I253A; and one or both of the third and sixth Fc domain monomers comprises the amino acid substitution R292P.

In some embodiments, each of the first Fc domain and third Fc domain include the amino acid substitutions I253A and R292P, and the second Fc domain includes the amino acid substitution I253A. In some embodiments, one or both of the first and fifth Fc domain monomers comprises the amino acid substitution I253A; one or both of the first and fifth Fc domain monomers comprises the amino acid substitution R292P; one or both of the third and sixth Fc domain monomers comprises the amino acid substitution I253A; one or both of the third and sixth Fc domain monomers comprises the amino acid substitution R292P; and one or both of the second and fourth Fc domain monomers comprises the amino acid substitution I253A. In some embodiments, each of the first Fc domain, second Fc domain, and third Fc domain include the amino acid substitution R292P. In some embodiments, one or both of the first and fifth Fc domain monomers comprises the amino acid substitution R292P; one or both of the second and fourth Fc domain monomers comprises the amino acid substitution R292P; and one or both of the third and sixth Fc domain monomers comprises the amino acid substitution R292P.

In some embodiments, each of the first Fc domain and third Fc domain include the amino acid substitution R292P, and the second Fc domain includes the amino acid substitutions I253A and R292P. In some embodiments, one or both of the first and fifth Fc domain monomers comprises the amino acid substitution R292P; one or both of the third and sixth Fc domain monomers comprises the amino acid substitution R292P; one or both of the second and fourth Fc domain monomers comprises the amino acid substitution I253A; and one or both of the second and fourth Fc domain monomers comprises the amino acid substitution R292P. In some embodiments, each of the first Fc domain, second Fc domain, and third Fc domain include the amino acid substitutions I253A and R292P. In some embodiments, one or both of the first and fifth Fc domain monomers comprises the amino acid substitution I253A; one or both of the first and fifth Fc domain monomers comprises the amino acid substitution R292P; one or both of the second and fourth Fc domain monomers comprises the amino acid substitution I253A; one or both of the second and fourth Fc domain monomers comprises the amino acid substitution R292P; one or both of the third and sixth Fc domain monomers comprises the amino acid substitution I253A; and one or both of the third and sixth Fc domain monomers comprises the amino acid substitution R292P.

In some embodiments, the first Fc domain monomer and the fifth Fc domain monomer include complementary dimerization selectivity modules that promote dimerization between the first Fc domain monomer and the fifth Fc domain monomer. In some embodiments, the second Fc domain monomer and the fourth Fc domain monomer include complementary dimerization selectivity modules that promote dimerization between the second Fc domain monomer and the fourth Fc domain monomer. In some embodiments, the third Fc domain monomer and the sixth Fc domain monomer include complementary dimerization selectivity modules that promote dimerization between the third Fc domain monomer and the sixth Fc domain monomer. In some embodiments, the first polypeptide and the second polypeptide comprise, consist of, or consist essentially of the same amino acid sequence and wherein the third polypeptide and the fourth polypeptide comprise, consist of, or consist essentially of the same amino acid sequence. In some embodiments, each of the second Fc domain monomer and fourth Fc domain monomer includes D399K and either K409D or K409E. In some embodiments, each of the second Fc domain monomer and fourth Fc domain monomer includes K392D and D399K. In some embodiments, each of the second Fc domain monomer and fourth Fc domain monomer includes E357K and K370E. In some embodiments, each of the second Fc domain monomer and fourth Fc domain monomer includes D356K and K439D. In some embodiments, each of the second Fc domain monomer and fourth Fc domain monomer includes K392E and D399K. In some embodiments, each of the second Fc domain monomer and fourth Fc domain monomer includes E357K and K370D. In some embodiments, each of the second Fc domain monomer and fourth Fc domain monomer includes D356K and K439E. In some embodiments, each of the first Fc domain monomer and third Fc domain monomer includes S354C and T366W and the fifth Fc domain monomer and sixth Fc domain monomer each include Y349C, T366S, L368A, and Y407V. In some embodiments, each of the third and fourth polypeptides includes S354C and T366W and the first Fc domain monomer and third Fc domain monomer each include Y349C, T366S, L368A, and Y407V. In some embodiments, each of the first Fc domain monomer and third Fc domain monomer includes E357K or E357R and the fifth Fc domain monomer and sixth Fc domain monomer each include K370D or K370E. In some embodiments, the first Fc domain monomer and third Fc domain monomer include K370D or K370E and the fifth Fc domain monomer and sixth Fc domain monomer each include E357K or E357R. In some embodiments, each of the first Fc domain monomer and third Fc domain monomer include K409D or K409E and the fifth Fc domain monomer and sixth Fc domain monomer each include D399K or D399R. In some embodiments, the first Fc domain monomer and third Fc domain monomer include D399K or D399R and the fifth Fc domain monomer and sixth Fc domain monomer each include K409D or K409E.

In some embodiments, the linker (e.g., spacer) includes a polypeptide having the sequence GGGGGGGGGGGGGGGGGGGG (SEQ ID NO: 23), GGGGS (SEQ ID NO: 1), GGSG (SEQ ID NO: 2), SGGG (SEQ ID NO: 3), GSGS (SEQ ID NO: 4), GSGSGS (SEQ ID NO: 5), GSGSGSGS (SEQ ID NO: 6), GSGSGSGSGS (SEQ ID NO: 7), GSGSGSGSGSGS (SEQ ID NO: 8), GGSGGS (SEQ ID NO: 9), GGSGGSGGS (SEQ ID NO: 10), GGSGGSGGSGGS (SEQ ID NO: 11), GGSGGGSG (SEQ ID NO: 12), GGSGGGSGGGSG (SEQ ID NO: 13), GGSGGGSGGGSGGGSG (SEQ ID NO: 14), GGSGGGSGGGSGGGGGSGGGGSGGGGSGGGGS (SEQ ID NO: 80), GENLYFQSGG (SEQ ID NO: 28), SACYCELS (SEQ ID NO: 29), RSIAT (SEQ ID NO: 30), RPACKIPNDLKQKVMNH (SEQ ID NO: 31), GGSAGGSGSGSSGGSSGASGTGTAGGTGSGSGTGSG (SEQ ID NO: 32), AAANSSIDLISVPVDSR (SEQ ID NO: 33), GGSGGGSEGGGSEGGGSEGGGSEGGGSEGGGSGGGS (SEQ ID NO: 34), GGGSGGGSGGGS (SEQ ID NO: 35), SGGGSGGGSGGGSGGGSGGG (SEQ ID NO: 18), GGSGGGSGGGSGGGSGGS (SEQ ID NO: 36), GGGG (SEQ ID NO: 19), GGGGGGGG (SEQ ID NO: 20), GGGGGGGGGGGG (SEQ ID NO: 21), or GGGGGGGGGGGGGGGG (SEQ ID NO: 22). In other embodiments, one or more linkers in an Fc construct described herein is a spacer, e.g., an amino acid spacer of 2-200 amino acids (e.g., 2-100, 3-200, 3-150, 3-100, 3-60, 3-50, 3-40, 3-30, 3-20, 3-10, 3-8, 3-5, 4-30, 5-30, 6-30, 8-30, 10-20, 10-30, 12-30, 14-30, 20-30, 15-25, 15-30, 18-22, and 20-30 amino acids). In some cases, the amino acid spacer includes only glycine, only serine, or only serine and glycine. In some embodiments, the amino acid spacer includes only glycine.

In some embodiments, each of the first polypeptide and the second polypeptide comprises, consists of, or consists essentially of the sequence DKTHTCPPCPAPELLGGPSVFLFPPKPKDTLMASRTPEVTCVVVDVSHEDPEVKFNWYVDGVEVHNAKTKPPEEQYNSTYRVVSVLTVLHQDWLNGKEYKCKVSNKALPAPIEKTISKAKGQPREPQVYTLPPCRDKLTKNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGGGDKTHTCPPCPAPELLGGPSVFLFPPK PKDTLMISRTPEVTCVVVDVSHEDPEVKFNWYVDGVEVHNAKTKPPEEQYNSTYRVVSVLTVLHQDWLN GKEYKCKVSNKALPAPIEKTISKAKGQPREPQVYTLPPSRDELTKNQVSLTCLVKGFYPSDIAVEWESNG QPENNYKTTPPVLKSDGSFFLYSDLTVDKSRWQQGNVFSCSVMHEALHNHYTQKSLSLSPG (SEQ ID NO: 78). In some embodiments, each of the first polypeptide and the second polypeptide comprises, consists of, or consists essentially of the sequence DKTHTCPPCPAPELLGGPSVFLFPPKPKDTLMASRTPEVTCVVVDVSHEDPEVKFNWYVDGVEVHNAKTKPPEEQYNSTYRVVSVLTVLHQDWLNGKEYKCKVSNKALPAPIEKTISKAKGQPREPQVYTLPPCRDKLTKNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGGGDKTHTCPPCPAPELLGGPSVFLFPPK PKDTLMISRTPEVTCVVVDVSHEDPEVKFNWYVDGVEVHNAKTKPPEEQYNSTYRVVSVLTVLHQDWLN GKEYKCKVSNKALPAPIEKTISKAKGQPREPQVYTLPPSRDELTKNQVSLTCLVKGFYPSDIAVEWESNG QPENNYKTTPPVLKSDGSFFLYSDLTVDKSRWQQGNVFSCSVMHEALHNHYTQKSLSLSPG (SEQ ID NO: 78) with up to 10 (9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 78 with up to 10 (e.g., no more than 1, no more than 2, no more than 3, no more than 4, no more than 5, no more than 6, no more than 7, no more than 8, no more than 9) single amino acid modifications in the region outside of the linker (e.g., outside the subsequence GGGGGGGGGGGGGGGGGGGG (SEQ ID NO: 23). The linker within SEQ ID NO:78 can be replaced with an alternative linker. In some embodiments, each of the first polypeptide and the second polypeptide comprises, consists of, or consists essentially of the sequence of SEQ ID NO: 78 with up to 10 single amino acid modifications, provided that position 33 of SEQ ID NO: 78 is alanine, position 72 of SEQ ID NO: 78 is proline, and position 319 of SEQ ID NO: 78 is proline.

In some embodiments, each of the first polypeptide and the second polypeptide comprises, consists of, or consists essentially of the sequence DKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPCRDKLTKNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGGGDKTHTCPPCPAPELLGGPSVFLFPPK PKDTLMISRTPEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCLVKGFYPSDIAVEWESNG QPENNYKTTPPVLKSDGSFFLYSDLTVDKSRWQQGNVFSCSVMHEALHNHYTQKSLSLSPG (SEQ ID NO: 49). In some embodiments, each of the first polypeptide and the second polypeptide comprises, consists of, or consists essentially of the sequence SEQ ID NO: 49 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 49 with up to 10 single amino acid modifications, provided that none of the up to 10 (e.g., no more than 1, no more than 2, no more than 3, no more than 4, no more than 5, no more than 6, no more than 7, no more than 8, no more than 9) single amino acid modifications in the region outside the linker (e.g., outside the subsequence GGGGGGGGGGGGGGGGGGGG (SEQ ID NO: 23). The linker within SEQ ID NO:49 can be replaced with an alternative linker. In some embodiments, each of the first polypeptide and the second polypeptide comprises, consists of, or consists essentially of the sequence of SEQ ID NO: 49 with up to 10 single amino acid modifications, provided that position 134 of SEQ ID NO: 49 is cysteine, position 137 of SEQ ID NO: 49 is lysine, position 146 of SEQ ID NO: 49 is tryptophan, position 426 of SEQ ID NO: 49 is lysine, and position 436 of SEQ ID NO: 49 is aspartic acid.

In some embodiments, each of the first polypeptide and the second polypeptide comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMASRTPE-VTCVVVDVSHEDPE-VKFNWYVDGVEVHNAKTKPREEQYN-STYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVFS-CSVMHEALHNHYTQKSLSLSPG (SEQ ID NO: 62). In some embodiments, each of the first polypeptide and the second polypeptide comprises, consists of, or consists essentially of the sequence SEQ ID NO: 62 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 62 with up to 10 (e.g., no more than 1, no more than 2, no more than 3, no more than 4, no more than 5, no more than 6, no more than 7, no more than 8, no more than 9) single amino acid modifications in the region outside the linker (e.g., outside the subsequence GGGGGGGGGGGGGGGGGGGG (SEQ ID NO: 23). The linker within SEQ ID NO:62 can be replaced with an alternative linker. In some embodiments, each of the first polypeptide and the second polypeptide comprises, consists of, or consists essentially of the sequence of SEQ ID NO: 62 with up to 10 single amino acid modifications, provided that position 134 of SEQ ID NO: 62 is cysteine, position 137 of SEQ ID NO: 62 is lysine, position 146 of SEQ ID NO: 62 is tryptophan, position 280 of SEQ ID NO: 62 is alanine, position 426 of SEQ ID NO: 62 is lysine, and position 436 of SEQ ID NO: 62 is aspartic acid.

In some embodiments, each of the first polypeptide and the second polypeptide comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMISRTPE-VTCVVVDVSHEDPE-VKFNWYVDGVEVHNAKTKPREEQYN-STYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQG-NVFSCSVMHEALHNHYTQKSLSLSPG (SEQ ID NO: 64). In some embodiments, each of the first polypeptide and the second polypeptide comprises, consists of, or consists essentially of the sequence SEQ ID NO: 64 with up to 10 (e.g., no more than 1, no more than 2, no more than 3, no more than 4, no more than 5, no more than 6, no more than 7, no more than 8, no more than 9) single amino acid modifications (e.g., substitutions, e.g., conservative substitutions). In some embodiments, each of the first polypeptide and the second polypeptide comprises, consists of, or consists essentially of the sequence of SEQ ID NO: 64 with up to 10 single amino acid modifications in the region outside the linker (e.g., outside the subsequence GGGGGGGGGGGGGGGGGGGG (SEQ ID NO: 23). The linker within SEQ ID NO: 64 can be replaced with an alternative linker. In some embodiments, each of the first polypeptide and the second polypeptide comprises, consists of, or consists essentially of the sequence of SEQ ID NO: 64 with up to 10 single amino acid modifications, provided that position 33 of SEQ ID NO: 64 is alanine.

In some embodiments, each of the first polypeptide and the second polypeptide comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMASRTPE-VTCVVVDVSHEDPE-VKFNWYVDGVEVHNAKTKPREEQYN-STYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNV-FSCSVMHEALHNHYTQKSLSLSPG (SEQ ID NO: 65). In some embodiments, each of the first polypeptide and the second polypeptide comprises, consists of, or consists essentially of the sequence SEQ ID NO: 65 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 65 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:65 can be replaced with an alternative linker. In some embodiments, each of the first polypeptide and the second polypeptide comprises, consists of, or consists essentially of the sequence of SEQ ID NO: 65 with up to 10 single amino acid modifications, provided that position 33 of SEQ ID NO: 65 is alanine, position 134 of SEQ ID NO: 65 is cysteine, position 137 of SEQ ID NO: 65 is lysine, position 146 of SEQ ID NO: 65 is tryptophan, position 280 of SEQ ID NO: 65 is alanine, position 426 of SEQ ID NO: 65 is lysine, and position 436 of SEQ ID NO: 65 is aspartic acid.

In some embodiments, each of the first polypeptide and the second polypeptide comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPP-CPAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVF-SCSVMHEALHNHYTQKSLSLSPG (SEQ ID NO: 66). In some embodiments, each of the first polypeptide and the second polypeptide comprises, consists of, or consists essentially of the sequence SEQ ID NO: 66 with up to 10 (e.g., no more than 1, no more than 2, no more than 3, no more than 4, no more than 5, no more than 6, no more than 7, no more than 8, no more than 9) single amino acid modifications (e.g., substitutions, e.g., conservative substitutions). In some embodiments, each of the first polypeptide and the second polypeptide comprises, consists of, or consists essentially of the sequence of SEQ ID NO: 66 with up to 10 single amino acid modifications in the region outside the linker the linker (e.g., outside the subsequence GGGGGGGGGGGGGGGGGGGG (SEQ ID NO: 23). The linker within SEQ ID NO:66 can be replaced with an alternative linker. In some embodiments, each of the first polypeptide and the second polypeptide comprises, consists of, or consists essentially of the sequence of SEQ ID NO: 66 with up to 10 single amino acid modifications, provided that position 134 of SEQ ID NO: 66 is cysteine, position 137 of SEQ ID NO: 66 is lysine, position 146 of SEQ ID NO: 66 is tryptophan, position 319 of SEQ ID NO: 66 is proline, position 426 of SEQ ID NO: 66 is lysine, and position 436 of SEQ ID NO: 66 is aspartic acid.

In some embodiments, each of the first polypeptide and the second polypeptide comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPP-CPAPELLGGPSVFLFPPK PKDTLMASRTPE-VTCVVVDVSHEDPEVKFNWYVDGVEVHNAKTKP-PEEQYNSTYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVF-SCSVMHEALHNHYTQKSLSLSPG (SEQ ID NO: 67). In some embodiments, each of the first polypeptide and the second polypeptide comprises, consists of, or consists essentially of the sequence SEQ ID NO: 67 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 67 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:67 can be replaced with an alternative linker. In some embodiments, each of the first polypeptide and the second polypeptide comprises, consists of, or consists essentially of the sequence of SEQ ID NO: 67 with up to 10 single amino acid modifications, provided that position 134 of SEQ ID NO: 67 is cysteine, position 137 of SEQ ID NO: 67 is lysine, position 146 of SEQ ID NO: 67 is tryptophan, position 280 of SEQ ID NO: 67 is alanine, position 318 of SEQ ID NO: 67 is proline, position 426 of SEQ ID NO: 67 is lysine, and position 436 of SEQ ID NO: 67 is aspartic acid.

In some embodiments, each of the first polypeptide and the second polypeptide comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPP-CPAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVF-SCSVMHEALHNHYTQKSLSLSPG (SEQ ID NO: 68). In some embodiments, each of the first polypeptide and the second polypeptide comprises, consists of, or consists essentially of the sequence SEQ ID NO: 68 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 68 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:68 can be replaced with an alternative linker. In some embodiments, each of the first polypeptide and the second polypeptide comprises, consists of, or consists essentially of the sequence of SEQ ID NO: 68 with up to 10 single amino acid modifications, provided that position 33 of SEQ ID NO: 68 is alanine, position 134 of SEQ ID NO: 68 is cysteine, position 137 of SEQ ID NO: 68 is lysine, position 146 of SEQ ID NO: 68 is tryptophan, position 319 of SEQ ID NO: 68 is proline, position 426 of SEQ ID NO: 68 is lysine, and position 436 of SEQ ID NO: 68 is aspartic acid.

In some embodiments, each of the first polypeptide and the second polypeptide comprises, consists of, or consists essentially of the sequence DKTHTCPPCPAPELLGGPSVFLFPPKPKDTLMASRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLPPCRDKLT KNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGGGDKTHTCPPCPAPELLGGPSVFLFPPK PKDTLMASRTPEVTCVVVDVSHEDPEVKFNWYVDGVEVHNAKTKPPEEQYNSTYRVVSVLTVLHQDWL NGKEYKCKVSNKALPAPIEKTISKAKGQPREPQVYTLPPSRDELTKNQVSLTCLVKGFYPSDIAVEWESN GQPENNYKTTPPVLKSDGSFFLYSDLTVDKSRWQQGNVFSCSVMHEALHNHYTQKSLSLSPG (SEQ ID NO: 69). In some embodiments, each of the first polypeptide and the second polypeptide comprises, consists of, or consists essentially of the sequence SEQ ID NO: 69 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 69 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:69 can be replaced with an alternative linker. In some embodiments, each of the first polypeptide and the second polypeptide comprises, consists of, or consists essentially of the sequence of SEQ ID NO: 69 with up to 10 single amino acid modifications, provided that position 33 of SEQ ID NO: 69 is alanine, position 134 of SEQ ID NO: 69 is cysteine, position 137 of SEQ ID NO: 69 is lysine, position 146 of SEQ ID NO: 69 is tryptophan, position 280 of SEQ ID NO: 69 is alanine, position 319 of SEQ ID NO: 69 is proline, position 426 of SEQ ID NO: 69 is lysine, and position 436 of SEQ ID NO: 69 is aspartic acid.

In some embodiments, each of the first polypeptide and the second polypeptide comprises, consists of, or consists essentially of the sequence DKTHTCPPCPAPELLGGPSVFLFPPKPKDTLMISRTPEVTCVVVDVSHEDPEVKFNWYVDGVEVHNAKT KPPEEQYNSTYRVVSVLTVLHQDWLNGKEYKCKVSNKALPAPIEKTISKAKGQPREPQVYTLPPCRDKLT KNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGGGDKTHTCPPCPAPELLGGPSVFLFPPK PKDTLMISRTPEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCLVKGFYPSDIAVEWESNG QPENNYKTTPPVLKSDGSFFLYSDLTVDKSRWQQGNVFSCSVMHEALHNHYTQKSLSLSPG (SEQ ID NO: 71). In some embodiments, each of the first polypeptide and the second polypeptide comprises, consists of, or consists essentially of the sequence SEQ ID NO: 71 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 71 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:71 can be replaced with an alternative linker. n some embodiments, each of the first polypeptide and the second polypeptide comprises, consists of, or consists essentially of the sequence of SEQ ID NO: 71 with up to 10 single amino acid modifications, provided that position 71 of SEQ ID NO: 71 is proline, 134 of SEQ ID NO: 71 is cysteine, position 137 of SEQ ID NO: 71 is lysine, position 146 of SEQ ID NO: 71 is tryptophan, position 426 of SEQ ID NO: 71 is lysine, and position 436 of SEQ ID NO: 71 is aspartic acid.

In some embodiments, each of the first polypeptide and the second polypeptide comprises, consists of, or consists essentially of the sequence DKTHTCPPCPAPELLGGPSVFLFPPKPKDTLMISRTPEVTCVVVDVSHEDPEVKFNWYVDGVEVHNAKT KPPEEQYNSTYRVVSVLTVLHQDWLNGKEYKCKVSNKALPAPIEKTISKAKGQPREPQVYTLPPCRDKLT KNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGGGDKTHTCPPCPAPELLGGPSVFLFPPK PKDTLMASRTPEVTCVVVDVSHEDPEVKFNWYVDGVEVHNAKTKPREEQYNSTYRVVSVLTVLHQDWL NGKEYKCKVSNKALPAPIEKTISKAKGQPREPQVYTLPPSRDELTKNQVSLTCLVKGFYPSDIAVEWESN GQPENNYKTTPPVLKSDGSFFLYSDLTVDKSRWQQGNVFSCSVMHEALHNHYTQKSLSLSPG (SEQ ID NO: 72). In some embodiments, each of the first polypeptide and the second polypeptide comprises, consists of, or consists essentially of the sequence SEQ ID NO: 72 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 72 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:72 can be replaced with an alternative linker. In some embodiments, each of the first polypeptide and the second polypeptide comprises, consists of, or consists essentially of the sequence of SEQ ID NO: 72 with up to 10 single amino acid modifications, provided that position 72 of SEQ ID NO: 72 is proline, position 134 of SEQ ID NO: 72 is cystine, position 137 of SEQ ID NO: 72 is lysine, position 146 of SEQ ID NO: 72 is tryptophan, position 426 of SEQ ID NO: 72 is lysine, and positioned 436 of SEQ ID NO: 72 is aspartic acid.

In some embodiments, each of the first polypeptide and the second polypeptide comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMISRTPE-VTCVVVDVSHEDPE-VKFNWYVDGVEVHNAKTKPREEQYN-STYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVFS-CSVMHEALHNHYTQKSLSLSPG (SEQ ID NO: 74). In some embodiments, each of the first polypeptide and the second polypeptide comprises, consists of, or consists essentially of the sequence SEQ ID NO: 74 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 74 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:74 can be replaced with an alternative linker. In some embodiments, each of the first polypeptide and the second polypeptide comprises, consists of, or consists essentially of the sequence of SEQ ID NO: 74 with up to 10 single amino acid modifications, provided that position 33 of SEQ ID NO: 74 is alanine, position 72 of SEQ ID NO: 74 is proline, position 134 of SEQ ID NO: 74 is cysteine, position 137 of SEQ ID NO: 74 is lysine, position 146 of SEQ ID NO: 74 is tryptophan, position 426 of SEQ ID NO: 74 is lysine, and position 436 of SEQ ID NO: 74 is aspartic acid.

In some embodiments, each of the first polypeptide and the second polypeptide comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMASRTPE-VTCVVVDVSHEDPE-VKFNWYVDGVEVHNAKTKPREEQYN-STYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVF-SCSVMHEALHNHYTQKSLSLSPG (SEQ ID NO: 75). In some embodiments, each of the first polypeptide and the second polypeptide comprises, consists of, or consists essentially of the sequence SEQ ID NO: 75 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 75 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:75 can be replaced with an alternative linker. In some embodiments, each of the first polypeptide and the second polypeptide comprises, consists of, or consists essentially of the sequence of SEQ ID NO: 75 with up to 10 single amino acid modifications, provided that position 33 of SEQ ID NO: 75 is alanine, position 72 of SEQ ID NO: 75 is proline, position 134 of SEQ ID NO: 75 is cysteine, position 137 of SEQ ID NO: 75 is lysine, position 146 of SEQ ID NO: 75 is tryptophan, position 280 of SEQ ID NO: 75 is alanine, position 426 of SEQ ID NO: 75 is lysine, and position 436 of SEQ ID NO: 75 is aspartic acid.

In some embodiments, each of the first polypeptide and the second polypeptide comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVF-SCSVMHEALHNHYTQKSLSLSPG (SEQ ID NO: 76). In some embodiments, each of the first polypeptide and the second polypeptide comprises, consists of, or consists essentially of the sequence SEQ ID NO: 76 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 76 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:76 can be replaced with an alternative linker. In some embodiments, each of the first polypeptide and the second polypeptide comprises, consists of, or consists essentially of the sequence of SEQ ID NO: 76 with up to 10 single amino acid modifications, provided that position 72 of SEQ ID NO: 76 is a proline and position 319 of SEQ ID NO: 76 is a proline. In some embodiments, each of the first polypeptide and the second polypeptide comprises, consists of, or consists essentially of the sequence DKTHTCPPCPA- PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPPC-PAPELLGGPSVFLFPPK PKDTLMASRTPE-VTCVVVDVSHEDPEVKFNWYVDGVEVHNAKTKP-PEEQYNSTYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVFS-CSVMHEALHNHYTQKSLSLSPG (SEQ ID NO: 77). In some embodiments, each of the first polypeptide and the second polypeptide comprises, consists of, or consists essentially of the sequence SEQ ID NO: 77 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 77 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:77 can be replaced with an alternative linker. In some embodiments, each of the first polypeptide and the second polypeptide comprises, consists of, or consists essentially of the sequence of SEQ ID NO: 77 with up to 10 single amino acid modifications, provided that position 72 of SEQ ID NO: 77 is proline, position 134 of SEQ ID NO: 77 is cysteine, position 137 of SEQ ID NO: 77 is lysine, position 146 of SEQ ID NO: 77 is tryptophan, position 280 of SEQ ID NO: 77 is alanine, position 319 of SEQ ID NO: 77 is proline, position 426 of SEQ ID NO: 77 is lysine, and positioned 436 of SEQ ID NO: 77 is aspartic acid.

In some embodiments, each of the first polypeptide and the second polypeptide comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPPC-PAPELLGGPSVFLFPPK PKDTLMASRTPE-VTCVVVDVSHEDPEVKFNWYVDGVEVHNAKTKP-PEEQYNSTYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVFS-CSVMHEALHNHYTQKSLSLSPG (SEQ ID NO: 79). In some embodiments, each of the first polypeptide and the second polypeptide comprises, consists of, or consists essentially of the sequence SEQ ID NO: 79 with up to 10 (e.g., up to 9, 8, 7, 6, 5, 4, 3, 2, or 1) single amino acid modifications (e.g., substitutions, e.g., conservative substitutions). In some embodiments, each of the first polypeptide and the second polypeptide comprises, consists of, or consists essentially of the sequence of SEQ ID NO: 79 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:79 can be replaced with an alternative linker. In some embodiments, each of the first polypeptide and the second polypeptide comprises, consists of, or consists essentially of the sequence of SEQ ID NO: 79 with up to 10 single amino acid modifications, provided that position 33 of SEQ ID NO: 79 is alanine, position 72 of SEQ ID NO: 79 is proline, position 280 of SEQ ID NO: 79 is alanine, and position 319 of SEQ ID NO: 79 is proline.

In some embodiments, each of the third polypeptide and the fourth polypeptide comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDS-DGSFFLVSKLTVDKSRWQQGNVFSCSV MHEALHN-HYTQKSLSLSPG (SEQ ID NO: 73). In some embodiments, each of the third polypeptide and the fourth polypeptide comprises, consists of, or consists essentially of the sequence SEQ ID NO: 73 with up to 10 (e.g., up to 9, 8, 7, 6, 5, 4, 3, 2, or 1) single amino acid modifications (e.g., substitutions, e.g., conservative substitutions). In some embodiments, each of the third polypeptide and the fourth polypeptide comprises, consists of, or consists essentially of the sequence SEQ ID NO: 73 with up to 10 single amino acid modifications, provided that position 33 of SEQ ID NO: 73 is an alanine and position 72 of SEQ ID NO: 73 is a proline.

In some embodiments, each of the third polypeptide and the fourth polypeptide comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDSD-GSFFLVSKLTVDKSRWQQGNVFSCSV MHEALHN-HYTQKSLSLSPG (SEQ ID NO: 61). In some embodiments, each of the third polypeptide and the fourth polypeptide comprises, consists of, or consists essentially of the sequence SEQ ID NO: 61 with up to 10 (e.g., up to 9, 8, 7, 6, 5, 4, 3, 2, or 1) single amino acid modifications (e.g., substitutions, e.g., conservative substitutions). In some embodiments, each of the third polypeptide and the fourth polypeptide comprises, consists of, or consists essentially of the sequence SEQ ID NO: 61 with up to 10 single amino acid modifications, provided that position 129 of SEQ ID NO: 61 is cysteine, position 146 of SEQ ID NO: 61 is serine, position 148 of SEQ ID NO: 61 is alanine, position 150 of SEQ ID NO: 61 is aspartic acid, and position 187 of SEQ ID NO: 61 is valine.

In some embodiments, each of the third polypeptide and the fourth polypeptide comprises, consists of, or consists essentially of the sequence DKTHTCPPCPA- PELLGGPSVFLFPPKPKDTLMASRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVCTLPPSRDELT KNQVSLSCAVDGFYPSDIAVEWESNGQPENNYKTTPPVLDSDGSFFLVSKLTVDKSRWQQGNVFSCSV MHEALHNHYTQKSLSLSPG (SEQ ID NO: 63). In some embodiments, each of the third polypeptide and the fourth polypeptide comprises, consists of, or consists essentially of the sequence SEQ ID NO: 63 with up to 10 (e.g., up to 9, 8, 7, 6, 5, 4, 3, 2, or 1) single amino acid modifications (e.g., substitutions, e.g., conservative substitutions). In some embodiments, each of the third polypeptide and the fourth polypeptide comprises, consists of, or consists essentially of the sequence SEQ ID NO: 63 with up to 10 single amino acid modifications, provided that position 33 of SEQ ID NO: 63 is alanine.

In some embodiments, each of the third polypeptide and the fourth polypeptide comprises, consists of, or consists essentially of the sequence DKTHTCPPCPAPELLGGPSVFLFPPKPKDTLMISRTPEVTCVVVDVSHEDPEVKFNWYVDGVEVHNAKT KPPEEQYNSTYRVVSVLTVLHQDWLNGKEYKCKVSNKALPAPIEKTISKAKGQPREPQVCTLPPSRDELT KNQVSLSCAVDGFYPSDIAVEWESNGQPENNYKTTPPVLDSDGSFFLVSKLTVDKSRWQQGNVFSCSV MHEALHNHYTQKSLSLSPG (SEQ ID NO: 70). In some embodiments, each of the third polypeptide and the fourth polypeptide comprises, consists of, or consists essentially of the sequence SEQ ID NO: 70 with up to 10 (e.g., up to 9, 8, 7, 6, 5, 4, 3, 2, or 1) single amino acid modifications (e.g., substitutions, e.g., conservative substitutions). In some embodiments, each of the third polypeptide and the fourth polypeptide comprises, consists of, or consists essentially of the sequence SEQ ID NO: 70 with up to 10 single amino acid modifications, provided that position 72 of SEQ ID NO: 70 is a proline.

In some embodiments, each of the first and second polypeptides comprises, consists of, or consists essentially of the sequence DKTHTCPPCPAPELLGGPSVFLFPPKPKDTLMASRTPEVTCVVVDVSHEDPEVKFNWYVDGVEVHNAKT KPPEEQYNSTYRVVSVLTVLHQDWLNGKEYKCKVSNKALPAPIEKTISKAKGQPREPQVYTLPPCRDKLT KNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGGGDKTHTCPPCPAPELLGGPSVFLFPPK PKDTLMISRTPEVTCVVVDVSHEDPEVKFNWYVDGVEVHNAKTKPPEEQYNSTYRVVSVLTVLHQDWLN GKEYKCKVSNKALPAPIEKTISKAKGQPREPQVYTLPPSRDELTKNQVSLTCLVKGFYPSDIAVEWESNG QPENNYKTTPPVLKSDGSFFLYSDLTVDKSRWQQGNVFSCSVMHEALHNHYTQKSLSLSPG (SEQ ID NO: 78), and each of the third and fourth polypeptides comprises, consists of, or consists essentially of the sequence DKTHTCPPCPAPELLGGPSVFLFPPKPKDTLMASRTPEVTCVVVDVSHEDPEVKFNWYVDGVEVHNAKT KPPEEQYNSTYRVVSVLTVLHQDWLNGKEYKCKVSNKALPAPIEKTISKAKGQPREPQVCTLPPSRDELT KNQVSLSCAVDGFYPSDIAVEWESNGQPENNYKTTPPVLDSDGSFFLVSKLTVDKSRWQQGNVFSCSV MHEALHNHYTQKSLSLSPG (SEQ ID NO: 73). In some embodiments, each of the first and second polypeptides comprises, consists of, or consists essentially of the sequence SEQ ID NO: 78 with up to 10 (e.g., up to 9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 73 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 78 with up to 10 single amino acid modifications, provided that none of the up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23). The linker within SEQ ID NO:78 can be replaced with an alternative linker. In some embodiments, each of the first and second polypeptides comprises, consists of, or consists essentially of the sequence SEQ ID NO: 78 with up to 10 single amino acid modifications, provided that position 33 of SEQ ID NO: 78 is alanine, position 72 of SEQ ID NO: 78 is proline, and position 319 of SEQ ID NO: 78 is proline, and each of the third and fourth polypeptides comprises, consists of, or consists essentially of the sequence SEQ ID NO: 73 with up to 10 single amino acid modifications, provided that position 33 of SEQ ID NO: 73 is an alanine and position 72 of SEQ ID NO: 73 is a proline.

In some embodiments, each of the first and second polypeptides comprises, consists of, or consists essentially of the sequence DKTHTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVYTLPPCRDKLT KNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGGGDKTHTCPPCPAPELLGGPSVFLFPPK PKDTLMISRTPEVTCVVVDVSHEDPEVKFNWYVDGVEVHNAKTKPREEQYNSTYRVVSVLTVLHQDWLN GKEYKCKVSNKALPAPIEKTISKAKGQPREPQVYTLPPSRDELTKNQVSLTCLVKGFYPSDIAVEWESNG QPENNYKTTPPVLKSDGSFFLYSDLTVDKSRWQQGNVFSCSVMHEALHNHYTQKSLSLSPG (SEQ ID NO: 49), and each of the third and fourth polypeptides comprises, consists of, or consists essentially of the sequence DKTHTCPPCPAPELLGGPSVFLFPPKPKDTLMISRTPEVTCVVVDVSHEDPEVKFNWYVDGVEVHNAKT KPREEQYNSTYRVVSVLTVLHQDWLNGKEYKCKVSNKALPAPIEKTISKAKGQPREPQVCTLPPSRDELT KNQVSLSCAVDGFYPSDIAVEWESNGQPENNYKTTPPVLDSDGSFFLVSKLTVDKSRWQQGNVFSCSV MHEALHNHYTQKSLSLSPG (SEQ ID NO: 61). In some embodiments, each of the first and second polypeptides comprises, consists of, or consists essentially of the sequence SEQ ID NO: 49 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 61 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 49 with up to (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:76 can be replaced with an alternative linker) and each of the third and fourth polypeptides comprises, consists of, or consists essentially of the sequence SEQ ID NO: 61 with up to 10 single amino acid modifications. In some embodiments, each of the first and second polypeptides comprises, consists of, or consists essentially of the sequence SEQ ID NO: 49 with up to 10 single amino acid modifications, provided that position 134 of SEQ ID NO: 49 is cysteine, position 137 of SEQ ID NO: 49 is lysine, position 146 of SEQ ID NO: 49 is tryptophan, position 426 of SEQ ID NO: 49 is lysine, and position 436 of SEQ ID NO: 49 is aspartic acid; and each of the third and fourth polypeptides comprises, consists of, or consists essentially of the sequence SEQ ID NO: 61 with up to 10 single amino acid modifications, provided that position 129 of SEQ ID NO: 61 is cysteine, position 146 of SEQ ID NO: 61 is serine, position 148 of SEQ ID NO: 61 is alanine, position 150 of SEQ ID NO: 61 is aspartic acid, and position 187 of SEQ ID NO: 61 is valine.

In some embodiments, each of the first and second polypeptides comprises, consists of, or consists essentially of the sequence DKTHTCPPCPA- PELLGGPSVFLFPPKPKDTLMISRTPE- VTCVVVDVSHEDPEVKFNWYVDGVEVHNAKT KPREEQYN- STYRVVSVLTVLHQDWLNGKEYKCKVSNKALPA- PIEKTISKAKGQPREPQVYTLPPCRDKLT KNQVSLWCLVKGFYPSDIAVEWESNGQPEN- NYKTTPPVLDSDGSFFLYSK- LTVDKSRWQQGNVFSCSV MHEALHNHYTQKSLSL- SPGKGGGGGGGGGGGGGGGGGGGGDKTHTCPP- CPAPELLGGPSVFLFPPK PKDTLMASRTPE- VTCVVVDVSHEDPE- VKFNWYVDGVEVHNAKTKPREEQYN- STYRVVSVLTVLHQDWL NGKEYKCKVSNKALPA- PIEKTISKAKGQPREPQVYTLPPSRDELTKNQVSLT- CLVKGFYPSDIAVEWESN GQPEN- NYKTTPPVLKSDGSFFLYSDLTVDKSRWQQGNVFS- CSVMHEALHNHYTQKSLSLSPG (SEQ ID NO: 62), and each of the third and fourth polypeptides comprises, consists of, or consists essentially of the sequence DKTHTCPPCPA- PELLGGPSVFLFPPKPKDTLMISRTPE- VTCVVVDVSHEDPEVKFNWYVDGVEVHNAKT KPREEQYN- STYRVVSVLTVLHQDWLNGKEYKCKVSNKALPA- PIEKTISKAKGQPREPQVCTLPPSRDELT KNQVSLS- CAVDGFYPSDIAVEWESNGQPENNYKTTPPVLDSD- GSFFLVSKLTVDKSRWQQGNVFSCSV MHEALHN- HYTQKSLSLSPG (SEQ ID NO: 61). In some embodiments, each of the first and second polypeptides comprises, consists of, or consists essentially of the sequence SEQ ID NO: 62 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 61 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 62 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:62 can be replaced with an alternative linker) and each of the third and fourth polypeptides comprises, consists of, or consists essentially of the sequence SEQ ID NO: 61 with up to 10 single amino acid modifications. In some embodiments, each of the first and second polypeptides comprises, consists of, or consists essentially of the sequence SEQ ID NO: 62 with up to 10 single amino acid modifications, provided that position 134 of SEQ ID NO: 62 is cysteine, position 137 of SEQ ID NO: 62 is lysine, position 146 of SEQ ID NO: 62 is tryptophan, position 280 of SEQ ID NO: 62 is alanine, position 426 of SEQ ID NO: 62 is lysine, and position 436 of SEQ ID NO: 62 is aspartic acid; and each of the third and fourth polypeptides comprises, consists of, or consists essentially of the sequence SEQ ID NO: 61 with up to 10 single amino acid modifications, provided that position 129 of SEQ ID NO: 61 is cysteine, position 146 of SEQ ID NO: 61 is serine, position 148 of SEQ ID NO: 61 is alanine, position 150 of SEQ ID NO: 61 is aspartic acid, and position 187 of SEQ ID NO: 61 is valine.

In some embodiments, each of the first and second polypeptides comprises, consists of, or consists essentially of the sequence DKTHTCPPCPA- PELLGGPSVFLFPPKPKDTLMASRTPE- VTCVVVDVSHEDPEVKFNWYVDGVEVHNAKT KPREEQYN- STYRVVSVLTVLHQDWLNGKEYKCKVSNKALPA- PIEKTISKAKGQPREPQVYTLPPCRDKLT KNQVSLWCLVKGFYPSDIAVEWESNGQPEN- NYKTTPPVLDSDGSFFLYSK- LTVDKSRWQQGNVFSCSV MHEALHNHYTQKSLSL- SPGKGGGGGGGGGGGGGGGGGGGGDKTHTCPPC- PAPELLGGPSVFLFPPK PKDTLMISRTPE- VTCVVVDVSHEDPE- VKFNWYVDGVEVHNAKTKPREEQYN- STYRVVSVLTVLHQDWLN GKEYKCKVSNKALPA- PIEKTISKAKGQPREPQVYTLPPSRDELTKNQVSLT- CLVKGFYPSDIAVEWESNG QPEN- NYKTTPPVLKSDGSFFLYSDLTVDKSRWQQGNVFS- CSVMHEALHNHYTQKSLSLSPG (SEQ ID NO: 64), and each of the third and fourth polypeptides comprises, consists of, or consists essentially of the sequence DKTHTCPPCPA- PELLGGPSVFLFPPKPKDTLMASRTPE- VTCVVVDVSHEDPEVKFNWYVDGVEVHNAKT KPREEQYN- STYRVVSVLTVLHQDWLNGKEYKCKVSNKALPA- PIEKTISKAKGQPREPQVCTLPPSRDELT KNQVSLS- CAVDGFYPSDIAVEWESNGQPENNYKTTPPVLDS- DGSFFLVSKLTVDKSRWQQGNVFSCSV MHEALHN- HYTQKSLSLSPG (SEQ ID NO: 63). In some embodiments, each of the first and second polypeptides comprises, consists of, or consists essentially of the sequence SEQ ID NO: 64 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 63 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 64 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:64 can be replaced with an alternative linker) and each of the third and fourth polypeptides comprises, consists of, or consists essentially of the sequence SEQ ID NO: 63 with up to 10 single amino acid modifications. In some embodiments, each of the first and second polypeptides comprises, consists of, or consists essentially of the sequence SEQ ID NO: 64 with up to 10 single amino acid modifications, provided that position 33 of SEQ ID NO: 64 is alanine, and each of the third and fourth polypeptides comprises, consists of, or consists essentially of the sequence SEQ ID NO: 63 with up to 10 single amino acid modifications, provided that position 33 of SEQ ID NO: 63 is alanine.

In some embodiments, each of the first and second polypeptides comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPPC-PAPELLGGPSVFLFPPK PKDTLMASRTPE-VTCVVVDVSHEDPE-VKFNWYVDGVEVHNAKTKPREEQYN-STYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVFS-CSVMHEALHNHYTQKSLSLSPG (SEQ ID NO: 65), and each of the third and fourth polypeptides comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDSD-GSFFLVSKLTVDKSRWQQGNVFSCSV MHEALHN-HYTQKSLSLSPG (SEQ ID NO: 63). In some embodiments, each of the first and second polypeptides comprises, consists of, or consists essentially of the sequence SEQ ID NO: 65 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 63 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 65 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:65 can be replaced with an alternative linker) and each of the third and fourth polypeptides comprises, consists of, or consists essentially of the sequence SEQ ID NO: 63 with up to 10 single amino acid modifications. In some embodiments, each of the first and second polypeptides comprises, consists of, or consists essentially of the sequence SEQ ID NO: 65 with up to 10 single amino acid modifications, provided that position 33 of SEQ ID NO: 65 is alanine, position 134 of SEQ ID NO: 65 is cysteine, position 137 of SEQ ID NO: 65 is lysine, position 146 of SEQ ID NO: 65 is tryptophan, position 280 of SEQ ID NO: 65 is alanine, position 426 of SEQ ID NO: 65 is lysine, and position 436 of SEQ ID NO: 65 is aspartic acid, and each of the third and fourth polypeptides comprises, consists of, or consists essentially of the sequence SEQ ID NO: 63 with up to 10 single amino acid modifications, provided that position 33 of SEQ ID NO: 63 is alanine.

In some embodiments, each of the first and second polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPP-CPAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVFS-CSVMHEALHNHYTQKSLSLSPG (SEQ ID NO: 66), and each of the third and fourth polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDSDG-SFFLVSKLTVDKSRWQQGNVFSCSV MHEALHN-HYTQKSLSLSPG (SEQ ID NO: 61). In some embodiments, each of the first and second polypeptides comprises, consists of, or consists essentially of the sequence SEQ ID NO: 66 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 61 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 66 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:66 can be replaced with an alternative linker) and each of the third and fourth polypeptides comprises, consists of, or consists essentially of the sequence SEQ ID NO: 61 with up to 10 single amino acid modifications. In some embodiments, each of the first and second polypeptides comprises, consists of, or consists essentially of the sequence SEQ ID NO: 66 with up to 10 single amino acid modifications, provided that position 134 of SEQ ID NO: 66 is cysteine, position 137 of SEQ ID NO: 66 is lysine, position 146 of SEQ ID NO: 66 is tryptophan, position 319 of SEQ ID NO: 66 is proline, position 426 of SEQ ID NO: 66 is lysine, and position 436 of SEQ ID NO: 66 is aspartic acid, and each of the third and fourth polypeptides comprises, consists of, or consists essentially of the sequence SEQ ID NO: 61 with up to 10 single amino acid modifications, provided that position 129 of SEQ ID NO: 61 is cysteine, position 146 of SEQ ID NO: 61 is serine, position 148 of SEQ ID NO: 61 is alanine, position 150 of SEQ ID NO: 61 is aspartic acid, and position 187 of SEQ ID NO: 61 is valine.

In some embodiments, each of the first and second polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMASRTPE-VTCVVVDVSHEDPEVKFNWYVDGVEVHNAKTKP-PEEQYNSTYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLY-SDLTVDKSRWQQGNVFSCSVMHEALHN-HYTQKSLSLSPG (SEQ ID NO: 67), and each of the third and fourth polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDSD-GSFFLVSKLTVDKSRWQQGNVFSCSV MHEALHN-HYTQKSLSLSPG (SEQ ID NO: 61). In some embodiments, each of the first and second polypeptides comprises, consists of, or consists essentially of the sequence SEQ ID NO: 67 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 61 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 67 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23; the linker within SEQ ID NO:67 can be replaced with an alternative linker), and each of the third and fourth polypeptides comprises, consists of, or consists essentially of the sequence SEQ ID NO: 61 with up to 10 single amino acid modifications. In some embodiments, each of the first and second polypeptides comprises, consists of, or consists essentially of the sequence SEQ ID NO: 67 with up to 10 single amino acid modifications, provided that position 134 of SEQ ID NO: 67 is cysteine, position 137 of SEQ ID NO: 67 is lysine, position 146 of SEQ ID NO: 67 is tryptophan, position 280 of SEQ ID NO: 67 is alanine, position 318 of SEQ ID NO: 67 is proline, position 426 of SEQ ID NO: 67 is lysine, and position 436 of SEQ ID NO: 67 is aspartic acid, and each of the third and fourth polypeptides comprises, consists of, or consists essentially of the sequence SEQ ID NO: 61 with up to 10 single amino acid modifications provided that position 129 of SEQ ID NO: 61 is cysteine, position 146 of SEQ ID NO: 61 is serine, position 148 of SEQ ID NO: 61 is alanine, position 150 of SEQ ID NO: 61 is aspartic acid, and position 187 of SEQ ID NO: 61 is valine.

In some embodiments, each of the first and second polypeptides comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPPCPA-PELLGGPSVFLFPPK PKDTLMISRTPEVTCVVVDVSHEDPE-VKFNWYVDGVEVHNAKTKPPEEQYN-STYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLY-SDLTVDKSRWQQGNVFSCSVMHEALHN-HYTQKSLSLSPG (SEQ ID NO: 68), and each of the third and fourth polypeptides comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDS-DGSFFLVSKLTVDKSRWQQGNVFSCSV MHEALHN-HYTQKSLSLSPG (SEQ ID NO: 63). In some embodiments, each of the first and second polypeptides comprises, consists of, or consists essentially of the sequence SEQ ID NO: 68 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 63 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 68 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGG (SEQ ID NO: 23); the linker within SEQ ID NO:68 can be replaced with an alternative linker), and each of the third and fourth polypeptides comprises, consists of, or consists essentially of the sequence SEQ ID NO: 63 with up to 10 single amino acid modifications. In some embodiments, each of the first and second polypeptides comprises, consists of, or consists essentially of the sequence SEQ ID NO: 68 with up to 10 single amino acid modifications, provided that position 33 of SEQ ID NO: 68 is alanine, position 134 of SEQ ID NO: 68 is cysteine, position 137 of SEQ ID NO: 68 is lysine, position 146 of SEQ ID NO: 68 is tryptophan, position 319 of SEQ ID NO: 68 is proline, position 426 of SEQ ID NO: 68 is lysine, and position 436 of SEQ ID NO: 68 is aspartic acid, and each of the third and fourth polypeptides comprises, consists of, or consists essentially of the sequence SEQ ID NO: 63 with up to 10 single amino acid modifications, provided that position 33 of SEQ ID NO: 63 is alanine.

In some embodiments, each of the first and second polypeptides comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCP-PCPAPELLGGPSVFLFPPK PKDTLMASRTPE-VTCVVVDVSHEDPEVKFNWYVDGVEVHNAKTKP-PEEQYNSTYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVF-SCSVMHEALHNHYTQKSLSLSPG (SEQ ID NO: 69), and each of the third and fourth polypeptides comprises, consists of, or consists essentially of the sequence DKTH-TCPPCPAPELLGGPSVFLFPPKPKDTLMASRTPE-VTCVVVDVSHEDPEVKFNWYVDGVEVHNAKT KPREEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDSD-GSFFLVSKLTVDKSRWQQGNVFSCSV MHEALHN-HYTQKSLSLSPG (SEQ ID NO: 63). In some embodiments, each of the first and second polypeptides comprises, consists of, or consists essentially of the sequence SEQ ID NO: 69 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 63 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 69 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGG (SEQ ID NO: 23); the linker within SEQ ID NO:69 can be replaced with an alternative linker), and each of the third and fourth polypeptides comprises, consists of, or consists essentially of the sequence SEQ ID NO: 63 with up to 10 single amino acid modifications. In some embodiments, each of the first and second polypeptides comprises, consists of, or consists essentially of the sequence SEQ ID NO: 69 with up to 10 single amino acid modifications, provided that position 33 of SEQ ID NO: 69 is alanine, position 134 of SEQ ID NO: 69 is cysteine, position 137 of SEQ ID NO: 69 is lysine, position 146 of SEQ ID NO: 69 is tryptophan, position 280 of SEQ ID NO: 69 is alanine, position 319 of SEQ ID NO: 69 is proline, position 426 of SEQ ID NO: 69 is lysine, and position 436 of SEQ ID NO: 69 is aspartic acid, and each of the third and fourth polypeptides comprises, consists of, or consists essentially of the sequence SEQ ID NO: 63 with up to 10 single amino acid modifications, provided that position 33 of SEQ ID NO: 63 is alanine.

In some embodiments, each of the first and second polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMISRTPE-VTCVVVDVSHEDPE-VKFNWYVDGVEVHNAKTKPREEQYN-STYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVF-SCSVMHEALHNHYTQKSLSLSPG (SEQ ID NO: 71), and each of the third and fourth polypeptides comprises, consists of, or consists essentially of the sequence DKTH-TCPPCPAPELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLD-SDGSFFLVSKLTVDKSRWQQGNVFSCSV MHEALHN-HYTQKSLSLSPG (SEQ ID NO: 70). In some embodiments, each of the first and second polypeptides comprises, consists of, or consists essentially of the sequence SEQ ID NO: 71 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 70 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 71 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGG (SEQ ID NO: 23); the linker within SEQ ID NO:71 can be replaced with an alternative linked), and each of the third and fourth polypeptides comprises, consists of, or consists essentially of the sequence SEQ ID NO: 70 with up to 10 single amino acid modifications. In some embodiments, each of the first and second polypeptides comprises, consists of, or consists essentially of the sequence SEQ ID NO: 71 with up to 10 single amino acid modifications, provided that position 71 of SEQ ID NO: 71 is proline, 134 of SEQ ID NO: 71 is cysteine, position 137 of SEQ ID NO: 71 is lysine, position 146 of SEQ ID NO: 71 is tryptophan, position 426 of SEQ ID NO: 71 is lysine, and position 436 of SEQ ID NO: 71 is aspartic acid, and each of the third and fourth polypeptides comprises, consists of, or consists essentially of the sequence SEQ ID NO: 70 with up to 10 single amino acid modifications, provided that position 72 of SEQ ID NO: 70 is a proline.

In some embodiments, each of the first and second polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPPC-PAPELLGGPSVFLFPPK PKDTLMASRTPE-VTCVVVDVSHEDPE-VKFNWYVDGVEVHNAKTKPREEQYN-STYRVVSVLTVLHQDWL NGKEYKCKVSNKALPA-PIEKTISKAKGQPREPQVYTLPPSRDELTKNQVSL-TCLVKGFYPSDIAVEWESN GQPEN-NYKTTPPVLKSDGSFFLY-SDLTVDKSRWQQGNVFSCSVMHEALHN-HYTQKSLSLSPG (SEQ ID NO: 72), and each of the third and fourth polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDSD-GSFFLVSKLTVDKSRWQQGNVFSCSV MHEALHN-HYTQKSLSLSPG (SEQ ID NO: 70). In some embodiments, each of the first and second polypeptides comprises, consists of, or consists essentially of the sequence SEQ ID NO: 72 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 70 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 72 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:72 can be replaced with an alternative linker), and each of the third and fourth polypeptides comprises, consists of, or consists essentially of the sequence SEQ ID NO: 70 with up to 10 single amino acid modifications. In some embodiments, each of the first and second polypeptides comprises, consists of, or consists essentially of the sequence SEQ ID NO: 72 with up to 10 single amino acid modifications, provided that position 72 of SEQ ID NO: 72 is proline, position 134 of SEQ ID NO: 72 is cystine, position 137 of SEQ ID NO: 72 is lysine, position 146 of SEQ ID NO: 72 is tryptophan, position 426 of SEQ ID NO: 72 is lysine, and positioned 436 of SEQ ID NO: 72 is aspartic acid, and each of the third and fourth polypeptides comprises, consists of, or consists essentially of the sequence SEQ ID NO: 70 with up to 10 single amino acid modifications, and each of the third and fourth polypeptides comprises, consists of, or consists essentially of the sequence SEQ ID NO: 70 with up to 10 single amino acid modifications, provided that position 72 of SEQ ID NO: 70 is a proline.

In some embodiments, each of the first and second polypeptides comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGDKTHTCPP-CPAPELLGGPSVFLFPPK PKDTLMISRTPE-VTCVVVDVSHEDPE-VKFNWYVDGVEVHNAKTKPREEQYN-STYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVFS-CSVMHEALHNHYTQKSLSLSPG (SEQ ID NO: 74), and each of the third and fourth polypeptides comprises, consists of, or consists essentially of the sequence DKTHTCPPCPA-PELLGGPSVFLFPPKPKDTLMASRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLD-SDGSFFLVSKLTVDKSRWQQGNVFSCSV MHEALHN-HYTQKSLSLSPG (SEQ ID NO: 73). In some embodiments, each of the first and second polypeptides comprises, consists of, or consists essentially of the sequence SEQ ID NO: 74 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 73 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 74 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:74 can be replaced with an alternative linker), and each of the third and fourth polypeptides comprises, consists of, or consists essentially of the sequence SEQ ID NO: 73 with up to 10 single amino acid modifications. In some embodiments, each of the first and second polypeptides comprises, consists of, or consists essentially of the sequence SEQ ID NO: 74 with up to 10 single amino acid modifications, provided that position 33 of SEQ ID NO: 74 is alanine, position 72 of SEQ ID NO: 74 is proline, position 134 of SEQ ID NO: 74 is cysteine, position 137 of SEQ ID NO: 74 is lysine, position 146 of SEQ ID NO: 74 is tryptophan, position 426 of SEQ ID NO: 74 is lysine, and position 436 of SEQ ID NO: 74 is aspartic acid, and each of the third and fourth polypeptides comprises, consists of, or consists essentially of the sequence SEQ ID NO: 73 with up to 10 single amino acid modifications, provided that position 33 of SEQ ID NO: 73 is an alanine and position 72 of SEQ ID NO: 73 is a proline.

In some embodiments, each of the first and second polypeptides comprises, consists of, or consists essentially of the sequence DKTHTCPPCPAPELLGGPSVFLFPPKPKDTLMASRTPEVTCVVVDVSHEDPEVKFNWYVDGVEVHNAKTKPPEEQYNSTYRVVSVLTVLHQDWLNGKEYKCKVSNKALPAPIEKTISKAKGQPREPQVYTLPPCRDKLTKNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGDKTHTCPPCPAPELLGGPSVFLFPPK PKDTLMASRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESN GQPENNYKTTPPVLKSDGSFFLYSDLTVDKSRWQQGNVFSCSVMHEALHNHYTQKSLSLSPG (SEQ ID NO: 75), and each of the third and fourth polypeptides comprises, consists of, or consists essentially of the sequence DKTHTCPPCPAPELLGGPSVFLFPPKPKDTLMASRTPEVTCVVVDVSHEDPEVKFNWYVDGVEVHNAKTKPPEEQYNSTYRVVSVLTVLHQDWLNGKEYKCKVSNKALPAPIEKTISKAKGQPREPQVCTLPPSRDELT KNQVSLSCAVDGFYPSDIAVEWESNGQPENNYKTTPPVLDSDGSFFLVSKLTVDKSRWQQGNVFSCSV MHEALHNHYTQKSLSLSPG (SEQ ID NO: 73). In some embodiments, each of the first and second polypeptides comprises, consists of, or consists essentially of the sequence SEQ ID NO: 75 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 73 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 75 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:75 can be replaced with an alternative linker), and each of the third and fourth polypeptides comprises, consists of, or consists essentially of the sequence SEQ ID NO: 73 with up to 10 single amino acid modifications. In some embodiments, each of the first and second polypeptides comprises, consists of, or consists essentially of the sequence SEQ ID NO: 75 with up to 10 single amino acid modifications, provided that position 33 of SEQ ID NO: 75 is alanine, position 72 of SEQ ID NO: 75 is proline, position 134 of SEQ ID NO: 75 is cysteine, position 137 of SEQ ID NO: 75 is lysine, position 146 of SEQ ID NO: 75 is tryptophan, position 280 of SEQ ID NO: 75 is alanine, position 426 of SEQ ID NO: 75 is lysine, and position 436 of SEQ ID NO: 75 is aspartic acid, and each of the third and fourth polypeptides comprises, consists of, or consists essentially of the sequence SEQ ID NO: 73 with up to 10 single amino acid modifications, provided that position 33 of SEQ ID NO: 73 is an alanine and position 72 of SEQ ID NO: 73 is a proline.

In some embodiments, each of the first and second polypeptides comprises, consists of, or consists essentially of the sequence DKTHTCPPCPAPELLGGPSVFLFPPKPKDTLMISRTPEVTCVVVDVSHEDPEVKFNWYVDGVEVHNAKTKPPEEQYNSTYRVVSVLTVLHQDWLNGKEYKCKVSNKALPAPIEKTISKAKGQPREPQVYTLPPCRDKLTKNQVSLWCLVKGFYPSDIAVEWESNGQPENNYKTTPPVLDSDGSFFLYSKLTVDKSRWQQGNVFSCSV MHEALHNHYTQKSLSLSPGKGGGGGGGGGGGGGGGGGGDKTHTCPPCPAPELLGGPSVFLFPPK PKDTLMISRTPEVTCVVVDVSHEDPEVKFNWYVDGVEVHNAKTKPPEEQYNSTYRVVSVLTVLHQDWLNGKEYKCKVSNKALPAPIEKTISKAKGQPREPQVYTLPPSRDELTKNQVSLTCLVKGFYPSDIAVEWESNG QPENNYKTTPPVLKSDGSFFLYSDLTVDKSRWQQGNVFSCSVMHEALHNHYTQKSLSLSPG (SEQ ID NO: 76), and each of the third and fourth polypeptides comprises, consists of, or consists essentially of the sequence DKTHTCPPCPAPELLGGPSVFLFPPKPKDTLMISRTPEVTCVVVDVSHEDPEVKFNWYVDGVEVHNAKTKPPEEQYNSTYRVVSVLTVLHQDWLNGKEYKCKVSNKALPAPIEKTISKAKGQPREPQVCTLPPSRDELT KNQVSLSCAVDGFYPSDIAVEWESNGQPENNYKTTPPVLDSDGSFFLVSKLTVDKSRWQQGNVFSCSV MHEALHNHYTQKSLSLSPG (SEQ ID NO: 70). In some embodiments, each of the first and second polypeptides comprises, consists of, or consists essentially of the sequence SEQ ID NO: 76 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 70 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 76 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:76 can be replaced with an alternative linker), and each of the third and fourth polypeptides comprises, consists of or consists essentially of the sequence SEQ ID NO: 70 with up to 10 single amino acid modifications. In some embodiments, each of the first and second polypeptides comprises, consists of, or consists essentially of the sequence SEQ ID NO: 76 with up to 10 single amino acid modifications, provided that position 72 of SEQ ID NO: 76 is a proline and position 319 of SEQ ID NO: 76 is a proline, and each of the third and fourth polypeptides comprises, consists of, or consists essentially of the sequence SEQ ID NO: 70 with up to 10 single amino acid modifications, provided that position 72 of SEQ ID NO: 70 is a proline.

In some embodiments, each of the first and second polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELT-KNQVSLTCL-VKGFYPSDIAVEWESNG QPEN-NYKTTPPVLKSDGSFFLY-SDLTVDKSRWQQGNVFSCSVMHEALHN-HYTQKSLSLSPG (SEQ ID NO: 76), and each of the third and fourth polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDSD-GSFFLVSKLTVDKSRWQQGNVFSCSV MHEALHN-HYTQKSLSLSPG (SEQ ID NO: 70).

In some embodiments, each of the first and second polypeptides comprises, consists of, or consists essentially of the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCP-PCPAPELLGGPSVFLFPPK PKDTLMASRTPE-VTCVVVDVSHEDPEVKFNWYVDGVEVHNAKTKP-PEEQYNSTYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVF-SCSVMHEALHNHYTQKSLSLSPG (SEQ ID NO: 77), and each of the third and fourth polypeptides comprises, consists of, or consists essentially of the sequence DKTH-TCPPCPAPELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDS-DGSFFLVSKLTVDKSRWQQGNVFSCSV MHEALHN-HYTQKSLSLSPG (SEQ ID NO: 70). In some embodiments, each of the first and second polypeptides comprises, consists of, or consists essentially of the sequence SEQ ID NO: 77 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 70 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 77 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:77 can be replaced with an alternative linker), and each of the third and fourth polypeptides comprises, consists of, or consists essentially of the sequence SEQ ID NO: 70 with up to 10 single amino acid modifications. In some embodiments, each of the first and second polypeptides comprises, consists of, or consists essentially of the sequence SEQ ID NO: 77 with up to 10 single amino acid modifications, provided that position 72 of SEQ ID NO: 77 is proline, position 134 of SEQ ID NO: 77 is cysteine, position 137 of SEQ ID NO: 77 is lysine, position 146 of SEQ ID NO: 77 is tryptophan, position 280 of SEQ ID NO: 77 is alanine, position 319 of SEQ ID NO: 77 is proline, position 426 of SEQ ID NO: 77 is lysine, and positioned 436 of SEQ ID NO: 77 is aspartic acid, and each of the third and fourth polypeptides comprises, consists of, or consists essentially of the sequence SEQ ID NO: 70 with up to 10 single amino acid modifications, provided that position 72 of SEQ ID NO: 70 is a proline.

In some embodiments, each of the first and second polypeptides comprises, consists of, or consists essentially of the sequence DKTHTCPPCPAPELLGGPSVFLFPPKPKDTLMASRT-PEVTCVVVDVSHEDPEVKFNWYVDGVE VHNAKTKPPEEQYN-STYRVVSVLTVLHQDWLNGKEYKCKVSNKALPA-PIEKTISKAKGQPREPQVYTLPP CRDKLT-KNQVSLWCLVKGFYPSDIAVEWESNGQPENNY-KTTPPVLDSDGSFFLYSKLTVDKSRWQQGN VFSCSVMHEALHNHYTQKSLSL-SPGKGGGGGGGGGGGGGGGGGGGGDKTH-TCPPCPAPELLGGPSV FLFPPKPKDTLMASRTPE-VTCVVVDVSHEDPEVKFNWYVDGVEVHNAKTKP-PEEQYNSTYRVVSVLTVL HQDWLNGKEYKCKVSNKALPA-PIEKTISKAKGQPREPQVYTLPPSRDELTKNQVSLT-CLVKGFYPSDIAV EWESNGQPEN-NYKTTPPVLKSDGSFFLYSDLTVDKSRWQQGNVFS-CSVMHEALHNHYTQKSLSLSPG (SEQ ID NO: 79), and each of the third and fourth polypeptides comprises, consists of, or consists essentially of the sequence DKTHTCPPCPAPELLGGPSVFLFPPKPKDTLMASRT-PEVTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVL-DSDGSFFLVSKLTVDKSRWQQGNVFSCSV MHEALHNHYTQKSLSLSPG (SEQ ID NO: 73). In some embodiments, each of the first and second polypeptides comprises, consists of, or consists essentially of the sequence SEQ ID NO: 79 with up to 10 (9, 8, 7, 6, 5, 4, 3, 2, or 1) single amino acid modifications (e.g., substitutions, e.g., conservative substitutions), and each of the third and fourth polypeptides comprises, consists of, or consists essentially of the sequence SEQ ID NO: 73 with up to 10 (9, 8, 7, 6, 5, 4, 3, 2, or 1) single amino acid modifications (e.g., substitutions, e.g., conservative substitutions). In some embodiments, each of the first and second polypeptides comprises, consists of, or consists essentially of the sequence SEQ ID NO: 79 with up to 10 (e.g., no more than 1, no more than 2, no more than 3, no more than 4, no more than 5, no more than 6, no more than 7, no more than 8, no more than 9) single amino acid modifications in the region outside the linker (e.g., the subsequence GGGGGGGGGGGGGGGGGGGG (SEQ ID NO: 23); the linker within SEQ ID NO:79 can be replaced with an alternative linker), and each of the third and fourth polypeptides comprises, consists of, or consists essentially of the sequence SEQ ID NO: 73 with up to 10 single amino acid modifications. In some embodiments, each of the first and second polypeptides comprises, consists of, or consists essentially of the sequence SEQ ID NO: 79 with up to 10 single amino acid modifications, provided that position 33 of SEQ ID NO: 79 is alanine, position 72 of SEQ ID NO: 79 is proline, position 280 of SEQ ID NO: 79 is alanine, and position 319 of SEQ ID NO: 79 is proline, and each of the third and fourth polypeptides comprises, consists of, or consists essentially of the sequence SEQ ID NO: 73 with up to 10 single amino acid modifications, provided that position 33 of SEQ ID NO: 73 is an alanine and position 72 of SEQ ID NO: 73 is a proline. In some embodiments, the Fc construct is construct 4, construct 5, construct 6, construct 7, construct 8, construct 9, construct 10, construct 11, construct 12, construct 13, construct 14, construct 15, construct 16, construct 17, construct 18, or construct 19.

In some embodiments, the Fc construct is construct 5, construct 6, construct 7, construct 9, construct 10, construct 11, construct 13, construct 14, construct 15, construct 16, construct 17, construct 18, or construct 19.

In some embodiments, each of the first polypeptide, second polypeptide, third polypeptide, and/or fourth polypeptide includes an N-terminal D to Q amino acid substitution.

In a second aspect, an Fc construct of the disclosure including (i) a first Fc domain including a first Fc domain monomer and a second Fc domain monomer and (ii) a second Fc domain including a third Fc domain monomer and a fourth Fc domain monomer, wherein at least one Fc domain includes an amino acid modification at position I253. In another aspect, an Fc construct of the disclosure including (i) a first Fc domain including a first Fc domain monomer and a second Fc domain monomer and (ii) a second Fc domain including a third Fc domain monomer and a fourth Fc domain monomer, wherein at least one Fc domain monomer includes an amino acid substitution at position I253. In some embodiments, each of the amino acid modifications (e.g., substitutions) at position I253 is independently selected from the group consisting of I253A, I253C, I253D, I253E, I253F, I253G, I253H, I253I, I253K, I253L, I253M, I253N, I253P, I253Q, I253R, I253S, I253T, I253V, I253W, and I253Y. In some embodiments, the amino acid modification (e.g., substitution) at position I253 is I253A. In some embodiments, the Fc construct includes at least one amino acid modification (e.g., substitution) at position R292. In some embodiments, the amino acid modification (e.g., substitution) at position R292 is selected from the group consisting of R292D, R292E, R292L, R292P, R292Q, R292R, R292T, and R292Y. In some embodiments, the amino acid modification (e.g., substitution) at position R292 is R292P.

In some embodiments, the first Fc domain monomer and the third Fc domain monomer are joined by a linker (e.g., a spacer). In some embodiments, the second Fc domain monomer and the fourth Fc domain monomer are joined by a linker (e.g., a spacer). In some embodiments, each linker (e.g., spacer) is independently selected from a polypeptide having the sequence GGGGGGGGGGGGGGGGGGGG (SEQ ID NO: 23), GGGGS (SEQ ID NO: 1), GGSG (SEQ ID NO: 2), SGGG (SEQ ID NO: 3), GSGS (SEQ ID NO: 4), GSGSGS (SEQ ID NO: 5), GSGSGSGS (SEQ ID NO: 6), GSGSGSGSGS (SEQ ID NO: 7), GSGSGSGSGSGS (SEQ ID NO: 8), GGSGGS (SEQ ID NO: 9), GGSGGSGGS (SEQ ID NO: 10), GGSGGSGGSGGS (SEQ ID NO: 11), GGSGGGSG (SEQ ID NO: 12), GGSGGGSGGGSG (SEQ ID NO: 13), GGSGGGSGGGSGGGSG (SEQ ID NO: 14), GGSGGGSGGGSGGGGGSGGGGSGGGGSGGGGS (SEQ ID NO: 80), GENLYFQSGG (SEQ ID NO: 28), SACYCELS (SEQ ID NO: 29), RSIAT (SEQ ID NO: 30), RPACKIPNDLKQKVMNH (SEQ ID NO: 31), GGSAGGSGSGSSGGSSGASGTGTAGGTGSGSGTGSG (SEQ ID NO: 32), AAANSSIDLISVPVDSR (SEQ ID NO: 33), GGSGGGSEGGGSEGGGSEGGGSEGGGSEGGGSGGGS (SEQ ID NO: 34), GGGSGGGSGGGS (SEQ ID NO: 35), SGGGSGGGSGGGSGGGSGGG (SEQ ID NO: 18), GGSGGGSGGGSGGGSGGS (SEQ ID NO: 36), GGGG (SEQ ID NO: 19), GGGGGGGG (SEQ ID NO: 20), GGGGGGGGGGGG (SEQ ID NO: 21), or GGGGGGGGGGGGGGGG (SEQ ID NO: 22).

In some embodiments, the first Fc domain monomer and the second Fc domain monomer include complementary dimerization selectivity modules that promote dimerization between the first Fc domain monomer and the second Fc domain monomer. In some embodiments, the third Fc domain monomer and fourth Fc domain monomer include complementary dimerization selectivity modules that promote dimerization between the third Fc domain monomer and the fourth Fc domain monomer.

In another aspect, the disclosure provides for an Fc construct including (i) a first Fc domain including a first F domain monomer and a second Fc domain monomer and (ii) a second Fc domain including a third Fc domain monomer and a fourth Fc domain monomer, wherein at least one Fc domain includes an amino acid modification at position R292. In another aspect, the disclosure provides for an Fc construct including (i) a first Fc domain including a first F domain monomer and a second Fc domain monomer and (ii) a second Fc domain including a third Fc domain monomer and a fourth Fc domain monomer, wherein at least one Fc domain monomer includes an amino acid substitution at position R292. In some embodiments, each of the amino acid modifications (e.g., substitutions) at position R292 is independently selected from the group consisting of R292D, R292E, R292L, R292P, R292Q, R292R, R292T, and R292Y. In some embodiments, the amino acid modification (e.g., substitution) at position R292 is R292P. In some embodiments, the first Fc domain monomer and the third Fc domain monomer are joined by a linker.

In some embodiments, the second Fc domain monomer and the fourth Fc domain monomer are joined by a linker. In some embodiments, each linker is independently selected from a polypeptide having the sequence GGGGGGGGGGGGGGGGGGGG (SEQ ID NO: 23), GGGGS (SEQ ID NO: 1), GGSG (SEQ ID NO: 2), SGGG (SEQ ID NO: 3), GSGS (SEQ ID NO: 4), GSGSGS (SEQ ID NO: 5), GSGSGSGS (SEQ ID NO: 6), GSGSGSGSGS (SEQ ID NO: 7), GSGSGSGSGSGS (SEQ ID NO: 8), GGSGGS (SEQ ID NO: 9), GGSGGSGGS (SEQ ID NO: 10), GGSGGSGGSGGS (SEQ ID NO: 11), GGSGGGSG (SEQ ID NO: 12), GGSGGGSGGGSG (SEQ ID NO: 13), GGSGGGSGGGSGGGSG (SEQ ID NO: 14), GGSGGGSGGGSGGGGGSGGGGSGGGGSGGGGS (SEQ ID NO: 80), GENLYFQSGG (SEQ ID NO: 28), SACYCELS (SEQ ID NO: 29), RSIAT (SEQ ID NO: 30), RPACKIPNDLKQKVMNH (SEQ ID NO: 31), GGSAGGSGSGSSGGSSGASGTGTAGGTGSGSGTGSG (SEQ ID NO: 32), AAANSSIDLISVPVDSR (SEQ ID NO: 33), GGSGGGSEGGGSEGGGSEGGGSEGGGSEGGGSGGGS (SEQ ID NO: 34), GGGSGGGSGGGS (SEQ ID NO: 35), SGGGSGGGSGGGSGGGSGGG (SEQ ID NO: 18), GGSGGGSGGGSGGGSGGS (SEQ ID NO: 36), GGGG (SEQ ID NO: 19), GGGGGGGG (SEQ ID NO: 20), GGGGGGGGGGGG (SEQ ID NO: 21), or GGGGGGGGGGGGGGGG (SEQ ID NO: 22). In some embodiments, the linker is GGGGGGGGGGGGGGGGGGGG (SEQ ID NO: 23).

In some embodiments, the first Fc domain monomer and the second Fc domain monomer comprise complementary dimerization selectivity modules that promote dimerization between the first Fc domain monomer and the second Fc domain monomer. In some embodiments, the third Fc domain monomer and fourth Fc domain monomer comprise complementary dimerization selectivity modules that promote dimerization between the third Fc domain monomer and the fourth Fc domain monomer.

In another aspect, the disclosure features a method of preparing an Fc construct described herein. The method includes: a) providing a host cell including polynucleotides encoding the polypeptides of the disclosure; b) expressing the polypeptides in the host cell under conditions that allow for the formation of the Fc construct; and c) recovering the Fc construct.

In another aspect, the disclosure provides for an Fc construct comprising: a) a first polypeptide comprising i). a first Fc domain monomer; ii). a second Fc domain monomer; and iii). a linker joining the first Fc domain monomer to the second Fc domain monomer; b). a second polypeptide comprising i). a third Fc domain monomer; ii). a fourth Fc domain monomer; and iii). a linker joining the third Fc domain monomer to the fourth Fc domain monomer; c). a third polypeptide comprises a fifth Fc domain monomer; and d). a fourth polypeptide comprises a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein at least one Fc domain comprises an amino acid modification at position I253; wherein each of the first and second polypeptides comprises the sequence DKTHTCPPCPAPELLGGPSVFLFPPKPKDTLMASRT-PEVTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPPC-PAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVF-SCSVMHEALHNHYTQKSLSLSPG (SEQ ID NO: 78), and each of the third and fourth polypeptides comprises the sequence DKTHTCPPCPAPELLGGPSVFLFPPKPKDTLMASRT-PEVTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDS-DGSFFLVSKLTVDKSRWQQGNVFSCSV MHEALHN-HYTQKSLSLSPG (SEQ ID NO: 73). In another aspect, the disclosure provides for an Fc construct comprising: a) a first polypeptide comprising i). a first Fc domain monomer; ii). a second Fc domain monomer; and iii). a linker joining the first Fc domain monomer to the second Fc domain monomer; b). a second polypeptide comprising i). a third Fc domain monomer; ii). a fourth Fc domain monomer; and iii). a linker joining the third Fc domain monomer to the fourth Fc domain monomer; c). a third polypeptide comprises a fifth Fc domain monomer; and d). a fourth polypeptide comprises a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein each of the first and second polypeptides comprises the sequence DKTHTCPPCPA-PELLGGPSVFLFPPKPKDTLMASRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVFS-CSVMHEALHNHYTQKSLSLSPG (SEQ ID NO: 78), and each of the third and fourth polypeptides comprises the sequence DKTHTCPPCPAPELLGGPSVFLFPPKPKDTL-MASRTPEVTCVVVDVSHEDPE-VKFNWYVDGVEVHNAKT KPPEEQYN-STYRVVSVLTVLHQDWLNGKEYKCKVSNKALPAP-IEKTISKAKGQPREPQVCTLPPSRDELT KNQVSLS-CAVDGFYPSDIAVEWESNGQPEN-NYKTTPPVLDSDGSFFLVSK-LTVDKSRWQQGNVFSCSV MHEALHNHYTQKSLSLSPG (SEQ ID NO: 73).

In another aspect, the disclosure provides for an Fc construct comprising a) a first polypeptide comprising i). a first Fc domain monomer; ii). a second Fc domain monomer; and iii). a linker joining the first Fc domain monomer to the second Fc domain monomer; b). a second polypeptide comprising i). a third Fc domain monomer; ii). a fourth Fc domain monomer; and iii). a linker joining the third Fc domain monomer to the fourth Fc domain monomer; c). a third polypeptide comprises a fifth Fc domain monomer; and d). a fourth polypeptide comprises a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein at least one Fc domain comprises an amino acid modification at position I253; wherein each of the first and second polypeptides comprises the sequence DKTHTCPPCPAPELLGGPSVFLFPPKPKDTLMASRT-PEVTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCP-PCPAPELLGGPSVFLFPPK PKDTLMASRTPE-VTCVVVDVSHEDPEVKFNWYVDGVEVHNAKTKP-PEEQYNSTYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVF-SCSVMHEALHNHYTQKSLSLSPG (SEQ ID NO: 79), and each of the third and fourth polypeptides comprises the sequence DKTHTCPPCPAPELLGGPSVFLFPPKPKDTLMASRT-PEVTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDSD-GSFFLVSKLTVDKSRWQQGNVFSCSV MHEALHN-HYTQKSLSLSPG (SEQ ID NO: 73). In another aspect, the disclosure provides for an Fc construct comprising a) a first polypeptide comprising i). a first Fc domain monomer; ii). a second Fc domain monomer; and iii). a linker joining the first Fc domain monomer to the second Fc domain monomer; b). a second polypeptide comprising i). a third Fc domain monomer; ii). a fourth Fc domain monomer; and iii). a linker joining the third Fc domain monomer to the fourth Fc domain monomer; c). a third polypeptide comprises a fifth Fc domain monomer; and d). a fourth polypeptide comprises a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein each of the first and second polypeptides comprises the sequence DKTHTCPPCPA-PELLGGPSVFLFPPKPKDTLMASRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMASRTPE-VTCVVVDVSHEDPEVKFNWYVDGVEVHNAKTKP-PEEQYNSTYRVVSVLTVLHQDWL NGKEYKCKVSNKALPA-PIEKTISKAKGQPREPQVYTLPPSRDELTKNQVSLT-CLVKGFYPSDIAVEWESN GQPEN-NYKTTPPVLKSDGSFFLYSDLTVDKSRWQQGNVF-SCSVMHEALHNHYTQKSLSLSPG (SEQ ID NO: 79), and each of the third and fourth polypeptides comprises the sequence DKTHTCPPCPAPELLGGPSVFLFPPKPKDTL-MASRTPEVTCVVVDVSHEDPE-VKFNWYVDGVEVHNAKT KPPEEQYN-STYRVVSVLTVLHQDWLNGKEYKCKVSNKALPAP-IEKTISKAKGQPREPQVCTLPPSRDELT KNQVSLS-CAVDGFYPSDIAVEWESNGQPEN-NYKTTPPVLDSDGSFFLVSK-LTVDKSRWQQGNVFSCSV MHEALHNHYTQKSLSLSPG (SEQ ID NO: 73).

In another aspect, the disclosure provides for an Fc construct including: a) a first polypeptide including i). a first Fc domain monomer; ii). a second Fc domain monomer; and iii). a linker joining the first Fc domain monomer to the second Fc domain monomer; b). a second polypeptide including i). a third Fc domain monomer; ii). a fourth Fc domain monomer; and iii). a linker joining the third Fc domain monomer to the fourth Fc domain monomer; c). a third polypeptide comprises a fifth Fc domain monomer; and d). a fourth polypeptide comprises a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein at least one Fc domain comprises an amino acid modification at position R292; wherein each of the first and second polypeptides includes the sequence DKTHTCPPCPAPELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVF-SCSVMHEALHNHYTQKSLSLSPG (SEQ ID NO: 76), and each of the third and fourth polypeptides includes the sequence DKTHTCPPCPAPELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLD-SDGSFFLVSKLTVDKSRWQQGNVFSCSV MHEALHN-HYTQKSLSLSPG (SEQ ID NO: 70). In another aspect, the disclosure provides for an Fc construct including: a) a first polypeptide including i). a first Fc domain monomer; ii). a second Fc domain monomer; and iii). a linker joining the first Fc domain monomer to the second Fc domain monomer; b). a second polypeptide including i). a third Fc domain monomer; ii). a fourth Fc domain monomer; and iii). a linker joining the third Fc domain monomer to the fourth Fc domain monomer; c). a third polypeptide comprises a fifth Fc domain monomer; and d). a fourth polypeptide comprises a sixth Fc domain monomer; wherein the first Fc domain monomer and fifth Fc domain monomer combine to form a first Fc domain, the second Fc domain monomer and fourth Fc domain monomer combine to form a second Fc domain, and the third Fc domain monomer and sixth Fc domain monomer combine to form a third Fc domain, and wherein each of the first and second polypeptides includes the sequence DKTHTCPPCPAPELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVYTLPPCRDKLT KNQVSLWCLVKGFYPSDIAVEWESNGQPEN-NYKTTPPVLDSDGSFFLYSK-LTVDKSRWQQGNVFSCSV MHEALHNHYTQKSLSL-SPGKGGGGGGGGGGGGGGGGGGGGDKTHTCPP-CPAPELLGGPSVFLFPPK PKDTLMISRTPE-VTCVVVDVSHEDPEVKFNWYVDGVEVHNAKTKP-PEEQYNSTYRVVSVLTVLHQDWLN GKEYKCKVSNKALPA-PIEKTISKAKGQPREPQVYTLPPSRDELTKNQVSLT-CLVKGFYPSDIAVEWESNG QPEN-NYKTTPPVLKSDGSFFLYSDLTVDKSRWQQGNVF-SCSVMHEALHNHYTQKSLSLSPG (SEQ ID NO: 76), and each of the third and fourth polypeptides includes the sequence DKTHTCPPCPA-PELLGGPSVFLFPPKPKDTLMISRTPE-VTCVVVDVSHEDPEVKFNWYVDGVEVHNAKT KPPEEQYN-STYRVVSVLTVLHQDWLNGKEYKCKVSNKALPA-PIEKTISKAKGQPREPQVCTLPPSRDELT KNQVSLS-CAVDGFYPSDIAVEWESNGQPENNYKTTPPVLDS-DGSFFLVSKLTVDKSRWQQGNVFSCSV MHEALHN-HYTQKSLSLSPG (SEQ ID NO: 70).

In some embodiments of any of the Fc constructs described herein each Fc domain is independently an IgG1 Fc domain, an IgG2 Fc domain, an IgG3 Fc domain, an IgG4 Fc domain, or a combination thereof. In some embodiments of any of the Fc constructs described herein each Fc domain is independently an IgG1 Fc domain, an IgG2 Fc domain, an IgG3 Fc domain, an IgG4 Fc domain, or a combination thereof with up to 10 (e.g., up to 1, 2, 3, 4, 5, 6, 7, 8, 9, or 10) single amino acid modifications. In some embodiments, each Fc domain is an IgG1 Fc domain. In some embodiments, each Fc domain is an IgG2 Fc domain. In some embodiments, each Fc domain is an IgG3 Fc domain. In some embodiments, each of the first, second, and third Fc domains are IgG1 Fc domains. In some embodiments, each Fc domain is a human IgG1 Fc domain. In some embodiments, each Fc domain comprises SEQ ID NO: 42 with up to 10 (e.g., no more than 1, no more than 2, no more than 3, no more than 4, no more than 5, no more than 6, no more than 7, no more than 8, no more than 9) single amino acid modifications.

In some embodiments of any of the Fc constructs described herein one or more of the Fc domain monomers is a human IgG Fc domain monomer having up to ten (e.g., up to 1, 2, 3, 4, 5, 6, 7, 8, 9, or 10) amino acid modifications. In some embodiments of any of the Fc constructs described herein each Fc domain monomer has no more than ten (e.g., no more than 1, 2, 3, 4, 5, 6, 7, 8, 9, or 10) amino acid modifications. In some embodiments of any of the Fc constructs described herein each Fc monomer comprises the sequence of SEQ ID NO: 42 with no more than ten (e.g., no more than 1, 2, 3, 4, 5, 6, 7, 8, 9, or 10) amino acid modifications. In some embodiments of any of the Fc constructs described herein, each Fc monomer comprises the sequence of SEQ ID NO: 42 with 5 amino acid modifications. In some embodiments of any of the Fc constructs described herein, each Fc monomer comprises the sequence of SEQ ID NO: 42 with 10 amino acid modifications. In some embodiments of any of the Fc constructs described herein, each Fc monomer comprises the sequence of SEQ ID NO: 42 with 8 amino acid modifications. In each case the modifications can include one or both of the amino acid substitutions I253A and R292P.

In another aspect, the disclosure features a host cell that expresses an Fc construct described herein. The host cell includes polynucleotides encoding the polypeptides of the disclosure, wherein the polynucleotides are expressed in the host cell.

In another aspect, the disclosure provides for a polypeptide comprising an amino acid sequence selected from the group consisting of SEQ ID NO: 43-79. In another aspect, the disclosure provides for a polypeptide comprising an amino acid sequence selected from the group consisting of SEQ ID NO: 49 and SEQ ID NO: 61-79.

In another aspect, the disclosure provides for a composition comprising or consisting of the sequence: SEQ ID NO: 78 and a polypeptide comprising or consisting of the sequence: SEQ ID NO: 73. In another aspect, the disclosure provides for a composition comprising or consisting of the sequence: SEQ ID NO: 49 and a polypeptide comprising or consisting of the sequence: SEQ ID NO: 61. In another aspect, the disclosure provides for a composition comprising or consisting of the sequence: SEQ ID NO: 62 and a polypeptide comprising or consisting of the sequence: SEQ ID NO: 61. In another aspect, the disclosure provides for a composition comprising or consisting of the sequence: SEQ ID NO: 64 and a polypeptide comprising or consisting of the sequence: SEQ ID NO: 63. In another aspect, the disclosure provides for a composition comprising or consisting of the sequence: SEQ ID NO: 65 and a polypeptide comprising or consisting of the sequence: SEQ ID NO: 63. In another aspect, the disclosure provides for a composition comprising or consisting of the sequence: SEQ ID NO: 67 and a polypeptide comprising or consisting of the sequence: SEQ ID NO: 61. In another aspect, the disclosure provides for a composition comprising or consisting of the sequence: SEQ ID NO: 68 and a polypeptide comprising or consisting of the sequence: SEQ ID NO: 63. In another aspect, the disclosure provides for a composition comprising or consisting of the sequence: SEQ ID NO: 69 and a polypeptide comprising or consisting of the sequence: SEQ ID NO: 63. In another aspect, the disclosure provides for a composition comprising or consisting of the sequence: SEQ ID NO: 72 and a polypeptide comprising or consisting of the sequence: SEQ ID NO: 70. In another aspect, the disclosure provides for a composition comprising or consisting of the sequence: SEQ ID NO: 74 and a polypeptide comprising or consisting of the sequence: SEQ ID NO: 73. In another aspect, the disclosure provides fora composition comprising or consisting of the sequence: SEQ ID NO: 75 and a polypeptide comprising or consisting of the sequence: SEQ ID NO: 73. In another aspect, the disclosure provides for a composition comprising or consisting of the sequence: SEQ ID NO: 77 and a polypeptide comprising or consisting of the sequence: SEQ ID NO: 70. In another aspect, the disclosure provides for a composition comprising or consisting of the sequence: SEQ ID NO: 79 and a polypeptide comprising or consisting of the sequence: SEQ ID NO: 73. In another aspect, the disclosure provides for a composition comprising or consisting of the sequence: SEQ ID NO: 76 and a polypeptide comprising or consisting of the sequence: SEQ ID NO: 70.

In some embodiments, the compositions include the first and second listed polypeptides present at a molar ratio between 1.1:1 and 1:1.1.

In another aspect, the disclosure provides for a method of treating a patient comprising administering to the patient any one of the compositions described herein.

In another aspect, the disclosure features a pharmaceutical composition including a substantially homogenous (e.g., at least 85%, 90%, 95%, 97%, 98%, 99% homogeneous) population of an Fc construct described herein (e.g., an Fc construct having three Fc domains) or a composition including a substantially homogenous population of an Fc construct described herein (e.g., a composition including a substantially homogenous population of an Fc construct having three Fc domains) and one or more pharmaceutically acceptable carriers or excipients. Such pharmaceutical compositions can be produced without substantial aggregation or unwanted multimerization of Fc constructs.

In some aspects, the disclosure provides for a composition including a polypeptide including SEQ ID NO: 76 and a polypeptide including SEQ ID NO: 70. In some aspects, the disclosure provides for a composition comprising a polypeptide including SEQ ID NO: 78 and a polypeptide including SEQ ID NO: 73. In some aspects, the disclosure provides for a composition comprising a polypeptide including SEQ ID NO: 79 and a polypeptide including SEQ ID NO: 73.

In some aspects, the disclosure provides for a method of treating a patient including administering to the patient any one of the compositions described herein.

In some aspects, the disclosure provides for a cell including a nucleic acid sequence encoding SEQ ID NO: 76 and a nucleic acid sequence encoding SEQ ID NO: 70. In some aspects, the disclosure provides for a cell including a nucleic acid sequence encoding SEQ ID NO: 78 and a nucleic acid sequence encoding SEQ ID NO: 73. In some aspects, the disclosure provides for a cell including a nucleic acid sequence encoding SEQ ID NO: 79 and a nucleic acid sequence encoding SEQ ID NO: 73. In some aspects, the disclosure provides for a cell including a nucleic acid sequence encoding any one of the Fc constructs described herein.

In another aspect, the disclosure features a method of reducing immune cell activation of the immune response in a subject, including administering to the subject an Fc construct described herein (e.g., an Fc construct having three Fc domains) or a composition including a substantially homogenous population of an Fc construct described herein (e.g., a composition including a substantially homogenous population of an Fc construct having three Fc domains). In some embodiments, the subject has an autoimmune disease.

In another aspect, the disclosure features a method of treating inflammation or an inflammatory disease in a subject, including administering to the subject an Fc construct described herein (e.g., an Fc construct having three Fc domains) or a composition including a substantially homogenous population of an Fc construct described herein (e.g., a composition including a substantially homogenous population of an Fc construct having three Fc domains).

In another aspect, the disclosure features a method of promoting clearance of autoantibodies and/or suppressing antigen presentation in a subject, including administering to the subject an Fc construct described herein (e.g., an Fc construct having three Fc domains) or a composition including a substantially homogenous population of an Fc construct described herein (e.g., a composition including a substantially homogenous population of an Fc construct having three Fc domains).

In some embodiments, exemplary diseases that may be treated by administering an Fc construct described herein (e.g., an Fc construct having three Fc domains) include: rheumatoid arthritis (RA); systemic lupus erythematosus (SLE); ANCA-associated vasculitis; antiphospholipid antibody syndrome; autoimmune hemolytic anemia; chronic inflammatory demyelinating neuropathy; clearance of anti-allo in transplant, anti-self in GVHD, anti-replacement, IgG therapeutics, IgG paraproteins; dermatomyositis; Goodpasture's Syndrome; organ system-targeted type II hypersensitivity syndromes mediated through antibody-dependent cell-mediated cytotoxicity, e.g., Guillain Barre syndrome, CIDP, dermatomyositis, Felty's syndrome, antibody-mediated rejection, autoimmune thyroid disease, ulcerative colitis, autoimmune liver disease; idiopathic thrombocytopenia purpura; Myasthenia Gravis, neuromyelitis optica; pemphigus and other autoimmune blistering disorders; Sjogren's Syndrome; autoimmune cytopenias and other disorders mediated through antibody-dependent phagocytosis; other FcR-dependent inflammatory syndromes, e.g., synovitis, dermatomyositis, systemic vasculitis, glomerulitis and vasculitis.

In some embodiments, the Fc constructs described herein do not include an antigen-recognition region, e.g., a variable domain or a complementarity determining region (CDR). In some embodiments, the Fc construct (or an Fc domain within an Fc construct) is formed entirely or in part by association of Fc domain monomers that are present in different polypeptides. In some embodiments, the Fc constructs described herein include an antigen-recognition region, e.g., a variable domain or a CDR. In certain embodiments, the Fc construct does not include an additional domain (e.g., an IgM tailpiece or an IgA tailpiece) that promotes association of two polypeptides. In other embodiments, covalent linkages are present in the Fc construct only between two Fc domain monomers that join to form an Fc domain. In other embodiments, the Fc construct does not include covalent linkages between Fc domains. In still other embodiments, the Fc construct provides for sufficient structural flexibility such that all or substantially all of the Fc domains in the Fc construct are capable of simultaneously interacting with an Fc receptor on a cell surface. In one embodiment, the domain monomers are different in primary sequence from wild-type or from each other in that they have dimerization selectivity modules.

The Fc domain monomers of an Fc domain of the construct can have the same primary amino acid sequence. For example, both Fc domain monomers of an Fc domain may have the same dimerization selectivity module, e.g., both Fc domain monomers of an Fc domain may have identical reverse charge mutations in at least two positions within the ring of charged residues at the interface between $C_H3$ domains. In some embodiments, the first polypeptide and the second polypeptides have the same amino acid sequence. In some embodiments, the third and the fourth polypeptides have the same amino acid sequence. In some embodiments, the sequence of the first Fc domain monomer is different from the sequence of the fifth Fc domain monomer. In some embodiments, the sequence of the third Fc domain monomer is different from the sequence of the sixth Fc domain monomer. In some embodiments, the sequence of the second Fc domain monomer is the same as the sequence of the fourth Fc domain monomer.

In any of the Fc constructs described herein, the Fc domain monomers of an Fc domain of a construct can have different sequences, e.g., sequences that differ by no more than 20 amino acids (e.g., no more than 15, 10 amino acids), e.g., no more than 20, 15, 10, 8, 7, 6, 5, 4, 3 or 2 amino acids, between two Fc domain monomers (i.e., between the Fc domain monomer and another monomer of the Fc construct). For example, Fc domain monomer sequences of a construct described herein may be different because complementary dimerization selectivity modules of any of the Fc constructs can include an engineered cavity in the $C_H3$ antibody constant domain of one of the domain monomers and an engineered protuberance in the $C_H3$ antibody constant domain of the other of the Fc domain monomers, wherein the engineered cavity and the engineered protuberance are positioned to form a protuberance-into-cavity pair of Fc domain monomers. In some embodiments, the Fc constructs include amino acid modifications in the $C_H3$ domain. In some embodiments, the Fc constructs includes amino acid modifications in the $C_H3$ domain of the Fc domain monomers (one or more of the Fc domain monomers) for selective dimerization. Exemplary engineered cavities and protuberances are shown in Table 1. In other embodiments, the complementary dimerization selectivity modules include an engineered (substituted) negatively-charged amino acid in the $C_H3$ antibody constant domain of one of the domain monomers and an engineered (substituted) positively-charged amino acid in the $C_H3$ antibody constant domain of the other of the Fc domain monomers, wherein the negatively-charged amino acid and the positively-charged amino acid are positioned to promote formation of an Fc domain between complementary domain monomers. Exemplary complementary amino acid changes are shown in Tables 2A-2C. In some embodiments, one or more of the Fc domain monomers are the same sequence. In some embodiments, one or more of the Fc domain monomers have the same modifications. In some embodiments, only one, two, three, or four of the Fc domain monomers have the same modifications.

In some cases, the Fc domain includes at least one amino acid modification, wherein the amino acid modifications alter one or more of (i) binding affinity to one or more Fc receptors, (ii) effector functions, (iii) the level of Fc domain sulfation, (iv) half-life, (v) protease resistance, (vi) Fc domain stability, and/or (vii) susceptibility to degradation (e.g., when compared to the unmodified Fc domain). In some cases, the Fc domain includes no more than 16 amino acid modifications (e.g., no more than 2, 3, 4, 5, 6, 7, 8, 9, 10, 11, 12, 13, 14, 15, or 16 amino acid modifications). In some cases, the Fc domain includes no more than 16 amino acid modifications (e.g., no more than 2, 3, 4, 5, 6, 7, 8, 9, 10, 11, 12, 13, 14, 15, or 16 amino acid modifications in the $C_H3$ domain).

The disclosure also features a pharmaceutical composition that includes a substantially homogenous population of any Fc construct described herein. In one embodiment, a sterile syringe or vial qualified for pharmaceutical use contains a pharmaceutical composition wherein the only or primary active ingredient is a substantially homogenous population of any one of the Fc constructs described herein. The pharmaceutical composition may include one or more inactive ingredients, e.g., selected from salts, detergents, surfactants, bulking agents, polymers, preservatives, and other pharmaceutical excipients.

In some embodiments, the Fc construct is formed at least in part by association of Fc domain monomers that are present in different polypeptides. In certain embodiments, the Fc construct is formed by association of Fc domain monomers that are present in different polypeptides. In these embodiments, the Fc construct does not include an additional domain that promotes association of two polypeptides (e.g., an IgM tailpiece or an IgA tailpiece). In other embodiments, covalent linkages (e.g., disulfide bridges) are present only between two Fc domain monomers that join to form an Fc domain. In other embodiments, the Fc construct does not include covalent linkages (e.g., disulfide bridges) between Fc domains. In still other embodiments, the Fc construct provides for sufficient structural flexibility such that all or substantially all of the Fc domains in the Fc construct are capable of simultaneously interacting with an Fc receptor on a cell surface. In certain examples of any of these embodiments, the Fc construct includes at least two Fc domains joined through a linker (e.g., a flexible amino acid spacer).

In another aspect, the disclosure features compositions and methods for promoting selective dimerization of Fc domain monomers. The disclosure includes an Fc domain wherein the two Fc domain monomers of the Fc domain include identical mutations in at least two positions within the ring of charged residues at the interface between $C_H3$ antibody constant domains. The disclosure also includes a method of making such an Fc domain, including introducing complementary dimerization selectivity modules having identical mutations in two Fc domain monomer sequences in at least two positions within the ring of charged residues at the interface between $C_H3$ antibody constant domains. The interface between $C_H3$ antibody constant domains consists of a hydrophobic patch surrounded by a ring of charged residues. When one $C_H3$ antibody constant domain comes together with another, these charged residues pair with residues of the opposite charge. By reversing the charge of both members of two or more complementary pairs of residues, mutated Fc domain monomers remain complementary to Fc domain monomers of the same mutated sequence, but have a lower complementarity to Fc domain monomers without those mutations. In this embodiment, the identical dimerization selectivity modules promotes homodimerization. Such Fc domains include Fc domain monomers containing the double mutants K409D/D399K, K392D/D399K, E357K/K370E, D356K/K439D, K409E/D399K, K392E/D399K, E357K/K370D, or D356K/K439E. In another embodiment, an Fc domain includes Fc domain monomers including quadruple mutants combining any pair of the double mutants, e.g., K409D/D399K/E357K/K370E.

In another embodiment, in addition to the identical dimerization selectivity modules, the Fc domain monomers of the Fc domain include complementary dimerization selectivity modules having non-identical mutations that promote specific association (e.g., engineered cavity and protuberance). As a result, the two Fc domain monomers include two dimerization selectivity modules and remain complementary to each other, but have a decreased complementarity to other Fc domain monomers. This embodiment promotes heterodimerization between a cavity-containing Fc domain and a protuberance-containing Fc domain monomer. In one example, the complementary dimerization selectivity modules having non-identical mutations in charged pair residues of both Fc domain monomers are combined with a protuberance on one Fc domain monomer and a cavity on the other Fc domain monomer.

In any of the Fc constructs described herein, it is understood that the order of the Fc domain monomers is interchangeable. For example, in a polypeptide having the a first Fc domain monomer connected to a second Fc domain monomer by a linker, the carboxy terminus of the first Fc domain monomer can be joined to the amino terminus of the linker, which in turn is joined at its carboxy terminus to the amino terminus of the second Fc domain monomer. Alternatively, the carboxy terminus of the second Fc domain monomer can be joined to the amino terminus of the linker, which in turn is joined at its carboxy terminus to the amino terminus of the first domain monomer. Both of these configurations are encompassed by the disclosure.

Definitions

As used herein, the term "Fc domain monomer" refers to a polypeptide chain that includes at least a hinge domain (or portion thereof) and second and third antibody constant domains ($C_H2$ and $C_H3$) or functional fragments thereof (e.g., fragments that that capable of (i) dimerizing with another Fc domain monomer to form an Fc domain, and (ii) binding to an Fc receptor). The Fc domain monomer can be of different origins, e.g., human, mouse, or rat. The Fc domain monomer can be any immunoglobulin antibody isotype, including IgG, IgE, IgM, IgA, or IgD (e.g., IgG). Additionally, the Fc domain monomer can be an IgG subtype (e.g., IgG1, IgG2a, IgG2b, IgG3, or IgG4) (e.g., IgG1). An Fc domain monomer does not include any portion of an immunoglobulin that is capable of acting as an antigen-recognition region, e.g., a variable domain or a complementarity determining region (CDR). Fc domain monomers can contain as many as ten changes (e.g., single amino acids modifications) from a wild-type Fc domain monomer sequence (e.g., 1-10, 1-8, 1-6, 1-4 amino acid substitutions, additions, or deletions) that alter the interaction between an Fc domain and an Fc receptor. Examples of suitable changes are known in the art.

As used herein, the term "Fc domain" refers to a dimer of two Fc domain monomers that is capable of binding an Fc receptor. In the wild-type Fc domain, the two Fc domain monomers dimerize by the interaction between the two $C_H3$ antibody constant domains, as well as one or more disulfide bonds that form between the hinge domains of the two dimerizing Fc domain monomers.

In the present disclosure, the term "Fc construct" refers to associated polypeptide chains forming Fc domains as described herein (e.g., an Fc construct having three Fc domains). Fc constructs described herein can include Fc domain monomers that have the same or different sequences. For example, an Fc construct can have three Fc domains, two of which includes IgG1 or IgG1-derived Fc domain monomers, and a third which includes IgG2 or IgG2-derived Fc domain monomers. In another example, an Fc construct can have three Fc domains, two of which comprises a "protuberance-into-cavity pair" and a third which does not comprise a "protuberance-into-cavity pair." In the present disclosure, an Fc domain does not include a variable region of an antibody, e.g., $V_H$, $V_L$, CDR, or HVR. An Fc domain forms the minimum structure that binds to an Fc receptor, e.g., FcγRI, FcγRIIa, FcγRIIb, FcγRIIIa, FcγRIIIb, FcγRIV. In some embodiments, the Fc constructs described herein do not include an antigen-recognition region, e.g., a variable domain or a complementarity determining region (CDR). In some embodiments, the Fc constructs described herein include an antigen-recognition region, e.g., a variable domain or a CDR.

As used herein, the term "antibody constant domain" refers to a polypeptide that corresponds to a constant region domain of an antibody (e.g., a CL antibody constant domain, a $C_H1$ antibody constant domain, a $C_H2$ antibody constant domain, or a $C_H3$ antibody constant domain).

As used herein, the term "promote" means to encourage and to favor, e.g., to favor the formation of an Fc domain from two Fc domain monomers which have higher binding affinity for each other than for other, distinct Fc domain monomers. As is described herein, two Fc domain monomers that combine to form an Fc domain can have compatible amino acid modifications (e.g., engineered protuberances and engineered cavities) at the interface of their respective $C_H3$ antibody constant domains. The compatible amino acid modifications promote or favor the selective interaction of such Fc domain monomers with each other relative to with other Fc domain monomers which lack such amino acid modifications or with incompatible amino acid modifications. This occurs because, due to the amino acid modifications at the interface of the two interacting $C_H3$ antibody constant domains, the Fc domain monomers to have a higher affinity toward each other than to other Fc domain monomers lacking amino acid modifications.

As used herein, the term "a dimerization selectivity module" refers to a sequence of the Fc domain monomer that facilitates the favored pairing between two Fc domain monomers. "Complementary" dimerization selectivity modules are dimerization selectivity modules that promote or favor the selective interaction of two Fc domain monomers with each other. Complementary dimerization selectivity modules can have the same or different sequences. Exemplary complementary dimerization selectivity modules are described herein.

As used herein, the term "engineered cavity" refers to the substitution of at least one of the original amino acid residues in the $C_H3$ antibody constant domain with a different amino acid residue having a smaller side chain volume than the original amino acid residue, thus creating a three dimensional cavity in the $C_H3$ antibody constant domain. The term "original amino acid residue" refers to a naturally occurring amino acid residue encoded by the genetic code of a wild-type $C_H3$ antibody constant domain.

As used herein, the term "engineered protuberance" refers to the substitution of at least one of the original amino acid residues in the $C_H3$ antibody constant domain with a different amino acid residue having a larger side chain volume than the original amino acid residue, thus creating a three dimensional protuberance in the $C_H3$ antibody constant domain. The term "original amino acid residues" refers to naturally occurring amino acid residues encoded by the genetic code of a wild-type $C_H3$ antibody constant domain.

As used herein, the term "protuberance-into-cavity pair" describes an Fc domain including two Fc domain monomers, wherein the first Fc domain monomer includes an engineered cavity in its $C_H3$ antibody constant domain, while the second Fc domain monomer includes an engineered protuberance in its $C_H3$ antibody constant domain. In a protuberance-into-cavity pair, the engineered protuberance in the $C_H3$ antibody constant domain of the first Fc domain monomer is positioned such that it interacts with the engineered cavity of the $C_H3$ antibody constant domain of the second Fc domain monomer without significantly perturbing the normal association of the dimer at the inter-$C_H3$ antibody constant domain interface.

As used herein, the term "heterodimer Fc domain" refers to an Fc domain that is formed by the heterodimerization of two Fc domain monomers, wherein the two Fc domain monomers contain different reverse charge mutations (see, e.g., mutations in Table 2A) that promote the favorable formation of these two Fc domain monomers. As shown in FIGS. 1 and 2, in an Fc construct having three Fc domains—one carboxyl terminal "stem" Fc domain and two amino terminal "branch" Fc domains—each of the amino terminal "branch" Fc domains may be a heterodimeric Fc domain (also called a "branch heterodimeric Fc domain") (e.g., a heterodimeric Fc domain formed by Fc domain monomers 106 and 114 or Fc domain monomers 112 and 116 in FIG. 1; a heterodimeric Fc domain formed by Fc domain monomers 206 and 214 or Fc domain monomers 212 and 216 in FIG. 2).

As used herein, the term "homodimeric Fc domain" refers to an Fc domain that is formed by the homodimerization of two Fc domain monomers, wherein the two Fc domain monomers contain the same reverse charge mutations (see, e.g., mutations in Tables 2B and 2C). As shown in FIGS. 1 and 2, in an Fc construct having three Fc domains—one carboxyl terminal "stem" Fc domain and two amino terminal "branch" Fc domains—the carboxy terminal "stem" Fc domain may be a homodimeric Fc domain (also called a "stem homodimeric Fc domain") (e.g., a homodimeric Fc domain formed by Fc domain monomers 104 and 110 in FIG. 1; a homodimeric Fc domain formed by Fc domain monomers 204 and 210 in FIG. 2).

As used herein, the term "heterodimerizing selectivity module" refers to engineered protuberances, engineered cavities, and certain reverse charge amino acid substitutions that can be made in the $C_H3$ antibody constant domains of Fc domain monomers in order to promote favorable heterodimerization of two Fc domain monomers that have compatible heterodimerizing selectivity modules. Fc domain monomers containing heterodimerizing selectivity modules may combine to form a heterodimeric Fc domain. Examples of heterodimerizing selectivity modules are shown in Table 1 and 2A.

As used herein, the term "homodimerizing selectivity module" refers to reverse charge mutations in an Fc domain monomer in at least two positions within the ring of charged residues at the interface between $C_H3$ domains that promote homodimerization of the Fc domain monomer to form a homodimeric Fc domain. Examples of homodimerizing selectivity modules are shown in Tables 2A and 2B.

As used herein, the term "joined" is used to describe the combination or attachment of two or more elements, components, or protein domains, e.g., polypeptides, by means including chemical conjugation, recombinant means, and chemical bonds, e.g., disulfide bonds and amide bonds. For example, two single polypeptides can be joined to form one contiguous protein structure through chemical conjugation, a chemical bond, a peptide linker, or any other means of covalent linkage. In some embodiments, a first Fc domain monomer is joined to a second Fc domain monomer by way of a peptide linker, wherein the N-terminus of the peptide linker is joined to the C-terminus of the first Fc domain monomer through a chemical bond, e.g., a peptide bond, and the C-terminus of the peptide linker is joined to the N-terminus of the second Fc domain monomer through a chemical bond, e.g., a peptide bond. In other embodiments, the N-terminus of an albumin-binding peptide is joined to the C-terminus of the $C_H3$ antibody constant domain of an Fc domain monomer by way of a linker in the same fashion as mentioned above.

As used herein, the term "associated" is used to describe the interaction, e.g., hydrogen bonding, hydrophobic interaction, or ionic interaction, between polypeptides (or sequences within one single polypeptide) such that the polypeptides (or sequences within one single polypeptide) are positioned to form an Fc construct described herein (e.g., an Fc construct having three Fc domains). For example, in some embodiments, four polypeptides, e.g., two polypeptides each including two Fc domain monomers and two polypeptides each including one Fc domain monomer, associate to form an Fc construct that has three Fc domains (e.g., as depicted in FIGS. 1 and 2). The four polypeptides can associate through their respective Fc domain monomers. The association between polypeptides does not include covalent interactions.

As used herein, the term "linker" refers to a linkage between two elements, e.g., protein domains. A linker can be a covalent bond or a spacer. The term "bond" refers to a chemical bond, e.g., an amide bond or a disulfide bond, or any kind of bond created from a chemical reaction, e.g., chemical conjugation. The term "spacer" refers to a moiety (e.g., a polyethylene glycol (PEG) polymer) or an amino acid sequence (e.g., a 3-200 amino acid, 3-150 amino acid, 3-100 amino acid, 3-60 amino acid, 3-50 amino acid, 3-40 amino acid, 3-30 amino acid, 3-20 amino acid, 3-10 amino acid, 3-8 amino acid, 3-5 amino acid, 4-30 amino acid, 5-30 amino acid, 6-30 amino acid, 8-30 amino acid, 10-20 amino acid, 10-30 amino acid, 12-30 amino acid, 14-30 amino acid, 20-30 amino acid, 15-25 amino acid, 15-30 amino acid, 18-22 amino acid, and 20-30 amino acid sequence) occurring between two polypeptides or polypeptide domains to provide space and/or flexibility between the two polypeptides or polypeptide domains. An amino acid spacer is part of the primary sequence of a polypeptide (e.g., joined to the spaced polypeptides or polypeptide domains via the polypeptide backbone). The formation of disulfide bonds, e.g., between two hinge regions or two Fc domain monomers that form an Fc domain, is not considered a linker.

As used herein, the term "glycine spacer" refers to a linker containing only glycines that joins two Fc domain monomers in tandem series. A glycine spacer may contain at least 4, 8, 12, 14, 16, 18, or 20 glycines (e.g., 4-30, 8-30, 12-30, 12-50, 12-100, or 12-200 glycines; e.g., 12-30, 4, 5, 6, 7, 8, 9, 10, 11, 12, 13, 14, 15, 16, 17, 18, 19, 20, 21, 22, 23, 24, 25, 26, 27, 28, 29, or 30 glycines). In some embodiments, a glycine spacer comprises, consists of, or consists essentially of the sequence GGGGGGGGGGGGGGGGGGGG (SEQ ID NO: 27).

As used herein, the term "albumin-binding peptide" refers to an amino acid sequence of 12 to 16 amino acids that has affinity for and functions to bind serum albumin. An albumin-binding peptide can be of different origins, e.g., human, mouse, or rat. In some embodiments of the present disclosure, an albumin-binding peptide is fused to the C-terminus of an Fc domain monomer to increase the serum half-life of the Fc construct. An albumin-binding peptide can be fused, either directly or through a linker, to the N- or C-terminus of an Fc domain monomer.

As used herein, the term "purification peptide" refers to a peptide of any length that can be used for purification, isolation, or identification of a polypeptide. A purification peptide may be joined to a polypeptide to aid in purifying the polypeptide and/or isolating the polypeptide from, e.g., a cell lysate mixture. In some embodiments, the purification peptide binds to another moiety that has a specific affinity for the purification peptide. In some embodiments, such moieties which specifically bind to the purification peptide are attached to a solid support, such as a matrix, a resin, or agarose beads. Examples of purification peptides that may be joined to an Fc construct are described in further detail herein.

As used herein, the term "multimer" refers to a molecule including at least two associated Fc constructs described herein.

As used herein, the term "antigen-recognition region" refers to the portions of the light and heavy chains of an antibody that are responsible for the recognition and binding of an antibody to an antigen. The antigen-recognition region includes the variable domains of the light and heavy chains (Fab), which include the complementary determining regions (CDRs, e.g., CDR L1, CDR L2, CDR L3, CDR H1, CDR H2, and CDR H3) and framework regions (FRs).

As used herein, the phrase "immune cell activation of the immune response" refers to an immune response that is induced or activated by the binding of an immune complex or an Fc construct to an Fcγ receptor (FcγR) (e.g., an activating FcγR, e.g., FcγRI, FcγRIIa, FcγRIIc, FcγRIIIa, or FcγRIIIb) on a cell (e.g., an immune cell (e.g., a monocyte)). An immune complex is an antigen-antibody complex formed from the binding of an antibody to an antigen. An immune complex often has multiple Fc domains, which aggregate FcγRs and inhibit or activate cellular processes that play critical roles in inflammation, infection, and other diseases. In some embodiments, Fc constructs of the disclosure are able to bind to FcγRs and induce activating FcγR (e.g., FcγRI, FcγRIIa, FcγRIIc, FcγRIIIa, or FcγRIIIb) signaling on immune cells (e.g., a monocyte). Measurement of certain downstream signaling events, such as kinase phosphorylation (e.g., Syk phosphorylation) and calcium influx in the FcγR-expressing cell may be used to detect immune cell activation of an immune response caused by the binding of an immune complex or an Fc construct. For example, immune cell activation of the immune response is induced if the level of kinase phosphorylation (e.g., Syk phosphorylation) or the level of calcium influx of the cell is at least 5 fold, e.g., 5-100 fold (e.g., 5-100, 10-95, 15-90, 20-85, 25-80, 30-75, 35-70, 40-65, 45-60, or 50-55 fold; e.g., 5-, 6-, 7-, 8-, 9-, 10-, 11-, 12-, 13-, 14-, 15-, 16-, 17-, 18-, 19-, 20-, 21-, 22-, 23-, 24-, 25-, 26-, 27-, 28-, 29-, 30-, 31-, 32-, 33-, 34-, 35-, 36-, 37-, 38-, 39-, 40-, 41-, 42-, 43-, 44-, 45-, 46-, 47-, 48-, 49-, 50-, 51-, 52-, 53-, 54-, 55-, 56-, 57-, 58-, 59-, 60-, 61-, 62-, 63-, 64-, 65-, 66-, 67-, 68-, 69-, 70-, 71-, 72-, 73-, 74-, 75-, 76-, 77-, 78-, 79-, 80-, 81-, 82-, 83-, 84-, 85-, 86-, 87-, 88-, 89-, 90-, 91-, 92-, 93-, 94-, 95-, 96-, 97-, 98-, 99-, or 100-fold) higher than the level of kinase phosphorylation (e.g., Syk phosphorylation) or calcium influx of the cell without any activation by the immune complex or the Fc construct.

As used herein, the term "phagocytosis" refers a form of endocytosis, in which a cell, often a phagocyte (e.g., a monocyte), engulfs another cell, a particle, or a pathogen (e.g., a microbe or a parasite) to form a phagosome. In the immune system, phagocytosis is a major mechanism used to remove diseased cells (e.g., a cancer cell, an infected cell, or a dead cell), pathogens, and cell debris. A cell that is targeted to be phagocytosed by another cell (e.g., a phagocyte (e.g., a monocyte)) is referred to as a target cell. For example, an immune cell (e.g., a monocyte) activated by the binding of an Fc construct of the disclosure to the FcγRs (e.g., FcγRI, FcγRIIa, FcγRIIc, FcγRIIIa, or FcγRIIIb) on the immune cell may phagocytose a target cell, which may be a cancer cell or an infected cell in a subject.

As used herein, "increase" or "increasing" phagocytosis of a target cell refers to the increase in phagocytosis induced by the binding of an Fc construct of the disclosure to FcγRs (e.g., FcγRI, FcγRIIa, FcγRIIc, FcγRIIIa, or FcγRIIIb) on an immune cell (e.g., a monocyte) relative the level of phagocytosis that occur without Fc construct induction. For example, phagocytosis of a target cell is increased if the level of phagocytosis is at least 10%, e.g., 10-100% (e.g., 10-100%, 15-95%, 20-90%, 25-85%, 30-80%, 35-75%, 40-70%, 45-65%, or 50-60%; e.g., 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%) higher than the level of phagocytosis that occur without Fc construct induction.

As used herein, the term "treating cancer" refers to a therapeutic treatment of cancer in a subject. A therapeutic treatment slows the progression of cancer, improves the subject's outcome, and/or eliminates the cancer.

As used herein, the term "treating an infection" refers to a therapeutic treatment of an infection in a subject. A therapeutic treatment slows the progression of the infection, improves the subject's outcome, and/or eliminates the infection.

As used herein, the term "infection" refers to the invasion of a subject's cells, tissues, and/or organs by a pathogen, such as bacteria, viruses, fungi, helminths, protozoans, arthropods, and other microbes, parasites, and worms. In some embodiments, the pathogen may grow, multiply, and/or produce toxins in the subject's cells, tissues, and/or organs. In some embodiments, the subject may develop a negative reaction (i.e., an allergic reaction or an immune response) to the pathogen. Examples of infections include, but are not limited to, a bacterial infection, a viral infection, a fungal infection, a helmintic infection, and a protozoal infection.

As used herein, the term "bacterial infection" refers to an infection caused by one or more bacteria. Examples of infection-causing bacteria are well-known in the art and include, but are not limited to, bacteria in the genus *Streptococcus* (e.g., *Streptococcus pyogenes*), bacteria in the genus *Escherichia* (e.g., *Escherichia coli*), bacteria in the genus *Vibrio* (e.g., *Vibrio cholerae*), bacteria in the genus *Enteritis* (e.g., *Enteritis salmonella*), and bacteria in the genus *Salmonella* (e.g., *Salmonella typhi*).

As used herein, the term "viral infection" refers to an infection caused by one or more viruses. Examples of infection-causing viruses are well-known in the art and include, but are not limited to, viruses in the family Retroviridae (e.g., human immunodeficiency virus (HIV)), viruses in the family Adenoviridae (e.g., adenovirus), viruses in the family Herpesviridae (e.g., herpes simplex virus types 1 and 2), viruses in the family Papillomaviridae (e.g., human papillomavirus (HPV)), viruses in the family Poxviridae (e.g., smallpox), viruses in the family Picornaviridae (e.g., hepatitis A virus, poliovirus, rhinovirus), viruses in the family Hepadnaviridae (e.g., hepatitis B virus), viruses in the family Flaviviridae virus (e.g., hepatitis C virus, yellow fever virus, West Nile virus), viruses in the family Togaviridae (e.g., rubella virus), viruses in the family Orthomyxoviridae (e.g., influenza virus), viruses in the family Filoviridae (e.g., ebola virus, marburg virus), and viruses in the family Paramyxoviridae (e.g., measles virus, mumps virus).

As used herein, the term "fungal infection" refers to an infection caused one or more fungi. Examples of infection-causing fungi are well-known in the art and include, but are not limited to, fungi in the genus *Aspergillus* (e.g., *Aspergillus fumigatus, A. flavus, A. terreus. A. niger, A. candidus, A. clavatus, A. ochraceus*), fungi in the genus *Candida* (e.g., *Candida albicans, C. parapsilosis, C. glabrata, C. guilliermondii, C. krusei, C. lusitaniae, C. tropicalis*), fungi in the genus *Cryptococcus* (e.g., *Cryptococcus neoformans*), and fungi in the genus *Fusarium* (e.g., *Fusarium solani, F. verticiffioides, F. oxysporum*).

As used herein, the term "helmintic infection" refers to an infection caused by one or more helminths. Examples of helminths include, but are not limited to, tapeworms (cestodes), roundworms (nematodes), flukes (trematodes), and monogeneans.

As used herein, the term "protozoal infection" refers to an infection caused by one or more protozoans. Examples of protozoans include, but are not limited to, protozoans in the genus *Entamoeba* (e.g., *Entamoeba histolytica*), protozoans in the genus *Plasmodium* (e.g., *Plasmodium falciparum, P. malariae*), protozoans in the genus *Giardia* (e.g., *Giardia lamblia*), and protozoans in the genus *Trypanosoma* (e.g., *Trypanosoma brucei*).

As used herein, the term "polynucleotide" refers to an oligonucleotide, or nucleotide, and fragments or portions thereof, and to DNA or RNA of genomic or synthetic origin, which may be single- or double-stranded, and represent the sense or anti-sense strand. A single polynucleotide is translated into a single polypeptide.

As used herein, the term "polypeptide" describes a single polymer in which the monomers are amino acid residues which are joined together through amide bonds. A polypeptide is intended to encompass any amino acid sequence, either naturally occurring, recombinant, or synthetically produced.

As used herein, the term "amino acid positions" refers to the position numbers of amino acids in a protein or protein domain. The amino acid positions for antibody or Fc constructs are numbered using the Kabat numbering system (Kabat et al., *Sequences of Proteins of Immunological Interest*, National Institutes of Health, Bethesda, Md., ed 5, 1991).

As used herein, the terms "amino acid mutation", "amino acid change" and "amino acid modification" are used interchangeably to refer to an alteration of an Fc domain polypeptide when compared to a reference Fc domain polypeptide (e.g., a wild-type, unmutated, or unmodified Fc sequence). The reference Fc domain polypeptide can be wild-type human IgG1 Fc domain polypeptide. An amino acid modification includes amino acid substitutions, deletions, and/or insertions. In some embodiments, an amino acid modification is the modification of a single amino acid. In other embodiment, the amino acid modification is the modification of multiple (e.g., more than one) amino acids. The amino acid modification may comprise a combination of amino acid substitutions, deletions, and/or insertions. Included in the description of amino acid modifications, are genetic (i.e., DNA and RNA) alterations such as point mutations (e.g., the exchange of a single nucleotide for another), insertions and deletions (e.g., the addition and/or removal of one or more nucleotides) of the nucleotide sequence that codes for an Fc polypeptide. An insertion, unless otherwise stated, is an addition of one or more amino acids directly following the amino acid position at which the insertion is specified to occur. The amino acid modification, e.g., a substitution, insertion, and/or deletion, unless otherwise stated, is incorporated into both of the Fc domain monomers that make up an Fc domain. In other embodiments, an Fc domain having a first and second Fc domain monomer may include, e.g., one or more (e.g., 1, 2, 3, 4, 5, 6, 7, 8, 9, 10, or more) amino acid modifications in the first Fc domain monomer that are different from the one or more (e.g., 1, 2, 3, 4, 5, 6, 7, 8, 9, 10, or more) amino acid modifications in the second Fc domain monomer. In some embodiments, an Fc domain may include Fc domain monomers, e.g., a first and second Fc domain monomer, with homogeneous amino acid modifications, e.g., at amino acid position I253 and/or R292. In other embodiments, an Fc domain may include Fc domain monomers, e.g., a first and second Fc domain monomer, with heterogeneous amino acid modifications, e.g., at amino acid position I253 and/or R292. In certain embodiments, at least one (e.g., 1, 2, 3, 4, 5, 6, 7, 8, 9, 10, or more) Fc domain within an Fc construct includes an amino acid modification. In some instances the at least one Fc domain includes one or more (e.g., 1, 2, 3, 4, 5, 6, 7, 8, 9, 10, or more) single amino acid modifications. In some instances, the Fc domain includes no more than sixteen single amino acid modifications (e.g., no more than one, two, three, four, five, six, seven, eight, nine, ten, eleven, twelve, thirteen, fourteen, fifteen, or sixteen amino acid modifications). In some cases, the Fc domain monomer includes no more than ten single amino acid modifications. In some cases, the Fc domain monomer includes no more than 12 single amino acid modifications. In some cases, the Fc domain monomer includes no more than 14 single amino acid modifications.

In certain embodiments, at least one (e.g., one, two, or three) Fc domain within an Fc construct includes an amino acid modification. In some instances the at least one Fc domain includes one or more (e.g., two, three, four, five, six, seven, eight, nine, ten, or twenty or more) amino acid modifications. In some instances the at least one Fc domain includes no more than ten single amino acid modifications.

As used herein, the term "percent (%) identity" refers to the percentage of amino acid (or nucleic acid) residues of a candidate sequence, e.g., the sequence an Fc domain monomer in an Fc construct described herein, that are identical to the amino acid (or nucleic acid) residues of a reference sequence, e.g., the sequence a wild-type Fc domain monomer, after aligning the sequences and introducing gaps, if necessary, to achieve the maximum percent identity (i.e., gaps can be introduced in one or both of the candidate and reference sequences for optimal alignment and non-homologous sequences can be disregarded for comparison purposes). Alignment for purposes of determining percent identity can be achieved in various ways that are within the skill in the art, for instance, using publicly available computer software such as BLAST, ALIGN, or Megalign (DNASTAR) software. Those skilled in the art can determine appropriate parameters for measuring alignment, including any algorithms needed to achieve maximal alignment over the full length of the sequences being compared. In some embodiments, the percent amino acid (or nucleic acid) sequence identity of a given candidate sequence to, with, or against a given reference sequence (which can alternatively be phrased as a given candidate sequence that has or includes a certain percent amino acid (or nucleic acid) sequence identity to, with, or against a given reference sequence) is calculated as follows:

$$100\times(\text{fraction of } A/B)$$

where A is the number of amino acid (or nucleic acid) residues scored as identical in the alignment of the candidate sequence and the reference sequence, and where B is the total number of amino acid (or nucleic acid) residues in the reference sequence. In some embodiments where the length of the candidate sequence does not equal to the length of the reference sequence, the percent amino acid (or nucleic acid) sequence identity of the candidate sequence to the reference sequence would not equal to the percent amino acid (or nucleic acid) sequence identity of the reference sequence to the candidate sequence.

In particular embodiments, a reference sequence aligned for comparison with a candidate sequence may show that the candidate sequence exhibits from 50% to 100% identity (e.g., 50% to 100%, 60% to 100%, 70% to 100%, 80% to 100%, 90% to 100%, 92% to 100%, 95% to 100%, 97% to 100%, 99% to 100%, or 99.5% to 100% identity), across the full length of the candidate sequence or a selected portion of contiguous amino acid (or nucleic acid) residues of the candidate sequence. The length of the candidate sequence aligned for comparison purpose is at least 30%, e.g., at least 40%, e.g., at least 50%, 60%, 70%, 80%, 90%, or 100% of the length of the reference sequence. When a position in the candidate sequence is occupied by the same amino acid (or nucleic acid) residue as the corresponding position in the reference sequence, then the molecules are identical at that position.

In some embodiments, an Fc domain monomer in an Fc construct described herein (e.g., an Fc construct having three Fc domains) may comprise, consist of, or consist essentially of a sequence that is at least 95% identical (e.g., at least 97%, 99%, or 99.5% identical) to the sequence a wild-type Fc domain monomer (e.g., SEQ ID NO: 42). In some embodiments, an Fc domain monomer in an Fc construct described herein (e.g., an Fc construct having three Fc domains) may comprise, consist of, or consist essentially of a sequence that is at least 95% identical (e.g., at least 97%, 99%, or 99.5% identical) to the sequence any one of SEQ ID NOs: 44, 46, 48, and 50-53. In certain embodiments, an Fc domain monomer in the Fc construct may comprise, consist of, or consist essentially of a sequence that is at least 95% identical (e.g., at least 97%, 99%, or 99.5% identical) to the sequence SEQ ID NO: 48, 52, and 53.

In some cases, an Fc domain monomer in an Fc construct described herein may comprise, consist of, or consist essentially of a sequence that is at least 95% identical (e.g., at least 97%, 99%, or 99.5% identical) to any of the sequences described herein. In some cases, an Fc domain monomer in an Fc construct described herein may comprise, consist of, or consist essentially of a sequence that is any one of the sequences described herein with up to 10 (e.g., up to 9, 8, 7, 6, 5, 4, 3, 2, or 1) single amino acid modifications (e.g., substitutions, e.g., conservative substitutions).

In some embodiments, a polypeptide having two Fc domain monomers in an Fc construct described herein (e.g., polypeptides 102 and 108 in FIG. 1; polypeptides 202 and 208 in FIG. 2) may comprise, consist of, or consist essentially of a sequence that is at least 95% identical (e.g., at least 97%, 99%, or 99.5% identical) to the sequence any one of SEQ ID NOs: 43, 45, 47, and 49. In certain embodiments, a polypeptide having two Fc domain monomers in an Fc construct described herein may comprise, consist of, or consist essentially of a sequence that is at least 95% identical (e.g., at least 97%, 99%, or 99.5% identical) to the sequence SEQ ID NO: 49.

In some embodiments, a spacer between two Fc domain monomers may comprise, consist of, or consist essentially of a sequence that is at least 75% identical (e.g., 75%, 77%, 79%, 81%, 83%, 85%, 87%, 89%, 91%, 93%, 95%, 97%, 99%, 99.5%, or 100% identical) to the sequence any one of SEQ ID NOs: 1-36 (e.g., SEQ ID NOs: 17, 18, 26, and 27) described further herein.

As used herein, the term "host cell" refers to a vehicle that includes the necessary cellular components, e.g., organelles, needed to express proteins from their corresponding nucleic acids. The nucleic acids are typically included in nucleic acid vectors that can be introduced into the host cell by conventional techniques known in the art (transformation, transfection, electroporation, calcium phosphate precipitation, direct microinjection, etc.). A host cell may be a prokaryotic cell, e.g., a bacterial cell, or a eukaryotic cell, e.g., a mammalian cell (e.g., a CHO cell). As described herein, a host cell is used to express one or more polypeptides encoding desired domains which can then combine to form a desired Fc construct.

As used herein, the term "pharmaceutical composition" refers to a medicinal or pharmaceutical formulation that contains an active ingredient as well as one or more excipients and diluents to enable the active ingredient to be suitable for the method of administration. The pharmaceutical composition of the present disclosure includes pharmaceutically acceptable components that are compatible with the Fc construct. The pharmaceutical composition is typically in aqueous form for intravenous or subcutaneous administration.

As used herein, a "substantially homogenous population" of polypeptides or of an Fc construct is one in which at least 50% of the polypeptides or Fc constructs in a composition (e.g., a cell culture medium or a pharmaceutical composition) have the same number of Fc domains, as determined by non-reducing SDS gel electrophoresis or size exclusion chromatography. A substantially homogenous population of polypeptides or of an Fc construct may be obtained prior to purification, or after Protein A or Protein G purification, or after any Fab or Fc-specific affinity chromatography only. In various embodiments, at least 55%, 60%, 65%, 70%, 75%, 80%, or 85% of the polypeptides or Fc constructs in the composition have the same number of Fc domains. In other embodiments, up to 85%, 90%, 92%, or 95% of the polypeptides or Fc constructs in the composition have the same number of Fc domains. A substantially homogenous population or composition is at least 85% homogenous (e.g., at least 85%, 90%, or 95% homogenous).

As used herein, the term "pharmaceutically acceptable carrier" refers to an excipient or diluent in a pharmaceutical composition. The pharmaceutically acceptable carrier must be compatible with the other ingredients of the formulation and not deleterious to the recipient. In the present disclosure, the pharmaceutically acceptable carrier must provide adequate pharmaceutical stability to the Fc construct. The nature of the carrier differs with the mode of administration. For example, for oral administration, a solid carrier is preferred; for intravenous administration, an aqueous solution carrier (e.g., WFI, and/or a buffered solution) is generally used.

As used herein, "therapeutically effective amount" refers to an amount, e.g., pharmaceutical dose, effective in inducing a desired biological effect in a subject or patient or in treating a patient having a condition or disorder described herein. It is also to be understood herein that a "therapeutically effective amount" may be interpreted as an amount giving a desired therapeutic effect, either taken in one dose or in any dosage or route, taken alone or in combination with other therapeutic agents.

DESCRIPTION OF THE DRAWINGS

FIG. 19A is a graph showing cellular binding of IgG1 and construct 4, construct 6, construct 16, and construct 18 by TR-FRET to FcγRIIb (mean±standard deviation shown for 3-8 replicates).

FIG. 19B is a graph showing cellular binding of IgG1 and construct 4, construct 6, construct 16, and construct 18 by TR-FRET to FcγRI (mean±standard deviation shown for 3-8 replicates).

FIG. 19C is a graph showing cellular binding of IgG1 and construct 4, construct 6, construct 16, and construct 18 by TR-FRET to FcγRIIa (mean±standard deviation shown for 3-8 replicates).

FIG. 19D is a graph showing cellular binding of IgG1 and construct 4, construct 6, construct 16, and construct 18 by TR-FRET to FcγRIIIa (mean±standard deviation shown for 3-8 replicates).

DETAILED DESCRIPTION OF THE INVENTION

Figure 1:
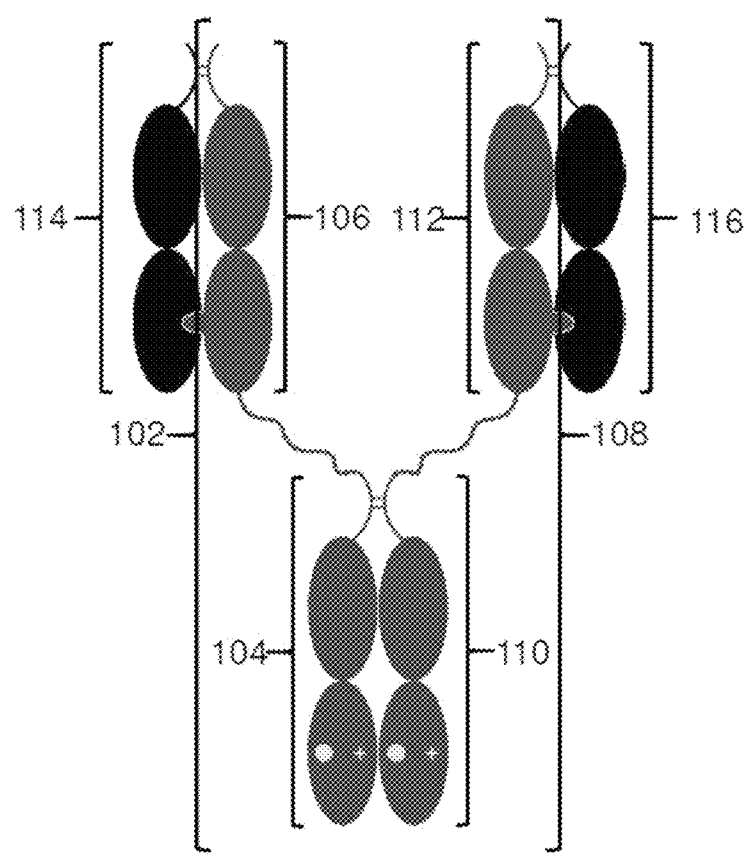
FIG. 1 is an illustration of Fc constructs (Fc construct 1, Fc construct 2, or Fc construct 3) containing three Fc domains formed from four polypeptides. The first polypeptide (102) contains one Fc domain monomer (104) containing different charged amino acids at the $C_H3$-$C_H3$ interface than the wild-type Fc domain monomer sequence joined in a tandem series with a protuberance-containing Fc domain monomer (106). The second polypeptide (108) contains an Fc domain monomer (110) containing different charged amino acids at the $C_H3$-$C_H3$ interface than the wild-type Fc domain monomer sequence joined in a tandem series with another protuberance-containing Fc domain monomer (112). The third and fourth polypeptides (114 and 116, respectively) each contain a cavity-containing Fc domain monomer.

Therapeutic proteins that include Fc domains of IgG can be used to treat inflammation and immunological and inflammatory diseases, cancers, and infections. The present disclosure features compositions and methods for preparing Fc constructs containing Fc domains (e.g., Fc constructs having 2-10 Fc domains, e.g., Fc constructs having 2, 3, 4, 5, 6, 7, 8, 9, or 10 Fc domains). The Fc constructs described herein facilitate the preparation of homogenous pharmaceutical compositions by incorporating structural features (for example, glycine spacers) that significantly improve manufacturing outcome.

Accordingly, the disclosure features pharmaceutical compositions that include a substantially homogenous population of an Fc construct described herein (e.g., an Fc construct having three Fc domains). Homogeneity is an important aspect of a pharmaceutical composition as it influences the pharmacokinetics and in vivo performance of the composition. Traditionally, in the manufacture of pharmaceutical products, there exists the problem of product heterogeneity that may be caused by several factors depending on how the product is produced. For example, the pharmaceutical product may undergo random product cleavage, proteolysis, degradation, and/or aggregation, off-target association of subunits, and/or inefficient protein folding. Different organisms having different biosynthetic processes or cellular machineries that are used to produce the pharmaceutical product may also cause heterogeneity in the product. Often, the initial culture containing the desired pharmaceutical product needs to undergo a rigorous purification process to produce a less heterogenous composition containing the pharmaceutical product.

The disclosure features, in one aspect, Fc constructs having structural features that significantly improve the folding efficiency of the Fc constructs and minimize off-target association of the subunits, thus, leading to pharmaceutical compositions containing these Fc constructs with high homogeneity. Having a high degree of homogeneity ensures the safety, efficacy, uniformity, and reliability of the pharmaceutical composition. Having a high degree of homogeneity also minimizes potential aggregation or degradation of the pharmaceutical product caused by unwanted materials (e.g., degradation products and/or aggregated products or multimers, as well as limiting off-target and adverse side effects caused by the unwanted materials.

As described in detail herein, the disclosure features substantially homogenous containing Fc constructs that all have the same number of Fc domains, as well as methods of preparing such substantially homogenous compositions.

The Fc constructs described herein include glycine spacers between Fc domains. As is well-known in the art, linkers containing both serines and glycines provide structural flexibility in a protein and are commonly used for joining two polypeptides. We have observed through experimentation (see Example 4) that linkers containing both serines and glycines undergo O-glycosylation (e.g., O-xylosylation) at multiple serines in the linker and proteolysis at the N-terminal side of serine. We aimed to optimize the linker sequence and length to further improve the homogeneity of the Fc constructs. We made Fc constructs in which all the linkers within the constructs are glycine spacers having only glycines (e.g., at least 12 glycines, e.g., 12-30 glycines; SEQ ID NO: 27). Having all glycine spacers in the Fc constructs further improved the homogeneity of the Fc constructs by removing O-glycosylation at serines and also decreasing the rate of proteolysis of the constructs (see Example 4). Consequently, we were able to achieve a more substantially homogenous population of Fc constructs by using all glycine spacers in the Fc constructs.

Homogeneity is the result of Fc construct components. For example, in a first approach ("approach (a)"), incorporation of linkers containing only glycines to join Fc domain monomers may be utilized. As we observed through experimentation, all-glycine spacers (e.g., at least 12 glycines, e.g., 12-30 glycines; SEQ ID NO: 27) in an Fc construct do not undergo O-glycosylation and are less susceptible to proteolysis as compared to traditional linkers that include serines and glycines (see Example 4).

In addition, in another approach ("approach (b)"), homogeneity of a composition containing an Fc construct described herein (e.g., an Fc construct having three Fc domains) is improved by removal of C-terminal lysines. Such C-terminal lysine residue are highly conserved in immunoglobulins across many species and may be fully or partially removed by the cellular machinery during protein production. Removal of the C-terminal lysines in the Fc constructs of the disclosure improves uniformity of the resulting composition and achieves a more homogenous Fc construct preparation (see Example 8). For example, in some embodiments of Fc constructs described herein (e.g., an Fc construct having three Fc domains), the codon of the C-terminal lysine is removed, thus, generating Fc constructs having polypeptides without C-terminal lysine residues and a resultant homogenous population.

A further approach ("approach (c)") to improve the homogeneity of a composition containing an Fc construct described herein (e.g., an Fc construct having three Fc domains), two sets of heterodimerizing selectivity modules were utilized: (i) heterodimerizing selectivity modules having different reverse charge mutations and (ii) heterodimerizing selectivity modules having engineered cavities and protuberances. We have observed through experimentation, e.g., see Example 6, that when trying to form a heterodimeric Fc domain in an Fc construct, having both (i) and (ii) further improved the homogeneity of the pharmaceutical composition produced by reducing uncontrolled association of Fc domain monomers, and therefore undesirable oligomers and multimers. In particular examples, an Fc domain monomer containing (i) at least one reverse charge mutation and (ii) at least one engineered cavity or at least one engineered protuberance may be produced and will selectively combine with another Fc domain monomer containing (i) at least one reverse charge mutation and (ii) at least one engineered protuberance or at least one engineered cavity to form an Fc domain. In another example, an Fc domain monomer containing reversed charge mutation K370D and engineered cavities Y349C, T366S, L368A, and Y407V and another Fc domain monomer containing reversed charge mutation E357K and engineered protuberances S354C and T366W may be produced and will selectively combine to form an Fc domain.

As described in detail herein, a substantially homogenous composition containing an Fc construct of the disclosure (e.g., an Fc construct having three Fc domains) may be achieved by using all-glycine spacers between two Fc domain monomers in the Fc construct (approach (a)), by using polypeptides that lack C-terminal lysines in the Fc construct (approach (b)), and/or by using two sets of heterodimerizing selectivity modules ((i) heterodimerizing selectivity modules having different reverse charge mutations and (ii) heterodimerizing selectivity modules having engineered cavities and protuberances) to promote heterodimeric Fc domain formation by some Fc domain monomers in the Fc construct (approach (c)).

In some embodiments, a substantially homogenous composition containing an Fc construct described herein (e.g., an Fc construct having three Fc domains) may be achieved through approach (a).

In some embodiments, a substantially homogenous composition containing an Fc construct described herein (e.g., an Fc construct having three Fc domains) may be achieved through approach (b).

In some embodiments, a substantially homogenous composition containing an Fc construct described herein (e.g., an Fc construct having three Fc domains) may be achieved through approach (c). In some embodiments, a substantially homogenous composition containing an Fc construct described herein (e.g., an Fc construct having three Fc domains) may be achieved through a combination of approaches (a) and (b).

In some embodiments, a substantially homogenous composition containing an Fc construct described herein (e.g., an Fc construct having three Fc domains) may be achieved through a combination of approaches (a) and (c).

In some embodiments, a substantially homogenous composition containing an Fc construct described herein (e.g., an Fc construct having three Fc domains) may be achieved through a combination of approaches (b) and (c).

In some embodiments, a substantially homogenous composition containing an Fc construct described herein (e.g., an Fc construct having three Fc domains) may be achieved through a combination of approaches (a), (b), and (c).

In some embodiments, to further improve the homogeneity of the pharmaceutical composition containing an Fc construct described herein, the N-terminal Asp in one or more of the polypeptides in the Fc construct in the composition is mutated to Gln. In some embodiments of a composition including a substantially homogenous population of an Fc construct described herein, the N-terminal Asp in each of the polypeptides in the Fc construct in the composition is mutated to Gln.

Furthermore, in Fc constructs of the disclosure (e.g., an Fc construct having three Fc domains), the length of the linkers that join Fc domain monomers influences the folding efficiency of the Fc constructs. In some embodiments, a linker having at least 4, 8, or 12 glycines (e.g., 4-30, 8-30, 12-30 glycines; SEQ ID NOs: 26 and 27) may be used to join Fc domain monomers in Fc constructs of the disclosure.

I. Fc Domain Monomers

An Fc domain monomer includes a hinge domain, a $C_H2$ antibody constant domain, and a $C_H3$ antibody constant domain. The Fc domain monomer can be of different origins, e.g., human, mouse, or rat. The Fc domain monomer can be of immunoglobulin antibody isotype IgG, IgE, IgM, IgA, or IgD. The Fc domain monomer may also be of any immunoglobulin antibody isotype (e.g., IgG1, IgG2a, IgG2b, IgG3, or IgG4). The Fc domain monomers may also be hybrids, e.g., with the hinge and $C_H2$ from IgG1 and the $C_H3$ from IgA, or with the hinge and $C_H2$ from IgG1 but the $C_H3$ from IgG3. A dimer of Fc domain monomers is an Fc domain (further defined herein) that can bind to an Fc receptor, e.g., FcγRIIIa, which is a receptor located on the surface of leukocytes. In the present disclosure, the $C_H3$ antibody constant domain of an Fc domain monomer may contain amino acid substitutions at the interface of the $C_H3$-$C_H3$ antibody constant domains to promote their association with each other. In other embodiments, an Fc domain monomer includes an additional moiety, e.g., an albumin-binding peptide or a purification peptide, attached to the N- or C-terminus. In the present disclosure, an Fc domain monomer does not contain any type of antibody variable region, e.g., $V_H$, $V_L$, a complementarity determining region (CDR), or a hypervariable region (HVR).

In some embodiments, an Fc domain monomer in an Fc construct described herein (e.g., an Fc construct having three Fc domains) may comprise, consist of, or consist essentially of a sequence that is at least 95% identical (e.g., at least 97%, 99%, or 99.5% identical) to the sequence a wild-type Fc domain monomer (SEQ ID NO: 42). In some embodiments, an Fc domain monomer in an Fc construct described herein (e.g., an Fc construct having three Fc domains) may comprise, consist of, or consist essentially of a sequence that is a wild-type Fc domain monomer (SEQ ID NO: 42) with up to 10 (9, 8, 7, 6, 5, 4, 3, 2, or 1) single amino acid modifications (e.g., substitutions, e.g., conservative substitutions). In some embodiments, an Fc domain monomer in an Fc construct described herein (e.g., an Fc construct having three Fc domains) may comprise, consist of, or consist essentially of a sequence that is at least 95% identical (e.g., at least 97%, 99%, or 99.5% identical) to the sequence any one of SEQ ID NOs: 44, 46, 48, and 50-53 (see Example 1, Tables 4 and 5). In some embodiments, an Fc domain monomer in an Fc construct described herein (e.g., an Fc construct having three Fc domains) may comprise, consist of, or consist essentially of a sequence that is any one of SEQ ID NOs: 44, 46, 48, and 50-53 (see Example 1, Tables 4 and 5) with up to 10 (9, 8, 7, 6, 5, 4, 3, 2, or 1) single amino acid modifications (e.g., substitutions, e.g., conservative substitutions). In some cases, these amino acid modifications are in addition to alteration in the length of the glycine spacer, i.e., the up to 10 (9, 8, 7, 6, 5, 4, 3, 2, or 1) single amino acid modifications are in addition to changes in the length of the all glycine spacer (SEQ ID NO:23). In certain embodiments, an Fc domain monomer in the Fc construct may comprise, consist of, or consist essentially of a sequence that is at least 95% identical (e.g., at least 97%, 99%, or 99.5% identical) to the sequence any one of SEQ ID NOs: 48, 52, and 53. In certain embodiments, an Fc domain monomer in the Fc construct may comprise, consist of, or consist essentially of a sequence that is any one of SEQ ID NOs: 48, 52, and 53 with up to 10 (9, 8, 7, 6, 5, 4, 3, 2, or 1) single amino acid modifications (e.g., substitutions, e.g., conservative substitutions).

```
SEQ ID NO: 42: wild-type human IgG1 Fc domain
monomer amino acid sequence
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE
```

-continued

```
YKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSR

WQQGNVFSCSVMHEALHNHYTQKSLSLSPGK

                                        SEQ ID NO: 44
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVCTLPPSRDELTKNQVSLSC

AVKGFYPSDIAVEWESNGQPENNYKTTPPVLDSDGSFFLVSKLTVDKSR

WQQGNVFSCSVMHEALHNHYTQKSLSLSPGK

                                        SEQ ID NO: 46
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVCTLPPSRDELTKNQVSLSC

AVKGFYPSDIAVEWESNGQPENNYKTTPPVLDSDGSFFLVSKLTVDKSR

WQQGNVFSCSVMHEALHNHYTQKSLSLSPG

                                        SEQ ID NO: 48
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVCTLPPSRDELTKNQVSLSC

AVDGFYPSDIAVEWESNGQPENNYKTTPPVLDSDGSFFLVSKLTVDKSR

WQQGNVFSCSVMHEALHNHYTQKSLSLSPG

                                        SEQ ID NO: 50
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPCRDELTKNQVSLWC

LVKGFYPSDIAVEWESNGQPENNYKTTPPVLDSDGSFFLYSKLTVDKSR

WQQGNVFSCSVMHEALHNHYTQKSLSLSPGK

                                        SEQ ID NO: 51
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLKSDGSFFLYSDLTVDKSR

WQQGNVFSCSVMHEALHNHYTQKSLSLSPGK

                                        SEQ ID NO: 52
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTC

LVKGFYPSDIAVEWESNGQPENNYKTTPPVLKSDGSFFLYSDLTVDKSR

WQQGNVFSCSVMHEALHNHYTQKSLSLSPG

                                        SEQ ID NO: 53
DKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKE
```

-continued

YKCKVSNKALPAPIEKTISKAKGQPREPQVYTLPPCRDKLTKNQVSLWC

LVKGFYPSDIAVEWESNGQPENNYKTTPPVLDSDGSFFLYSKLTVDKSR

WQQGNVFSCSVMHEALHNHYTQKSLSLSPGK

II. Fc Domains

As defined herein, an Fc domain includes two Fc domain monomers that are dimerized by the interaction between the $C_H3$ antibody constant domains. In the present disclosure, an Fc domain does not include a variable region of an antibody, e.g., $V_H$, $V_L$, CDR, or HVR. An Fc domain forms the minimum structure that binds to an Fc receptor, e.g., Fc-gamma receptors (i.e., Fcγ receptors (FcγR)), Fc-alpha receptors (i.e., Fcα receptors (FcαR)), Fc-epsilon receptors (i.e., Fcεreceptors (FcεR)), and/or the neonatal Fc receptor (FcRn). In some embodiments, an Fc domain of the present disclosure binds to an Fcγ receptor (e.g., FcγRI (CD64), FcγRIIa (CD32), FcγRIIb (CD32), FcγRIIIa (CD16a), FcγRIIIb (CD16b)), and/or FcγRIV and/or the neonatal Fc receptor (FcRn).

III. Fc Domain Modifications

An unmodified Fc domain monomer can be a naturally occurring human Fc domain monomer or a WT human Fc domain monomer. An Fc domain monomer can be a naturally occurring human Fc domain monomer comprising a hinge, a $C_H2$ domain, and a $C_H3$ domain; or a variant thereof having up to 16 (e.g., up to 2, 3, 4, 5, 6, 7, 8, 9, 10, 11, 12, 13, 14, 15, or 16) amino acid modifications (e.g., single amino acid modifications) to accommodate or promote directed dimerization. An Fc domain monomer can be an IgG1 Fc domain, an IgG2 Fc domain, an IgG3 Fc domain, an IgG4 Fc domain, or a combination thereof. An Fc domain monomer can be an IgG1 Fc domain, an IgG2 Fc domain, an IgG3 Fc domain, an IgG4 Fc domain, or a combination thereof with up to 10 (9, 8, 7, 6, 5, 4, 3, 2, or 1) single amino acid modifications (e.g., substitutions, e.g., conservative substitutions). In some cases, the Fc domain monomer is a human IgG Fc domain monomer having up to ten amino acid modifications (e.g., no more than 2, 3, 4, 5, 6, 7, 8, 9, 10, 11, 12, 13, 14, 15, or 16 amino acid modifications). In some cases, the Fc domain monomer comprises, consists of, or consists essentially of the sequence of SEQ ID NO: 42 with no more than ten amino acid modifications (e.g., no more than 2, 3, 4, 5, 6, 7, 8, 9, 10, 11, 12, 13, 14, 15, or 16 amino acid modifications). In some cases, the Fc domain includes at least one amino acid modification, wherein the amino acid modifications alter one or more of (i) binding affinity to one or more Fc receptors, (ii) effector functions, (iii) the level of Fc domain sulfation, (iv) half-life, (v) protease resistance, (vi) Fc domain stability, and/or (vii) susceptibility to degradation (e.g., when compared to the unmodified Fc domain). In some cases, the Fc domain includes no more than 16 amino acid modifications (e.g., no more than 2, 3, 4, 5, 6, 7, 8, 9, 10, 11, 12, 13, 14, 15, or 16 amino acid modifications in the $C_H3$ domain).

Figure 2:
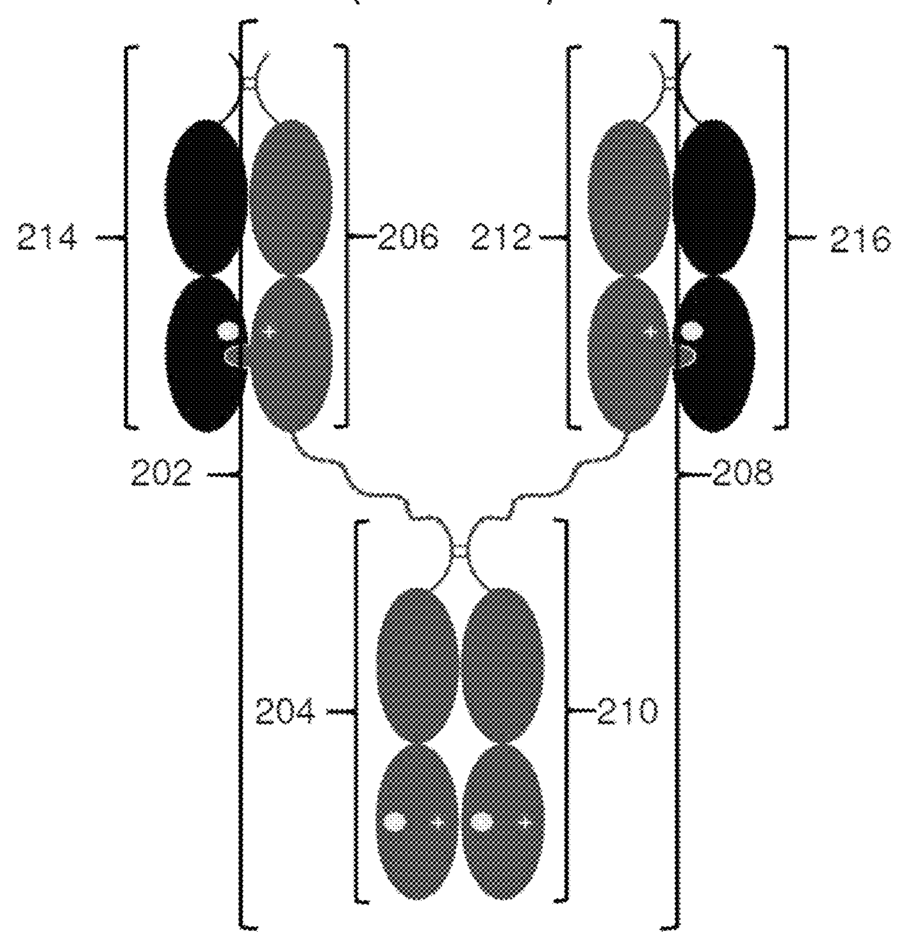
FIG. 2 is an illustration of an Fc construct (Fc construct 4) containing three Fc domains formed from four polypeptides. The first polypeptide (202) contains one Fc domain monomer (204) containing different charged amino acids at the $C_H3$-$C_H3$ interface than the wild-type Fc domain monomer sequence joined in a tandem series with another Fc domain monomer (206) containing different charged amino acids and a protuberance. The second polypeptide (208) contains an Fc domain monomer (210) containing different charged amino acids at the $C_H3$-$C_H3$ interface than the wild-type Fc domain monomer sequence joined in a tandem series with another Fc domain monomer (212) containing different charged amino acids and a protuberance. The third and fourth polypeptides (214 and 216, respectively) each contain an Fc domain monomer containing different charged amino acids and a cavity.
Figure 18A:
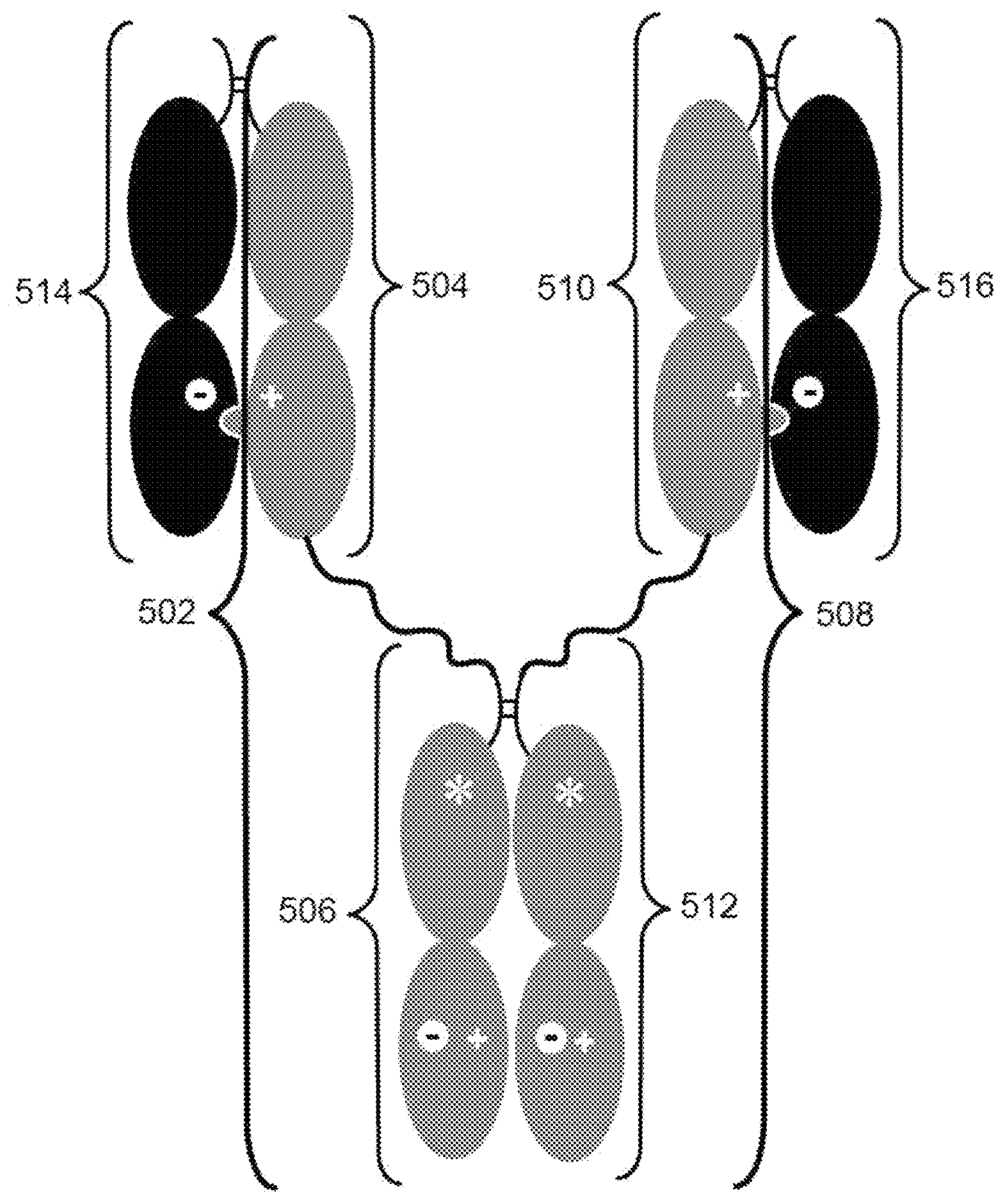
FIG. 18A is an illustration of an Fc construct (construct 5) containing three Fc domains formed from four polypeptides. Each of the first polypeptide (502) and the second polypeptide (508) contains one Fc domain monomer containing charged amino acids at the $C_H3$-$C_H3$ interface than the wild-type sequence (506 and 512, respectively) joined by way of a linker to a protuberance-containing Fc domain monomer (504 and 510, respectively). The third and fourth polypeptides (514 and 516, respectively) each contain a cavity-containing Fc domain monomer. Each of the first polypeptide (502) and the second polypeptide (508) also contain electrostatic steering mutations, e.g., E357K. Similarly, the third and fourth polypeptides (514 and 516, respectively) each contain electrostatic steering mutations, e.g., K370D. 506 and 512 each contain the amino acid modification I253A, which is represented as an asterisk. 502 and 508 each have the amino acid sequence of SEQ ID NO: 62. 514 and 516 each have the amino acid sequence of SEQ ID NO: 61.
Figure 18B:
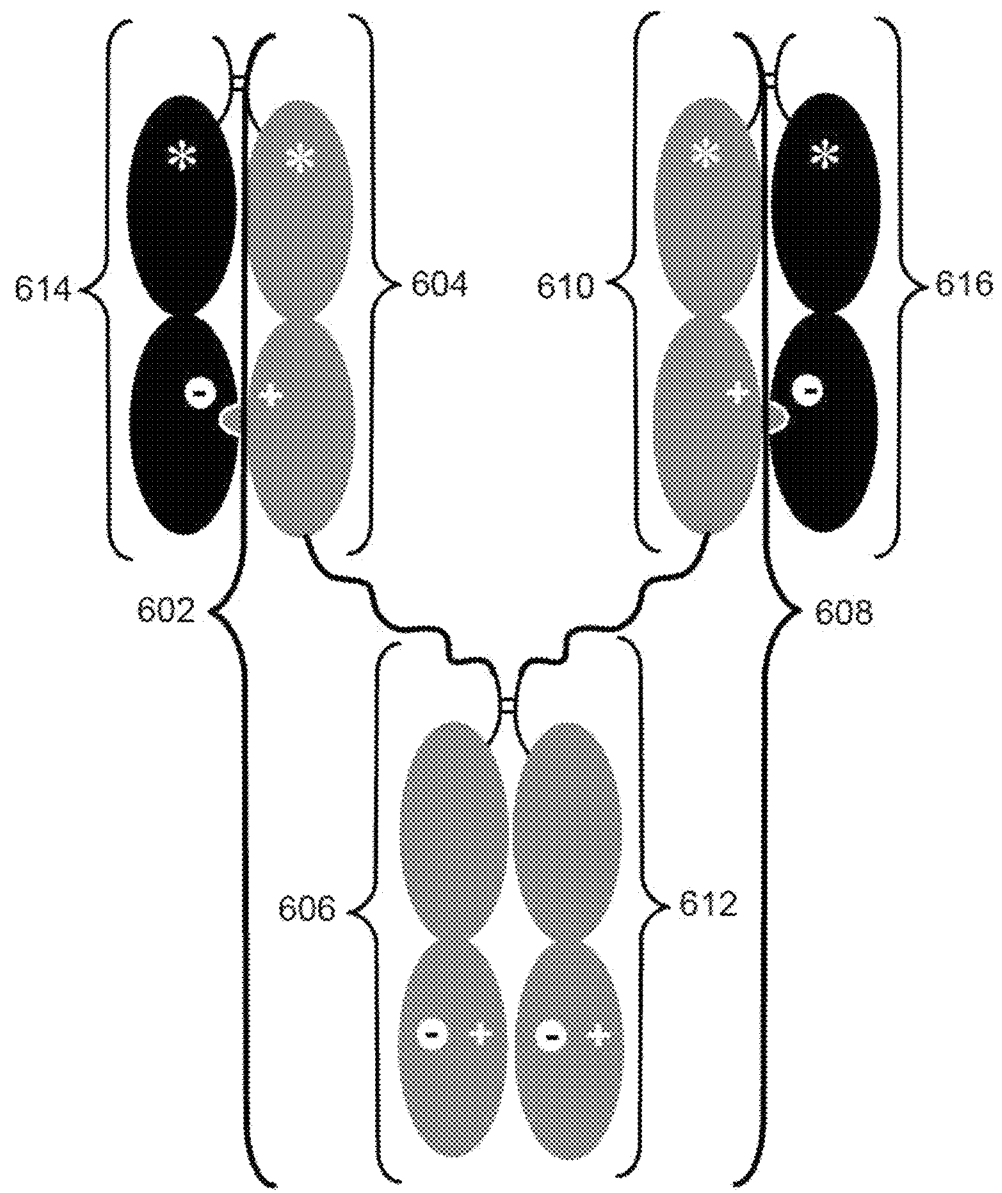
FIG. 18B is an illustration of an Fc construct (construct 6) containing three Fc domains formed from four polypeptides. Each of the first polypeptide (602) and the second polypeptide (608) contains one Fc domain monomer containing charged amino acids at the $C_H3$-$C_H3$ interface than the wild-type sequence (606 and 612, respectively) joined by way of a linker to a protuberance-containing Fc domain monomer (604 and 610, respectively). The third and fourth polypeptides (614 and 616, respectively) each contain a cavity-containing Fc domain monomer. Each of the first polypeptide (602) and the second polypeptide (608) also contain electrostatic steering mutations, e.g., E357K. Similarly, the third and fourth polypeptides (614 and 616, respectively) each contain electrostatic steering mutations, e.g., K370D. 604, 610, 614, and 616 each contain the amino acid modification I253A, which is represented as an asterisk. 602 and 608 each have the amino acid sequence of SEQ ID NO: 64. 614 and 616 each have the amino acid sequence of SEQ ID NO: 63.

At least one Fc domain of an Fc construct of the disclosure includes an amino acid modification at position I253 (e.g., I253A, I253C, I253D, I253E, I253F, I253G, I253H, I253I, I253K, I253L, I253M, I253N, I253P, I253Q, I253R, I253S, I253T, I253V, I253W, or I253Y) and/or at position R292 (e.g., R292P, R292D, R292E, R292L, R292Q, R292R, R292T, and R292Y). In some instances, at least one Fc domain includes an amino acid modification at position I253, e.g., I253A. In some instances, at least one Fc domain includes an amino acid modification at position R292, e.g., R292P. An Fc domain may include both an amino acid modification at position I253 (e.g., I253A) and at position R292 (e.g., R292P). For example, an Fc construct having three Fc domains may include an amino acid modification at position I253 (e.g., I253A) in one, two, or all three Fc domains and may additionally, or alternatively, include an amino acid modification at position R292 (e.g., R292P) in one, two, or all three Fc domains. Exemplary Fc constructs having I253A and/or R292P amino acid modifications are depicted in FIG. 2 and FIGS. 18B-18O.

In some embodiments, Fc domain modifications that alter half-life may decrease the binding of a modified Fc domain to FcRn, for example, by modification of the Fc domain at position I253.

Modifications at position I253 may include an amino acid substitution, wherein the amino acid at position I253 is substituted with a natural or non-natural amino acid; a deletion of the amino acid at position I253; or an insertion of one or more amino acid residues at position I253 of the Fc domain. Modification of amino acid I253 can be as part of a combination including multiple modifications (e.g., at other residue positions, e.g., R292), for example, a combination of one or more amino acid substitutions, deletions, and/or insertions. In particular embodiments, an Fc construct may contain, e.g., three Fc domains wherein at least one Fc domain contains a modification at position I253. For example, the wild-type amino acid residue, e.g., isoleucine (1), at position I253 may be substituted for a natural or non-natural amino acid, e.g., alanine (A). In some instances, each amino acid modification at position I253 is independently selected from, e.g., I253A, I253C, I253D, I253E, I253F, I253G, I253H, I253I, I253K, I253L, I253M, I253N, I253P, I253Q, I253R, I253S, I253T, I253V, I253W, and I253Y.

In other embodiments, Fc domain modifications that alter half-life may alter the binding of a modified Fc domain to FcγRIIb, for example, by modification of the Fc domain at position R292. Modifications at position R292 may include an amino acid substitution, wherein the amino acid at position R292 is substituted with a natural or non-natural amino acid; a deletion of the amino acid at position R292; or an insertion of one or more amino acid residues at position R292 of the Fc domain. Modification of amino acid 292 can be as part of a combination including multiple modifications (e.g., at other residue positions, e.g., I253), for example, a combination of one or more amino acid substitutions, deletions, and/or insertions. In particular embodiments, an Fc construct may contain, e.g., three Fc domains wherein at least one Fc domain contains a modification at position R292. For example, the wild-type amino acid residue, e.g., arginine (R), at position 292 may be substituted for a natural or non-natural amino acid, e.g., proline (P). In some instances, each amino acid modification at position R292 is independently selected from, e.g., R292P, R292D, R292E, R292L, R292Q, R292R, R292T, and R292Y.

Exemplary Fc domains with altered binding affinity to Fc receptors include Fc monomers containing the double mutants S267E/L328F. S267E/L328F mutations have been previously shown to significantly and specifically enhance IgG1 binding to the FcγRIIb receptor (Chu et al. Molecular Immunology 45 2008).

An amino acid modification, e.g., to alter the half-life, at position I253, e.g., I253A, may occur in at least one (e.g., 1, 2, 3, 4, or 5) Fc domain of an Fc construct, e.g., construct 4 (FIG. 2). In other embodiments, an amino acid modification at position R292, e.g., R292P, may occur in at least one (e.g., 1, 2, 3, 4, or 5) Fc domain of an Fc construct, e.g., construct 4 (FIG. 2). In some embodiments, for example, an amino acid modification may occur at both position I253, e.g., I253A, and position R292, e.g., R292P. For example, an Fc construct, e.g., construct 4 (FIG. 2), may contain one Fc domain with an amino acid modification at I253, e.g., I253A, and contain at least one (e.g., 1, 2, or 3) Fc domain with an amino acid modification at R292, e.g., R292P. In another embodiment, an Fc construct, e.g., construct 4 (FIG. 2), may contain two Fc domains with an amino acid modification at I253, e.g., I253A, and contain at least one (e.g., 1, 2, or 3) Fc domain with an amino acid modification at R292, e.g., R292P. In yet another embodiment, an Fc construct, e.g., construct 4, may contain three Fc domains with an amino modification at I253, e.g., I293A, and contain at least one (e.g., 1, 2, or 3) Fc domain with an amino acid modification at R292, e.g., R292P. Exemplary Fc constructs having modifications at amino acid position I253 and/or R292, e.g., I293A and/or R292P, respectively, are depicted in FIGS. 18A-18O. Not depicted in FIG. 18A-18O, but contemplated by the disclosure, are Fc constructs having heterogeneous combinations of amino acid modifications, e.g., at amino acid positions I253 and/or R292, within the Fc domain monomers constituting an Fc domain.

IV. Dimerization Selectivity Modules

In the present disclosure, a dimerization selectivity module is the part of the Fc domain monomer that facilitates the preferred pairing of two Fc domain monomers to form an Fc domain. Specifically, a dimerization selectivity module is that part of the $C_H3$ antibody constant domain of an Fc domain monomer which includes amino acid substitutions positioned at the interface between interacting $C_H3$ antibody constant domains of two Fc domain monomers. In a dimerization selectivity module, the amino acid substitutions make favorable the dimerization of the two $C_H3$ antibody constant domains as a result of the compatibility of amino acids chosen for those substitutions. The ultimate formation of the favored Fc domain is selective over other Fc domains which form from Fc domain monomers lacking dimerization selectivity modules or with incompatible amino acid substitutions in the dimerization selectivity modules. This type of amino acid substitution can be made using conventional molecular cloning techniques well-known in the art, such as QuikChange® mutagenesis.

In some embodiments, a dimerization selectivity module includes an engineered cavity (described further herein) in the $C_H3$ antibody constant domain. In other embodiments, a dimerization selectivity module includes an engineered protuberance (described further herein) in the $C_H3$ antibody constant domain. To selectively form an Fc domain, two Fc domain monomers with compatible dimerization selectivity modules, e.g., one $C_H3$ antibody constant domain containing an engineered cavity and the other $C_H3$ antibody constant domain containing an engineered protuberance, combine to form a protuberance-into-cavity pair of Fc domain monomers. Engineered protuberances and engineered cavities are examples of heterodimerizing selectivity modules, which can be made in the $C_H3$ antibody constant domains of Fc domain monomers in order to promote favorable heterodimerization of two Fc domain monomers that have compatible heterodimerizing selectivity modules.

In other embodiments, an Fc domain monomer with a dimerization selectivity module containing positively-charged amino acid substitutions and an Fc domain monomer with a dimerization selectivity module containing negatively-charged amino acid substitutions may selectively combine to form an Fc domain through the favorable electrostatic steering (described further herein) of the charged amino acids. In some embodiments, an Fc domain monomer may include one of the following positively-charged and negatively-charged amino acid substitutions: K392D, K392E, D399K, K409D, K409E, K439D, and K439E. In one example, an Fc domain monomer containing a positively-charged amino acid substitution, e.g., D356K or E357K, and an Fc domain monomer containing a negatively-charged amino acid substitution, e.g., K370D or K370E, may selectively combine to form an Fc domain through favorable electrostatic steering of the charged amino acids. In another example, an Fc domain monomer containing E357K and an Fc domain monomer containing K370D may selectively combine to form an Fc domain through favorable electrostatic steering of the charged amino acids. In some embodiments, reverse charge amino acid substitutions may be used as heterodimerizing selectivity modules, wherein two Fc domain monomers containing different, but compatible, reverse charge amino acid substitutions combine to form a heterodimeric Fc domain. Specific dimerization selectivity modules are further listed, without limitation, in Tables 1 and 2A described further below.

In other embodiments, two Fc domain monomers include homodimerizing selectivity modules containing identical reverse charge mutations in at least two positions within the ring of charged residues at the interface between $C_H3$ domains. Homodimerizing selectivity modules are reverse charge amino acid substitutions that promote the homodimerization of Fc domain monomers to form a homodimeric Fc domain. By reversing the charge of both members of two or more complementary pairs of residues in the two Fc domain monomers, mutated Fc domain monomers remain complementary to Fc domain monomers of the same mutated sequence, but have a lower complementarity to Fc domain monomers without those mutations. In one embodiment, an Fc domain includes Fc domain monomers including the double mutants K409D/D399K, K392D/D399K, E357K/K370E, D356K/K439D, K409E/D399K, K392E/D399K, E357K/K370D, or D356K/K439E. In another embodiment, an Fc domain includes Fc domain monomers including quadruple mutants combining any pair of the double mutants, e.g., K409D/D399K/E357K/K370E. Examples of homodimerizing selectivity modules are further shown in Tables 2B and 2C.

In further embodiments, an Fc domain monomer containing (i) at least one reverse charge mutation and (ii) at least one engineered cavity or at least one engineered protuberance may selectively combine with another Fc domain monomer containing (i) at least one reverse charge mutation and (ii) at least one engineered protuberance or at least one engineered cavity to form an Fc domain. For example, an Fc domain monomer containing reversed charge mutation K370D and engineered cavities Y349C, T366S, L368A, and Y407V and another Fc domain monomer containing reversed charge mutation E357K and engineered protuberances S354C and T366W may selectively combine to form an Fc domain. The formation of such Fc domains is promoted by the compatible amino acid substitutions in the $C_H3$ antibody constant domains. Two dimerization selectivity modules containing incompatible amino acid substitutions, e.g., both containing engineered cavities, both containing engineered protuberances, or both containing the same charged amino acids at the $C_H3$-$C_H3$ interface, will not promote the formation of a heterodimeric Fc domain.

Furthermore, other methods used to promote the formation of Fc domains with defined Fc domain monomers include, without limitation, the LUZ-Y approach (U.S. Patent Application Publication No. WO2011034605) which includes C-terminal fusion of a monomer α-helices of a leucine zipper to each of the Fc domain monomers to allow heterodimer formation, as well as strand-exchange engineered domain (SEED) body approach (Davis et al., *Protein Eng Des Sel.* 23:195-202, 2010) that generates Fc domain with heterodimeric Fc domain monomers each including alternating segments of IgA and IgG $C_H3$ sequences.

V. Engineered Cavities and Engineered Protuberances

The use of engineered cavities and engineered protuberances (or the "knob-into-hole" strategy) is described by Carter and co-workers (Ridgway et al., *Protein Eng.* 9:617-612, 1996; Atwell et al., *J Mol Biol.* 270:26-35, 1997; Merchant et al., *Nat Biotechnol.* 16:677-681, 1998). The knob and hole interaction favors heterodimer formation, whereas the knob-knob and the hole-hole interaction hinder homodimer formation due to steric clash and deletion of favorable interactions. The "knob-into-hole" technique is also disclosed in U.S. Pat. No. 5,731,168.

In the present disclosure, engineered cavities and engineered protuberances are used in the preparation of the Fc constructs described herein. An engineered cavity is a void that is created when an original amino acid in a protein is replaced with a different amino acid having a smaller side-chain volume.

An engineered protuberance is a bump that is created when an original amino acid in a protein is replaced with a different amino acid having a larger side-chain volume. Specifically, the amino acid being replaced is in the $C_H3$ antibody constant domain of an Fc domain monomer and is involved in the dimerization of two Fc domain monomers. In some embodiments, an engineered cavity in one $C_H3$ antibody constant domain is created to accommodate an engineered protuberance in another $C_H3$ antibody constant domain, such that both $C_H3$ antibody constant domains act as dimerization selectivity modules (e.g., heterodimerizing selectivity modules) (described above) that promote or favor the dimerization of the two Fc domain monomers. In other embodiments, an engineered cavity in one $C_H3$ antibody constant domain is created to better accommodate an original amino acid in another $C_H3$ antibody constant domain. In yet other embodiments, an engineered protuberance in one $C_H3$ antibody constant domain is created to form additional interactions with original amino acids in another $C_H3$ antibody constant domain.

An engineered cavity can be constructed by replacing amino acids containing larger side chains such as tyrosine or tryptophan with amino acids containing smaller side chains such as alanine, valine, or threonine. Specifically, some dimerization selectivity modules (e.g., heterodimerizing selectivity modules) (described further above) contain engineered cavities such as Y407V mutation in the $C_H3$ antibody constant domain. Similarly, an engineered protuberance can be constructed by replacing amino acids containing smaller side chains with amino acids containing larger side chains. Specifically, some dimerization selectivity modules (e.g., heterodimerizing selectivity modules) (described further above) contain engineered protuberances such as T366W mutation in the $C_H3$ antibody constant domain. In the present disclosure, engineered cavities and engineered protuberances are also combined with inter-$C_H3$ domain disulfide bond engineering to enhance heterodimer formation. In one example, an Fc domain monomer containing engineered cavities Y349C, T366S, L368A, and Y407V may selectively combine with another Fc domain monomer containing engineered protuberances S354C and T366W to form an Fc domain. In another example, an Fc domain monomer containing engineered cavity Y349C and an Fc domain monomer containing engineered protuberance S354C may selectively combine to form an Fc domain. Other engineered cavities and engineered protuberances, in combination with either disulfide bond engineering or structural calculations (mixed HA-TF) are included, without limitation, in Table 1.

TABLE 1

| Strategy | $CH_3$ antibody constant domain of Fc domain monomer 1 | $CH_3$ antibody constant domain of Fc domain monomer 2 | Reference |
|---|---|---|---|
| Engineered cavities and protuberances ("knob-into-hole") | Y407T | T366Y | U.S. Pat. No. 8,216,805 |
| | Y407A | T366W | U.S. Pat. No. 8,216,805 |
| | F405A | T394W | U.S. Pat. No. 8,216,805 |
| | Y407T | T366Y | U.S. Pat. No. 8,216,805 |
| | T394S | F405W | U.S. Pat. No. 8,216,805 |
| | T394W:Y407T | T366Y:F405A | U.S. Pat. No. 8,216,805 |
| | T394S:Y407A | T366W:F405W | U.S. Pat. No. 8,216,805 |
| | T366W:T394S | F405W:Y407A | U.S. Pat. No. 8,216,805 |
| Engineered cavities and protuberances ("knob-into-hole"), S-S engineering | T366S:L368A: Y407V:Y349C | T366W:S354C | Zeidler et al., *J Immunol.* 163: 1246-52, 1999 |
| Mixed HA-TF | S364H:F405A | Y349T:T394F | WO2006106905 |

Replacing an original amino acid residue in the $C_H3$ antibody constant domain with a different amino acid residue can be achieved by altering the nucleic acid encoding the original amino acid residue. The upper limit for the number of original amino acid residues that can be replaced is the total number of residues in the interface of the $C_H3$ antibody constant domains, given that sufficient interaction at the interface is still maintained. In some cases, the $C_H3$ antibody constant domain has no more than 16 (e.g., no more than 2, 4, 6, 8, 10, 12, 14, or 16) single amino acid modifications.

VI. Electrostatic Steering

Electrostatic steering is the utilization of favorable electrostatic interactions between oppositely charged amino acids in peptides, protein domains, and proteins to control the formation of higher ordered protein molecules. A method of using electrostatic steering effects to alter the interaction of antibody domains to reduce for formation of homodimer in favor of heterodimer formation in the generation of bi-specific antibodies is disclosed in U.S. Patent Application Publication No. 2014-0024111.

In the present disclosure, electrostatic steering is used to control the dimerization of Fc domain monomers and the formation of Fc constructs. In particular, to control the dimerization of Fc domain monomers using electrostatic steering, one or more amino acid residues that make up the $C_H3$-$C_H3$ interface are replaced with positively- or negatively-charged amino acid residues such that the interaction becomes electrostatically favorable or unfavorable depending on the specific charged amino acids introduced. In some embodiments, a positively-charged amino acid in the interface, such as lysine, arginine, or histidine, is replaced with a negatively-charged amino acid such as aspartic acid or glutamic acid. In other embodiments, a negatively-charged amino acid in the interface is replaced with a positively-charged amino acid. The charged amino acids may be introduced to one of the interacting $C_H3$ antibody constant domains, or both. By introducing charged amino acids to the interacting $C_H3$ antibody constant domains, dimerization selectivity modules (described further above) are created that can selectively form dimers of Fc domain monomers as controlled by the electrostatic steering effects resulting from the interaction between charged amino acids.

In some embodiments, to create a dimerization selectivity module including reversed charges that can selectively form dimers of Fc domain monomers as controlled by the electrostatic steering effects, the two Fc domain monomers may be selectively formed through heterodimerization or homodimerization.

Heterodimerization of Fc Domain Monomers

Heterodimerization of Fc domain monomers can be promoted by introducing different, but compatible, mutations in the two Fc domain monomers, such as the charge residue pairs included, without limitation, in Table 2A. In some embodiments, an Fc domain monomer may include one of the following positively-charged and negatively-charged amino acid substitutions: D356K, D356R, E357K, E357R, K370D, K370E, K392D, K392E, D399K, K409D, K409E, K439D, and K439E. In one example, an Fc domain monomer containing a positively-charged amino acid substitution, e.g., D356K or E357K, and an Fc domain monomer containing a negatively-charged amino acid substitution, e.g., K370D or K370E, may selectively combine to form an Fc domain through favorable electrostatic steering of the charged amino acids. In another example, an Fc domain monomer containing E357K and an Fc domain monomer containing K370D may selectively combine to form an Fc domain through favorable electrostatic steering of the charged amino acids.

For example, in an Fc construct having three Fc domains, two of the three Fc domains may be formed by the heterodimerization of two Fc domain monomers, as promoted by the electrostatic steering effects. A "heterodimeric Fc domain" refers to an Fc domain that is formed by the heterodimerization of two Fc domain monomers, wherein the two Fc domain monomers contain different reverse charge mutations (heterodimerizing selectivity modules) (see, e.g., mutations in Table 2A) that promote the favorable formation of these two Fc domain monomers. As shown in FIGS. 1 and 2, in an Fc construct having three Fc domains—one carboxyl terminal "stem" Fc domain and two amino terminal "branch" Fc domains—each of the amino terminal "branch" Fc domains may be a heterodimeric Fc domain (also called a "branch heterodimeric Fc domain") (e.g., a heterodimeric Fc domain formed by Fc domain monomers 106 and 114 or Fc domain monomers 112 and 116 in FIG. 1; a heterodimeric Fc domain formed by Fc domain monomers 206 and 214 or Fc domain monomers 212 and 216 in FIG. 2). A branch heterodimeric Fc domain may be formed by an Fc domain monomer containing E357K and another Fc domain monomer containing K370D.

TABLE 2A

| Reverse charge mutation(s) in $C_H3$ antibody constant domain of Fc domain monomer 1 | Reverse charge mutation(s) in $C_H3$ antibody constant domain of Fc domain monomer 2 |
|---|---|
| K409D | D399K |
| K409D | D399R |
| K409E | D399K |
| K409E | D399R |
| K392D | D399K |
| K392D | D399R |
| K392E | D399K |
| K392E | D399R |
| K370D | E357K |
| K370D | E357R |
| K370E | E357K |
| K370E | E357R |
| K370D | D356K |
| K370D | D356R |
| K370E | D356K |
| K370E | D356R |
| K409D, K392D | D399K, E356K |
| K370E, K409D, K439E | E356K, E357K, D399K |

Homodimerization of Fc domain monomers Homodimerization of Fc domain monomers can be promoted by introducing the same electrostatic steering mutations (homodimerizing selectivity modules) in both Fc domain monomers in a symmetric fashion. In some embodiments, two Fc domain monomers include homodimerizing selectivity modules containing identical reverse charge mutations in at least two positions within the ring of charged residues at the interface between $C_H3$ domains. By reversing the charge of both members of two or more complementary pairs of residues in the two Fc domain monomers, mutated Fc domain monomers remain complementary to Fc domain monomers of the same mutated sequence, but have a lower complementarity to Fc domain monomers without those mutations. Electrostatic steering mutations that may be introduced into an Fc domain monomer to promote its homodimerization are shown, without limitation, in Tables 2B and 2C. In one embodiment, an Fc domain includes two Fc domain monomers each including the double reverse charge mutants (Table 2B), e.g., K409D/D399K. In another embodiment, an Fc domain includes two Fc domain monomers each including quadruple reverse mutants (Table 2C), e.g., K409D/D399K/K370D/E357K.

For example, in an Fc construct having three Fc domains, one of the three Fc domains may be formed by the homodimerization of two Fc domain monomers, as promoted by the electrostatic steering effects. A "homodimeric Fc domain" refers to an Fc domain that is formed by the homodimerization of two Fc domain monomers, wherein the two Fc domain monomers contain the same reverse charge mutations (see, e.g., mutations in Tables 2B and 2C). As shown in FIGS. 1 and 2, in an Fc construct having three Fc domains—one carboxyl terminal "stem" Fc domain and two amino terminal "branch" Fc domains—the carboxy terminal "stem" Fc domain may be a homodimeric Fc domain (also called a "stem homodimeric Fc domain") (e.g., a homodimeric Fc domain formed by Fc domain monomers 104 and 110 in FIG. 1; a homodimeric Fc domain formed by Fc domain monomers 204 and 210 in FIG. 2). A stem homodimeric Fc domain may be formed by two Fc domain monomers each containing the double mutants K409D/D399K.

TABLE 2B

| Reverse charge mutation(s) in $C_H3$ antibody constant domain of each of the two Fc domain monomers in a homodimeric Fc domain |
|---|
| K409D/D399K |
| K409D/D399R |
| K409E/D399K |
| K409E/D399R |
| K392D/D399K |
| K392D/D399R |
| K392E/D399K |
| K392E/D399R |
| K370D/E357K |
| K370D/E357R |
| K370E/E357K |
| K370E/E357R |
| K370D/D356K |
| K370D/D356R |
| K370E/D356K |
| K370E/D356R |

TABLE 2C

| Reverse charge mutation(s) in $C_H3$ antibody constant domain of each of the two Fc domain monomers in a homodimeric Fc domain | Reverse charge mutation(s) in CH3 antibody constant domain of each of the two Fc domain monomers in a homodimeric Fc domain |
|---|---|
| K409D/D399K/K370D/E357K | K392D/D399K/K370D/E357K |
| K409D/D399K/K370D/E357R | K392D/D399K/K370D/E357R |
| K409D/D399K/K370E/E357K | K392D/D399K/K370E/E357K |
| K409D/D399K/K370E/E357R | K392D/D399K/K370E/E357R |
| K409D/D399K/K370D/D356K | K392D/D399K/K370D/D356K |
| K409D/D399K/K370D/D356R | K392D/D399K/K370D/D356R |
| K409D/D399K/K370E/D356K | K392D/D399K/K370E/D356K |
| K409D/D399K/K370E/D356R | K392D/D399K/K370E/D356R |
| K409D/D399R/K370D/E357K | K392D/D399R/K370D/E357K |
| K409D/D399R/K370D/E357R | K392D/D399R/K370D/E357R |
| K409D/D399R/K370E/E357K | K392D/D399R/K370E/E357K |
| K409D/D399R/K370E/E357R | K392D/D399R/K370E/E357R |
| K409D/D399R/K370D/D356K | K392D/D399R/K370D/D356K |
| K409D/D399R/K370D/D356R | K392D/D399R/K370D/D356R |
| K409D/D399R/K370E/D356K | K392D/D399R/K370E/D356K |
| K409D/D399R/K370E/D356R | K392D/D399R/K370E/D356R |
| K409E/D399K/K370D/E357K | K392E/D399K/K370D/E357K |
| K409E/D399K/K370D/E357R | K392E/D399K/K370D/E357R |
| K409E/D399K/K370E/E357K | K392E/D399K/K370E/E357K |
| K409E/D399K/K370E/E357R | K392E/D399K/K370E/E357R |
| K409E/D399K/K370D/D356K | K392E/D399K/K370D/D356K |
| K409E/D399K/K370D/D356R | K392E/D399K/K370D/D356R |
| K409E/D399K/K370E/D356K | K392E/D399K/K370E/D356K |
| K409E/D399K/K370E/D356R | K392E/D399K/K370E/D356R |
| K409E/D399R/K370D/E357K | K392E/D399R/K370D/E357K |
| K409E/D399R/K370D/E357R | K392E/D399R/K370D/E357R |
| K409E/D399R/K370E/E357K | K392E/D399R/K370E/E357K |
| K409E/D399R/K370E/E357R | K392E/D399R/K370E/E357R |
| K409E/D399R/K370D/D356K | K392E/D399R/K370D/D356K |
| K409E/D399R/K370D/D356R | K392E/D399R/K370D/D356R |
| K409E/D399R/K370E/D356K | K392E/D399R/K370E/D356K |
| K409E/D399R/K370E/D356R | K392E/D399R/K370E/D356R |

Replacing an original amino acid residue in the $C_H3$ antibody constant domain with a different amino acid residue can be achieved by altering the nucleic acid encoding the original amino acid residue. The upper limit for the number of original amino acid residues that can be replaced is the total number of residues in the interface of the $C_H3$ antibody constant domains, given that sufficient interaction at the interface is still maintained. In some cases, the $C_H3$ antibody constant domain has no more than 16 (e.g., no more than 2, 4, 6, 8, 10, 12, 14, or 16) single amino acid modifications.

VII. Linkers

In the present disclosure, a linker is used to describe a linkage or connection between polypeptides or protein domains and/or associated non-protein moieties. In some embodiments, a linker is a linkage or connection between at least two Fc domain monomers, for which the linker connects the C-terminus of the $C_H3$ antibody constant domain of a first Fc domain monomer to the N-terminus of the hinge domain of a second Fc domain monomer, such that the two Fc domain monomers are joined to each other in tandem series. In other embodiments, a linker is a linkage between an Fc domain monomer and any other protein domains that are attached to it. For example, a linker can attach the C-terminus of the $C_H3$ antibody constant domain of an Fc domain monomer to the N-terminus of an albumin-binding peptide.

A linker can be a simple covalent bond, e.g., a peptide bond, a synthetic polymer, e.g., a polyethylene glycol (PEG) polymer, or any kind of bond created from a chemical reaction, e.g., chemical conjugation. In the case that a linker is a peptide bond, the carboxylic acid group at the C-terminus of one protein domain can react with the amino group at the N-terminus of another protein domain in a condensation reaction to form a peptide bond. Specifically, the peptide bond can be formed from synthetic means through a conventional organic chemistry reaction well-known in the art, or by natural production from a host cell, wherein a polynucleotide sequence encoding the DNA sequences of both proteins, e.g., two Fc domain monomer, in tandem series can be directly transcribed and translated into a contiguous polypeptide encoding both proteins by the necessary molecular machineries, e.g., DNA polymerase and ribosome, in the host cell.

In the case that a linker is a synthetic polymer, e.g., a PEG polymer, the polymer can be functionalized with reactive chemical functional groups at each end to react with the terminal amino acids at the connecting ends of two proteins.

In the case that a linker (except peptide bond mentioned above) is made from a chemical reaction, chemical functional groups, e.g., amine, carboxylic acid, ester, azide, or other functional groups commonly used in the art, can be attached synthetically to the C-terminus of one protein and the N-terminus of another protein, respectively. The two functional groups can then react to through synthetic chemistry means to form a chemical bond, thus connecting the two proteins together. Such chemical conjugation procedures are routine for those skilled in the art.

Spacer

In the present disclosure, a linker between two Fc domain monomers can be an amino acid spacer including 3-200 amino acids (e.g., 3-200, 3-180, 3-160, 3-140, 3-120, 3-100, 3-90, 3-80, 3-70, 3-60, 3-50, 3-45, 3-40, 3-35, 3-30, 3-25, 3-20, 3-15, 3-10, 3-9, 3-8, 3-7, 3-6, 3-5, 3-4, 4-200, 5-200, 6-200, 7-200, 8-200, 9-200, 10-200, 15-200, 20-200, 25-200, 30-200, 35-200, 40-200, 45-200, 50-200, 60-200, 70-200, 80-200, 90-200, 100-200, 120-200, 140-200, 160-200, or 180-200 amino acids)(e.g., 3-150, 3-100, 3-60, 3-50, 3-40, 3-30, 3-20, 3-10, 3-8, 3-5, 4-30, 5-30, 6-30, 8-30, 10-20, 10-30, 12-30, 14-30, 20-30, 15-25, 15-30, 18-22, and 20-30 amino acid). In some embodiments, a linker between two Fc domain monomers is an amino acid spacer containing at least 12 amino acids, such as 12-200 amino acids (e.g., 12-200, 12-180, 12-160, 12-140, 12-120, 12-100, 12-90, 12-80, 12-70, 12-60, 12-50, 12-40, 12-30, 12-20, 12-19, 12-18, 12-17, 12-16, 12-15, 12-14, or 12-13 amino acids) (e.g., 14-200, 16-200, 18-200, 20-200, 30-200, 40-200, 50-200, 60-200, 70-200, 80-200, 90-200, 100-200, 120-200, 140-200, 160-200, 180-200, or 190-200 amino acids). In some embodiments, a linker between two Fc domain monomers is an amino acid spacer containing 12-30 amino acids (e.g., 12, 13, 14, 15, 16, 17, 18, 19, 20, 21, 22, 23, 24, 25, 26, 27, 28, 29, or 30 amino acids). Suitable peptide spacers are known in the art, and include, for example, peptide linkers containing flexible amino acid residues such as glycine and serine. In certain embodiments, a spacer can contain motifs, e.g., multiple or repeating motifs, of GS, GGS, GGGGS (SEQ ID NO: 1), GGSG (SEQ ID NO: 2), or SGGG (SEQ ID NO: 3). In certain embodiments, a spacer can contain 2 to 12 amino acids including motifs of GS, e.g., GS, GSGS (SEQ ID NO: 4), GSGSGS (SEQ ID NO: 5), GSGSGSGS (SEQ ID NO: 6), GSGSGSGSGS (SEQ ID NO: 7), or GSGSGSGSGSGS (SEQ ID NO: 8). In certain other embodiments, a spacer can contain 3 to 12 amino acids including motifs of GGS, e.g., GGS, GGSGGS (SEQ ID NO: 9), GGSGGSGGS (SEQ ID NO: 10), and GGSGGSGGSGGS (SEQ ID NO: 11). In yet other embodiments, a spacer can contain 4 to 20 amino acids including motifs of GGSG (SEQ ID NO: 2), e.g., GGSGGGSG (SEQ ID NO: 12), GGSGGGSGGGSG (SEQ ID NO: 13), GGSGGGSGGGSGGGSG (SEQ ID NO: 14), or GGSGGGSGGGSGGGSGGGSG (SEQ ID NO: 15). In other embodiments, a spacer can contain motifs of GGGGS (SEQ ID NO: 1), e.g., GGGGSGGGGS (SEQ ID NO: 16) or GGGGSGGGGSGGGGS (SEQ ID NO: 17). In certain embodiments, a spacer is SGGGSGGGSGGGSGGGSGGG (SEQ ID NO: 18).

In some embodiments, a spacer between two Fc domain monomers contains only glycine residues, e.g., at least 4 glycine residues (e.g., 4-200, 4-180, 4-160, 4-140, 4-40, 4-100, 4-90, 4-80, 4-70, 4-60, 4-50, 4-40, 4-30, 4-20, 4-19, 4-18, 4-17, 4-16, 4-15, 4-14, 4-13, 4-12, 4-11, 4-10, 4-9, 4-8, 4-7, 4-6 or 4-5 glycine residues) (e.g., 4-200, 6-200, 8-200, 10-200, 12-200, 14-200, 16-200, 18-200, 20-200, 30-200, 40-200, 50-200, 60-200, 70-200, 80-200, 90-200, 100-200, 120-200, 140-200, 160-200, 180-200, or 190-200 glycine residues). In certain embodiments, a spacer has 4-30 glycine residues (e.g., 4, 5, 6, 7, 8, 9, 10, 11, 12, 13, 14, 15, 16, 17, 18, 19, 20, 21, 22, 23, 24, 25, 26, 27, 28, 29, or 30 glycine residues). In some embodiments, a spacer containing only glycine residues may not be glycosylated (e.g., O-linked glycosylation, also referred to as O-glycosylation) or may have a decreased level of glycosylation (e.g., a decreased level of O-glycosylation) (e.g., a decreased level of O-glycosylation with glycans such as xylose, mannose, sialic acids, fucose (Fuc), and/or galactose (Gal) (e.g., xylose)) as compared to, e.g., a spacer containing one or more serine residues (e.g., SGGGSGGGSGGGSGGGSGGG (SEQ ID NO: 18)) (see Example 4).

In some embodiments, a spacer containing only glycine residues may not be O-glycosylated (e.g., O-xylosylation) or may have a decreased level of O-glycosylation (e.g., a decreased level of O-xylosylation) as compared to, e.g., a spacer containing one or more serine residues (e.g., SGGGSGGGSGGGSGGGSGGG (SEQ ID NO: 18)).

In some embodiments, a spacer containing only glycine residues may not undergo proteolysis or may have a decreased rate of proteolysis as compared to, e.g., a spacer containing one or more serine residues (e.g., SGGGSGGGSGGGSGGGSGGG (SEQ ID NO: 18)) (see Example 4).

In certain embodiments, a spacer can contain motifs of GGGG (SEQ ID NO: 19), e.g., GGGGGGGG (SEQ ID NO: 20), GGGGGGGGGGGG (SEQ ID NO: 21), GGGGGGGGGGGGGGGG (SEQ ID NO: 22), or GGGGGGGGGGGGGGGGGGGG (SEQ ID NO: 23). In certain embodiments, a spacer can contain motifs of GGGGG (SEQ ID NO: 24), e.g., GGGGGGGGGG (SEQ ID NO: 25), or GGGGGGGGGGGGGGG (SEQ ID NO: 26). In certain embodiments, a spacer is GGGGGGGGGGGGGGGGGGGG (SEQ ID NO: 27).

In other embodiments, a spacer can also contain amino acids other than glycine and serine, e.g., GENLYFQSGG (SEQ ID NO: 28), SACYCELS (SEQ ID NO: 29), RSIAT (SEQ ID NO: 30), RPACKIPNDLKQKVMNH (SEQ ID NO: 31), GGSAGGSGSGSSGGSSGASGTGTAGGTGSGSGTGSG (SEQ ID NO: 32), AAANSSIDLISVPVDSR (SEQ ID NO: 33), or GGSGGGSEGGGSEGGGSEGGGSEGGGSEGGGSGGGS (SEQ ID NO: 34).

In certain embodiments in the present disclosure, a 12- or 20-amino acid peptide spacer is used to connect two Fc domain monomers in tandem series (e.g., polypeptides 102 and 108 in FIG. 1; polypeptides 202 and 208 in FIG. 2), the 12- and 20-amino acid peptide spacers consisting of sequences GGGSGGGSGGGS (SEQ ID NO: 35) and SGGGSGGGSGGGSGGGSGGG (SEQ ID NO: 18), respectively. In other embodiments, an 18-amino acid peptide spacer consisting of sequence GGSGGGSGGGSGGGSGGS (SEQ ID NO: 36) may be used.

In some embodiments, a spacer between two Fc domain monomers may comprise, consist of, or consist essentially of a sequence that is at least 75% identical (e.g., at least 77%, 79%, 81%, 83%, 85%, 87%, 89%, 91%, 93%, 95%, 97%, 99%, or 99.5% identical) to the sequence any one of SEQ ID NOs: 1-36 described above. In some embodiments, a spacer between two Fc domain monomers may comprise, consist of, or consist essentially of a sequence that is any one of SEQ ID NOs: 1-36 described above with up to 10 (9, 8, 7, 6, 5, 4, 3, 2, or 1) single amino acid modifications (e.g., substitutions, e.g., conservative substitutions). In certain embodiments, a spacer between two Fc domain monomers may comprise, consist of, or consist essentially of a sequence that is at least 80% identical (e.g., at least 82%, 85%, 87%, 90%, 92%, 95%, 97%, 99%, or 99.5% identical) to the sequence any one of SEQ ID NOs: 17, 18, 26, and 27. In certain embodiments, a spacer between two Fc domain monomers may comprise, consist of, or consist essentially of a sequence that is any one of SEQ ID NOs: 17, 18, 26, and 27 with up to 10 (9, 8, 7, 6, 5, 4, 3, 2, or 1) single amino acid modifications (e.g., substitutions, e.g., conservative substitutions). In certain embodiments, a spacer between two Fc domain monomers may comprise, consist of, or consist essentially of a sequence that is at least 80% identical (e.g., at least 82%, 85%, 87%, 90%, 92%, 95%, 97%, 99%, or 99.5%) to the sequence SEQ ID NO: 18 or 27. In certain embodiments, a spacer between two Fc domain monomers may comprise, consist of, or consist essentially of a sequence that is sequence SEQ ID NO: 18 or 27 with up to 10 (9, 8, 7, 6, 5, 4, 3, 2, or 1) single amino acid modifications (e.g., substitutions, e.g., conservative substitutions).

VIII. Serum Protein-Binding Peptides

Binding to serum protein peptides can improve the pharmacokinetics of protein pharmaceuticals, and in particular the Fc constructs described here may be fused with serum protein-binding peptides As one example, albumin-binding peptides that can be used in the methods and compositions described here are generally known in the art. In one embodiment, the albumin binding peptide includes the sequence DICLPRWGCLW (SEQ ID NO: 37). In some embodiments, the albumin binding peptide comprises, consists of, or consists essentially of a sequence that is at least 80% identical (e.g., 80%, 90%, or 100% identical) to the sequence SEQ ID NO: 37. In some embodiments, the albumin binding peptide comprises, consists of, or consists essentially of a sequence that is the sequence SEQ ID NO: 37 with up to 10 (9, 8, 7, 6, 5, 4, 3, 2, or 1) single amino acid modifications (e.g., substitutions, e.g., conservative substitutions).

In the present disclosure, albumin-binding peptides may be attached to the N- or C-terminus of certain polypeptides in the Fc construct. In one embodiment, an albumin-binding peptide may be attached to the C-terminus of one or more polypeptides in Fc constructs 1-4 (FIGS. 1 and 2). In another embodiment, an albumin-binding peptide can be fused to the C-terminus of the polypeptide encoding two Fc domain monomers linked in tandem series in Fc constructs 1-4 (e.g., polypeptide 102 and 108 in FIG. 1 and polypeptides 202 and 208 in FIG. 2). In yet another embodiment, an albumin-binding peptide can be attached to the C-terminus of Fc domain monomer (e.g., Fc domain monomers 114 and 116 in FIG. 1; Fc domain monomers 214 and 216 in FIG. 2) which is joined to the second Fc domain monomer in the polypeptide encoding the two Fc domain monomers linked in tandem series. Albumin-binding peptides can be fused genetically to Fc constructs or attached to Fc constructs through chemical means, e.g., chemical conjugation. If desired, a spacer can be inserted between the Fc construct and the albumin-binding peptide. Without being bound to a theory, it is expected that inclusion of an albumin-binding peptide in an Fc construct of the disclosure may lead to prolonged retention of the therapeutic protein through its binding to serum albumin.

IX. Fc Constructs

In general, the disclosure features Fc constructs having Fc domains (e.g., an Fc construct having three Fc domains). These may have greater binding affinity and/or avidity than a single wild-type Fc domain for an Fc receptor, e.g., FcγRIIIa. The disclosure discloses methods of engineering amino acids at the interface of two interacting $C_H3$ antibody constant domains such that the two Fc domain monomers of an Fc domain selectively form a dimer with each other, thus preventing the formation of unwanted multimers or aggregates. An Fc construct includes an even number of Fc domain monomers, with each pair of Fc domain monomers forming an Fc domain. An Fc construct includes, at a minimum, one functional Fc domain formed from a dimer of two Fc domain monomers. In some embodiments, the Fc constructs described herein do not include an antigen-recognition region, e.g., a variable domain (e.g., $V_H$, $V_L$, a hypervariable region (HVR)) or a complementarity determining region (CDR). In some embodiments, the Fc constructs described herein include an antigen-recognition region, e.g., a variable domain (e.g., $V_H$, $V_L$, a HVR) or a CDR.

An Fc construct containing three Fc domains may form from four polypeptides (FIGS. 1 and 2). The first and second polypeptides (e.g., polypeptides 102 and 108 in FIG. 1; polypeptides 202 and 208 in FIG. 2) can be the same or different, as can the third and fourth polypeptides (e.g., polypeptides 114 and 116 in FIG. 1; polypeptides 214 and 216 in FIG. 2). In FIG. 1, the first and second polypeptides both encode two Fc domain monomers (e.g., Fc domain monomers 104, 106, 110, and 112) connected by way of a linker in tandem series, wherein one Fc domain monomer contains charged amino acid substitutions in the $C_H3$ antibody constant domain (e.g., Fc domain monomers 104 and 110) while the other Fc domain monomer contains a protuberance in the $C_H3$ antibody constant domain (e.g., Fc domain monomers 106 and 112). The third and fourth polypeptides both encode an Fc domain monomer with a cavity (e.g., Fc domain monomers 114 and 116). A stem homodimeric Fc domain may be formed by combining Fc domain monomers 104 and 110, each of which contains the same reverse charge mutations in its $C_H3$ antibody constant domain (e.g., each of Fc domain monomers 104 and 110 contains D399K and K409D.

A first branch heterodimeric Fc domain may be formed by combining Fc domain monomers 106 and 114 (e.g., Fc domain monomer 106 contains engineered protuberances S354C and T366W, and Fc domain monomer 114 contains engineered cavities Y349C, T366S, L368A, and Y409V). A second heterodimeric Fc domain may be formed by combining Fc domain monomers 112 and 116 (e.g., Fc domain monomer 112 contains engineered protuberances S354C and T366W, and Fc domain monomer 116 contains engineered cavities Y349C, T366S, L368A, and Y409V).

In FIG. 2, the first and second polypeptides both encode two Fc domain monomers (e.g., Fc domain monomers 204, 206, 210, and 212) connected by way of a linker in tandem series, wherein one Fc domain monomer contains charged amino acid substitutions in the $C_H3$ antibody constant domain (e.g., Fc domain monomers 204 and 210) while the other Fc domain monomer contains a protuberance and charged amino acid substitutions in the $C_H3$ antibody constant domain (e.g., Fc domain monomers 206 and 212). The third and fourth polypeptides both encode an Fc domain monomer with a cavity and charged amino acid substitutions (e.g., Fc domain monomers 214 and 216). A stem homodimeric Fc domain may be formed by combining Fc domain monomers 204 and 210, each of which contains the same reverse charge mutations in its $C_H3$ antibody constant domain (e.g., each of Fc domain monomers 204 and 210 contains D399K and K409D. A first branch heterodimeric Fc domain may be formed by combining Fc domain monomers 206 and 214 (e.g., Fc domain monomer 206 contains engineered protuberances S354C and T366W and reverse charge mutation E357K, and Fc domain monomer 214 contains engineered cavities Y349C, T366S, L368A, and Y409V and reverse charge mutation K370D). A second heterodimeric Fc domain may be formed by combining Fc domain monomers 212 and 216 (e.g., Fc domain monomer 212 contains engineered protuberances S354C and T366W and reverse charge mutation E357K, and Fc domain monomer 216 contains engineered cavities Y349C, T366S, L368A, and Y409V and reverse charge mutation K370D).

In further embodiments, an Fc domain monomer containing (i) at least one reverse charge mutation and (ii) at least one engineered cavity or at least one engineered protuberance may selectively combine with another Fc domain monomer containing (i) at least one reverse charge mutation and (ii) at least one engineered protuberance or at least one engineered cavity to form an Fc domain. For example, an Fc domain monomer containing reversed charge mutation K370D and engineered cavities Y349C, T366S, L368A, and Y407V and another Fc domain monomer containing reversed charge mutation E357K and engineered protuberances S354C and T366W may selectively combine to form an Fc domain.

In some embodiments, in an Fc construct including: a) a first polypeptide having the formula A-L-B; wherein i) A includes a first Fc domain monomer; ii) L is a linker; and iii) B includes a second Fc domain monomer; b) a second polypeptide having the formula A'-L'-B'; wherein i) A' includes a third Fc domain monomer; ii) L' is a linker; and iii) B' includes a fourth Fc domain monomer; c) a third polypeptide that includes a fifth Fc domain monomer; and d) a fourth polypeptide that includes a sixth Fc domain monomer; wherein B and B' combine to form a first Fc domain, A and the fifth Fc domain monomer combine to form a second Fc domain, and A' and the sixth Fc domain monomer combine to form a third Fc domain, examples of some amino acid mutations that can be incorporated into the Fc domain monomers in the Fc construct are shown in Tables 3A-3D. In some embodiments, each of the first, second, third, and fourth polypeptides in the Fc construct lacks a C-terminal lysine. In some embodiments, the N-terminal Asp in each of the first, second, third, and fourth polypeptides in the Fc construct is mutated to Gln. In some embodiments, each of L and L' comprises, consists of, or consists essentially of the sequence GGGGGGGGGGGGGGGGGGGG (SEQ ID NO: 27).

TABLE 3A

| Fc domain monomer | | Amino acid mutations (each column represents a set of mutations in an Fc construct having three Fc domains) | | | | | | | | | | | | | | | |
|---|---|---|---|---|---|---|---|---|---|---|---|---|---|---|---|---|---|
| A and A' | Engineered protuberance | S354C | S354C | S354C | S354C | S354C | S354C | S354C | S354C | S354C | S354C | S354C | S354C | S354C | S354C | S354C | S354C |
| | | T366W | T366W | T366W | T366W | T366W | T366W | T366W | T366W | T366W | T366W | T366W | T366W | T366W | T366W | T366W | T366W |
| | reversed charge mutation(s) | E357K | E357R | E357K | E357K | E357R | E357R | E357K | E357R | E357K | E357R | E357K | E357K | E357R | E357R | E357K | E357R |
| L and L' | | GGGGGGGGGGGGGGGGGGGG (SEQ ID NO: 27) | | | | | | | | | | | | | | | |
| B and B' | reversed charge mutation(s) | D399K | D399K | D399R | D399K | D399R | D399K | D399R | D399R | D399K | D399K | D399R | D399K | D399R | D399K | D399R | D399R |
| | | K409D | K409D | K409D | K409E | K409D | K409E | K409D | K409D | K409D | K409E | K409D | K409E | K409D | K409E | K409E | K409E |
| 5<sup>th</sup> and 6<sup>th</sup> Fc domain monomers | Engineered cavity | Y349C | Y349C | Y349C | Y349C | Y349C | Y349C | Y349C | Y349C | Y349C | Y349C | Y349C | Y349C | Y349C | Y349C | Y349C | Y349C |
| | | T366S | T366S | T366S | T366S | T366S | T366S | T366S | T366S | T366S | T366S | T366S | T366S | T366S | T366S | T366S | T366S |
| | | L368A | L368A | L368A | L368A | L368A | L368A | L368A | L368A | L368A | L368A | L368A | L368A | L368A | L368A | L368A | L368A |
| | | Y407V | Y407V | Y407V | Y407V | Y407V | Y407V | Y407V | Y407V | Y407V | Y407V | Y407V | Y407V | Y407V | Y407V | Y407V | Y407V |
| | reversed charge mutation(s) | K370D | K370D | K370D | K370D | K370D | K370D | K370D | K370D | K370E | K370E | K370E | K370E | K370E | K370E | K370E | K370E |

TABLE 3B

| Fc domain monomer | | Amino acid mutations (each column represents a set of mutations in an Fc construct having three Fc domains) | | | | | | | | | | | | | | | |
|---|---|---|---|---|---|---|---|---|---|---|---|---|---|---|---|---|---|
| A and A' | Engineered protuberance<br>reversed charge mutation(s) | S354C<br>T366W<br>K370D | S354C<br>T366W<br>K370D | S354C<br>T366W<br>K370D | S354C<br>T366W<br>K370D | S354C<br>T366W<br>K370D | S354C<br>T366W<br>K370D | S354C<br>T366W<br>K370D | S354C<br>T366W<br>K370D | S354C<br>T366W<br>K370E | S354C<br>T366W<br>K370E | S354C<br>T366W<br>K370E | S354C<br>T366W<br>K370E | S354C<br>T366W<br>K370E | S354C<br>T366W<br>K370E | S354C<br>T366W<br>K370E | S354C<br>T366W<br>K370E |
| L and L' | | GGGGGGGGGGGGGGGGGGGG (SEQ ID NO: 27) | | | | | | | | | | | | | | | |
| B and B' | reversed charge mutation(s) | D399K<br>K409D | D399K<br>K409D | D399R<br>K409D | D399K<br>K409E | D399R<br>K409D | D399K<br>K409E | D399R<br>K409D | D399R<br>K409D | D399K<br>K409D | D399K<br>K409E | D399R<br>K409D | D399K<br>K409E | D399R<br>K409D | D399K<br>K409E | D399R<br>K409E | D399R<br>K409E |
| 5th and 6th Fc domain monomers | Engineered cavity<br><br><br><br>reversed charge mutation(s) | Y349C<br>T366S<br>L368A<br>Y407V<br>E357K | Y349C<br>T366S<br>L368A<br>Y407V<br>E357R | Y349C<br>T366S<br>L368A<br>Y407V<br>E357K | Y349C<br>T366S<br>L368A<br>Y407V<br>E357K | Y349C<br>T366S<br>L368A<br>Y407V<br>E357R | Y349C<br>T366S<br>L368A<br>Y407V<br>E357R | Y349C<br>T366S<br>L368A<br>Y407V<br>E357K | Y349C<br>T366S<br>L368A<br>Y407V<br>E357R | Y349C<br>T366S<br>L368A<br>Y407V<br>E357K | Y349C<br>T366S<br>L368A<br>Y407V<br>E357R | Y349C<br>T366S<br>L368A<br>Y407V<br>E357K | Y349C<br>T366S<br>L368A<br>Y407V<br>E357K | Y349C<br>T366S<br>L368A<br>Y407V<br>E357R | Y349C<br>T366S<br>L368A<br>Y407V<br>E357R | Y349C<br>T366S<br>L368A<br>Y407V<br>E357K | Y349C<br>T366S<br>L368A<br>Y407V<br>E357R |

TABLE 3C

| Fc domain monomer | | Amino acid mutations (each column represents a set of mutations in an Fc construct having three Fc domains) | | | | | | | | | | | | | | | |
|---|---|---|---|---|---|---|---|---|---|---|---|---|---|---|---|---|---|
| A and A' | Engineered cavity | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V | Y349C<br>T366S<br>L368A<br>Y407V |
| | reversed charge mutation(s) | E357K | E357R | E357K | E357K | E357R | E357R | E357K | E357R | E357K | E357R | E357K | E357K | E357R | E357R | E357K | E357R |
| L and L' | | GGGGGGGGGGGGGGGGGG (SEQ ID NO: 27) | | | | | | | | | | | | | | | |
| B and B' | reversed charge mutation(s) | D399K<br>K409D | D399K<br>K409D | D399R<br>K409D | D399K<br>K409E | D399R<br>K409D | D399K<br>K409E | D399R<br>K409D | D399R<br>K409D | D399K<br>K409D | D399K<br>K409E | D399R<br>K409D | D399K<br>K409E | D399R<br>K409D | D399K<br>K409E | D399R<br>K409E | D399R<br>K409E |
| 5th and 6th Fc domain monomers | Engineered protuberance reversed charge mutation(s) | S354C<br>T366W<br>K370D | S354C<br>T366W<br>K370D | S354C<br>T366W<br>K370D | S354C<br>T366W<br>K370D | S354C<br>T366W<br>K370D | S354C<br>T366W<br>K370D | S354C<br>T366W<br>K370D | S354C<br>T366W<br>K370D | S354C<br>T366W<br>K370E | S354C<br>T366W<br>K370E | S354C<br>T366W<br>K370E | S354C<br>T366W<br>K370E | S354C<br>T366W<br>K370E | S354C<br>T366W<br>K370E | S354C<br>T366W<br>K370E | S354C<br>T366W<br>K370E |

TABLE 3D

| Fc domain monomer | | Amino acid mutations (each column represents a set of mutations in an Fc construct having three Fc domains) | | | | | | | | | | | | | | | |
|---|---|---|---|---|---|---|---|---|---|---|---|---|---|---|---|---|---|
| A and A' | Engineered cavity<br><br><br><br>reversed charge mutation(s) | Y349C<br>T366S<br>L368A<br>Y407V<br>K370D | Y349C<br>T366S<br>L368A<br>Y407V<br>K370D | Y349C<br>T366S<br>L368A<br>Y407V<br>K370D | Y349C<br>T366S<br>L368A<br>Y407V<br>K370D | Y349C<br>T366S<br>L368A<br>Y407V<br>K370D | Y349C<br>T366S<br>L368A<br>Y407V<br>K370D | Y349C<br>T366S<br>L368A<br>Y407V<br>K370D | Y349C<br>T366S<br>L368A<br>Y407V<br>K370D | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E | Y349C<br>T366S<br>L368A<br>Y407V<br>K370E |
| L and L' | | GGGGGGGGGGGGGGGGGGGG (SEQ ID NO: 27) | | | | | | | | | | | | | | | |
| B and B' | reversed charge mutation(s) | D399K<br>K409D | D399K<br>K409D | D399R<br>K409D | D399K<br>K409E | D399R<br>K409D | D399K<br>K409E | D399R<br>K409D | D399R<br>K409D | D399K<br>K409D | D399K<br>K409E | D399R<br>K409D | D399K<br>K409E | D399R<br>K409D | D399K<br>K409E | D399R<br>K409E | D399R<br>K409E |
| 5th and 6th Fc domain monomers | Engineered protuberance<br>reversed charge mutation(s) | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K | S354C<br>T366W<br>E357K |

Figure 13:
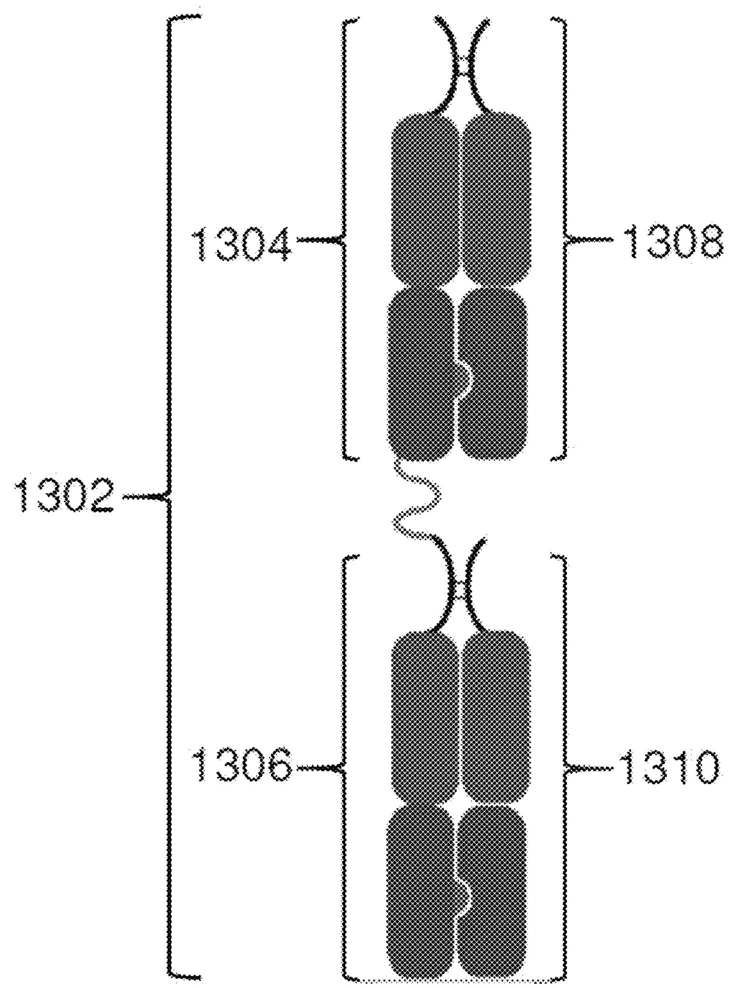
FIG. 13 is an illustration of an Fc construct containing two Fc domains formed from three polypeptides.

In some embodiments, an Fc construct contains two Fc domains formed from three polypeptides. The first polypeptide contains two Fc domain monomers joined in tandem series joined by way of a linker (e.g., a glycine spacer; SEQ ID NOs: 26 and 27), and the second and third polypeptides contain one Fc domain monomer. The second and third polypeptides may be the same polypeptide or may be different polypeptides. FIG. 13 depicts an example of such an Fc construct. The first polypeptide (1302) contains two Fc domain monomers (1304 and 1306) joined in tandem series by way of a linker (e.g., a glycine spacer; SEQ ID NOs: 26 and 27). Both Fc domain monomers 1304 and 1306 contain engineered protuberances in the $C_H3$ antibody constant domains. The second and third polypeptides (1308 and 1310) each contain one Fc domain monomer having engineered cavities in the $C_H3$ antibody constant domain. One of the Fc domain monomers (1304) in the first polypeptide forms a first heterodimeric Fc domain with the second polypeptide (1308), while the other Fc domain monomer (1306) in the first polypeptide forms a second heterodimeric Fc domain with the third polypeptide (1310). The second and third polypeptides are not attached or linked to each other. The engineered protuberance-into-cavity $C_H3$-$C_H3$ interface favors the formation of heterodimers of Fc domain monomers and prevents the uncontrolled formation of unwanted multimers. In some embodiments, each of the Fc domain monomers may further contain reverse charge mutations to promote heterodimerization. For example, Fc domain monomer 1304 having engineered protuberances and reverse charge mutations (e.g., E357K) may favorably form a heterodimeric Fc domain with Fc domain monomer 1308 having engineered cavities and reverse charge mutations (e.g., K370D).

Figure 14:
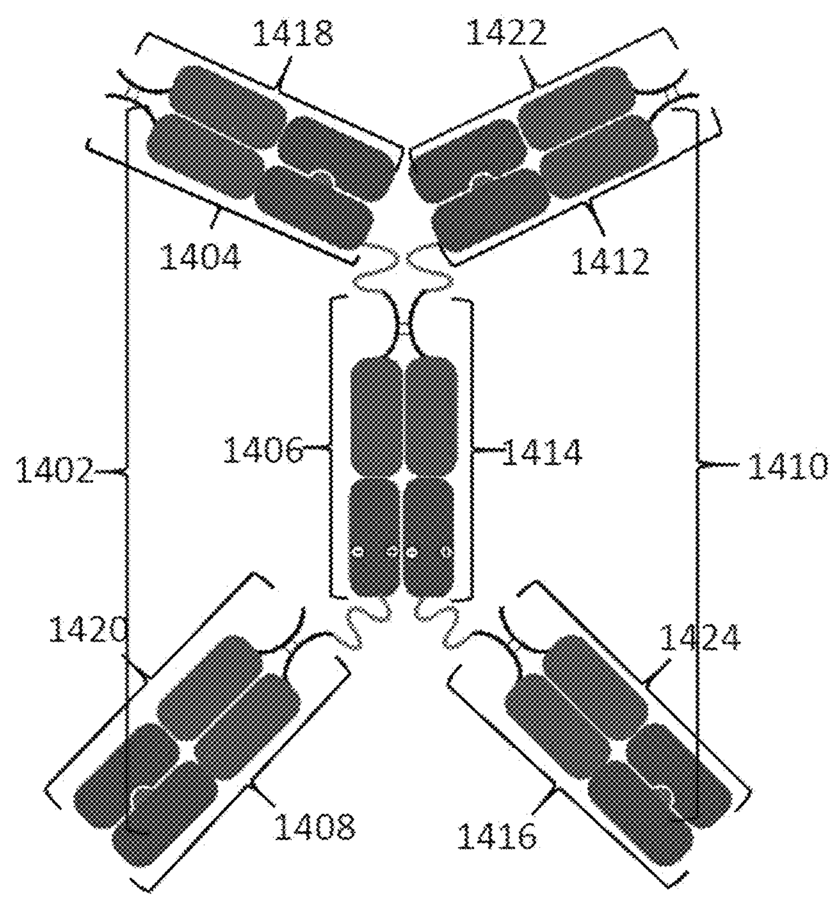
FIG. 14 is an illustration of an Fc construct containing five Fc domains formed from six polypeptides (Fc5X).
Figure 15:
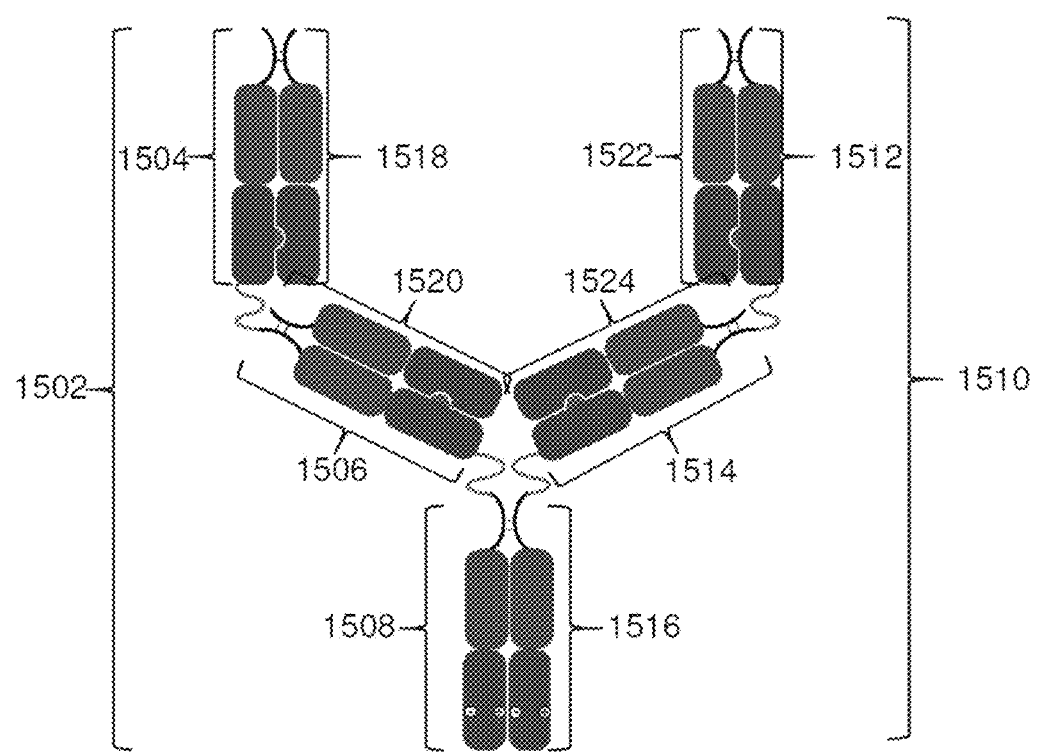
FIG. 15 is an illustration of an Fc construct containing five Fc domains formed from six polypeptides (Fc5Y).

In yet other embodiments, Fc constructs can contain five Fc domains formed from six polypeptides. Two examples are depicted in FIGS. 14 and 15. While these depicted Fc constructs are comprised of six polypeptides, four of the polypeptides can be encoded by the same nucleic acid, and the remaining two polypeptides can also be encoded by the same nucleic acid. As a result, these Fc constructs can be produced by the expression of two nucleic acids in a suitable host cell.

FIG. 14 is an illustration of an Fc construct containing five Fc domains formed from six polypeptides. The first and second polypeptides (1402 and 1410) each contain three Fc domain monomers (1404, 1406, 1408, and 1412, 1414, 1416, respectively) joined in a tandem series by way of a linker (e.g., a glycine spacer; SEQ ID NOs: 26 and 27). Specifically, in polypeptide 1402 or 1410, a first protuberance-containing Fc domain monomer (1404 or 1412) is connected to a second Fc domain monomer containing different charged amino acids at the $C_H3$-$C_H3$ interface (1406 or 1414) than the wild-type sequence, which is connected to a third protuberance-containing Fc domain monomer (1408 or 1416). Fc domain monomers 1406 and 1414 may each contain the same reverse charge mutations (e.g., D399K/K409D) that promote formation of a homodimeric Fc domain. The third through sixth polypeptides (1418, 1420, 1422, and 1424) each contain a cavity-containing Fc domain monomer and form a heterodimeric Fc domain with each of Fc domain monomers 1404, 1408, 1412 and 1416, respectively. In some embodiments, each of the Fc domain monomers 1404, 1408, 1412, 1416, 1418, 1420, 1422, and 1424 may further contain reverse charge mutations to promote heterodimerization. For example, Fc domain monomer 1408 having engineered protuberances and reverse charge mutations (e.g., E357K) may favorably form a heterodimeric Fc domain with Fc domain monomer 1420 having engineered cavities and reverse charge mutations (e.g., K370D).

FIG. 15 is an illustration of an Fc construct containing five Fc domains formed from six polypeptides. The first and second polypeptides (1502 and 1510) each contain three Fc domain monomers (1504, 1506, 1508, and 1512, 1514, 1516, respectively) joined in a tandem series by way of a linker (e.g., a glycine spacer; SEQ ID NOs: 26 and 27). Specifically, in polypeptide 1502 or 1510, a first protuberance-containing Fc domain monomer (1504 or 1512) is connected to a second protuberance-containing Fc domain monomer (1506 or 1514), which is connected to a third Fc domain monomer containing different charged amino acids at the $C_H3$-$C_H3$ interface (1508 or 1516) than the wild-type sequence. Fc domain monomers 1508 and 1516 may each contain the same reverse charge mutations (e.g., D399K/K409D) that promote formation of a homodimeric Fc domain. The third through sixth polypeptides (1518, 1520, 1522, and 1524) each contain a cavity-containing Fc domain monomer and form a heterodimeric Fc domain with each of Fc domain monomers 1504, 1506, 1512 and 1514, respectively. In some embodiments, each of the Fc domain monomers 1504, 1506, 1512, 1514, 1518, 1520, 1522, and 1524 may further contain reverse charge mutations to promote heterodimerization. For example, Fc domain monomer 1504 having engineered protuberances and reverse charge mutations (e.g., E357K) may favorably form a heterodimeric Fc domain with Fc domain monomer 1518 having engineered cavities and reverse charge mutations (e.g., K370D).

Figure 16:
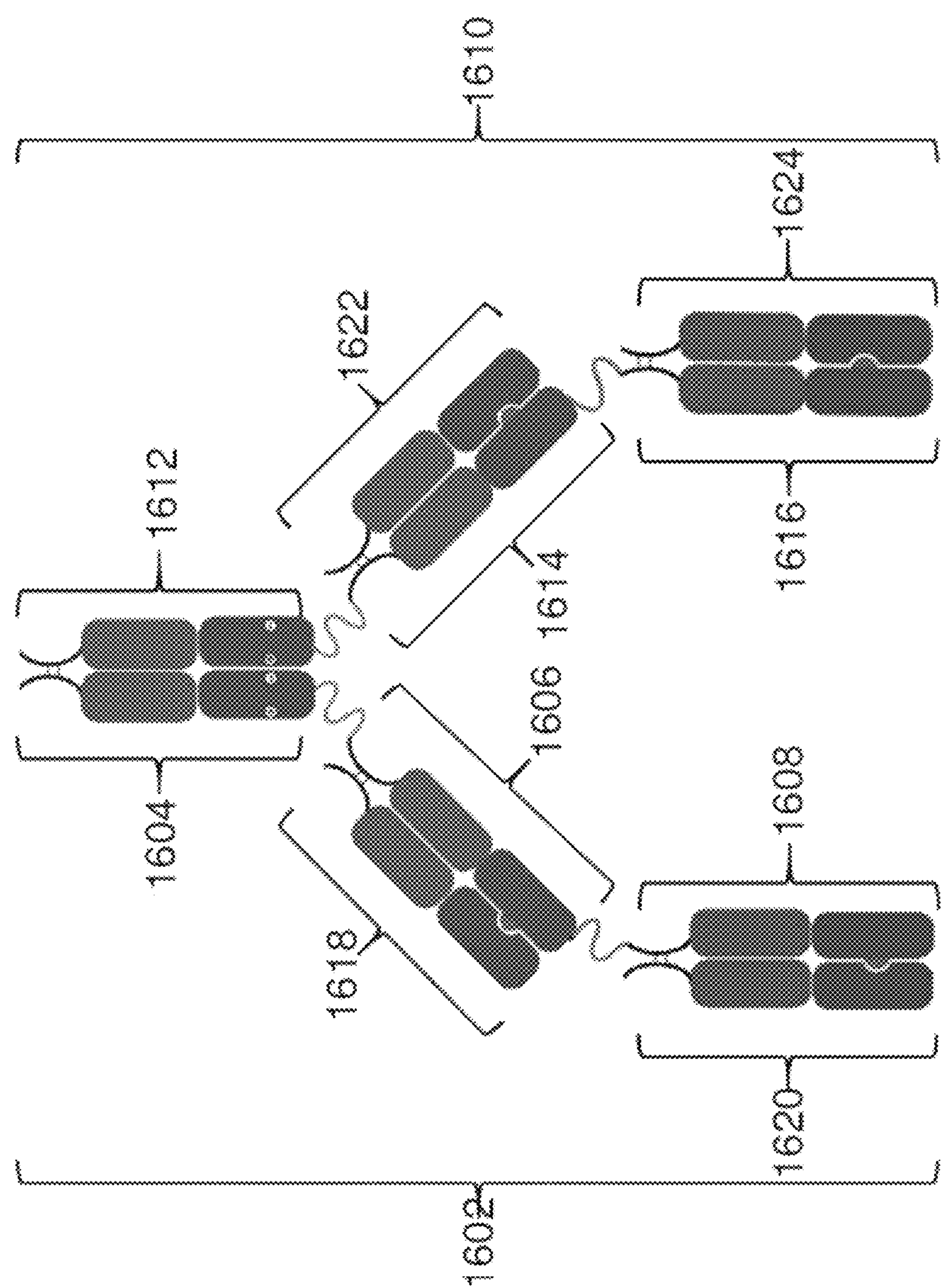
FIG. 16 is an illustration of an Fc construct containing five Fc domains formed from six polypeptides (Fc5Y-invert).

FIG. 16 is an illustration of another Fc construct containing five Fc domains formed from six polypeptides. The first and second polypeptides (1602 and 1610) each contain three Fc domain monomers (1604, 1606, 1608, and 1612, 1614, 1616, respectively) joined in a tandem series by way of a linker (e.g., a glycine spacer; SEQ ID NOs: 26 and 27). Specifically, in polypeptide 1602 or 1610, a first Fc domain monomer containing different charged amino acids at the $C_H3$-$C_H3$ interface (1604 or 1612) is connected to a second protuberance-containing Fc domain monomer (1606 or 1614), which is connected to a third protuberance-containing Fc domain monomer (1608 or 1616) than the wild-type sequence. Fc domain monomers 1604 and 1612 may each contain the same reverse charge mutations (e.g., D399K/K409D) that promote formation of a homodimeric Fc domain. The third through sixth polypeptides (1618, 1620, 1622, and 1624) each contain a cavity-containing Fc domain monomer and form a heterodimeric Fc domain with each of Fc domain monomers 1606, 1608, 1614 and 1616, respectively. In some embodiments, each of the Fc domain monomers 1606, 1608, 1614, 1616, 1618, 1620, 1622, and 1624 may further contain reverse charge mutations to promote heterodimerization. For example, Fc domain monomer 1608 having engineered protuberances and reverse charge mutations (e.g., E357K) may favorably form a heterodimeric Fc domain with Fc domain monomer 1620 having engineered cavities and reverse charge mutations (e.g., K370D).

Figure 17:
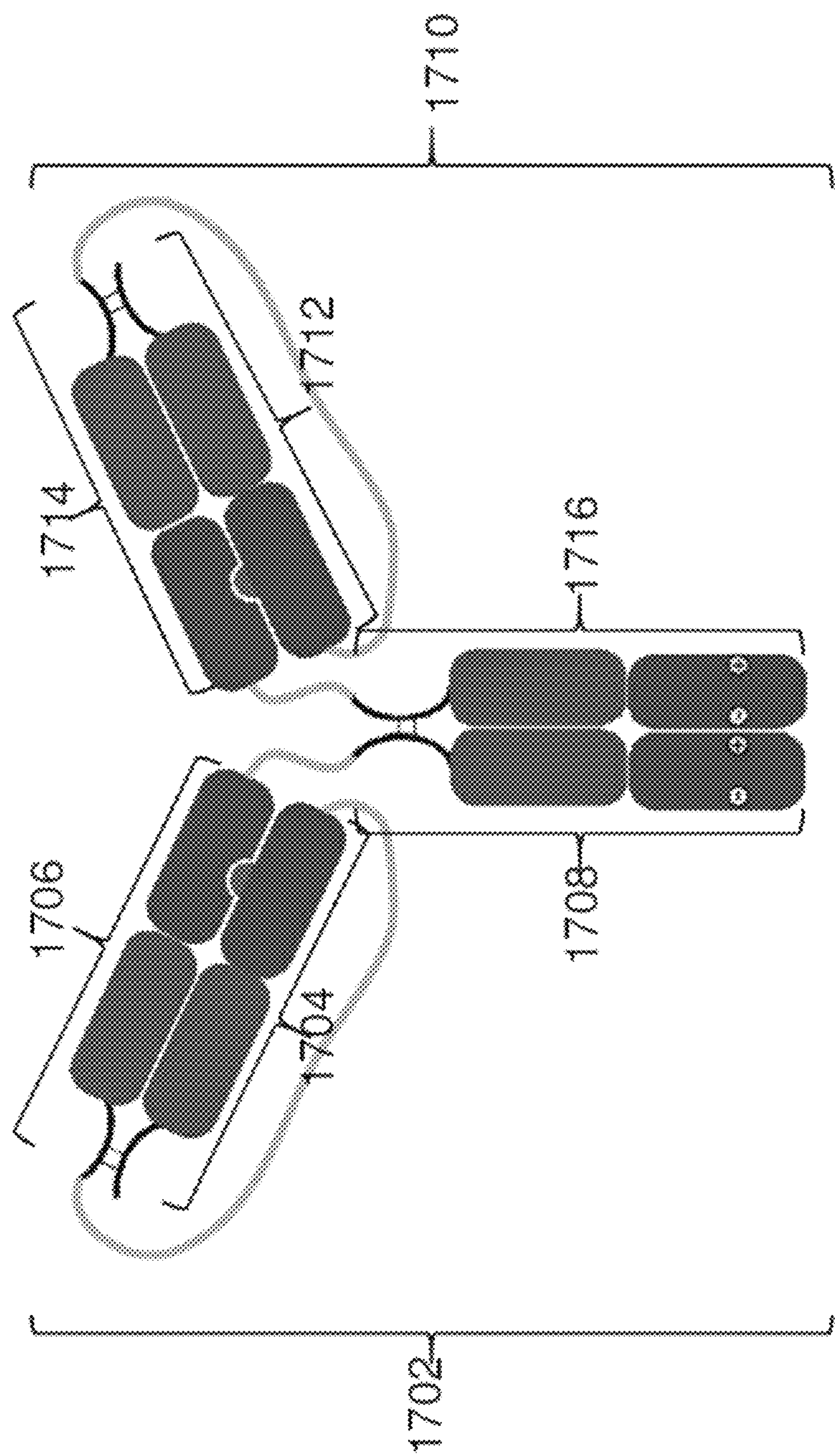
FIG. 17 is an illustration of an Fc construct containing three Fc domains formed from two polypeptides.

In another embodiment, an Fc construct containing two or more Fc domains can be formed from two polypeptides having the same primary sequence. Such a construct can be formed from expression of a single polypeptide sequence in a host cell. An example is depicted in FIG. 17. In this example, a single nucleic acid is sufficient to encode an Fc construct containing three Fc domains. Two Fc domain monomers that are part of the same polypeptide are permitted to form a heterodimeric Fc domain by the inclusion of a flexible linker of a sufficient length and flexibility. This same polypeptide also contains a third Fc domain monomer joined by way of a flexible linker (e.g., a glycine spacer; SEQ ID NOs: 26 and 27). This third Fc domain monomer (1708) is capable of joining to another Fc domain monomer (1716) to form a homodimeric Fc domain and to produce the Y-shaped Fc construct depicted in FIG. 17. Formation of Fc domains can be controlled through the use of dimerization selectivity modules, as is also depicted in FIG. 17. In some embodiments, each of the Fc domain monomers 1704, 1706, 1712, and 1714 may further contain reverse charge mutations to promote heterodimerization. For example, Fc domain monomer 1704 having engineered protuberances and reverse charge mutations (e.g., E357K) may favorably form a heterodimeric Fc domain with Fc domain monomer 1706 having engineered cavities and reverse charge mutations (e.g., K370D).

In some embodiments, one or more Fc polypeptides in an Fc construct (e.g., Fc construct 1-3 in FIG. 1; Fc construct 4 in FIG. 2) lack a C-terminal lysine residue. In some embodiments, all of the Fc polypeptides in an Fc construct lack a C-terminal lysine residue. In some embodiments, the absence of a C-terminal lysine in one or more Fc polypeptides in an Fc construct may improve the homogeneity of a population of an Fc construct (e.g., an Fc construct having three Fc domains), e.g., a population of an Fc construct having three Fc domains that is substantially homogeneous (see Example 8). In one example, the C-terminal lysine residue in an Fc polypeptide having the sequence any one of SEQ ID NOs: 43 and 44 (see Example 1, Table 6) may be removed to generate a corresponding Fc polypeptide that does not contain a C-terminal lysine residue.

In some embodiments, an Fc domain monomer in an Fc construct described herein (e.g., an Fc construct having three Fc domains) may comprise, consist of, or consist essentially of a sequence that is at least 95% identical (e.g., at least 97%, 99%, or 99.5% identical) to the sequence a wild-type Fc domain monomer (e.g., SEQ ID NO: 42). In some embodiments, an Fc domain monomer in an Fc construct described herein (e.g., an Fc construct having three Fc domains) may comprise, consist of, or consist essentially of a sequence that is the sequence a wild-type Fc domain monomer (e.g., SEQ ID NO: 42) with up to 10 (9, 8, 7, 6, 5, 4, 3, 2, or 1) single amino acid modifications (e.g., substitutions, e.g., conservative substitutions). In some embodiments, an Fc domain monomer in an Fc construct described herein (e.g., an Fc construct having three Fc domains) may comprise, consist of, or consist essentially of a sequence that is at least 95% identical (e.g., at least 97%, 99%, or 99.5% identical) to the sequence any one of SEQ ID NOs: 44, 46, 48, and 50-53. In some embodiments, an Fc domain monomer in an Fc construct described herein (e.g., an Fc construct having three Fc domains) may comprise, consist of, or consist essentially of a sequence that is the sequence any one of SEQ ID NOs: 44, 46, 48, and 50-53 with up to 10 (9, 8, 7, 6, 5, 4, 3, 2, or 1) single amino acid modifications (e.g., substitutions, e.g., conservative substitutions). In certain embodiments, an Fc domain monomer in the Fc construct may comprise, consist of, or consist essentially of a sequence that is at least 95% identical (e.g., at least 97%, 99%, or 99.5% identical) to the sequence SEQ ID NO: 48, 52, and 53. In certain embodiments, an Fc domain monomer in the Fc construct may comprise, consist of, or consist essentially of a sequence that is the sequence SEQ ID NO: 48, 52, and 53 with up to 10 (e.g., up to 9, 8, 7, 6, 5, 4, 3, 2, or 1) single amino acid modifications (e.g., substitutions, e.g., conservative substitutions).

In some embodiments, a polypeptide having two Fc domain monomers in an Fc construct described herein (e.g., polypeptides 102 and 108 in FIG. 1; polypeptides 202 and 208 in FIG. 2) may comprise, consist of, or consist essentially of a sequence that is at least 95% identical (e.g., at least 97%, 99%, or 99.5% identical) to the sequence any one of SEQ ID NOs: 43, 45, 47, and 49 (see Example 1, Table 6). In some embodiments, a polypeptide having two Fc domain monomers in an Fc construct described herein (e.g., polypeptides 102 and 108 in FIG. 1; polypeptides 202 and 208 in FIG. 2) may comprise, consist of, or consist essentially of a sequence that is the sequence any one of SEQ ID NOs: 43, 45, 47, and 49 (see Example 1, Table 6) with up to 10 (e.g., up to 9, 8, 7, 6, 5, 4, 3, 2, or 1) single amino acid modifications (e.g., substitutions, e.g., conservative substitutions). In certain embodiments, a polypeptide having two Fc domain monomers in an Fc construct described herein may comprise, consist of, or consist essentially of a sequence that is at least 95% identical (e.g., at least 97%, 99%, or 99.5% identical) to the sequence SEQ ID NOs: 49. In certain embodiments, a polypeptide having two Fc domain monomers in an Fc construct described herein may comprise, consist of, or consist essentially of a sequence that is the sequence SEQ ID NOs: 49 with up to 10 (e.g., up to 9, 8, 7, 6, 5, 4, 3, 2, or 1) single amino acid modifications (e.g., substitutions, e.g., conservative substitutions). In some embodiments, the amino acid mutations in a polypeptide having two Fc domain monomers in an Fc construct described herein (e.g., polypeptides 102 and 108 in FIG. 1; polypeptides 202 and 208 in FIG. 2) occur only in the Fc domain monomers (e.g., Fc domain monomers 104, 106, 110, and 112 in FIG. 1; Fc domain monomers 204, 206, 210, and 212 in FIG. 2) and do not occur in the spacer. For example, in the polypeptides shown in Table 8, additional amino acid mutations may be made in the Fc domain monomers having the sequences of SEQ ID NOs: 50-53 while the spacers having the sequences of SEQ ID NOs: 18, 26, and 27 do not change.

In some embodiments, the N-terminal Asp in one or more of the first, second, third and fourth polypeptides in an Fc construct described herein (e.g., polypeptides 102, 108, 114, and 116 in FIGS. 1; 202, 208, 214, and 216 in FIG. 2) may be mutated to Gln. In some embodiments, the N-terminal Asp in each of the first, second, third, and fourth polypeptides in an Fc construct described herein is mutated to Gln. In other embodiments, an Fc construct described herein (e.g., an Fc construct having three Fc domains) may include one or more Fc domain monomers having N-terminal Asp be mutated to Gln. In some embodiments, the mutation of N-terminal Asp to Gln in one or more of the first, second, third and fourth polypeptides in an Fc construct described herein may improve the homogeneity of a population of an Fc construct (e.g., an Fc construct having three Fc domains), e.g., a population of an Fc construct having three Fc domains that is substantially homogeneous. For example, Table 4 shows amino acid sequences of first, second, third, and fourth polypeptides that have N-terminal Asp mutated to Gln in an Fc construct having three Fc domains.

TABLE 4

| Fc construct with N-terminal Asp mutated to Gln in all four polypeptides | |
|---|---|
| First and second polypeptides | QKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVYTLPPCRDELTKNQVSLWCLVKGFYPSDIAVEWESNGQPENN<br>YKTTPPVLDSDGSFFLYSKLTVDKSRWQQGNVFSCSVMHEALHNHYTQKSLSLSPG<br>KSGGGSGGGSGGGSGGGSGGGDKTHTCPPCPAPELLGGPSVFLFPPKPKDTLMIS<br>RTPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSLTC<br>LVKGFYPSDIAVEWESNGQPENNYKTTPPVLKSDGSFFLYSDLTVDKSRWQQGNVF<br>SCSVMHEALHNHYTQKSLSLSPGK (SEQ ID NO: 54) |
| Third and fourth polypeptides | QKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVCTLPPSRDELTKNQVSLSCAVKGFYPSDIAVEWESNGQPENNY<br>KTTPPVLDSDGSFFLVSKLTVDKSRWQQGNVFSCSVMHEALHNHYTQKSLSLSPGK<br>(SEQ ID NO: 55) |
| Fc construct with N-terminal Asp mutated to Gln in all four polypeptides | |
| First and second polypeptides | QKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVYTLPPCRDELTKNQVSLWCLVKGFYPSDIAVEWESNGQPENN<br>YKTTPPVLDSDGSFFLYSKLTVDKSRWQQGNVFSCSVMHEALHNHYTQKSLSLSPG<br>KSGGGSGGGSGGGSGGGSGGGDKTHTCPPCPAPELLGGPSVFLFPPKPKDTLMIS<br>RTPEVTCVVVDVSHEDPEVKFNWYVDGVEVHNAKTKPREEQYNSTYRVVSVLTVLH<br>QDWLNGKEYKCKVSNKALPAPIEKTISKAKGQPREPQVYTLPPSRDELTKNQVSLTC<br>LVKGFYPSDIAVEwESNGQPENNYKTTPPVLKSDGSFFLYSDLTVDKSRWQQGNVF<br>SCSVMHEALHNHYTQKSLSLSPG (SEQ ID NO: 56) |
| Third and fourth polypeptides | QKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVCTLPPSRDELTKNQVSLSCAVKGFYPSDIAVEWESNGQPENNY<br>KTTPPVLDSDGSFFLVSKLTVDKSRWQQGNVFSCSVMHEALHNHYTQKSLSLSPG<br>(SEQ ID NO: 57) |
| Fc construct with N-terminal Asp mutated to Gln in all four polypeptides | |
| First and second polypeptides | QKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVYTLPPCRDKLTKNQVSLWCLVKGFYPSDIAVEWESNGQPENN<br>YKTTPPVLDSDGSFFLYSKLTVDKSRWQQGNVFSCSVMHEALHNHYTQKSLSLSPG<br>KGGGGGGGGGGGGGGGDKTHTCPPCPAPELLGGPSVFLFPPKPKDTLMISRTPEV<br>TCVVVDVSHEDPEVKFNWYVDGVEVHNAKTKPREEQYNSTYRVVSVLTVLHQDWLN<br>GKEYKCKVSNKALPAPIEKTISKAKGQPREPQVYTLPPSRDELTKNQVSLTCLVKGFY<br>PSDIAVEWESNGQPENNYKTTPPVLKSDGSFFLYSDLTVDKSRWQQGNVFSCSVMH<br>EALHNHYTQKSLSLSPG (SEQ ID NO: 58) |
| Third and fourth polypeptides | QKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVCTLPPSRDELTKNQVSLSCAVDGFYPSDIAVEWESNGQPENNY<br>KTTPPVLDSDGSFFLVSKLTVDKSRWQQGNVFSCSVMHEALHNHYTQKSLSLSPG<br>(SEQ ID NO: 59) |
| Fc construct with N-terminal Asp mutated to Gln in all four polypeptides | |
| First and second polypeptides | QKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVYTLPPCRDKLTKNQVSLWCLVKGFYPSDIAVEWESNGQPENN<br>YKTTPPVLDSDGSFFLYSKLTVDKSRWQQGNVFSCSVMHEALHNHYTQKSLSLSPG<br>KGGGGGGGGGGGGGGGGGGGGDKTHTCPPCPAPELLGGPSVFLFPPKPKDTLMI<br>SRTPEVTCVVVDVSHEDPEVKFNWYVDGVEVHNAKTKPREEQYNSTYRVVSVLTVL<br>HQDWLNGKEYKCKVSNKALPAPIEKTISKAKGQPREPQVYTLPPSRDELTKNQVSLT<br>CLVKGFYPSDIAVEWESNGQPENNYKTTPPVLKSDGSFFLYSDLTVDKSRWQQGNV<br>FSCSVMHEALHNHYTQKSLSLSPG (SEQ ID NO: 60) |
| Third and fourth polypeptides | QKTHTCPPCPAPELLGGPSVFLFPPKPKDTLMISRTPEVTCVVVDVSHEDPEVKFNW<br>YVDGVEVHNAKTKPREEQYNSTYRVVSVLTVLHQDWLNGKEYKCKVSNKALPAPIEK<br>TISKAKGQPREPQVCTLPPSRDELTKNQVSLSCAVDGFYPSDIAVEWESNGQPENNY<br>KTTPPVLDSDGSFFLVSKLTVDKSRWQQGNVFSCSVMHEALHNHYTQKSLSLSPG<br>(SEQ ID NO: 59) |

X. Host Cells and Protein Production

In the present disclosure, a host cell refers to a vehicle that includes the necessary cellular components, e.g., organelles, needed to express the polypeptides and constructs described herein from their corresponding nucleic acids. The nucleic acids may be included in nucleic acid vectors that can be introduced into the host cell by conventional techniques known in the art (transformation, transfection, electroporation, calcium phosphate precipitation, direct microinjection, etc.). Host cells can be of mammalian, bacterial, fungal, or insect origin. Mammalian host cells include, but are not limited to, CHO (or CHO-derived cell strains, e.g., CHO- K1, CHO-DXB11 CHO-DG44), murine host cells (e.g., NS0, Sp2/0), VERY, HEK (e.g., HEK293), BHK, HeLa, COS, MDCK, 293, 3T3, W138, BT483, Hs578T, HTB2, BT20 and T47D, CRL7O3O and HsS78Bst cells. Host cells can also be chosen that modulate the expression of the protein constructs, or modify and process the protein product in the specific fashion desired. Different host cells have characteristic and specific mechanisms for the post-translational processing and modification of protein products. Appropriate cell lines or host systems can be chosen to ensure the correct modification and processing of the protein expressed.

For expression and secretion of protein products from their corresponding DNA plasmid constructs, host cells may be transfected or transformed with DNA controlled by appropriate expression control elements known in the art, including promoter, enhancer, sequences, transcription terminators, polyadenylation sites, and selectable markers. Methods for expression of therapeutic proteins are known in the art. See, for example, Paulina Balbas, Argelia Lorence (eds.) *Recombinant Gene Expression: Reviews and Protocols* (*Methods in Molecular Biology*), Humana Press; 2nd ed. 2004 edition (Jul. 20, 2004); Vladimir Voynov and Justin A. Caravella (eds.) *Therapeutic Proteins: Methods and Protocols* (*Methods in Molecular Biology*) Humana Press; 2nd ed. 2012 edition (Jun. 28, 2012).

XI. Purification

An Fc construct can be purified by any method known in the art of protein purification, for example, by chromatography (e.g., ion exchange, affinity (e.g., Protein A affinity), and size-exclusion column chromatography), centrifugation, differential solubility, or by any other standard technique for the purification of proteins. For example, an Fc construct can be isolated and purified by appropriately selecting and combining affinity columns such as Protein A column with chromatography columns, filtration, ultra filtration, salting-out and dialysis procedures (see, e.g., Process Scale Purification of Antibodies, Uwe Gottschalk (ed.) John Wiley & Sons, Inc., 2009; and Subramanian (ed.) *Antibodies—Volume I—Production and Purification*, Kluwer Academic/Plenum Publishers, New York (2004)).

In some instances, an Fc construct can be conjugated to one or more purification peptides to facilitate purification and isolation of the Fc construct from, e.g., a whole cell lysate mixture. In some embodiments, the purification peptide binds to another moiety that has a specific affinity for the purification peptide. In some embodiments, such moieties which specifically bind to the purification peptide are attached to a solid support, such as a matrix, a resin, or agarose beads. Examples of purification peptides that may be joined to an Fc construct include, but are not limited to, a hexa-histidine peptide, a FLAG peptide, a myc peptide, and a hemagglutinin (HA) peptide. A hexa-histidine peptide (HHHHHH (SEQ ID NO: 38)) binds to nickel-functionalized agarose affinity column with micromolar affinity. In some embodiments, a FLAG peptide includes the sequence DYKDDDDK (SEQ ID NO: 39). In some embodiments, a FLAG peptide includes integer multiples of the sequence DYKDDDDK in tandem series, e.g., 3×DYKDDDDK. In some embodiments, a myc peptide includes the sequence EQKLISEEDL (SEQ ID NO: 40). In some embodiments, a myc peptide includes integer multiples of the sequence EQKLISEEDL in tandem series, e.g., 3×EQKLISEEDL. In some embodiments, an HA peptide includes the sequence YPYDVPDYA (SEQ ID NO: 41). In some embodiments, an HA peptide includes integer multiples of the sequence YPYDVPDYA in tandem series, e.g., 3×YPYDVPDYA. Antibodies that specifically recognize and bind to the FLAG, myc, or HA purification peptide are well-known in the art and often commercially available. A solid support (e.g., a matrix, a resin, or agarose beads) functionalized with these antibodies may be used to purify an Fc construct that includes a FLAG, myc, or HA peptide.

For the Fc constructs, Protein A column chromatography may be employed as a purification process. Protein A ligands interact with Fc constructs through the Fc region, making Protein A chromatography a highly selective capture process that is able to remove most of the host cell proteins. In the present disclosure, Fc constructs may be purified using Protein A column chromatography as described in Example 2.

XII. Pharmaceutical Compositions/Preparations

The disclosure features pharmaceutical compositions that include one or more Fc constructs described herein. In one embodiment, a pharmaceutical composition includes a substantially homogenous population of Fc constructs. In various examples, the pharmaceutical composition includes a substantially homogenous population of any one of Fc constructs 1-4.

A therapeutic protein construct, e.g., an Fc construct described herein (e.g., an Fc construct having three Fc domains), of the present disclosure can be incorporated into a pharmaceutical composition. Pharmaceutical compositions including therapeutic proteins can be formulated by methods know to those skilled in the art. The pharmaceutical composition can be administered parenterally in the form of an injectable formulation including a sterile solution or suspension in water or another pharmaceutically acceptable liquid. For example, the pharmaceutical composition can be formulated by suitably combining the Fc construct with pharmaceutically acceptable vehicles or media, such as sterile water for injection (WFI), physiological saline, emulsifier, suspension agent, surfactant, stabilizer, diluent, binder, excipient, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HCO-50, and the like commonly known in the art. Formulation methods for therapeutic protein products are known in the art, see e.g., Banga (ed.) *Therapeutic Peptides and Proteins: Formulation, Processing and Delivery Systems* (2d ed.) Taylor & Francis Group, CRC Press (2006).

XIII. Dosage

The pharmaceutical compositions are administered in a manner compatible with the dosage formulation and in such amount as is therapeutically effective to result in an improvement or remediation of the symptoms. The pharmaceutical compositions are administered in a variety of dosage forms, e.g., intravenous dosage forms, subcutaneous dosage forms, oral dosage forms such as ingestible solutions, drug release capsules, and the like. The appropriate dosage for the individual subject depends on the therapeutic objectives, the route of administration, and the condition of the patient. Generally, recombinant proteins are dosed at 1-200 mg/kg, e.g., 1-100 mg/kg, e.g., 20-100 mg/kg. Accordingly, it will be necessary for a healthcare provider to tailor and titer the dosage and modify the route of administration as required to obtain the optimal therapeutic effect.

XIV. Indications

The pharmaceutical compositions of the disclosure (e.g., those containing Fc constructs having 2, 3, or 4 Fc domains) are useful to reduce inflammation in a subject, to promote clearance of autoantibodies in a subject, to suppress antigen presentation in a subject, to reduce the immune response, e.g., to block immune complex-based activation of the immune response in a subject, and to treat immunological and inflammatory conditions or diseases in a subject. Exemplary conditions and diseases include rheumatoid arthritis (RA); systemic lupus erythematosus (SLE); ANCA-associated vasculitis; antiphospholipid antibody syndrome; autoimmune hemolytic anemia; chronic inflammatory demyelinating neuropathy; clearance of anti-allo in transplant, anti-self in GVHD, anti-replacement, IgG therapeutics, IgG paraproteins; dermatomyositis; Goodpasture's Syndrome; organ system-targeted type II hypersensitivity syndromes mediated through antibody-dependent cell-mediated cytotoxicity, e.g., Guillain Barre syndrome, CIDP, dermatomyositis, Felty's syndrome, antibody-mediated rejection, autoimmune thyroid disease, ulcerative colitis, autoimmune liver disease; idiopathic thrombocytopenia purpura; Myasthenia Gravis, neuromyelitis optica; pemphigus and other autoimmune blistering disorders; Sjogren's Syndrome; autoimmune cytopenias and other disorders mediated through antibody-dependent phagocytosis; other FcR-dependent inflammatory syndromes e.g., synovitis, dermatomyositis, systemic vasculitis, glomerulitis, and vasculitis.

In some embodiments, the pharmaceutical compositions of the disclosure containing Fc constructs having 5-10 Fc domains are also useful, e.g., to induce immune cell activation of the immune response in a subject, to increase phagocytosis of a target cell (i.e., a cancer cell or an infected cell) in a subject, and to treat diseases such as cancers and infections in a subject. Fc constructs and homogenous pharmaceutical compositions of the disclosure may bind to activating Fcγ receptors (e.g., FcγRI, FcγRIIa, FcγRIIc, FcγRIIIa, and FcγRIIIb) to induce an immune response. Fc constructs and homogenous pharmaceutical compositions of the disclosure may activate Syk phosphorylation and calcium flux from primary THP-1 monocytes. Activated monocytes and their differentiated macrophages have the ability to phagocytose or kill target cells. The disclosure therefore provides methods of treatment that may be used to treat subjects who are suffering from diseases and disorders such as cancers and infections. In some embodiments, Fc constructs and homogenous pharmaceutical compositions described herein may be administered to a subject in a therapeutically effective amount to phagocytose or kill cancer cells or infected cells in the subject.

Cancers that are amenable to treatment according to the methods of the disclosure include, but are not limited to, bladder cancer, pancreatic cancer, lung cancer, liver cancer, ovarian cancer, colon cancer, stomach cancer, breast cancer, prostate cancer, renal cancer, testicular cancer, thyroid cancer, uterine cancer, rectal cancer, a cancer of the respiratory system, a cancer of the urinary system, oral cavity cancer, skin cancer, leukemia, sarcoma, carcinoma, basal cell carcinoma, non-Hodgkin's lymphoma, acute myeloid leukemia (AML), chronic lymphocytic leukemia (CLL), B-cells chronic lymphocytic leukemia (B-CLL), multiple myeloma (MM), erythroleukemia, renal cell carcinoma, astrocytoma, oligoastrocytoma, biliary tract cancer, choriocarcinoma, CNS cancer, larynx cancer, small cell lung cancer, adenocarcinoma, giant (or oat) cell carcinoma, squamous cell carcinoma, anaplastic large cell lymphoma, non-small-cell lung cancer, neuroblastoma, rhabdomyosarcoma, neuroectodermal cancer, glioblastoma, breast carcinoma, melanoma, inflammatory myofibroblastic tumor cancer, and soft tissue tumor cancer.

Infections that are amenable to treatment according to the methods of the disclosure include, but are not limited to, a bacterial infection, a viral infection, a fungal infection, a helmintic infection, and a protozoal infection.

Examples of infection-causing bacteria are well-known in the art and include, but are not limited to, bacteria in the genus *Streptococcus* (e.g., *Streptococcus pyogenes*), bacteria in the genus *Escherichia* (e.g., *Escherichia coli*), bacteria in the genus *Vibrio* (e.g., *Vibrio cholerae*), bacteria in the genus *Enteritis* (e.g., *Enteritis salmonella*), and bacteria in the genus *Salmonella* (e.g., *Salmonella typhi*). Examples of infection-causing viruses are well-known in the art and include, but are not limited to, viruses in the family Retroviridae (e.g., human immunodeficiency virus (HIV)), viruses in the family Adenoviridae (e.g., adenovirus), viruses in the family Herpesviridae (e.g., herpes simplex virus types 1 and 2), viruses in the family Papillomaviridae (e.g., human papillomavirus (HPV)), viruses in the family Poxviridae (e.g., smallpox), viruses in the family Picornaviridae (e.g., hepatitis A virus, poliovirus, rhinovirus), viruses in the family Hepadnaviridae (e.g., hepatitis B virus), viruses in the family Flaviviridae virus (e.g., hepatitis C virus, yellow fever virus, West Nile virus), viruses in the family Togaviridae (e.g., rubella virus), viruses in the family Orthomyxoviridae (e.g., influenza virus), viruses in the family Filoviridae (e.g., ebola virus, marburg virus), and viruses in the family Paramyxoviridae (e.g., measles virus, mumps virus). Examples of infection-causing fungi are well-known in the art and include, but are not limited to, fungi in the genus *Aspergillus* (e.g., *Aspergillus fumigatus, A. flavus, A. terreus. A. niger, A. candidus, A. clavatus, A. ochraceus*), fungi in the genus *Candida* (e.g., *Candida albicans, C. parapsilosis, C. glabrata, C. guilliermondii, C. krusei, C. lusitaniae, C. tropicalis*), fungi in the genus *Cryptococcus* (e.g., *Cryptococcus neoformans*), and fungi in the genus *Fusarium* (e.g., *Fusarium solani, F. verticiffioides, F. oxysporum*). Examples of helminths include, but are not limited to, tapeworms (cestodes), roundworms (nematodes), flukes (trematodes), and monogeneans.

Examples of protozoans include, but are not limited to, protozoans in the genus *Entamoeba* (e.g., *Entamoeba histolytica*), protozoans in the genus *Plasmodium* (e.g., *Plasmodium falciparum, P. malariae*), protozoans in the genus *Giardia* (e.g., *Giardia lamblia*), and protozoans in the genus *Trypanosoma* (e.g., *Trypanosoma brucei*).

EXAMPLES

Example 1. Fc Constructs Design

Desirably, Fc constructs are designed to increase folding efficiencies, to minimize uncontrolled association of subunits, which may create unwanted high molecular weight oligomers and multimers, and to generate compositions that are substantially homogenous. With these goals in mind, we designed four Fc constructs (FIGS. 1 and 2), each including a long polypeptide including two Fc domain monomers separated by a spacer (polypeptides 102 and 108 in FIG. 1 and polypeptides 202 and 208 in FIG. 2) and a short polypeptide including a single Fc domain monomer (polypeptides 114 and 116 in FIG. 1 and polypeptides 214 and 216 in FIG. 2). Each is based on the IgG1 Fc sequence, with the inclusion of engineered cavity, engineered protuberance, and/or electrostatic steering modifications to control assembly of the polypeptides. DNA sequences encoding the long and short polypeptides were optimized for expression in mammalian cells and cloned into the pcDNA3.4 mammalian expression vector. The DNA plasmid constructs were transfected via liposomes into human embryonic kidney (HEK) 293 cells. A total of eight DNA plasmid constructs were used to assemble four Fc constructs each having three Fc domains.

For each Fc construct, the long and short polypeptides, when co-expressed, produce a branched molecule containing three Fc domains, with the C-terminal Fc monomers of the long polypeptides specifically associating with each other to form one C-terminal Fc domain and with the N-terminal Fc monomers of the long polypeptides specifically associating with the short polypeptides to form two N-terminal Fc domains. Fc constructs 1-4 and their design are described in Table 5 and FIGS. 1 and 2. The sequences utilized in each Fc construct are shown Table 6. Table 7 below further summarizes the characteristics of the long and short polypeptides in each of constructs 1-4.

TABLE 5

| Fc construct | Long Polypeptide #s (SEQ ID NO) | Short Polypeptide #s (SEQ ID NO) | FIG. |
|---|---|---|---|
| Fc construct 1 | 102 and 108 (SEQ ID NO: 43) | 114 and 116 (SEQ ID NO: 44) | FIG. 1 |
| Fc construct 2 | 102 and 108 (SEQ ID NO: 45) | 114 and 116 (SEQ ID NO: 46) | FIG. 1 |
| Fc construct 3 | 102 and 108 (SEQ ID NO: 47) | 114 and 116 (SEQ ID NO: 48) | FIG. 1 |
| Fc construct 4 | 202 and 208 (SEQ ID NO: 49) | 214 and 216 (SEQ ID NO: 48) | FIG. 2 |

TABLE 6

| SEQ ID NO | Amino Acid Sequence |
|---|---|
| SEQ ID NO: 43 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVYTLPPCRDELTKNQVSLWCLVKGFYPSDIAVEWESNGQPENNYKTTPPVLDSDG<br>SFFLYSKLTVDKSRWQQGNVFSCSVMHEALHNHYTQKSLSLSPGKSGGGSGGGSGGGSG<br>GGSGGGDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYKTTPPV<br>LKSDGSFFLYSDLTVDKSRWQQGNVFSCSVMHEALHNHYTQKSLSLSPGK |
| SEQ ID NO: 44 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVCTLPPSRDELTKNQVSLSCAVKGFYPSDIAVEWESNGQPENNYKTTPPVLDSDG<br>SFFLVSKLTVDKSRWQQGNVFSCSVMHEALHNHYTQKSLSLSPGK |
| SEQ ID NO: 45 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVYTLPPCRDELTKNQVSLWCLVKGFYPSDIAVEWESNGQPENNYKTTPPVLDSDG<br>SFFLYSKLTVDKSRWQQGNVFSCSVMHEALHNHYTQKSLSLSPGKSGGGSGGGSGGGSG<br>GGSGGGDKTHTCPPCPAPELLGGPSVFLFPPKPKDTLMISRTPEVTCVVVDVSHEDPEVKF<br>NWYVDGVEVHNAKTKPREEQYNSTYRVVSVLTVLHQDWLNGKEYKCKVSNKALPAPIEKTI<br>SKAKGQPREPQVYTLPPSRDELTKNQVSLTCLVKGFYPSDIAVEWESNGQPENNYKTTPPV<br>LKSDGSFFLYSDLTVDKSRWQQGNVFSCSVMHEALHNHYTQKSLSLSPG |
| SEQ ID NO: 46 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVCTLPPSRDELTKNQVSLSCAVKGFYPSDIAVEWESNGQPENNYKTTPPVLDSDG<br>SFFLVSKLTVDKSRWQQGNVFSCSVMHEALHNHYTQKSLSLSPG |
| SEQ ID NO: 47 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGDKTHTCPPCPAPELLGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPENNYKTTPPVLKSD<br>GSFFLYSDLTVDKSRWQQGNVFSCSVMHEALHNHYTQKSLSLSPG |
| SEQ ID NO: 48 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVCTLPPSRDELTKNQVSLSCAVDGFYPSDIAVEWESNGQPENNYKTTPPVLDSDG<br>SFFLVSKLTVDKSRWQQGNVFSCSVMHEALHNHYTQKSLSLSPG |
| SEQ ID NO: 49 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGGGGGGDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTT<br>PPVLKSDGSFFLYSDLTVDKSRWQQGNVFSCSVMHEALHNHYTQKSLSLSPG |

TABLE 7

| | Fc construct 1 | Fc construct 2 | Fc construct 3 | Fc construct 4 |
|---|---|---|---|---|
| Spacer in Long Polypeptide (102/202 and 108/208) | SGGGSGGGS GGGSGGGSG GG (SEQ ID NO: 18) | SGGGSGGGS GGGSGGGSG GG (SEQ ID NO: 18) | GGGGGGGGG GGGGGG (SEQ ID NO: 26) | GGGGGGGGG GGGGGGGGG GG (SEQ ID NO: 27) |
| C-terminal Lysine in Long Polypeptide (102/202 and 108/208) | Y | N | N | N |
| C-terminal Lysine in Short Polypeptide (114/214 and 116/216) | Y | N | N | N |
| Amino acid mutations in 106/206 and 108/208 | S354C* T366W | S354C T366W | S354C E357K T366W | S354C E357K T366W |
| Amino acid mutations in 104/204 and 110/210 | D399K K409D | D399K K409D | D399K K409D | D399K K409D |
| Amino acid mutations in 114/214 and 116/216 | Y349C T366S L368A Y407V | Y349C T366S L368A Y407V | Y349C T366S L368A K370D Y407V | Y349C T366S L368A K370D Y407V |
| Figure | FIG. 1 | FIG. 1 | FIG. 1 | FIG. 2 |

*Sequence positions are numbered according to the Kabat numbering system (Kabat et al., Sequences of Proteins of Immunological Interest, National Institutes of Health, Bethesda, Md., ed 5, 1991).

Each of the long polypeptides 102 and 108 in Fc constructs 1-3 (FIG. 1) and long polypeptides 202 and 208 in Fc construct 4 (FIG. 2) contains two Fc domain monomers joined in a tandem series by way of a spacer. Table 8 below provides the sequences of the Fc domain monomers in the long polypeptides and the spacers in Fc constructs 1-4.

TABLE 8

| Fc construct 1 polypeptides 102/108 | |
|---|---|
| N-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVMHEALHNHYTQK SLSLSPGK (SEQ ID NO: 50) |
| spacer | SGGGSGGGSGGGSGGGSGGG (SEQ ID NO: 18) |
| C-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLKSDGSFFLYSDLTVDKSRWQQGNVFSCSVMHEALHNHYTQKS LSLSPGK (SEQ ID NO: 51) |
| **Fc construct 2 polypeptides 102/108** | |
| N-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPCRDELTKNQVSLWCLVKGFYPSDIAVEWESNG QPENNYKTTPPVLDSDGSFFLYSKLTVDKSRWQQGNVFSCSVMHEALHNHYTQK SLSLSPGK (SEQ ID NO: 50) |
| spacer | SGGGSGGGSGGGSGGGSGGG (SEQ ID NO: 18) |
| C-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLKSDGSFFLYSDLTVDKSRWQQGNVFSCSVMHEALHNHYTQKS LSLSPG (SEQ ID NO: 52) |

TABLE 8-continued

| | |
|---|---|
| **Fc construct 3 polypeptides 102/108** | |
| N-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPCRDKLTKNQVSLWCLVKGFYPSDIAVEWESNG QPENNYKTTPPVLDSDGSFFLYSKLTVDKSRWQQGNVFSCSVMHEALHNHYTQK SLSLSPGK (SEQ ID NO: 53) |
| spacer | GGGGGGGGGGGGGGG (SEQ ID NO: 26) |
| C-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLKSDGSFFLYSDLTVDKSRWQQGNVFSCSVMHEALHNHYTQKS LSLSPG (SEQ ID NO: 52) |
| **Fc construct 4 polypeptides 202/208** | |
| N-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPCRDKLTKNQVSLWCLVKGFYPSDIAVEWESNG QPENNYKTTPPVLDSDGSFFLYSKLTVDKSRWQQGNVFSCSVMHEALHNHYTQK SLSLSPGK (SEQ ID NO: 53) |
| spacer | GGGGGGGGGGGGGGGGGGGG (SEQ ID NO: 27) |
| C-terminal Fc domain monomer | DKTHTCPPCPAPELLGGPSVFLFPPKPKDTLMISRTPEVTCVVVDVSHEDPEVKFN WYVDGVEVHNAKTKPREEQYNSTYRVVSVLTVLHQDWLNGKEYKCKVSNKALPA PIEKTISKAKGQPREPQVYTLPPSRDELTKNQVSLTCLVKGFYPSDIAVEWESNGQ PENNYKTTPPVLKSDGSFFLYSDLTVDKSRWQQGNVFSCSVMHEALHNHYTQKS LSLSPG (SEQ ID NO: 52) |

Example 2. Expression of Fc Constructs

The expressed proteins were purified from the cell culture supernatant by Protein A-based affinity column chromatography, using a Poros MabCapture A (LifeTechnologies) column. Captured Fc constructs were washed with phosphate buffered saline (low-salt wash) and eluted with 100 mM glycine, pH 3. The eluate was quickly neutralized by the addition of 1 M TRIS pH 7.4 and sterile filtered through a 0.2 μm filter.

The proteins were further fractionated by ion exchange chromatography using Poros XS resin (Applied Biosciences). The column was pre-equilibrated with 50 mM MES, pH 6 (buffer A), and the sample was eluted with a step gradient using 50 mM MES, 400 mM sodium chloride, pH 6 (buffer B) as the elution buffer.

After ion-exchange, the target fraction was buffer exchanged into PBS buffer using a 10 kDa cutoff polyether sulfone (PES) membrane cartridge on a tangential flow filtration system. The samples were concentrated to approximately 30 mg/mL and sterile filtered through a 0.2 μm filter.

Example 3. Experimental Assays Used to Characterize Fc Constructs

Peptide and Glycopeptide Liquid Chromatography-MS/MS

The proteins were diluted to 1 μg/μL in 6M guanidine (Sigma). Dithiothreitol (DTT) was added to a concentration of 10 mM, to reduce the disulfide bonds under denaturing conditions at 65° C. for 30 min. After cooling on ice, the samples were incubated with 30 mM iodoacetamide (IAM) for 1 h in the dark to alkylate (carbamidomethylate) the free thiols. The protein was then dialyzed across a 10-kDa membrane into 25 mM ammonium bicarbonate buffer (pH 7.8) to remove IAM, DTT and guanidine. The protein was digested with trypsin in a Barocycler (NEP 2320; Pressure Biosciences, Inc.). The pressure was cycled between 20,000 psi and ambient pressure at 37° C. for a total of 30 cycles in 1 h. LC-MS/MS analysis of the peptides was performed on an Ultimate 3000 (Dionex) Chromatography System and an Q-Exactive (Thermo Fisher Scientific) Mass Spectrometer. Peptides were separated on a BEH PepMap (Waters) Column using 0.1% FA in water and 0.1% FA in acetonitrile as the mobile phases. The singly xylosylated linker peptide was targeted based on the doubly charged ion (z=2) m/z 842.5 with a quadrupole isolation width of ±1.5 Da.

Intact Mass Spectrometry

The protein was diluted to a concentration of 2 μg/μL in the running buffer consisting of 78.98% water, 20% acetonitrile, 1% formic acid (FA), and 0.02% trifluoroacetic acid. Size exclusion chromatography separation was performed on two Zenix-C SEC-300 (Sepax Technologies, Newark, DE) 2.1×350 mm in tandem for a total length column length of 700 mm. The proteins were eluted from the SEC column using the running buffer described above at a flow rate of 80 μL/min. Mass spectra were acquired on an QSTAR Elite (Applied Biosystems) Q-ToF mass spectrometer operated in positive mode. The neutral masses under the individual size fractions were deconvoluted using Bayesian peak deconvolution by summing the spectra across the entire width of the chromatographic peak.

Capillary Electrophoresis-Sodium Dodecyl Sulfate (CE-SDS) Assay

Samples were diluted to 1 mg/mL and mixed with the HT Protein Express denaturing buffer (PerkinElmer). The mixture was incubated at 40° C. for 20 min. Samples were diluted with 70 μL of water and transferred to a 96-well plate. Samples were analyzed by a Caliper GXII instrument (PerkinElmer) equipped with the HT Protein Express LabChip (PerkinElmer). Fluorescence intensity was used to calculate the relative abundance of each size variant.

Non-Reducing SDS-PAGE

Samples were denatured in Laemmli sample buffer (4% SDS, Bio-Rad) at 95° C. for 10 min. Samples were run on a Criterion TGX stain-free gel (4-15% polyacrylamide, Bio-Rad). Protein bands were visualized by UV illumination or Coommassie blue staining. Gels were imaged by ChemiDoc MP Imaging System (Bio-Rad). Quantification of bands was performed using Imagelab 4.0.1 software (Bio-Rad).

Complement Dependent Cytotoxicity (CDC)

CDC was evaluated by a colorimetric assay in which Raji cells (ATCC) were coated with serially diluted Rituximab, Fc construct 4, or IVIg. Human serum complement (Quidel) was added to all wells at 25% v/v and incubated for 2 h at 37° C. Cells were incubated for 12 h at 37° C. after addition of WST-1 cell proliferation reagent (Roche Applied Science). Plates were placed on a shaker for 2 min and absorbance at 450 nm was measured.

Example 4. O-Glycosylation and Proteolysis of Linker Serine Residues

O-Glycosylation at Linker Serine Residues

As described in Example 1, we designed the Fc constructs to increase folding efficiencies, to minimize uncontrolled association of subunits, and to generate compositions for pharmaceutical use that are substantially homogenous. In an effort to achieve these goals, we investigated different linkers between the two Fc domain monomers in the long polypeptide (102 and 108 in FIGS. 1; 202 and 208 in FIG. 2). Fc construct 1 and Fc construct 2 each has a serine-glycine linker (SGGGSGGGSGGGSGGGSGGG (SEQ ID NO: 18)) between the two Fc domain monomers in the long polypeptide.

Figure 3:
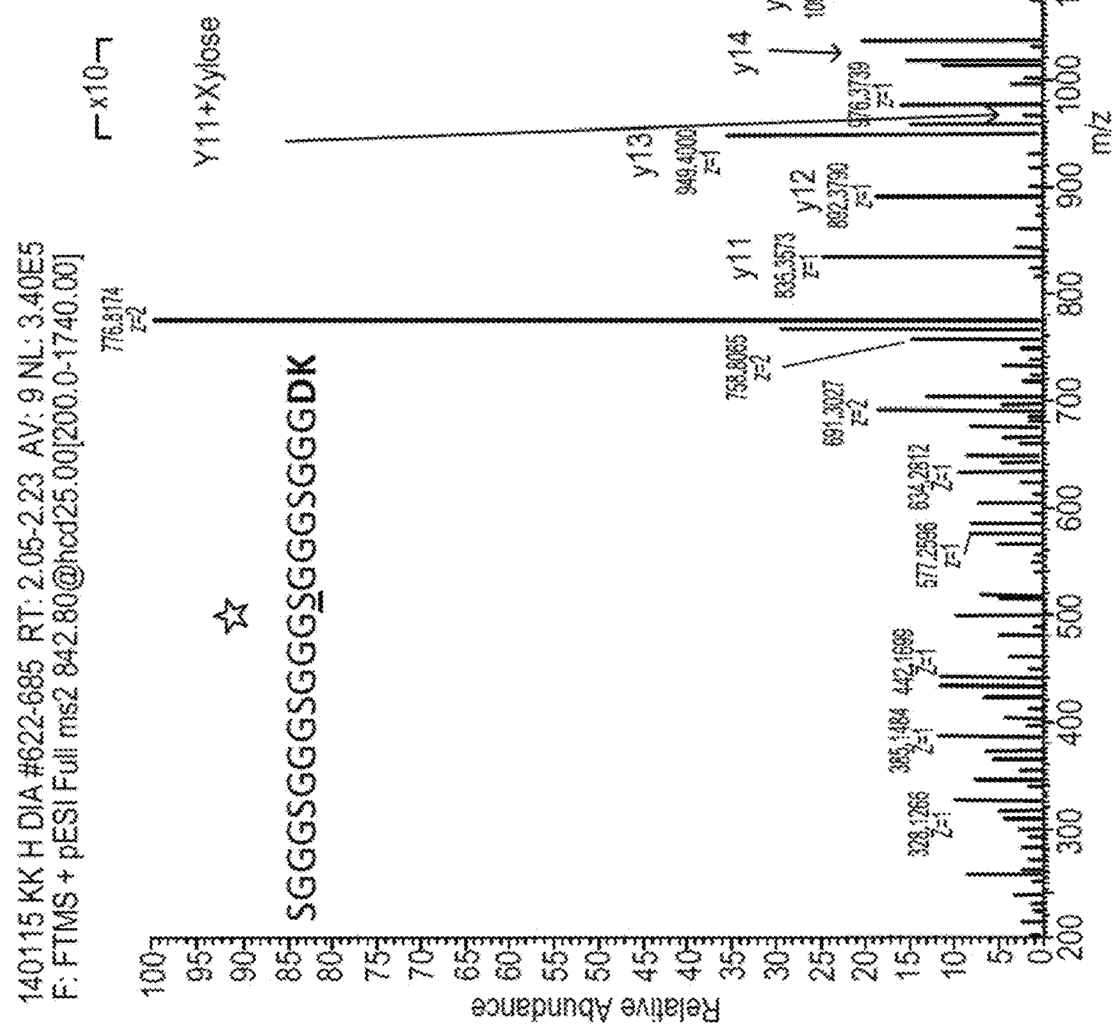
FIG. 3 shows identification of O-xylosylated Ser in the Fc construct 2 linker (SGGGSGGGSGGGSGGGSGGG (SEQ ID NO: 18)) by LC-MS/MS.

When Fc construct 2, which contains the linker SGGGSGGGSGGGSGGGSGGG (SEQ ID NO: 18) between the two Fc domain monomers in the long polypeptide, was analyzed by peptide LC-MS/MS, O-xylosylation was observed (FIG. 3). However, as fragments y2 to y9 do not contain xylose, the fifth serine in the linker is not O-xylosylated. There may be multiple sites that are O-xylosylated, but each peptide is only singly O-xylosylated. The extent and location of this post-translational modification may depend on both sequence and expression system.

Figure 4:
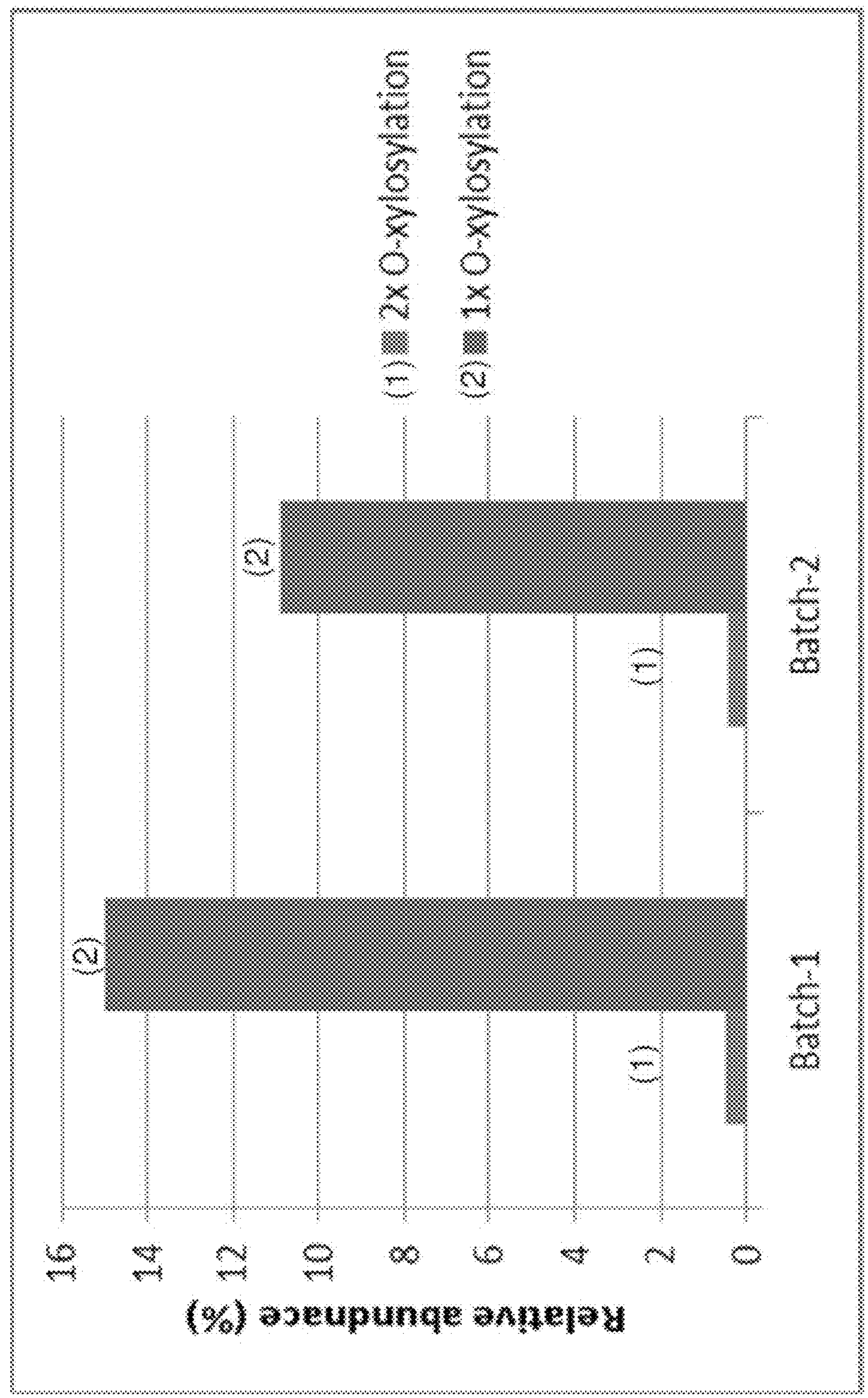
FIG. 4 shows the abundance of linker O-xylosylation in an Fc construct having two Fc domains (the Fc construct shown in FIG. 13) as determined by LC-MS/MS.

Likewise, O-xylosylation was observed in an Fc construct having two Fc domains (the Fc construct shown in FIG. 13) containing the same $(SG_3)_5$ linker (FIG. 4). Modification was observed at multiple sites, with up to two xylose modifications in each linker. Moreover, the level of modification was variable between batches.

After observing O-xylosylation at serine residues in the serine-glycine linker, we investigated alternative linkers that contained only glycine residues in order to further optimize linker sequence and improve the homogeneity of the Fc construct. As a result, an all-glycine spacer was selected for use in Fc construct 3 and Fc construct 4. Fc construct 3 has a 15-mer all-glycine spacer (GGGGGGGGGGGGGGG (SEQ ID NO: 26)) between the two Fc domain monomers in the long polypeptide. Fc construct 4 has a 20-mer all-glycine spacer (GGGGGGGGGGGGGGGGGGGG (SEQ ID NO: 27)) between the two Fc domain monomers in the long polypeptide.

Proteolysis at Linker Serine Residues

Figure 5:
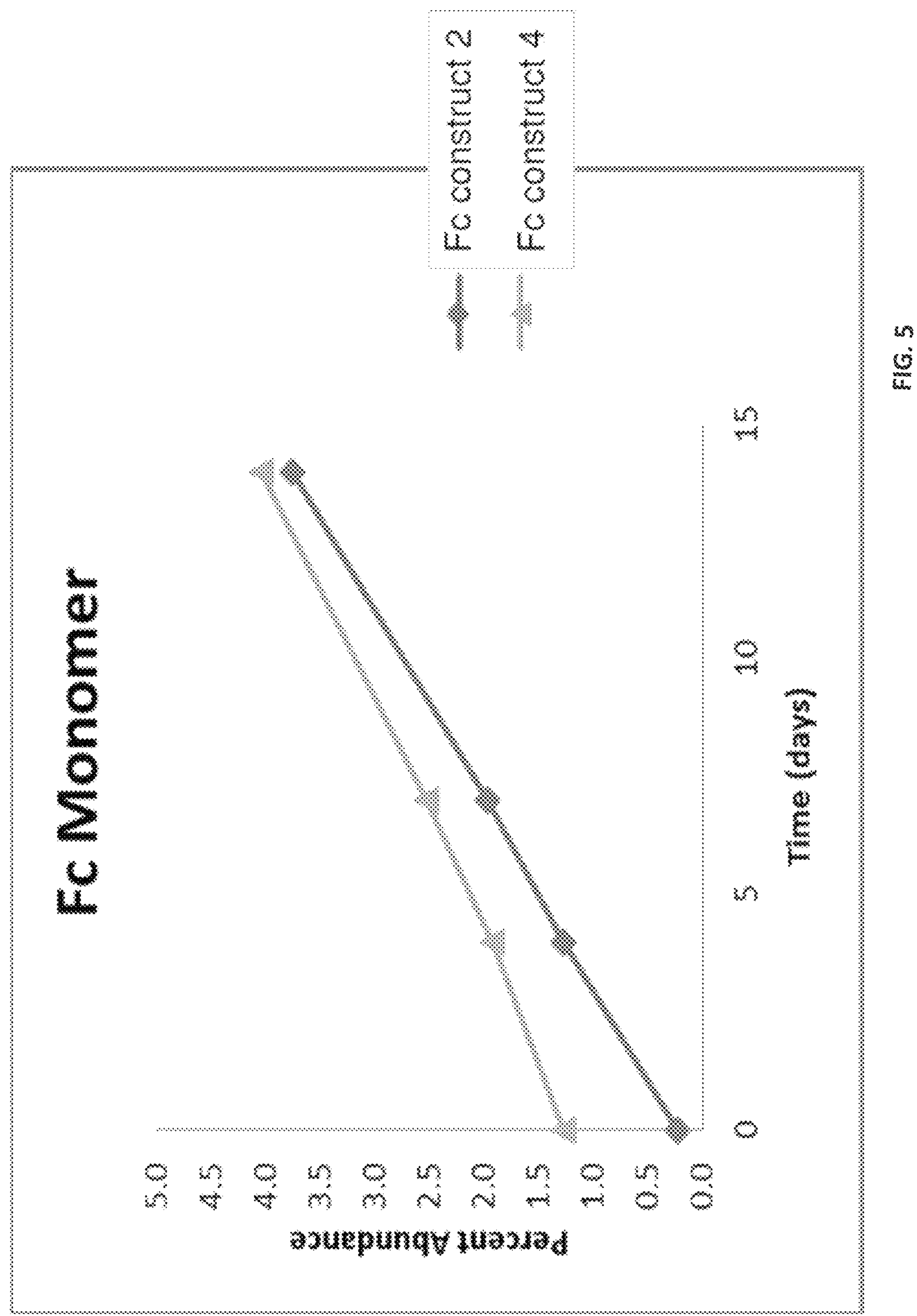
FIG. 5 shows the formation of monomeric Fc species from Fc constructs 2 and 4 upon storage at 45° C. as determined by CE-SDS.

In some embodiments, Fc constructs were found to undergo proteolysis in the linkers upon incubation at 45° C. in phosphate buffered saline, generating monomeric Fc products. The rate of monomer formation in Fc construct 2 (which contains the linker SGGGSGGGSGGGSGGGSGGG in each of the polypeptides 102 and 108) was faster than in Fc construct 4 (which contains the all-glycine spacer GGGGGGGGGGGGGGGGGGGG in each of the polypeptides 202 and 208) (FIG. 5), indicating that the all-glycine spacer is less susceptible to proteolysis. This effect was found to be general amongst branched Fc constructs having three Fc domains for multiple linker lengths; all-glycine spacers were proteolyzed more slowly than serine-glycine linkers (Table 9).

TABLE 9

| Linker Sequence | Rate of monomer formation (% monomer/day) |
|---|---|
| $G_8$ | 0.17 |
| $G_{15}$ | 0.21 |
| $G_{20}$ | 0.24 |
| $(SG_4)_4$ | 0.33 |
| $(S3_2)_5$ | 0.34 |

Figure 6:
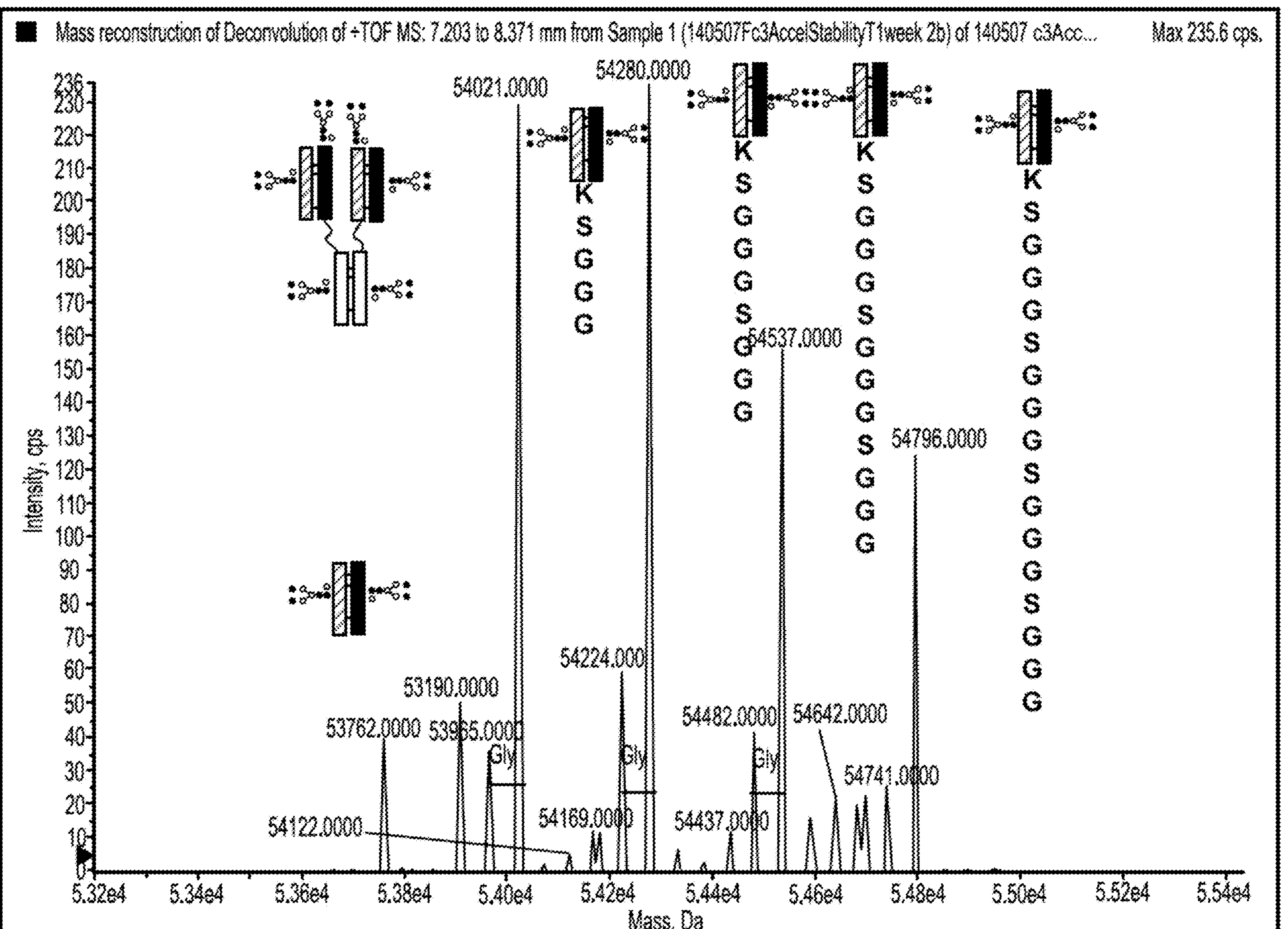
FIG. 6 shows proteolysis products of Fc construct 2 upon two weeks of storage at 45° C. as determined by LC-MS.
Figure 7:
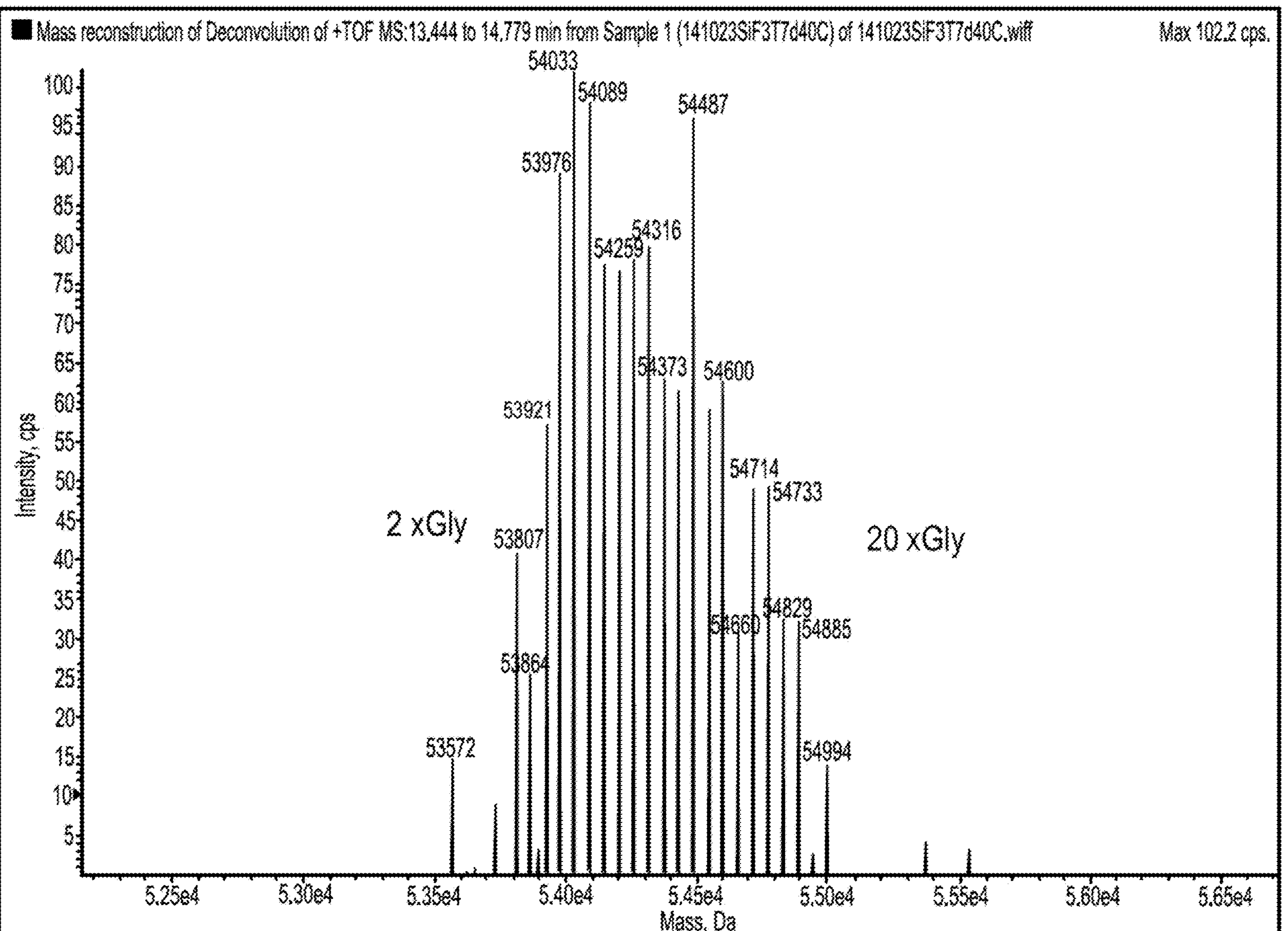
FIG. 7 shows proteolysis products of Fc construct 4 upon two weeks of storage at 45° C. as determined by LC-MS.

Furthermore, analyses by mass spectrometry of the monomeric Fc products in Fc construct 2, with an $(SG_3)_5$ linker in each of polypeptides 102 and 108, demonstrated that the dominant products were cleaved to the N-terminal side of serine, with all but the first serines susceptible to proteolysis (FIG. 6). In contrast, the cleavage products of Fc construct 4, with a $G_{20}$ spacer in each of polypeptides 202 and 208, did not show strong specificity for any particular spacer residue (FIG. 7). Together, these results indicated that the all-glycine spacer had a decreased susceptibility to proteolysis. To limit proteolysis, a serine-free spacer may be used, such as the $G_{20}$ spacer used in Fc construct 4. Use of such a glycine spacer substantially improves the homogeneity of the final Fc construct composition.

Example 5. Optimization of the Linker Length

To further optimized homogeneity, linker length was explored by preparing variations on the Fc construct 2 sequence in which the $(SG_3)_5$ linker was replaced with a $G_8$, $G_{15}$, or $G_{20}$ spacer. Analyses by in vitro assays indicated that the linker length impacted biological activity, presumably by altering the ability of the Fc construct to interact with Fcγ receptors.

Figure 8:
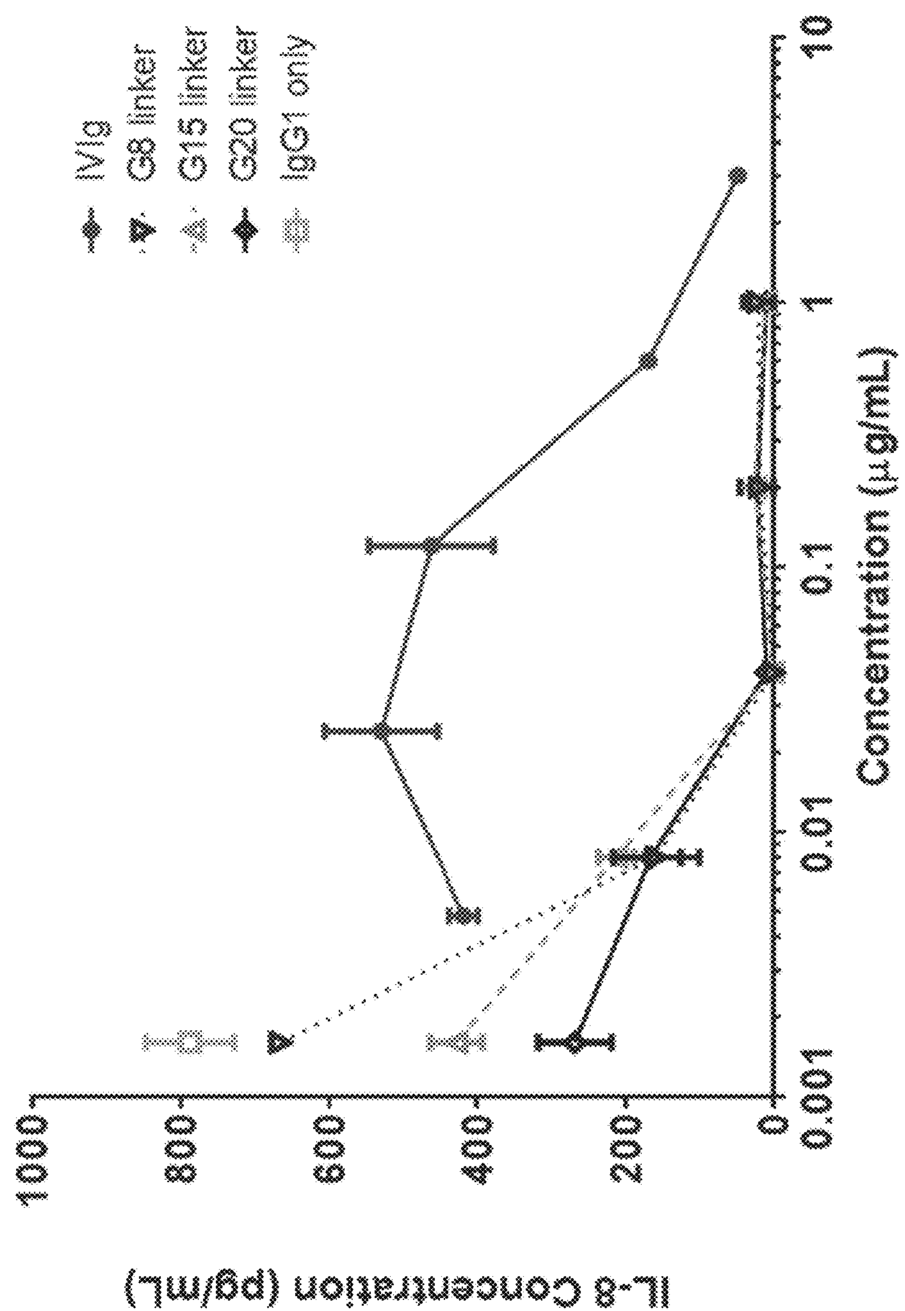
FIG. 8 shows the inhibition of IL-8 release by THP-1 cells by Fc construct 2 with varying linker lengths.

Inhibition of IL-8 release by THP-1 cells stimulated by plate-bound IgG was found to depend on linker length (FIG. 8). Inhibition at low Fc construct concentrations followed the order $G_8<G_{15}<G_{20}$, with Fc construct 2 having a $G_{20}$ spacer most strongly inhibiting IL-8 release by THP-1 cells.

Figure 9:
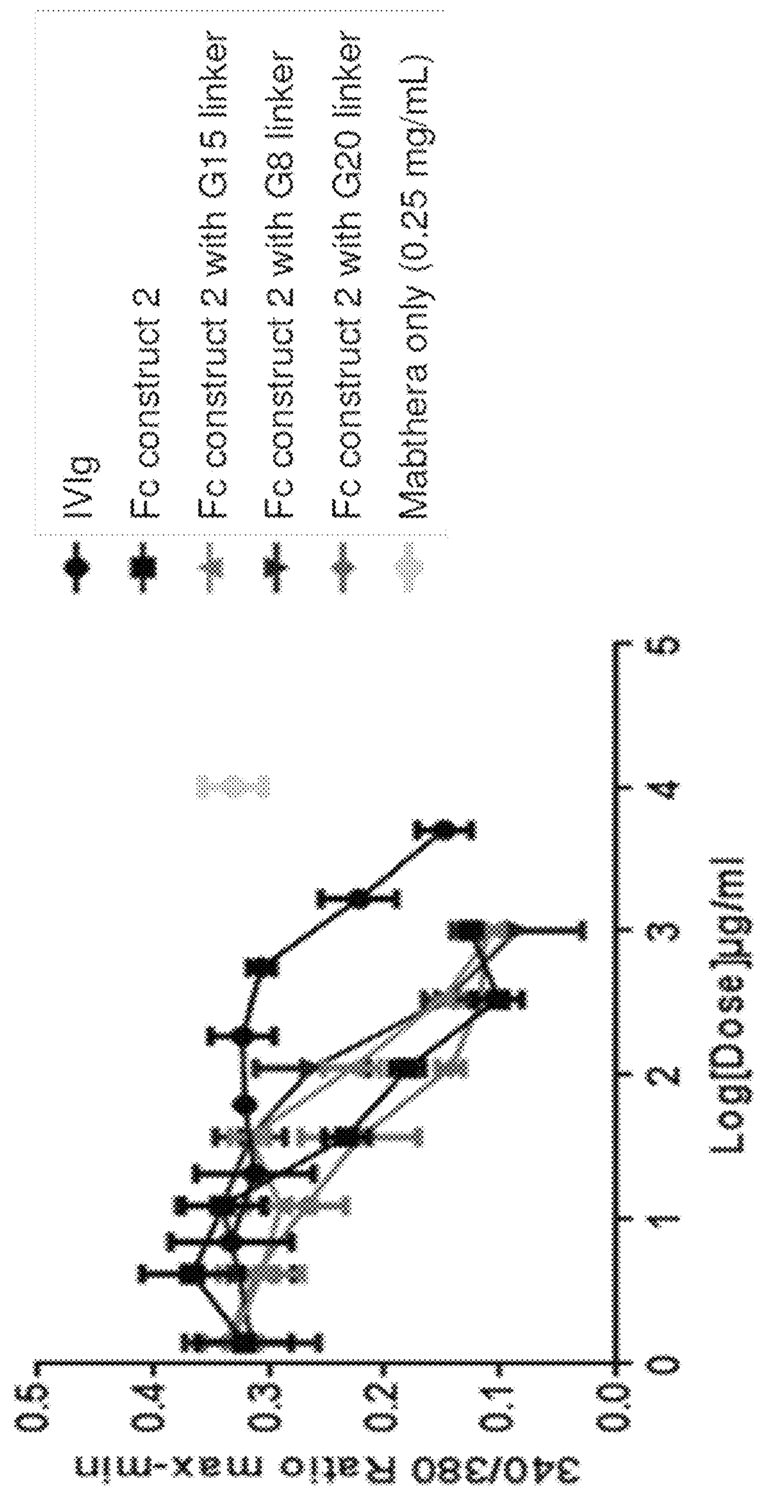
FIG. 9 shows the inhibition of calcium flux in neutrophils by Fc construct 2 with varying linker lengths.

Further, the inhibition of calcium flux in neutrophils was found to be dependent upon linker length (FIG. 9). Inhibition followed the order $G_8<G_{15}<G_{20}$, with Fc construct 2 having the $G_{20}$ spacer exhibiting the greatest inhibition of calcium flux in neutrophils.

Example 6. Optimization of Heterodimerization by Knob-into-Hole Technology

Figure 10:
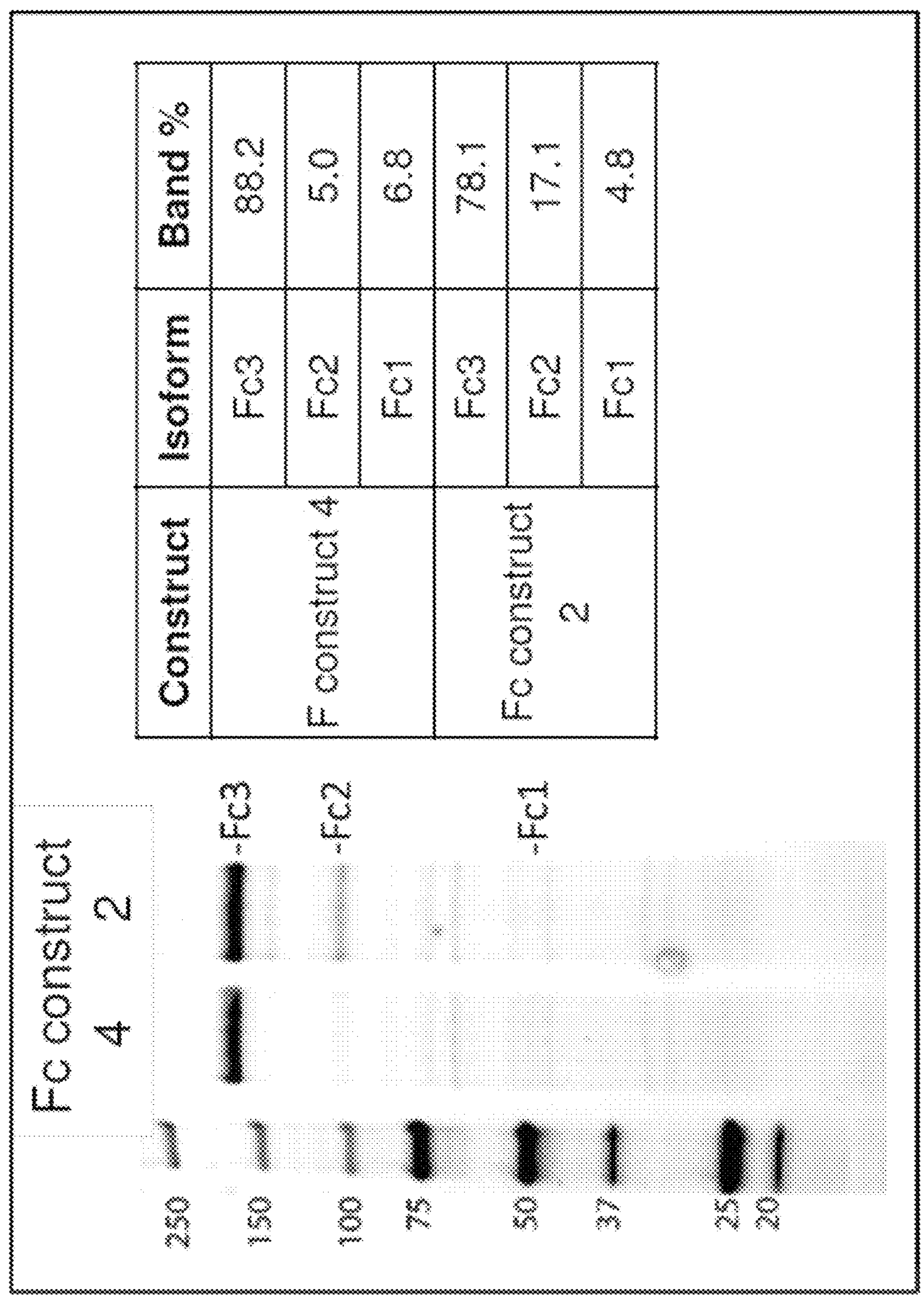
FIG. 10 shows the size distribution by non-reducing SDS-PAGE of Fc construct 2 and Fc construct 4 in unpurified media.

Plasmids expressing the Fc construct 2 long and short polypeptides (polypeptides 102, 108, 114, and 116 in FIG. 1) or Fc construct 4 long and short polypeptides (polypeptides 202, 208, 214, and 216 in FIG. 2) were transfected into HEK293 cells. Following seven days in culture, cells were cleared by centrifugation and raw media supernatants were separated by non-reducing SDS-PAGE (FIG. 10). Densitometric analysis of the visualized protein bands revealed that Fc construct 2 having three Fc domains and Fc construct 4 having three Fc domains (Fc3) are expressed at similar levels. However, the constructs for Fc construct 2 expressed significantly higher levels of contaminating dimer (Fc2) species (FIG. 10). Both sets of constructs expressed similar levels of the monomer species (Fc1). Additional bands present in the image represent media components that are present in mock transfected controls.

These results indicate that having both electrostatic steering mutations that promote heterodimerization and knob-into-hole mutations that promote heterodimerization in the "branch" subunits (e.g., Fc domain monomers 106, 114, 112, and 116 in FIG. 1; Fc domain monomers 206, 214, 212, and 216 in FIG. 2) enhances formation of a heterodimeric Fc domain in an Fc construct, optimizes the assembly of an Fc construct having three Fc domains, and improves the homogeneity of the composition containing the Fc construct.

Example 7. Electrostatic Steering for Control of Homodimerization

To minimize off-register association of subunits, which generates unwanted high molecular weight oligomers and multimers, mutations that favor heterodimerization (e.g., knobs and holes) were introduced into the "branch" subunits (e.g., Fc domain monomers 106, 112, 114, and 116 in FIG. 1; Fc domain monomers 206, 212, 214, and 216 in FIG. 2). These amino acid substitutions preserve the attraction of knobs subunits (e.g., Fc domain monomers 106 and 112 in FIG. 1; Fc domain monomers 206 and 212 in FIG. 2) for the holes counterparts (e.g., Fc domain monomers 114 and 116 in FIG. 1; Fc domain monomers 214 and 216 in FIG. 2) and at the same time hinder association between knobs subunits. Because the knobs mutations also inhibit assembly with wild-type Fc sequences, it calls into question the necessity of including additional mutations to further reduce affinity of the "stem" Fc subunits (e.g., Fc domain monomers 104 and 110 in FIG. 1; Fc domain monomers 204 and 210 in FIG. 2) for the knobs and holes "branch" subunits. To address this question, an Fc construct long polypeptide was generated which contained a wild-type Fc domain monomer sequence in the carboxyl terminal "stem" subunit and an Fc domain monomer carrying knob mutations in the amino terminal "branch" subunit. The corresponding short polypeptide was the Fc domain monomer carrying hole mutations. This Fc construct is based on the sequences of the polypeptides in Fc construct 2, but has a wild-type Fc domain monomer sequence in the carboxyl terminal "stem" subunit in each of the long polypeptides.

Figure 11:
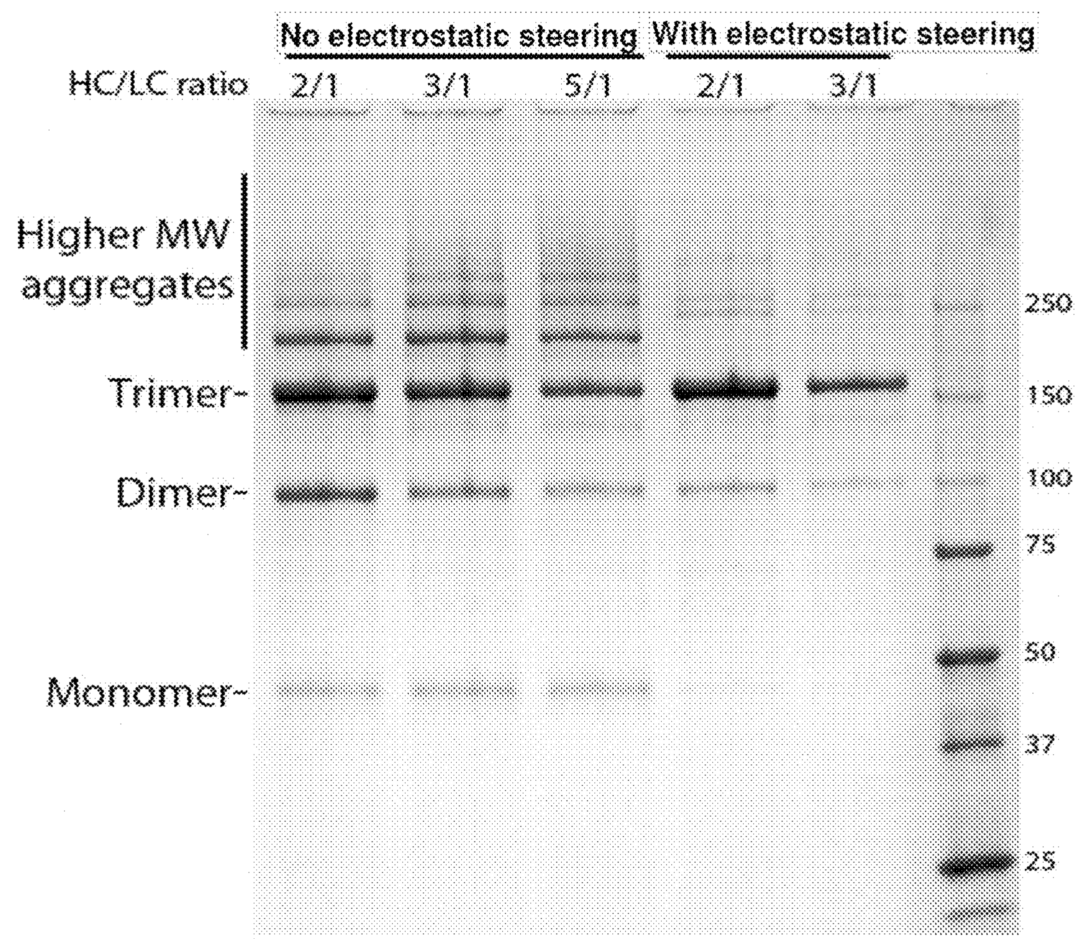
FIG. 11 shows the expression and assembly of Fc construct 2 ("With electrostatic steering") and another Fc construct having three Fc domains but without electrostatic steering mutations in the "stem" subunits ("No electrostatic steering").

HEK293 cells were co-transfected with plasmids expressing Fc construct 2 (which has homodimerizing electrostatic steering mutations in the Fc domain monomer in the carboxyl terminal "stem" subunit in each of the long polypeptides; see Tables 5 and 6 in Example 1), or an Fc construct based on Fc construct 2 in which the Fc domain monomer in the carboxyl terminal "stem" subunit in each of the long polypeptides was replaced with a wild-type Fc domain monomer sequence (SEQ ID NO: 42) (as described above). Following seven days in culture, cells were cleared by centrifugation and raw media supernatants were separated by non-reducing SDS-PAGE. Imaging of stained proteins revealed that the Fc construct without electrostatic steering mutations in the "stem" subunits (labeled "No electrostatic steering" (lanes 1-3) in FIG. 11) contained much higher levels of monomer (Fc1) and dimer (Fc2) than the Fc construct 2 counterpart (labeled "With electrostatic steering" (lanes 4 and 5) in FIG. 11). Furthermore, a much larger number of bands higher in molecular weight than the trimer can be detected (lanes 1-3 in FIG. 11).

These results confirm that having electrostatic steering mutations that promote homodimerization in the "stem" subunits (e.g., Fc domain monomers 104 and 110 in FIG. 1; Fc domain monomers 204 and 210 in FIG. 2) further enhances formation of a homodimeric Fc domain in the Fc construct, optimizes the assembly of an Fc construct having three Fc domains, and improves the homogeneity of the composition containing the Fc construct.

Figure 12:
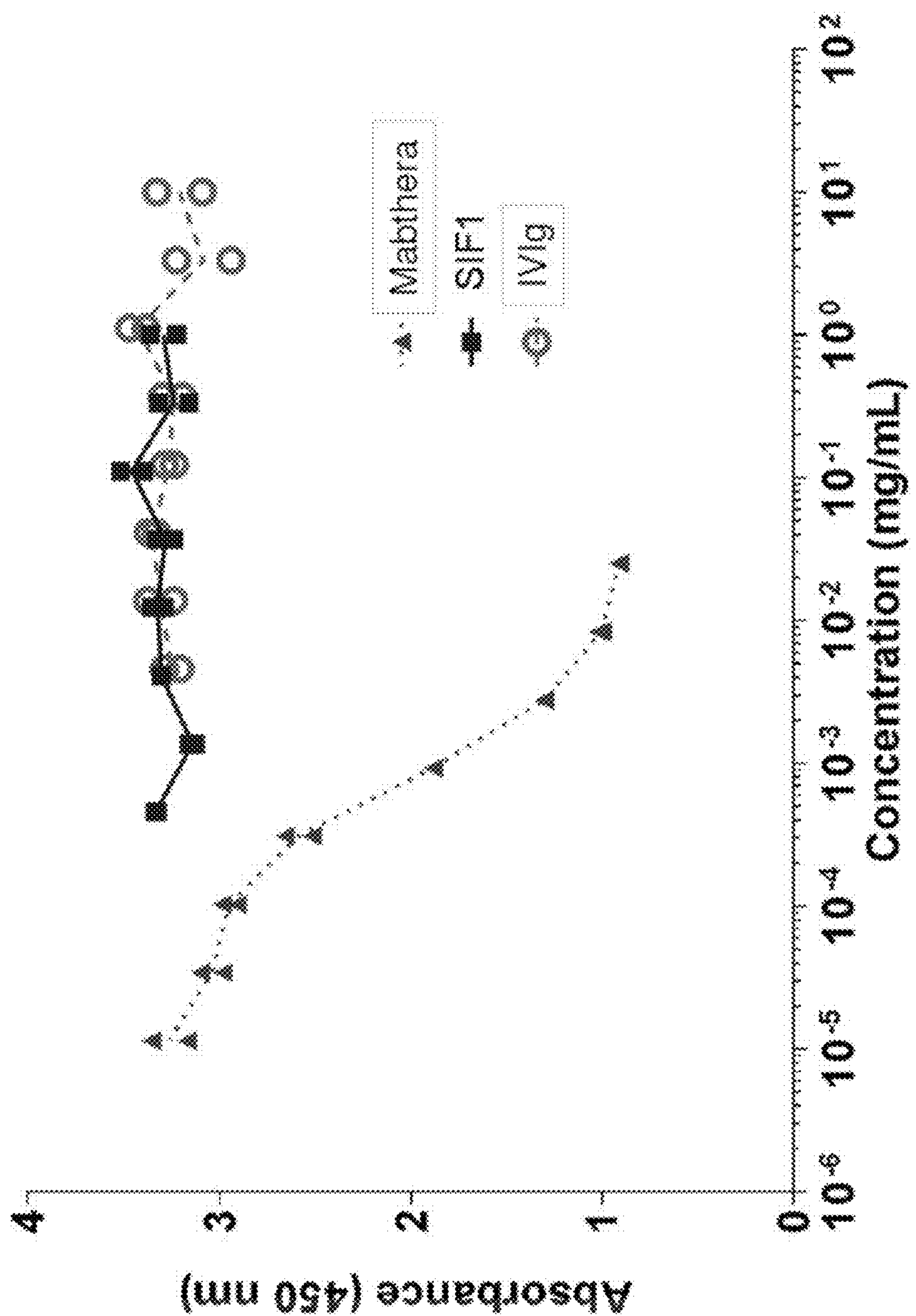
FIG. 12 shows that the removal of the C-terminal lysine to generate Fc construct 2 did not induce complement dependent cytotoxicity (CDC) in vitro.

Example 8. Optimization of Composition Homogeneity by Elimination of C-Terminal Lysine Residues The C-terminal lysine residue of immunoglobulins is highly conserved across many species. In some instances, C-terminal lysines in polypeptides are removed by the cellular machinery during protein production. We aimed to further improve the uniformity of the Fc constructs in the composition and to achieve a more homogenous composition containing an Fc construct described herein by removing the C-terminal lysine from the each of the polypeptides in the Fc construct. Fc construct 2 does not contain any C-terminal lysine residues in either its long polypeptides (102 and 108; see Example 1, Tables 5-7; FIG. 1) or short polypeptides (114 and 116). FIG. 12 shows that the removal of the C-terminal lysine to generate Fc construct 2 did not induce complement dependent cytotoxicity (CDC) in vitro. Thus, by removal of the C-terminal lysine residue, we were able to improve homogeneity of the Fc construct pharmaceutical composition without triggering adverse immunological side effects.

Example 9. Design of Fc Constructs Having I253 and/or R292 Amino Acid Modifications Fc constructs having an altered (e.g., increased) half-life were designed based on construct 4 (M230) and included amino acid modifications (e.g., single mutations or combinations of mutations) that alter binding affinity to FcRn (e.g., reduce binding to FcRn, e.g., by including an amino acid modification at position I253, e.g., I253A) and/or that alter binding affinity to FcγRIIb (e.g., reduced binding to FcγRIIb, e.g., by including an amino acid modification at position R292, e.g., R292P) (FIGS. 18A-18O).

Six Fc constructs (FIGS. 2, 18B, 18C, 18L, 18N, and 18O) were prepared, each including a long polypeptide including two Fc domain monomers separated by a spacer, e.g., an all-glycine linker, e.g., GGGGGGGGGGGGGGGGGGGG (SEQ ID NO: 23) and a short polypeptide including a single Fc domain monomer, and having different valency of amino acid modifications at positions I253 (e.g., I253A) and/or R292 (e.g., R292P). Each Fc construct is based on the IgG1 Fc sequence, with the inclusion of engineered cavity, engineered protuberance, and/or electrostatic steering modifications to control assembly of the polypeptides. DNA sequences encoding the long and short polypeptides were optimized for expression in mammalian cells and cloned into the pcDNA3.4 mammalian expression vector. The DNA plasmid constructs were transfected via liposomes into human embryonic kidney (HEK) 293 cells.

For each Fc construct, the long and short polypeptides, when co-expressed, produce a branched molecule containing three Fc domains, with the C-terminal Fc monomers of the long polypeptides specifically associating with each other to form one C-terminal Fc domain and with the N-terminal Fc monomers of the long polypeptides specifically associating with the short polypeptides to form two N-terminal Fc domains. Fc constructs 12-15, 24, 26, and 27 and their design are described in Table 10 and FIGS. 2 and 18B-18O. The sequences utilized in each Fc construct are shown in Table 11, where each I253A and/or R292P amino acid modification are bolded and underlined.

In construct 4, each of the long polypeptides contains one Fc domain monomer having charged amino acids (D399K and K409D) at the $C_H3$-$C_H3$ interface joined by way of a linker to a protuberance-containing (formed by the modifications S354C and T366W) Fc domain monomer. The protuberance-containing Fc domain monomer has an amino acid modification (E357K) that enhances assembly of the Fc domain. The short polypeptides each have a cavity-containing (formed by the modifications Y349C/T366S/L368A/Y407V) Fc domain monomer. The short polypeptides also have an amino acid modification (K370D) that enhance assembly of the Fc domains. Construct 4 is formed by expressing a first and second polypeptide having the amino acid sequence of SEQ ID NO: 49 and a third and fourth polypeptide having the amino acid sequence of SEQ ID NO: 61.

Constructs 13-27 (FIGS. 18A-18O) are identical to construct 4, except for certain modifications at positions I253 and/or R292, as described herein. Construct 5 is formed by expressing a first and second polypeptide having the amino acid sequence of SEQ ID NO: 62 and a third and fourth polypeptide having the amino acid sequence of SEQ ID NO: 61. Construct 6 is formed by expressing a first and second polypeptide having the amino acid sequence of SEQ ID NO: 64 and a third and fourth polypeptide having the amino acid sequence of SEQ ID NO: 57. Construct 7 is formed by expressing a first and second polypeptide having the amino acid sequence of SEQ ID NO: 65 and a third and fourth polypeptide having the amino acid sequence of SEQ ID NO: 57. Construct 8 is formed by expressing a first and second polypeptide having the amino acid sequence of SEQ ID NO: 66 and a third and fourth polypeptide having the amino acid sequence of SEQ ID NO: 61. Construct 9 is formed by expressing a first and second polypeptide having the amino acid sequence of SEQ ID NO: 67 and a third and fourth polypeptide having the amino acid sequence of SEQ ID NO: 61. Construct 10 is formed by expressing a first and second polypeptide having the amino acid sequence of SEQ ID NO: 68 and a third and fourth polypeptide having the amino acid sequence of SEQ ID NO: 57. Construct 11 is formed by expressing a first and second polypeptide having the amino acid sequence of SEQ ID NO: 69 and a third and fourth polypeptide having the amino acid sequence of SEQ ID NO: 57. Construct 12 is formed by expressing a first and second polypeptide having the amino acid sequence of SEQ ID NO: 71 and a third and fourth polypeptide having the amino acid sequence of SEQ ID NO: 70. Construct 13 is formed by expressing a first and second polypeptide having the amino acid sequence of SEQ ID NO: 72 and a third and fourth polypeptide having the amino acid sequence of SEQ ID NO: 70. Construct 14 is formed by expressing a first and second polypeptide having the amino acid sequence of SEQ ID NO: 74 and a third and fourth polypeptide having the amino acid sequence of SEQ ID NO: 73. Construct 15 is formed by expressing a first and second polypeptide having the amino acid sequence of SEQ ID NO: 75 and a third and fourth polypeptide having the amino acid sequence of SEQ ID NO: 73. Construct 16 is formed by expressing a first and second polypeptide having the amino acid sequence of SEQ ID NO: 76 and a third and fourth polypeptide having the amino acid sequence of SEQ ID NO: 70. Construct 17 is formed by expressing a first and second polypeptide having the amino acid sequence of SEQ ID NO: 77 and a third and fourth polypeptide having the amino acid sequence of SEQ ID NO: 70. Construct 18 is formed by expressing a first and second polypeptide having the amino acid sequence of SEQ ID NO: 78 and a third and fourth polypeptide having the amino acid sequence of SEQ ID NO: 73. Construct 19 is formed by expressing a first and second polypeptide having the amino acid sequence of SEQ ID NO: 79 and a third and fourth polypeptide having the amino acid sequence of SEQ ID NO: 73.

TABLE 10

Fc constructs having I253 and/or R292 amino acid modifications

Figure 18C:
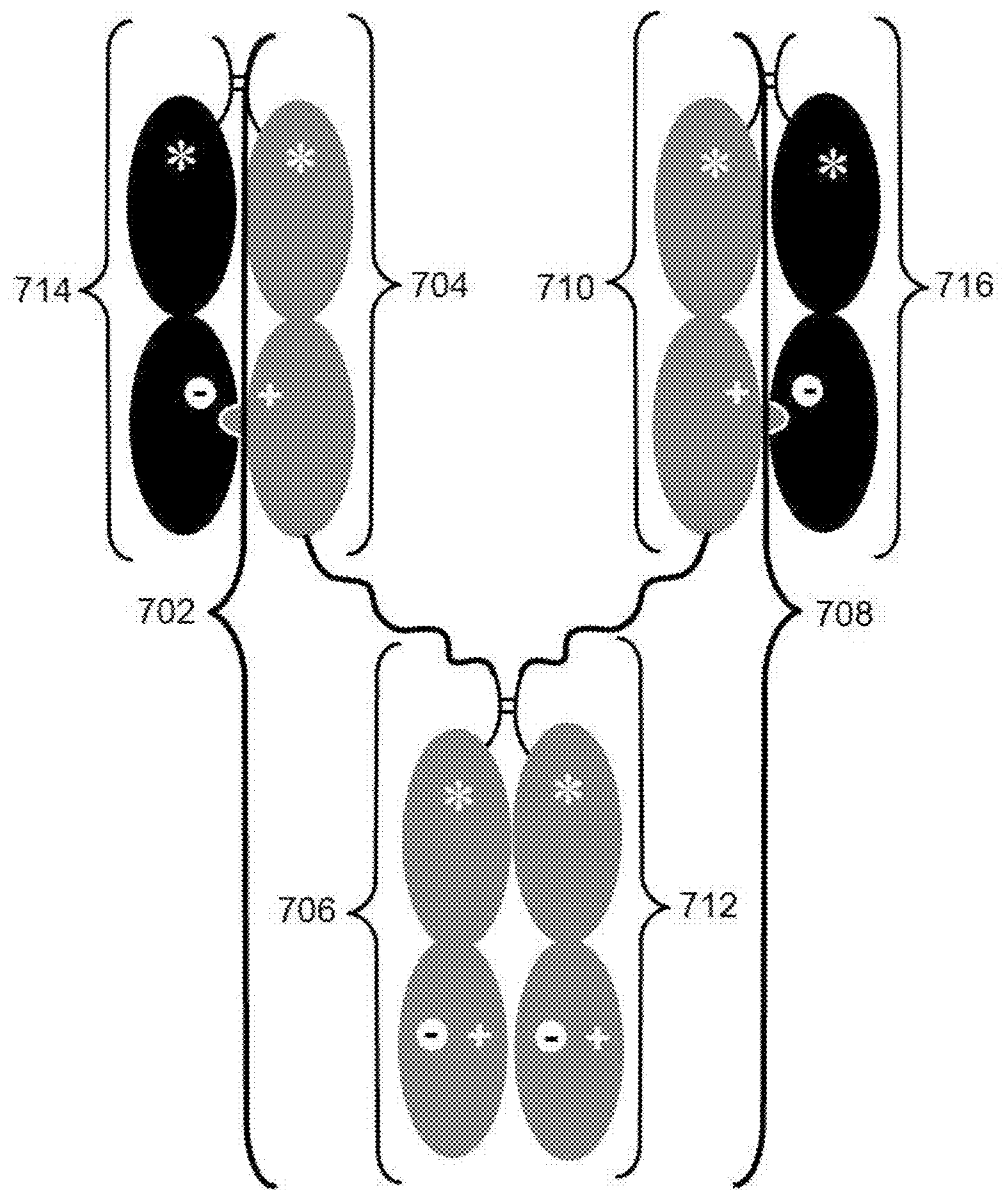
FIG. 18C is an illustration of an Fc construct (construct 7) containing three Fc domains formed from four polypeptides. Each of the first polypeptide (702) and the second polypeptide (708) contains one Fc domain monomer containing charged amino acids at the $C_H3$-$C_H3$ interface than the wild-type sequence (706 and 712, respectively) joined by way of a linker to a protuberance-containing Fc domain monomer (704 and 710, respectively). The third and fourth polypeptides (714 and 716, respectively) each contain a cavity-containing Fc domain monomer. Each of the first polypeptide (702) and the second polypeptide (708) also contain electrostatic steering mutations, e.g., E357K. Similarly, the third and fourth polypeptides (714 and 716, respectively) each contain electrostatic steering mutations, e.g., K370D. 704, 706, 710, 712, 714, and 716 each contain the amino acid modification I253A, which is represented as an asterisk. 702 and 708 each have the amino acid sequence of SEQ ID NO: 65. 714 and 716 each have the amino acid sequence of SEQ ID NO: 63.
Figure 18D:
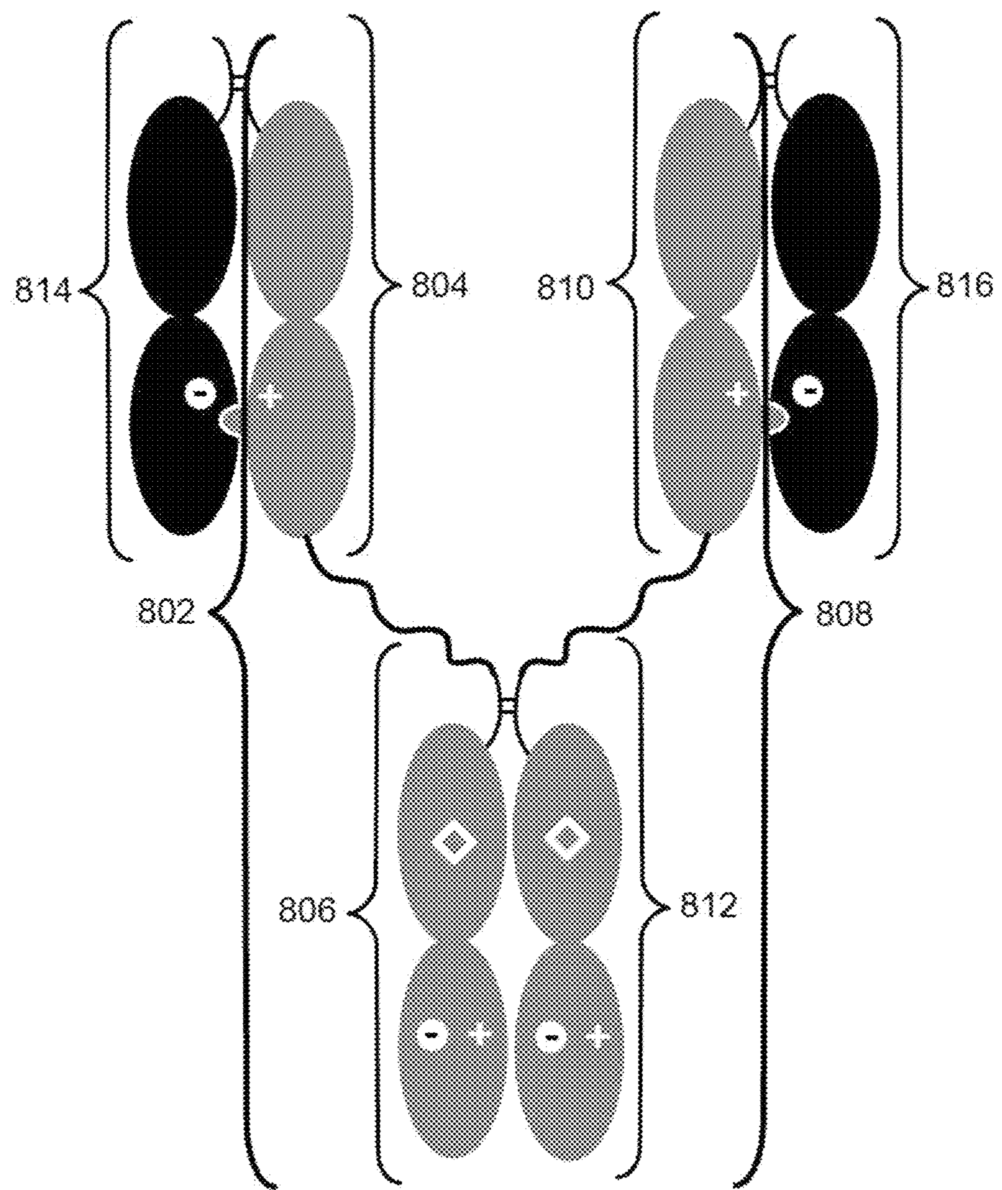
FIG. 18D is an illustration of an Fc construct (construct 8) containing three Fc domains formed from four polypeptides. Each of the first polypeptide (802) and the second polypeptide (808) contains one Fc domain monomer containing charged amino acids at the $C_H3$-$C_H3$ interface than the wild-type sequence (806 and 812, respectively) joined by way of a linker to a protuberance-containing Fc domain monomer (804 and 810, respectively). The third and fourth polypeptides (814 and 816, respectively) each contain a cavity-containing Fc domain monomer. Each of the first polypeptide (802) and the second polypeptide (808) also contain electrostatic steering mutations, e.g., E357K. Similarly, the third and fourth polypeptides (814 and 816, respectively) each contain electrostatic steering mutations, e.g., K370D. 806 and 812 each contain the amino acid modification R292P, which is represented as a diamond. 802 and 808 each have the amino acid sequence of SEQ ID NO: 66. 814 and 816 each have the amino acid sequence of SEQ ID NO: 61.
Figure 18E:
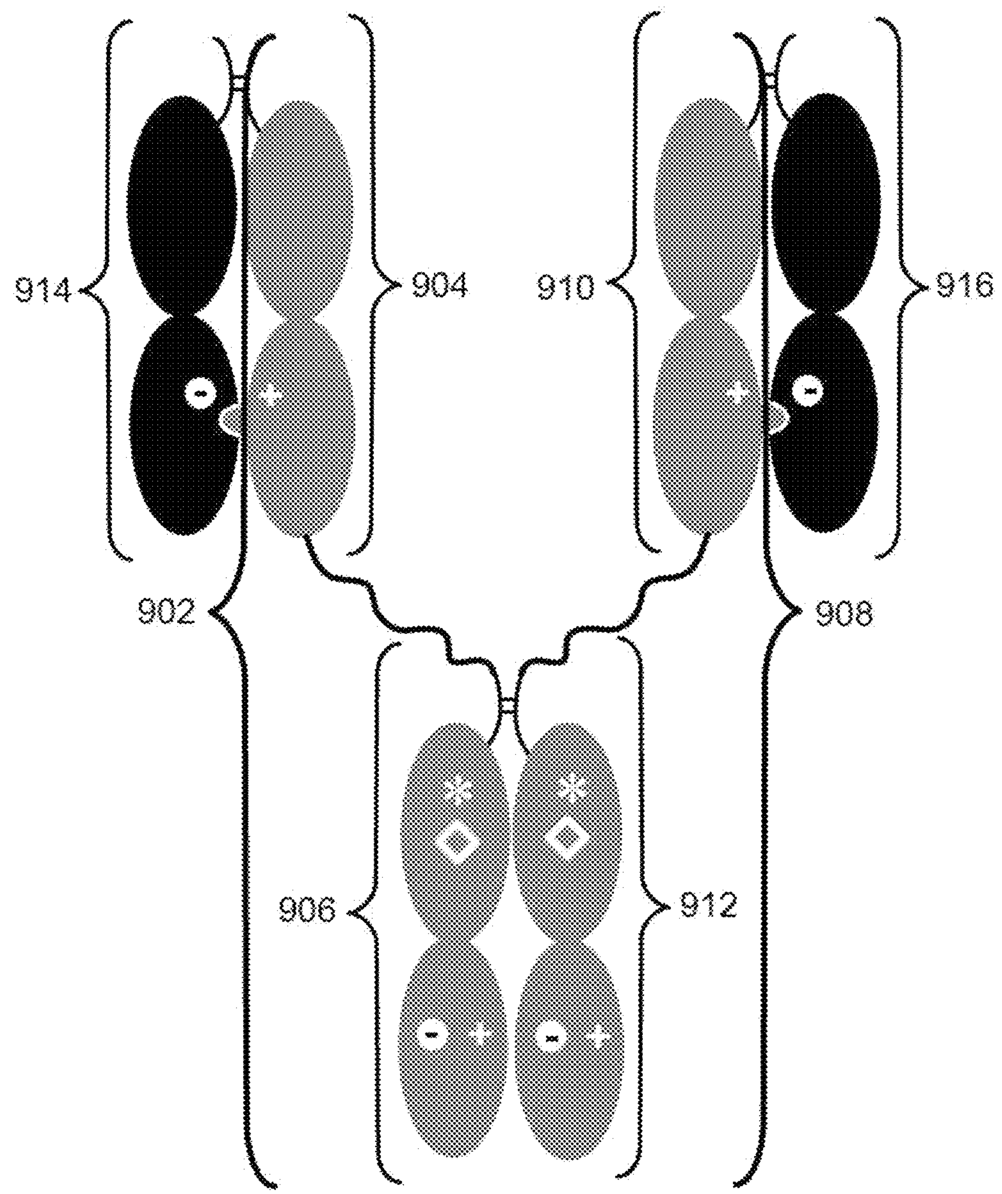
FIG. 18E is an illustration of an Fc construct (construct 9) containing three Fc domains formed from four polypeptides. Each of the first polypeptide (902) and the second polypeptide (908) contains one Fc domain monomer containing charged amino acids at the $C_H3$-$C_H3$ interface than the wild-type sequence (906 and 912, respectively) joined by way of a linker to a protuberance-containing Fc domain monomer (904 and 910, respectively). The third and fourth polypeptides (914 and 916, respectively) each contain a cavity-containing Fc domain monomer. Each of the first polypeptide (902) and the second polypeptide (908) also contain electrostatic steering mutations, e.g., E357K. Similarly, the third and fourth polypeptides (914 and 916, respectively) each contain electrostatic steering mutations, e.g., K370D. 906 and 912 each contain the amino acid modifications I253A, which is represented as an asterisk, and R292P, which is represented as a diamond. 902 and 908 each have the amino acid sequence of SEQ ID NO: 67. 914 and 916 each have the amino acid sequence of SEQ ID NO: 61.
Figure 18F:
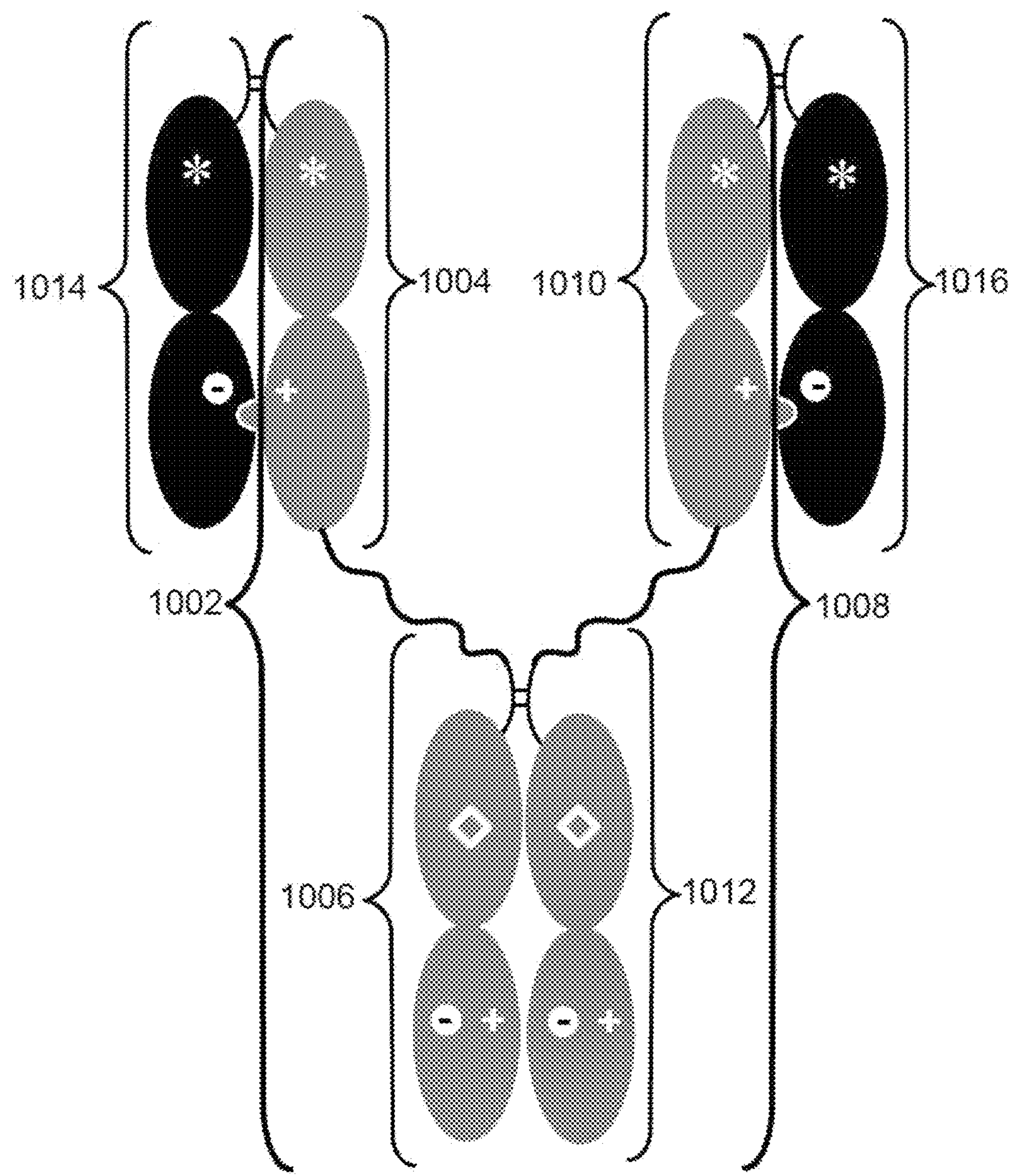
FIG. 18F is an illustration of an Fc construct (construct 10) containing three Fc domains formed from four polypeptides. Each of the first polypeptide (1002) and the second polypeptide (1008) contains one Fc domain monomer containing charged amino acids at the $C_H3$-$C_H3$ interface than the wild-type sequence (1006 and 1012, respectively) joined by way of a linker to a protuberance-containing Fc domain monomer (1004 and 1010, respectively). The third and fourth polypeptides (1014 and 1016, respectively) each contain a cavity-containing Fc domain monomer. Each of the first polypeptide (1002) and the second polypeptide (1008) also contain electrostatic steering mutations, e.g., E357K. Similarly, the third and fourth polypeptides (1014 and 1016, respectively) each contain electrostatic steering mutations, e.g., K370D. 1006 and 1012 each contain the amino acid modification R292P, which is represented as a diamond, and 1004, 1010, 1014, and 1016 each contain the amino acid modification I253A, which is represented as an asterisk. 1002 and 1008 each have the amino acid sequence of SEQ ID NO: 68. 1014 and 1016 each have the amino acid sequence of SEQ ID NO: 63.
Figure 18G:
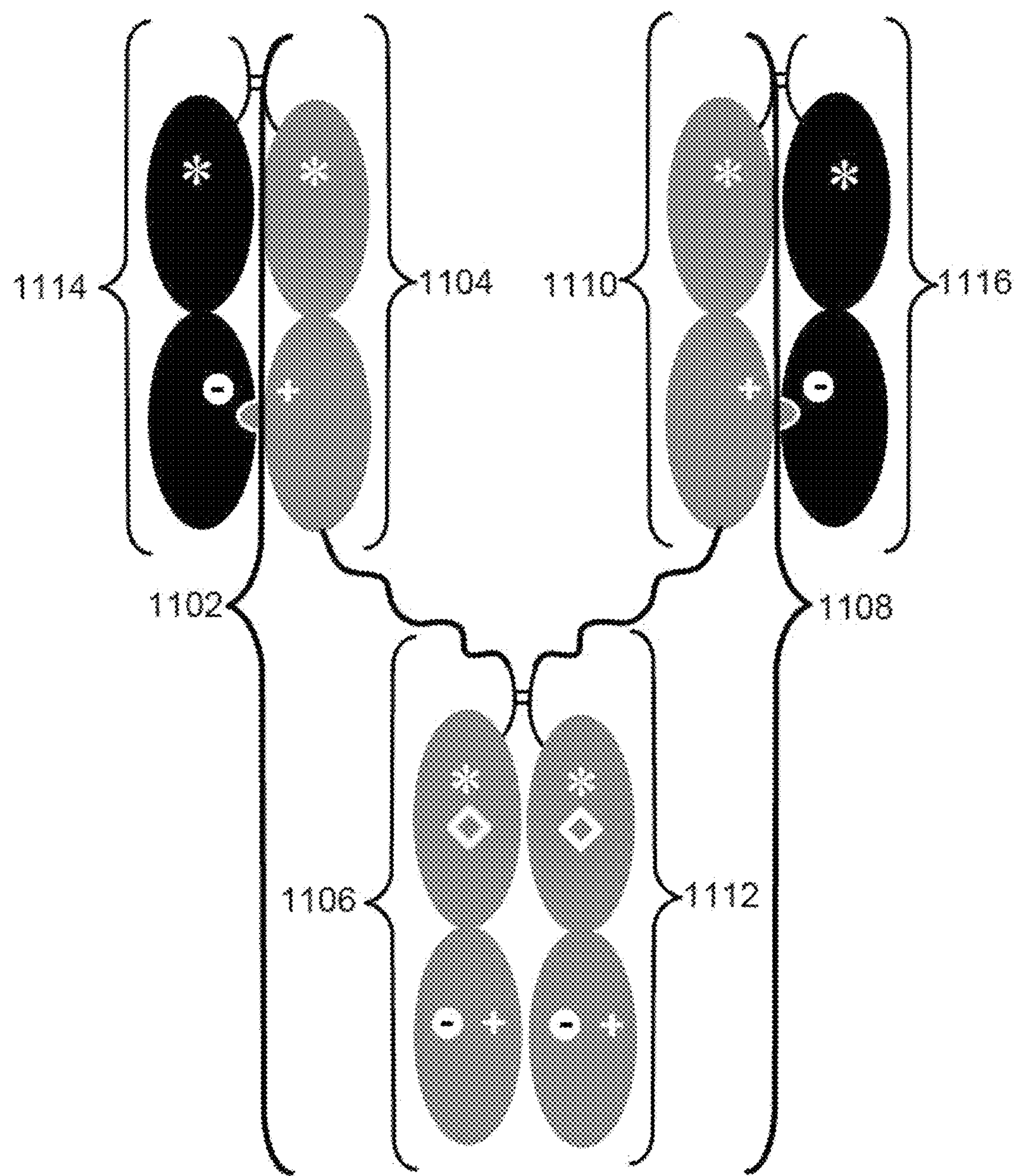
FIG. 18G is an illustration of an Fc construct (construct 11) containing three Fc domains formed from four polypeptides. Each of the first polypeptide (1102) and the second polypeptide (1108) contains one Fc domain monomer containing charged amino acids at the $C_H3$-$C_H3$ interface than the wild-type sequence (1106 and 1112, respectively) joined by way of a linker to a protuberance-containing Fc domain monomer (1104 and 1110, respectively). The third and fourth polypeptides (1114 and 1116, respectively) each contain a cavity-containing Fc domain monomer. Each of the first polypeptide (1102) and the second polypeptide (1108) also contain electrostatic steering mutations, e.g., E357K. Similarly, the third and fourth polypeptides (1114 and 1116, respectively) each contain electrostatic steering mutations, e.g., K370D. 1106 and 1112 each contain the amino acid modification R292P, which is represented as a diamond, and 1104, 1110, 1114, and 1116 each contain the amino acid modification I253A, which is represented as an asterisk. 1102 and 1108 each have the amino acid sequence of SEQ ID NO: 69. 1114 and 1116 each have the amino acid sequence of SEQ ID NO: 63.
Figure 18H:
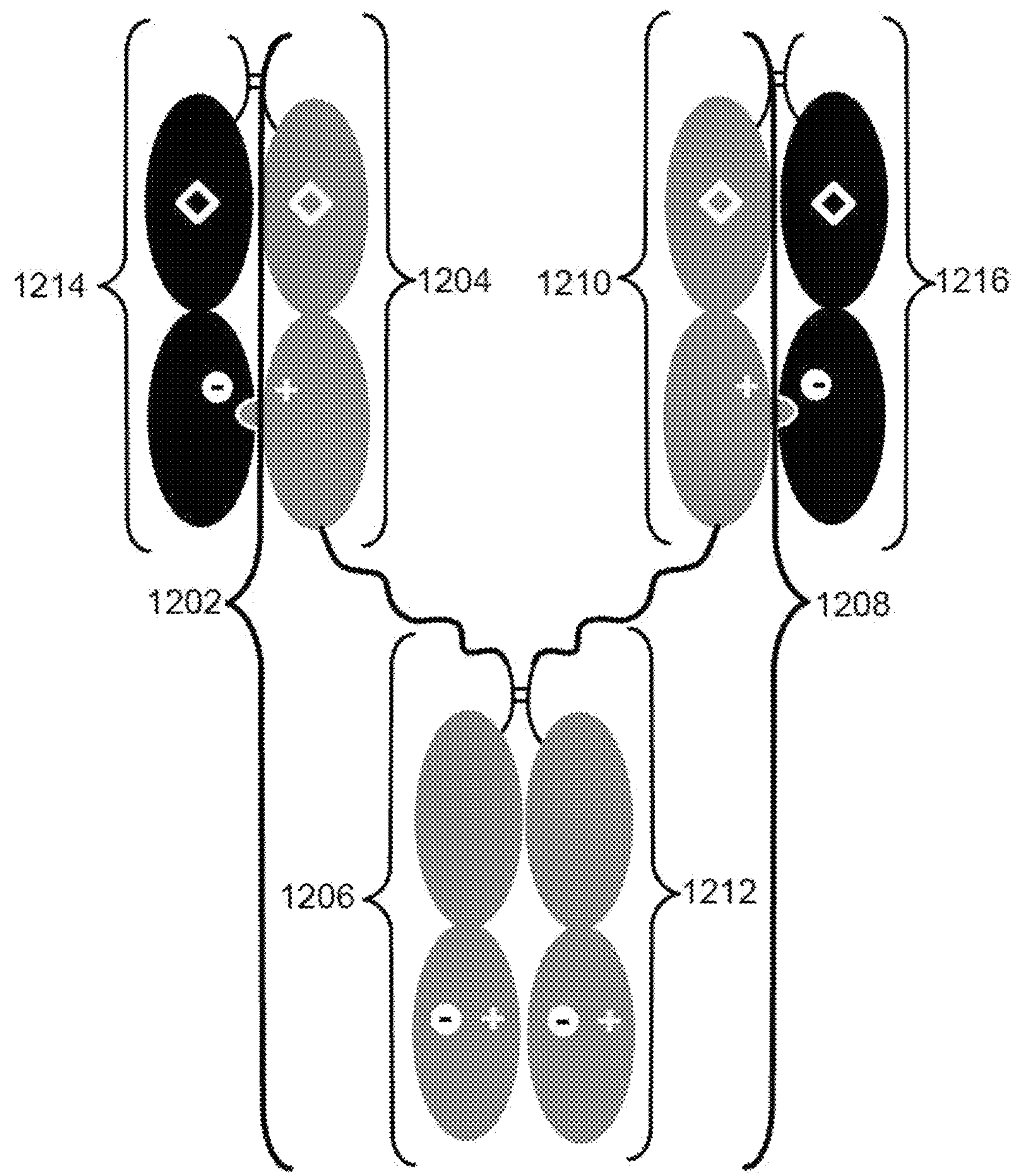
FIG. 18H is an illustration of an Fc construct (construct 12) containing three Fc domains formed from four polypeptides. Each of the first polypeptide (1202) and the second polypeptide (1208) contains one Fc domain monomer containing charged amino acids at the $C_H3$-$C_H3$ interface than the wild-type sequence (1206 and 1212, respectively) joined by way of a linker to a protuberance-containing Fc domain monomer (1204 and 1210, respectively). The third and fourth polypeptides (1214 and 1216, respectively) each contain a cavity-containing Fc domain monomer. Each of the first polypeptide (1202) and the second polypeptide (1208) also contain electrostatic steering mutations, e.g., E357K. Similarly, the third and fourth polypeptides (1214 and 1216, respectively) each contain electrostatic steering mutations, e.g., K370D. 1204, 1210, 1214, and 1216 each contain the amino acid modification R292P, which is represented as a diamond. 1202 and 1208 each have the amino acid sequence of SEQ ID NO: 71. 1214 and 1216 each have the amino acid sequence of SEQ ID NO: 70.

| Fc construct | FcγRIIb Binding Mutations[1] | FcRn Binding Mutations[2] | Long Polypeptide #s (SEQ ID NO) | Short Polypeptide #s (SEQ ID NO) | FIG. |
|---|---|---|---|---|---|
| Fc construct 4 | None | None | 1202 and 1208 (SEQ ID NO: 49) | 1214 and 1216 (SEQ ID NO: 61) | FIG. 2 |
| Fc construct 5 | None | C-terminal Fc domain only | 502 and 508 (SEQ ID NO: 62) | 514 and 516 (SEQ ID NO: 61) | FIG. 18A |
| Fc construct 6 | None | Two N-terminal Fc domains | 602 and 608 (SEQ ID NO: 64) | 614 and 616 (SEQ ID NO: 57) | FIG. 18B |
| Fc construct 7 | None | All three Fc domains | 702 and 708 (SEQ ID NO: 65) | 714 and 716 (SEQ ID NO: 57) | FIG. 18C |
| Fc construct 8 | C-terminal Fc domain only | None | 802 and 808 (SEQ ID NO: 66) | 814 and 816 (SEQ ID NO: 61) | FIG. 18D |
| Fc construct 9 | C-terminal Fc domain only | C-terminal Fc domain only | 902 and 908 (SEQ ID NO: 67) | 914 and 916 (SEQ ID NO: 61) | FIG. 18E |
| Fc construct 10 | C-terminal Fc domain only | Two N-terminal Fc domains | 1002 and 1008 (SEQ ID NO: 68) | 1014 and 1016 (SEQ ID NO: 57) | FIG. 18F |
| Fc construct 11 | C-terminal Fc domain only | All three Fc domains | 1102 and 1108 (SEQ ID NO: 69) | 1114 and 1116 (SEQ ID NO: 57) | FIG. 18G |
| Fc construct 12 | Two N-terminal Fc domains | None | 1202 and 1208 (SEQ ID NO: 71) | 1214 and 1216 (SEQ ID NO: 70) | FIG. 18H |

TABLE 10-continued

Fc constructs having I253 and/or R292 amino acid modifications

Figure 18I:
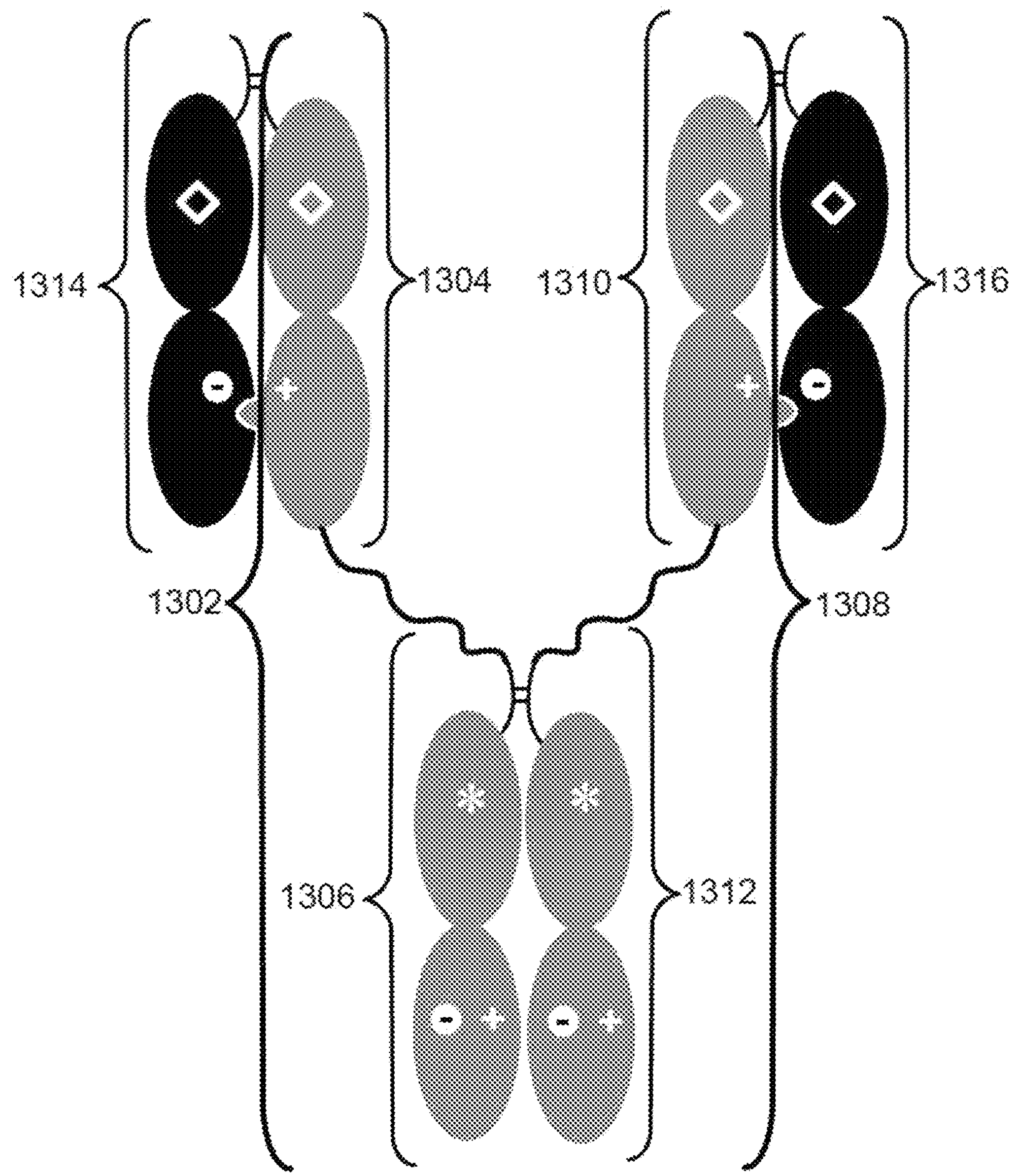
FIG. 18I is an illustration of an Fc construct (construct 13) containing three Fc domains formed from four polypeptides. Each of the first polypeptide (1302) and the second polypeptide (1308) contains one Fc domain monomer containing charged amino acids at the $C_H3$-$C_H3$ interface than the wild-type sequence (1306 and 1312, respectively) joined by way of a linker to a protuberance-containing Fc domain monomer (1304 and 1310, respectively). The third and fourth polypeptides (1314 and 1316, respectively) each contain a cavity-containing Fc domain monomer. Each of the first polypeptide (1302) and the second polypeptide (1308) also contain electrostatic steering mutations, e.g., E357K. Similarly, the third and fourth polypeptides (1314 and 1316, respectively) each contain electrostatic steering mutations, e.g., K370D. 1304, 1310, 1314, and 1316 each contain the amino acid modification R292P, which is represented as a diamond, and 1306 and 1132 each contain the amino acid modification I253A, which is represented as an asterisk. 1302 and 1308 each have the amino acid sequence of SEQ ID NO: 72. 1314 and 1316 each have the amino acid sequence of SEQ ID NO: 70.
Figure 18J:
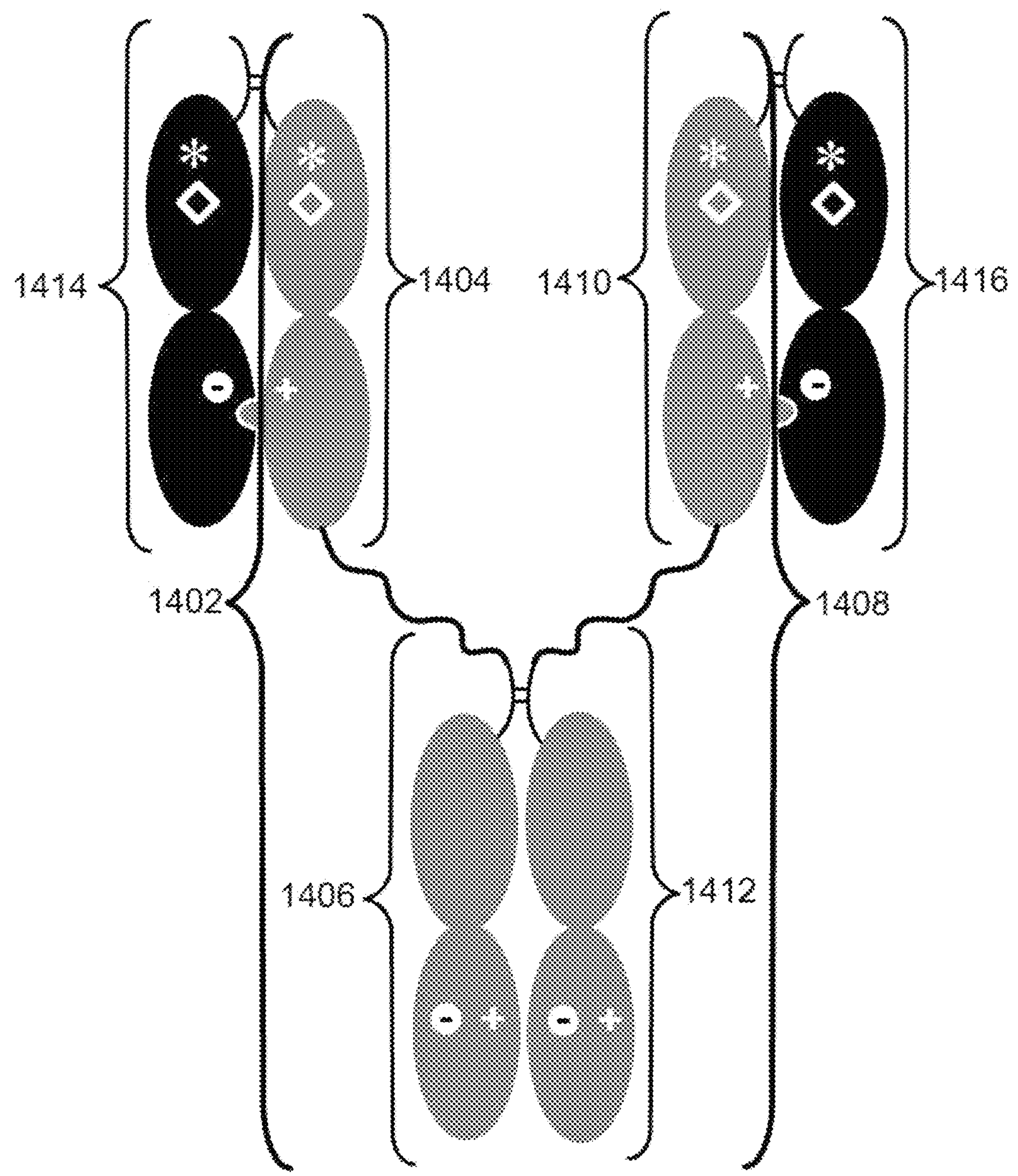
FIG. 18J is an illustration of an Fc construct (construct 14) containing three Fc domains formed from four polypeptides. Each of the first polypeptide (1402) and the second polypeptide (1408) contains one Fc domain monomer containing charged amino acids at the $C_H3$-$C_H3$ interface than the wild-type sequence (1406 and 1412, respectively) joined by way of a linker to a protuberance-containing Fc domain monomer (1404 and 1410, respectively). The third and fourth polypeptides (1414 and 1416, respectively) each contain a cavity-containing Fc domain monomer. Each of the first polypeptide (1402) and the second polypeptide (1408) also contain electrostatic steering mutations, e.g., E357K. Similarly, the third and fourth polypeptides (1414 and 1416, respectively) each contain electrostatic steering mutations, e.g., K370D. 1404, 1410, 1414, and 1416 each contain the amino acid modifications R292P, which is represented as a diamond, and I253A, which is represented as an asterisk. 1402 and 1408 each have the amino acid sequence of SEQ ID NO: 74. 1414 and 1416 each have the amino acid sequence of SEQ ID NO: 73.
Figure 18K:
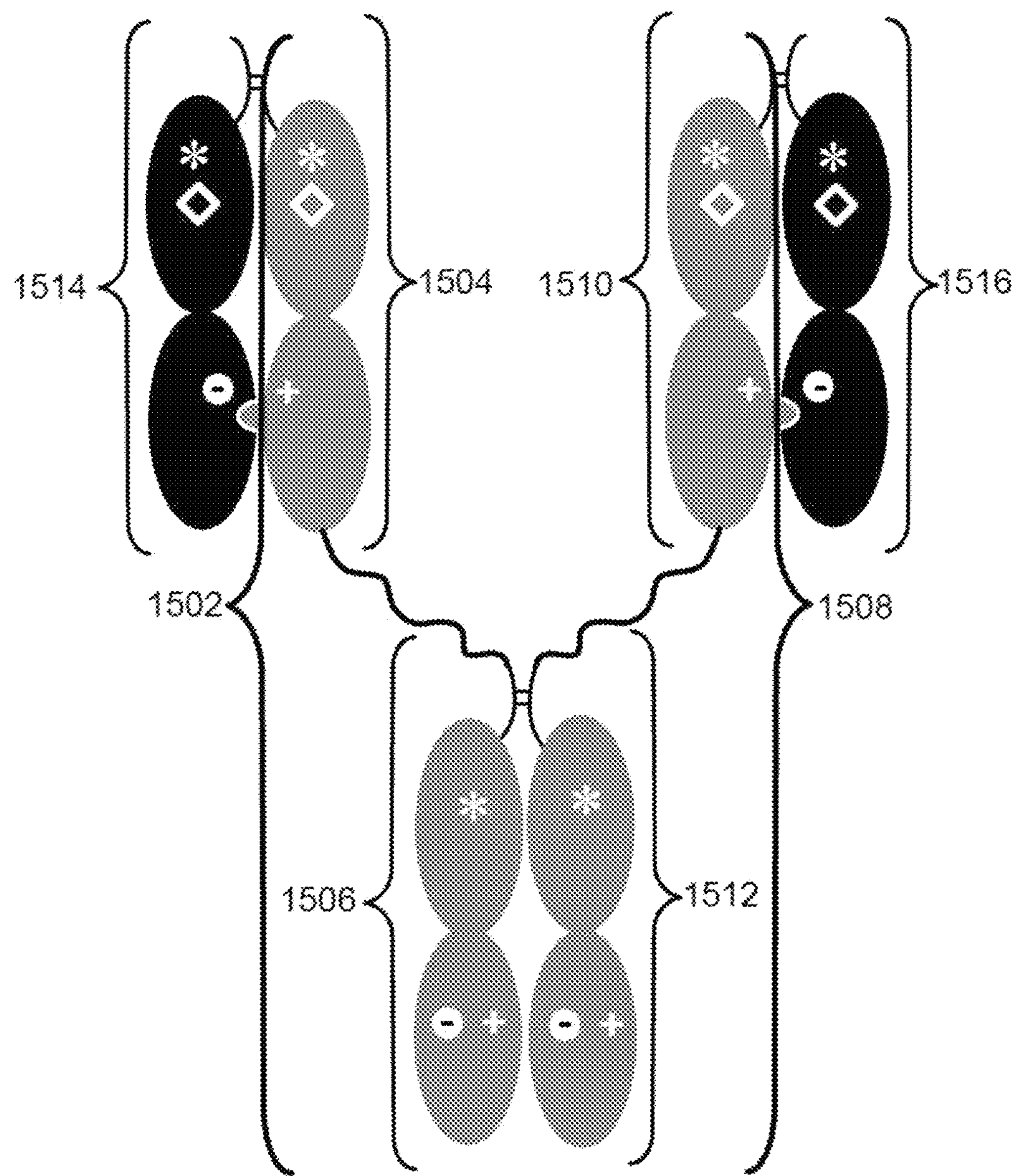
FIG. 18K is an illustration of an Fc construct (construct 15) containing three Fc domains formed from four polypeptides. Each of the first polypeptide (1502) and the second polypeptide (1508) contains one Fc domain monomer containing charged amino acids at the $C_H3$-$C_H3$ interface than the wild-type sequence (1506 and 1512, respectively) joined by way of a linker to a protuberance-containing Fc domain monomer (1504 and 1510, respectively). The third and fourth polypeptides (1514 and 1516, respectively) each contain a cavity-containing Fc domain monomer. Each of the first polypeptide (1502) and the second polypeptide (1508) also contain electrostatic steering mutations, e.g., E357K. Similarly, the third and fourth polypeptides (1514 and 1516, respectively) each contain electrostatic steering mutations, e.g., K370D. 1504, 1510, 1514, and 1516 each contain the amino acid modification R292P, which is represented as a diamond, and 1506 and 1512 each contain the amino acid modification I253A, which is represented as an asterisk. 1502 and 1508 each have the amino acid sequence of SEQ ID NO: 75. 1514 and 1516 each have the amino acid sequence of SEQ ID NO: 73.
Figure 18L:
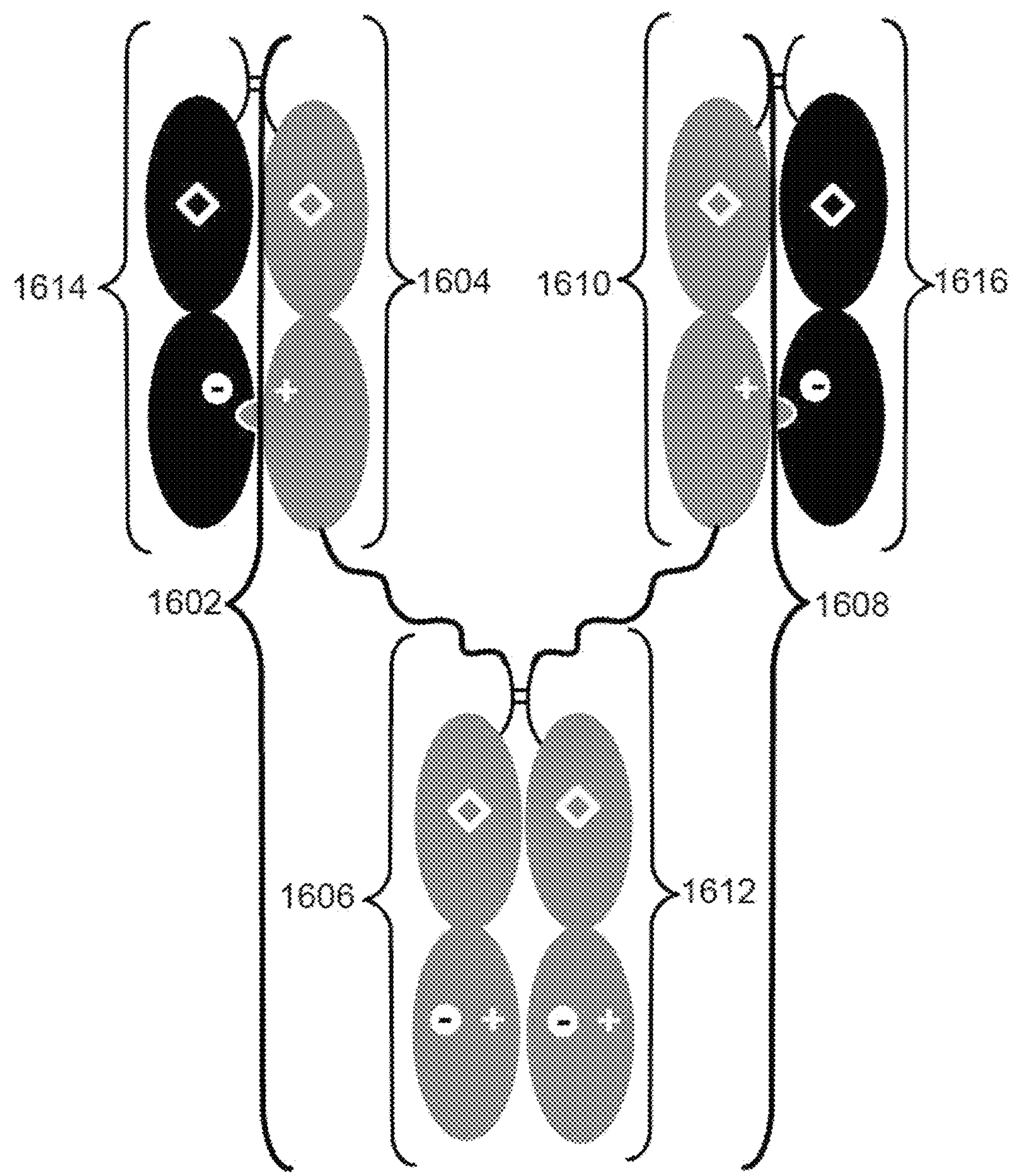
FIG. 18L is an illustration of an Fc construct (construct 16) containing three Fc domains formed from four polypeptides. Each of the first polypeptide (1602) and the second polypeptide (1608) contains one Fc domain monomer containing charged amino acids at the $C_H3$-$C_H3$ interface than the wild-type sequence (1606 and 1612, respectively) joined by way of a linker to a protuberance-containing Fc domain monomer (1604 and 1610, respectively). The third and fourth polypeptides (1614 and 1616, respectively) each contain a cavity-containing Fc domain monomer. Each of the first polypeptide (1602) and the second polypeptide (1608) also contain electrostatic steering mutations, e.g., E357K. Similarly, the third and fourth polypeptides (1614 and 1616, respectively) each contain electrostatic steering mutations, e.g., K370D. 1604, 1606, 1610, 1612, 1614, and 1616 each contain the amino acid modification R292P, which is represented by a diamond. 1602 and 1608 each have the amino acid sequence of SEQ ID NO: 76. 1614 and 1616 each have the amino acid sequence of SEQ ID NO: 70.
Figure 18M:
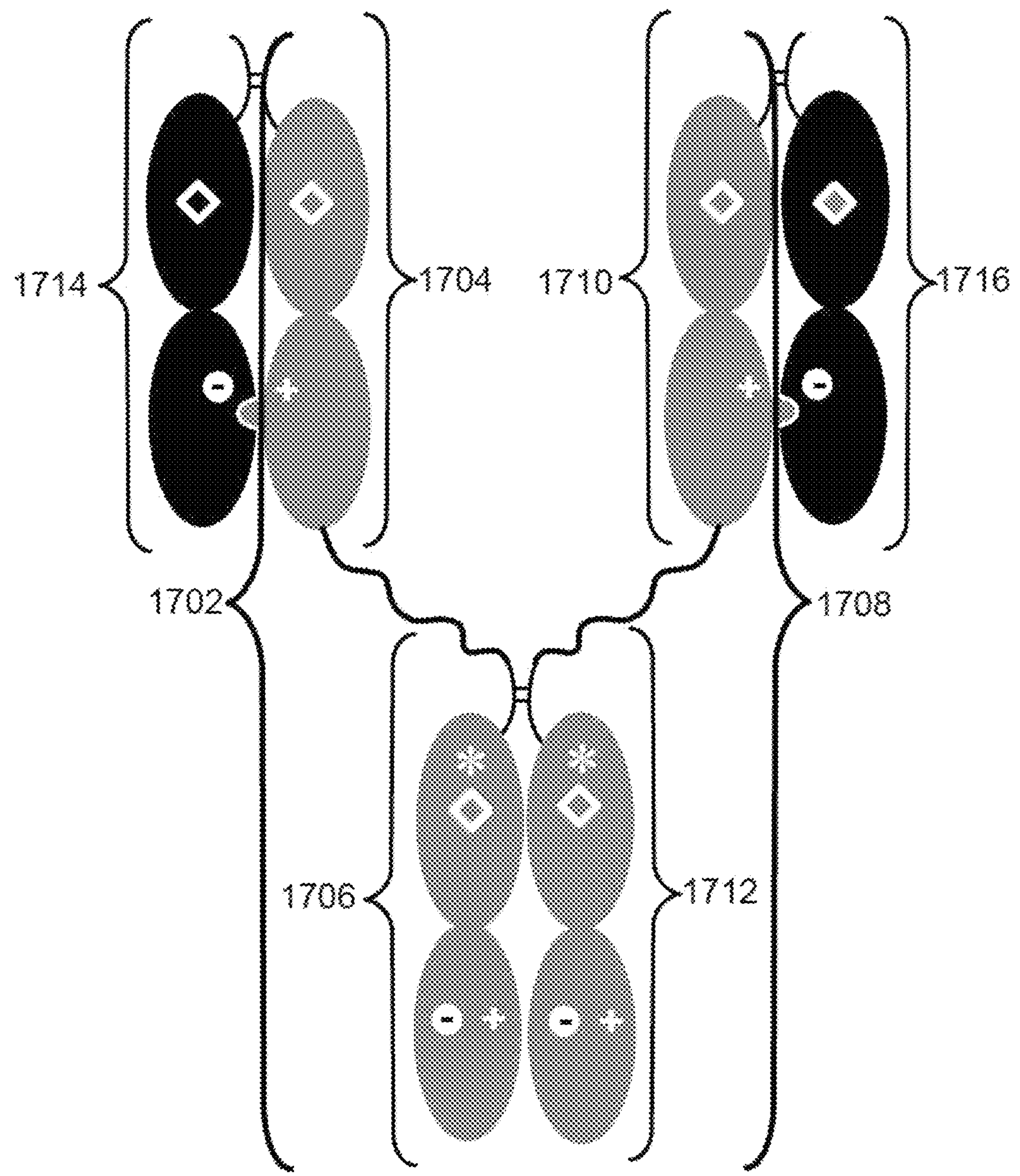
FIG. 18M is an illustration of an Fc construct (construct 17) containing three Fc domains formed from four polypeptides. Each of the first polypeptide (1702) and the second polypeptide (1708) contains one Fc domain monomer containing charged amino acids at the $C_H3$-$C_H3$ interface than the wild-type sequence (1706 and 1712, respectively) joined by way of a linker to a protuberance-containing Fc domain monomer (1704 and 1710, respectively). The third and fourth polypeptides (1714 and 1716, respectively) each contain a cavity-containing Fc domain monomer. Each of the first polypeptide (1702) and the second polypeptide (1708) also contain electrostatic steering mutations, e.g., E357K. Similarly, the third and fourth polypeptides (1714 and 1716, respectively) each contain electrostatic steering mutations, e.g., K370D. 1704, 1706, 1710, 1712, 1714, and 1716 each contain the amino acid modification R292P, which is represented by a diamond, and 1706 and 1712 each contain the amino acid modification I253A, which is represented by an asterisk. 1702 and 1708 each have the amino acid sequence of SEQ ID NO: 77. 1714 and 1716 each have the amino acid sequence of SEQ ID NO: 70.
Figure 18N:
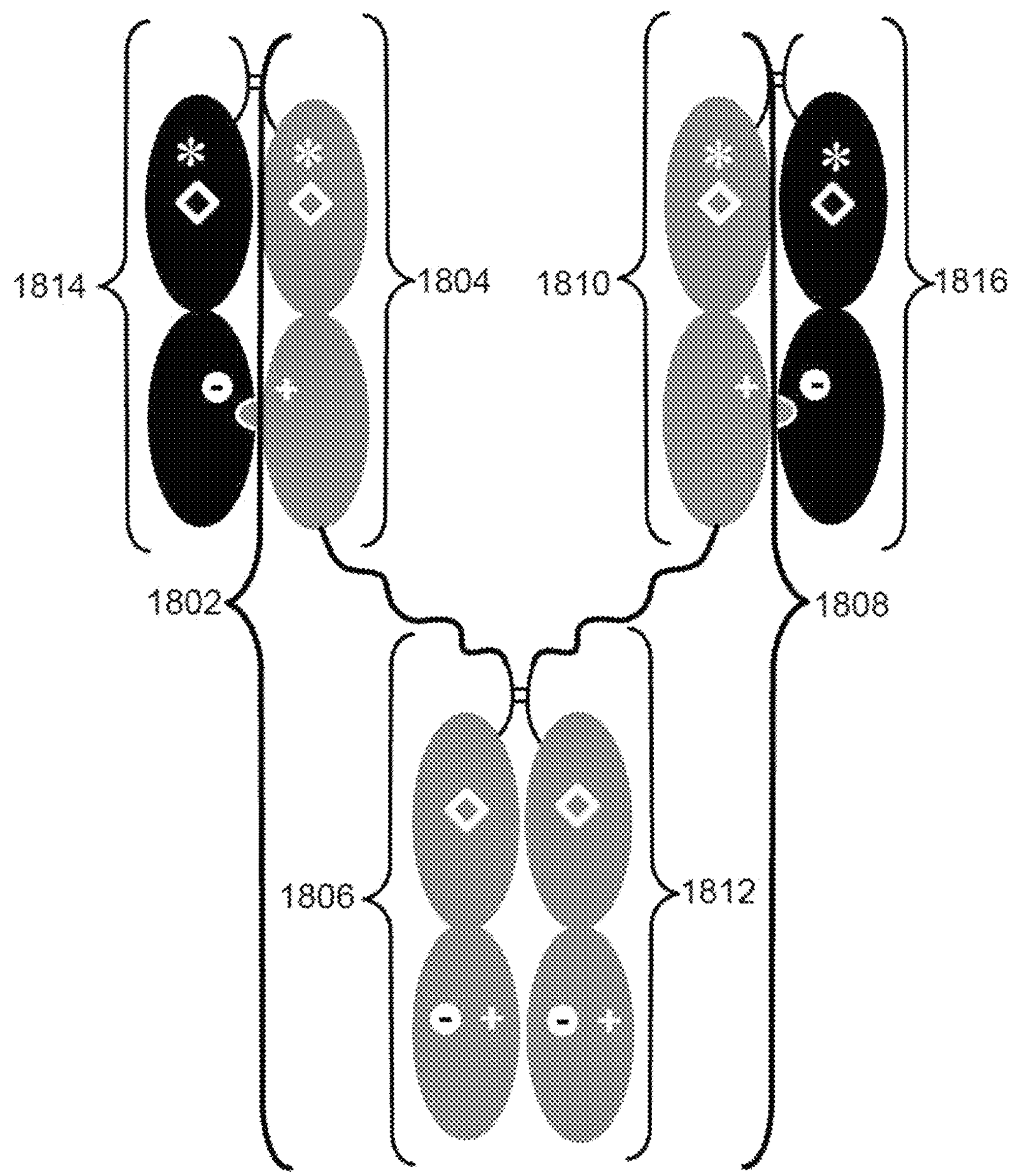
FIG. 18N is an illustration of an Fc construct (construct 18) containing three Fc domains formed from four polypeptides. Each of the first polypeptide (1802) and the second polypeptide (1808) contains one Fc domain monomer containing charged amino acids at the $C_H3$-$C_H3$ interface than the wild-type sequence (1806 and 1812, respectively) joined by way of a linker to a protuberance-containing Fc domain monomer (1804 and 1810, respectively). The third and fourth polypeptides (1814 and 1816, respectively) each contain a cavity-containing Fc domain monomer. Each of the first polypeptide (1802) and the second polypeptide (1808) also contain electrostatic steering mutations, e.g., E357K. Similarly, the third and fourth polypeptides (1814 and 1816, respectively) each contain electrostatic steering mutations, e.g., K370D. 1804, 1806, 1810, 1812, 1814, and 1816 each contain the amino acid modification R292P, which is represented by a diamond, and 1804, 1810, 1814, and 1816 each contain the amino acid modification I253A, which is represented by an asterisk. 1802 and 1808 each have the amino acid sequence of SEQ ID NO: 78. 1814 and 1816 each have the amino acid sequence of SEQ ID NO: 73.
Figure 18O:
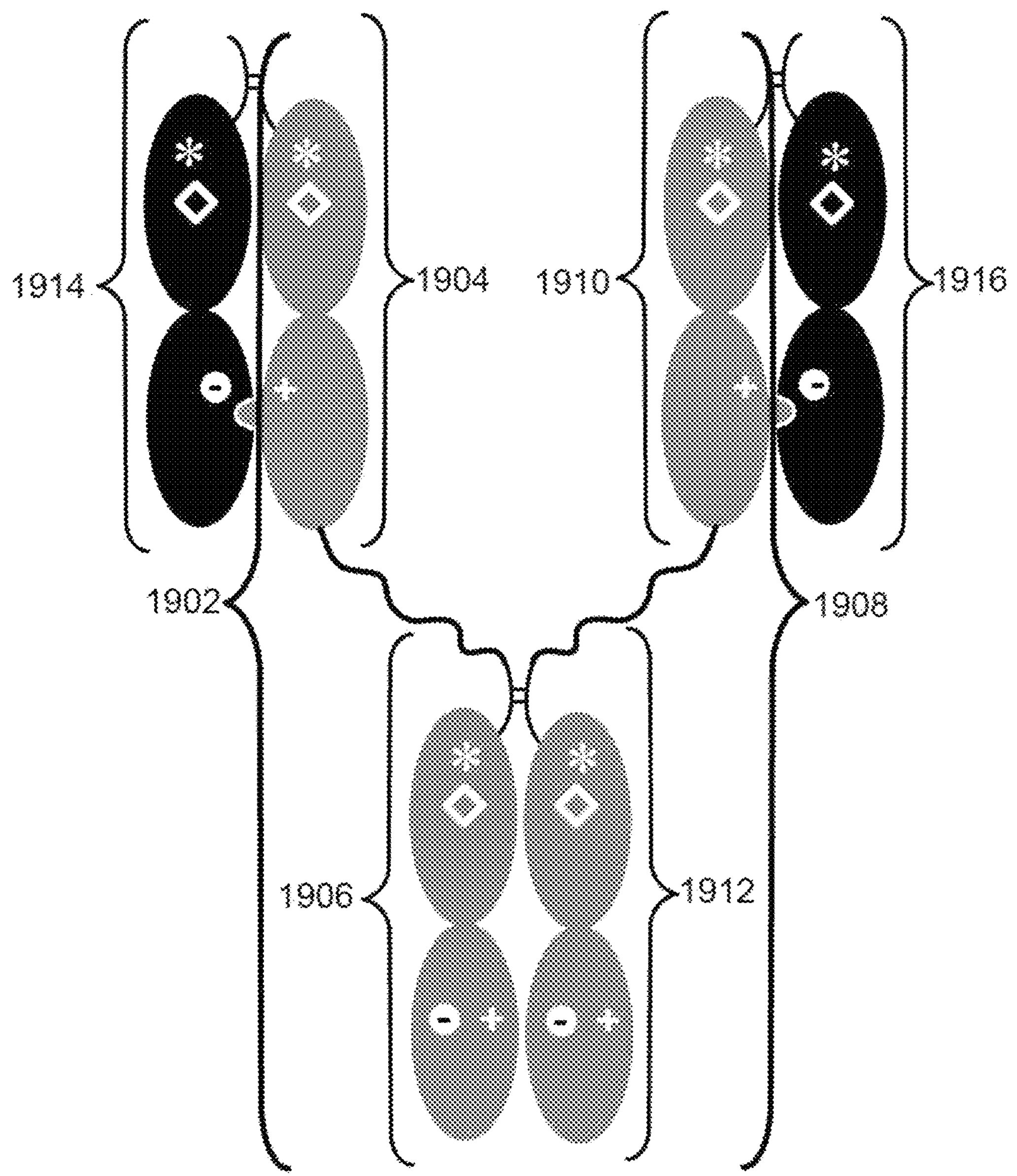
FIG. 18O is an illustration of an Fc construct (construct 19) containing three Fc domains formed from four polypeptides. Each of the first polypeptide (1902) and the second polypeptide (1908) contains one Fc domain monomer containing charged amino acids at the $C_H3$-$C_H3$ interface than the wild-type sequence (1906 and 1912, respectively) joined by way of a linker to a protuberance-containing Fc domain monomer (1904 and 1910, respectively). The third and fourth polypeptides (1914 and 1916, respectively) each contain a cavity-containing Fc domain monomer. Each of the first polypeptide (1902) and the second polypeptide (1908) also contain electrostatic steering mutations, e.g., E357K. Similarly, the third and fourth polypeptides (1914 and 1916, respectively) each contain electrostatic steering mutations, e.g., K370D. 1904, 1906, 1910, 1912, 1914, and 1916 each contain the amino acid modifications R292P, which is represented by a diamond, and I253A, which is represented by an asterisk. 1902 and 1908 each have the amino acid sequence of SEQ ID NO: 79. 1914 and 1916 each have the amino acid sequence of SEQ ID NO: 73.
Figure 18P:
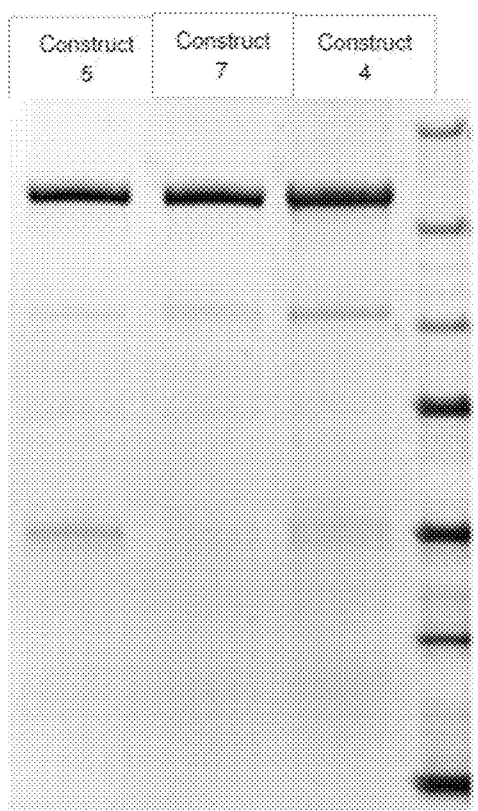
FIG. 18P is a western blot showing the expression of construct 4, construct 5, and construct 7.

| Fc construct | FcγRIIb Binding Mutations[1] | FcRn Binding Mutations[2] | Long Polypeptide #s (SEQ ID NO) | Short Polypeptide #s (SEQ ID NO) | FIG. |
|---|---|---|---|---|---|
| Fc construct 13 | Two N-terminal Fc domains | C-terminal Fc domain only | 1302 and 1308 (SEQ ID NO: 72) | 1314 and 1316 (SEQ ID NO: 70) | FIG. 18I |
| Fc construct 14 | Two N-terminal Fc domains | Two N-terminal Fc domains | 1402 and 1408 (SEQ ID NO: 74) | 1414 and 1416 (SEQ ID NO: 73) | FIG. 18J |
| Fc construct 15 | Two N-terminal Fc domains | All three Fc domains | 1502 and 1508 (SEQ ID NO: 75) | 1514 and 1516 (SEQ ID NO: 73) | FIG. 18K |
| Fc construct 16 | All three Fc domains | None | 1602 and 1608 (SEQ ID NO: 76) | 1614 and 1616 (SEQ ID NO: 70) | FIG. 18L |
| Fc construct 17 | All three Fc domains | C-terminal Fc domain only | 1702 and 1708 (SEQ ID NO: 77) | 1714 and 1716 (SEQ ID NO: 70) | FIG. 18M |
| Fc construct 18 | All three Fc domains | Two N-terminal Fc domains | 1804 and 1808 (SEQ ID NO: 78) | 1814 and 1816 (SEQ ID NO: 73) | FIG. 18N |
| Fc construct 19 | All three Fc domains | All three Fc domains | 1904 and 1908 (SEQ ID NO: 79) | 1914 and 1916 (SEQ ID NO: 73) | FIG. 18O |

[1]R292P mutation

[2]I253A mutation

TABLE 11

Amino acid sequences

| | Amino Acid Sequence |
|---|---|
| SEQ ID NO: 61 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVCTLPPSRDELTKNQVSLSCAVDGFYPSDIAVEWESNGQPENNYKTTPPVLDSDG<br>SFFLVSKLTVDKSRWQQGNVFSCSVMHEALHNHYTQKSLSLSPG |
| SEQ ID NO: 49 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGGGGGGDKTHTCPPCPAPELLGGPSVFLFPPKPKDTLMISRTPEVTCVVVDVSHEDPEV<br>KFNWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTT<br>PPVLKSDGSFFLYSDLTVDKSRWQQGNVFSCSVMHEALHNHYTQKSLSLSPG |
| SEQ ID NO: 62 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGGGGGGDKTHTCPPCPAPELLGGPSVFLFPPKPKDTLMASRTPEVTCVVVDVSHEDPEV<br>KFNWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTT<br>PPVLKSDGSFFLYSDLTVDKSRWQQGNVFSCSVMHEALHNHYTQKSLSLSPG |
| SEQ ID NO: 57 | DKTHTCPPCPAPELLGGPSVFLFPPKPKDTLMASRTPEVTCVVVDVSHEDPEVKFNWYVD<br>GVEVHNAKTKPREEQYNSTYRVVSVLTVLHQDWLNGKEYKCKVSNKALPAPIEKTISKAKG<br>QPREPQVCTLPPSRDELTKNQVSLSCAVDGFYPSDIAVEWESNGQPENNYKTTPPVLDSD<br>GSFFLVSKLTVDKSRWQQGNVFSCSVMHEALHNHYTQKSLSLSPG |
| SEQ ID NO: 64 | DKTHTCPPCPAPELLGGPSVFLFPPKPKDTLMASRTPEVTCVVVDVSHEDPEVKFNWYVD<br>GVEVHNAKTKPREEQYNSTYRVVSVLTVLHQDWLNGKEYKCKVSNKALPAPIEKTISKAKG<br>QPREPQVYTLPPCRDKLTKNQVSLWCLVKGFYPSDIAVEWESNGQPENNYKTTPPVLDSD<br>GSFFLYSKLTVDKSRWQQGNVFSCSVMHEALHNHYTQKSLSLSPGKGGGGGGGGGGGG<br>GGGGGGGGDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKT<br>TPPVLKSDGSFFLYSDLTVDKSRWQQGNVFSCSVMHEALHNHYTQKSLSLSPG |
| SEQ ID NO: 65 | DKTHTCPPCPAPELLGGPSVFLFPPKPKDTLMASRTPEVTCVVVDVSHEDPEVKFNWYVD<br>GVEVHNAKTKPREEQYNSTYRVVSVLTVLHQDWLNGKEYKCKVSNKALPAPIEKTISKAKG<br>QPREPQVYTLPPCRDKLTKNQVSLWCLVKGFYPSDIAVEWESNGQPENNYKTTPPVLDSD<br>GSFFLYSKLTVDKSRWQQGNVFSCSVMHEALHNHYTQKSLSLSPGKGGGGGGGGGGGG<br>GGGGGGGGDKTHTCPPCPAPELLGGPSVFLFPPKPKDTLMASRTPEVTCVVVDVSHEDPE<br>VKFNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKT<br>TPPVLKSDGSFFLYSDLTVDKSRWQQGNVFSCSVMHEALHNHYTQKSLSLSPG |

TABLE 11-continued

| Amino acid sequences | |
|---|---|
| | Amino Acid Sequence |
| SEQ ID NO: 66 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGGGGGGDKTHTCPPCPAPELLGGPSVFLFPPKPKDTLMISRTPEVTCVVVDVSHEDPEV<br>KFNWYVDGVEVHNAKTKP**P**EEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTT<br>PPVLKSDGSFFLYSDLTVDKSRWQQGNVFSCSVMHEALHNHYTQKSLSLSPG |
| SEQ ID NO: 67 | DKTHTCPPCPAPELLGGPSVFLFPPKPKDTLMISRTPEVTCVVVDVSHEDPEVKFNWYVDG<br>VEVHNAKTKPREEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGGGGGGDKTHTCPPCPAPELLGGPSVFLFPPKPKDTLM**A**SRTPEVTCVVVDVSHEDPEV<br>KFNWYVDGVEVHNAKTKP**P**EEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTT<br>PPVLKSDGSFFLYSDLTVDKSRWQQGNVFSCSVMHEALHNHYTQKSLSLSPG |
| SEQ ID NO: 68 | DKTHTCPPCPAPELLGGPSVFLFPPKPKDTLM**A**SRTPEVTCVVVDVSHEDPEVKFNWYVD<br>GVEVHNAKTKPREEQYNSTYRVVSVLTVLHQDWLNGKEYKCKVSNKALPAPIEKTISKAKG<br>QPREPQVYTLPPCRDKLTKNQVSLWCLVKGFYPSDIAVEWESNGQPENNYKTTPPVLDSD<br>GSFFLYSKLTVDKSRWQQGNVFSCSVMHEALHNHYTQKSLSLSPGKGGGGGGGGGGGG<br>GGGGGGGGDKTHTCPPCPAPELLGGPSVFLFPPKPKDTLMISRTPEVTCVVVDVSHEDPE<br>VKFNWYVDGVEVHNAKTKP**P**EEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKT<br>TPPVLKSDGSFFLYSDLTVDKSRWQQGNVFSCSVMHEALHNHYTQKSLSLSPG |
| SEQ ID NO: 69 | DKTHTCPPCPAPELLGGPSVFLFPPKPKDTLM**A**SRTPEVTCVVVDVSHEDPEVKFNWYVD<br>GVEVHNAKTKPREEQYNSTYRVVSVLTVLHQDWLNGKEYKCKVSNKALPAPIEKTISKAKG<br>QPREPQVYTLPPCRDKLTKNQVSLWCLVKGFYPSDIAVEWESNGQPENNYKTTPPVLDSD<br>GSFFLYSKLTVDKSRWQQGNVFSCSVMHEALHNHYTQKSLSLSPGKGGGGGGGGGGGG<br>GGGGGGGGDKTHTCPPCPAPELLGGPSVFLFPPKPKDTLM**A**SRTPEVTCVVVDVSHEDPE<br>VKFNWYVDGVEVHNAKTKP**P**EEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKT<br>TPPVLKSDGSFFLYSDLTVDKSRWQQGNVFSCSVMHEALHNHYTQKSLSLSPG |
| SEQ ID NO: 70 | DKTHTCPPCPAPELLGGPSVFLFPPKPKDTLMISRTPEVTCVVVDVSHEDPEVKFNWYVDG<br>VEVHNAKTKP**P**EEQYNSTYRVVSVLTVLHQDWLNGKEYKCKVSNKALPAPIEKTISKAKGQ<br>PREPQVCTLPPSRDELTKNQVSLSCAVDGFYPSDIAVEWESNGQPENNYKTTPPVLDSDG<br>SFFLVSKLTVDKSRWQQGNVFSCSVMHEALHNHYTQKSLSLSPG |
| SEQ ID NO: 71 | DKTHTCPPCPAPELLGGPSVFLFPPKPKDTLMISRTPEVTCVVVDVSHEDPEVKFNWYVDG<br>VEVHNAKTKP**P**EEQYNSTYRVVSVLTVLHQDWLNGKEYKCKVSNKALPAPIEKTISKAKGQ<br>PREPQVCTLPPSRDELTKNQVSLSCAVDGFYPSDIAVEWESNGQPENNYKTTPPVLDSDG<br>SFFLVSKLTVDKSRWQQGNVFSCSVMHEALHNHYTQKSLSLSPG |
| SEQ ID NO: 72 | DKTHTCPPCPAPELLGGPSVFLFPPKPKDTLMISRTPEVTCVVVDVSHEDPEVKFNWYVDG<br>VEVHNAKTKP**P**EEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGGGGGGDKTHTCPPCPAPELLGGPSVFLFPPKPKDTLM**A**SRTPEVTCVVVDVSHEDPEV<br>KFNWYVDGVEVHNAKTKPREEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTT<br>PPVLKSDGSFFLYSDLTVDKSRWQQGNVFSCSVMHEALHNHYTQKSLSLSPG |
| SEQ ID NO: 73 | DKTHTCPPCPAPELLGGPSVFLFPPKPKDTLM**A**SRTPEVTCVVVDVSHEDPEVKFNWYVD<br>GVEVHNAKTKP**P**EEQYNSTYRVVSVLTVLHQDWLNGKEYKCKVSNKALPAPIEKTISKAKG<br>QPREPQVCTLPPSRDELTKNQVSLSCAVDGFYPSDIAVEWESNGQPENNYKTTPPVLDSD<br>GSFFLVSKLTVDKSRWQQGNVFSCSVMHEALHNHYTQKSLSLSPG |
| SEQ ID NO: 74 | DKTHTCPPCPAPELLGGPSVFLFPPKPKDTLM**A**SRTPEVTCVVVDVSHEDPEVKFNWYVD<br>GVEVHNAKTKP**P**EEQYNSTYRVVSVLTVLHQDWLNGKEYKCKVSNKALPAPIEKTISKAKG<br>QPREPQVYTLPPCRDKLTKNQVSLWCLVKGFYPSDIAVEWESNGQPENNYKTTPPVLDSD<br>GSFFLYSKLTVDKSRWQQGNVFSCSVMHEALHNHYTQKSLSLSPGKGGGGGGGGGGGG<br>GGGGGGGGDKTHTCPPCPAPELLGGPSVFLFPPKPKDTLMISRTPEVTCVVVDVSHEDPE<br>VKFNWYVDGVEVHNAKTKPREEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKT<br>TPPVLKSDGSFFLYSDLTVDKSRWQQGNVFSCSVMHEALHNHYTQKSLSLSPG |
| SEQ ID NO: 75 | DKTHTCPPCPAPELLGGPSVFLFPPKPKDTLM**A**SRTPEVTCVVVDVSHEDPEVKFNWYVD<br>GVEVHNAKTKP**P**EEQYNSTYRVVSVLTVLHQDWLNGKEYKCKVSNKALPAPIEKTISKAKG<br>QPREPQVYTLPPCRDKLTKNQVSLWCLVKGFYPSDIAVEWESNGQPENNYKTTPPVLDSD<br>GSFFLYSKLTVDKSRWQQGNVFSCSVMHEALHNHYTQKSLSLSPGKGGGGGGGGGGGG<br>GGGGGGGGDKTHTCPPCPAPELLGGPSVFLFPPKPKDTLM**A**SRTPEVTCVVVDVSHEDPE<br>VKFNWYVDGVEVHNAKTKPREEQYNSTYRVVSVLTVLHQDWLNGKEYKCKVSNKALPAPI |

TABLE 11-continued

| Amino acid sequences | |
|---|---|
| | Amino Acid Sequence |
| | EKTISKAKGQPREPQVYTLPPSRDELTKNQVSLTCLVKGFYPSDIAVEWESNGQPENNYKT<br>TPPVLKSDGSFFLYSDLTVDKSRWQQGNVFSCSVMHEALHNHYTQKSLSLSPG |
| SEQ ID NO: 76 | DKTHTCPPCPAPELLGGPSVFLFPPKPKDTLMISRTPEVTCVVVDVSHEDPEVKFNWYVDG<br>VEVHNAKTKP**P**EEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGGGGGGDKTHTCPPCPAPELLGGPSVFLFPPKPKDTLMISRTPEVTCVVVDVSHEDPEV<br>KFNWYVDGVEVHNAKTKP**P**EEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTT<br>PPVLKSDGSFFLYSDLTVDKSRWQQGNVFSCSVMHEALHNHYTQKSLSLSPG |
| SEQ ID NO: 77 | DKTHTCPPCPAPELLGGPSVFLFPPKPKDTLMISRTPEVTCVVVDVSHEDPEVKFNWYVDG<br>VEVHNAKTKP**P**EEQYNSTYRVVSVLTVLHQDWLNGKEYKCKVSNKALPAPIEKTISKAKGQ<br>PREPQVYTLPPCRDKLTKNQVSLWCLVKGFYPSDIAVEWESNGQPENNYKTTPPVLDSDG<br>SFFLYSKLTVDKSRWQQGNVFSCSVMHEALHNHYTQKSLSLSPGKGGGGGGGGGGGGG<br>GGGGGGGDKTHTCPPCPAPELLGGPSVFLFPPKPKDTLM**A**SRTPEVTCVVVDVSHEDPEV<br>KFNWYVDGVEVHNAKTKP**P**EEQYNSTYRVVSVLTVLHQDWLNGKEYKCKVSNKALPAPIE<br>KTISKAKGQPREPQVYTLPPSRDELTKNQVSLTCLVKGFYPSDIAVEWESNGQPENNYKTT<br>PPVLKSDGSFFLYSDLTVDKSRWQQGNVFSCSVMHEALHNHYTQKSLSLSPG |
| SEQ ID NO: 78 | DKTHTCPPCPAPELLGGPSVFLFPPKPKDTLM**A**SRTPEVTCVVVDVSHEDPEVKFNWYVD<br>GVEVHNAKTKP**P**EEQYNSTYRVVSVLTVLHQDWLNGKEYKCKVSNKALPAPIEKTISKAKG<br>QPREPQVYTLPPCRDKLTKNQVSLWCLVKGFYPSDIAVEWESNGQPENNYKTTPPVLDSD<br>GSFFLYSKLTVDKSRWQQGNVFSCSVMHEALHNHYTQKSLSLSPGKGGGGGGGGGGGG<br>GGGGGGGGDKTHTCPPCPAPELLGGPSVFLFPPKPKDTLMISRTPEVTCVVVDVSHEDPE<br>VKFNWYVDGVEVHNAKTKP**P**EEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKT<br>TPPVLKSDGSFFLYSDLTVDKSRWQQGNVFSCSVMHEALHNHYTQKSLSLSPG |
| SEQ ID NO: 79 | DKTHTCPPCPAPELLGGPSVFLFPPKPKDTLM**A**SRTPEVTCVVVDVSHEDPEVKFNWYVD<br>GVEVHNAKTKP**P**EEQYNSTYRVVSVLTVLHQDWLNGKEYKCKVSNKALPAPIEKTISKAKG<br>QPREPQVYTLPPCRDKLTKNQVSLWCLVKGFYPSDIAVEWESNGQPENNYKTTPPVLDSD<br>GSFFLYSKLTVDKSRWQQGNVFSCSVMHEALHNHYTQKSLSLSPGKGGGGGGGGGGGG<br>GGGGGGGGDKTHTCPPCPAPELLGGPSVFLFPPKPKDTLM**A**SRTPEVTCVVVDVSHEDPE<br>VKFNWYVDGVEVHNAKTKP**P**EEQYNSTYRVVSVLTVLHQDWLNGKEYKCKVSNKALPAPI<br>EKTISKAKGQPREPQVYTLPPSRDELTKNQVSLTCLVKGFYPSDIAVEWESNGQPENNYKT<br>TPPVLKSDGSFFLYSDLTVDKSRWQQGNVFSCSVMHEALHNHYTQKSLSLSPG |

The I253A and R292P mutations (modifications) are indicated in bold and underlined (when present)

Example 10. Evaluation of I253A and R292P Amino Acid Modifications on Fc Receptor Binding Specificity A cell-based binding assay was utilized to confirm that the amino acid modifications at positions I253, e.g., I253A, and R292, e.g., R292P, were specific to the intended receptors, e.g., reduced binding affinity to the FcRn receptor and FcγRIIb receptor, respectively. Relative binding of Fc constructs and controls to Fc gamma receptors (FcγRs) was measured using cell-based homogeneous time-resolved fluorescence resonance energy transfer (TR-FRET) competition assays (CISBIO®) kits for FcγRI, FcγRIIa H131, FcγRIIb, and FcγRIIIa V158. Assay reagents were prepared according to the manufacturer's instructions. A 10-point, 3-fold serial dilution series, plus one blank per sample, was generated using an automated liquid handler (Freedom EVOware 150, TECAN®). Assay plates were read on a PHERAstar fluorescent reader (BMG Labtech GmbH) at 665 and 620 nm. An IgG1 sample was used as a control. FIG. 19 A-D shows that the R292P mutations in construct 16 and construct 18 dramatically reduced binding to FcγRIIb-expressing cells as compared to the IgG1 control, while having minimal impact on FcγRI, FcγRIIa, and FcγRIIIa binding. However, I253A mutations had minimal impact on binding to any Fc gamma receptor, as demonstrated by the similarity of the binding profiles of construct 6 and construct 4, and the similarity of the binding profiles of construct 18 and construct 16.

Figure 20:
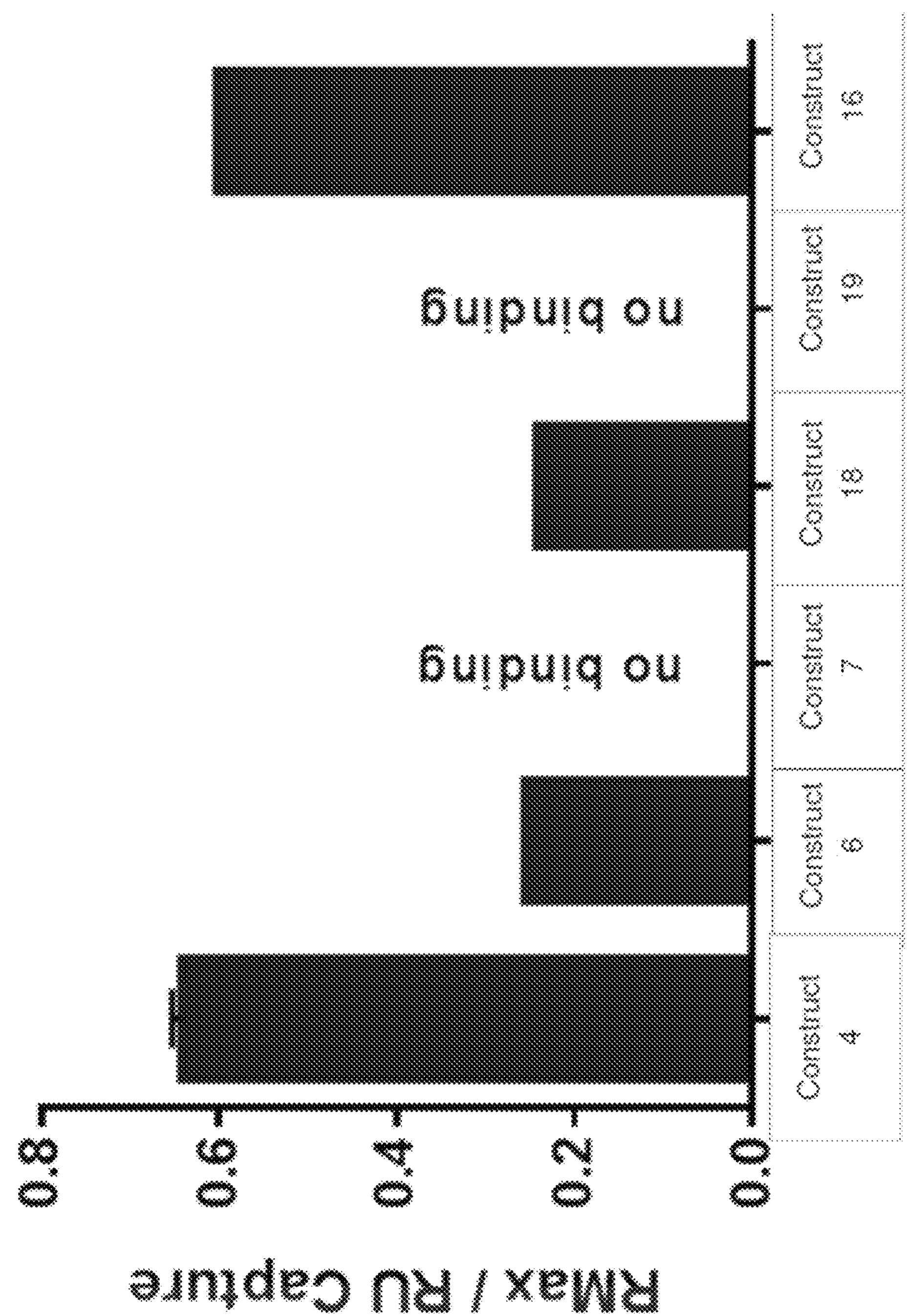
FIG. 20 is a graph showing binding of construct 4, construct 7, construct 6, construct 16, construct 18, and construct 19 by surface plasmon resonance (SPR) to FcRn at pH 6.0. The normalized maximum binding level is proportional to the number of domains functional to bind FcRn.

To assess the impact of the amino acid modifications at position I253, e.g., I253A, and R292, e.g., R292P, on FcRn binding a surface plasmon resonance (SPR) binding experiment was designed to measure the affinity and normalized binding level of solution-phase human FcRn to sensor-bound Fc constructs at pH 6.0. A goat anti-human IgG was immobilized on reference and test sensor surfaces using amine coupling chemistry. Fc constructs were captured on the test sensor surface. Recombinant human FcRn was flowed over the sensor surface in a dilution series with a top concentration of 1.0 μM. The sensor surface was regenerated at the end of each cycle with 10 mM glycine pH 1.7. Double-reference subtracted sensorgrams were subjected to equilibrium binding analysis; the maximum binding level (RMax) and the equilibrium dissociation constant ($K_D$) were estimated. The normalized maximum binding level was calculated by dividing the RMax by the FC-construct capture level. Construct 16 was captured at the same level as construct 4, indicating no loss of binding to FcRn as expected (FIG. 20). Construct 6 and construct 18 showed greatly reduced capture levels, consistent with two Fc domains losing affinity for FcRn as intended (FIG. 20). Likewise, construct 7 and construct 19, which had mutations in all three domains to limit FcRn binding, did not bind FcRn (FIG. 20).

Together, this data demonstrates that the mutation to reduce binding to FcγRIIb (e.g., an amino acid modification at position R292, e.g., R292P) had the intended effect with little impact on binding to other Fc gamma receptors and minimal impact on binding FcRn. Likewise, the mutation to reduce binding to FcRn (e.g., an amino acid modification at position I253, e.g., I253A) had the desired effect with minimal impact on Fc gamma receptor binding. Moreover, the two mutations (e.g., I253 and R292 mutations, such as I253A and R292P) could be combined to achieve diminished Fc construct binding to both FcγRIIb and FcRn.

Figure 21:
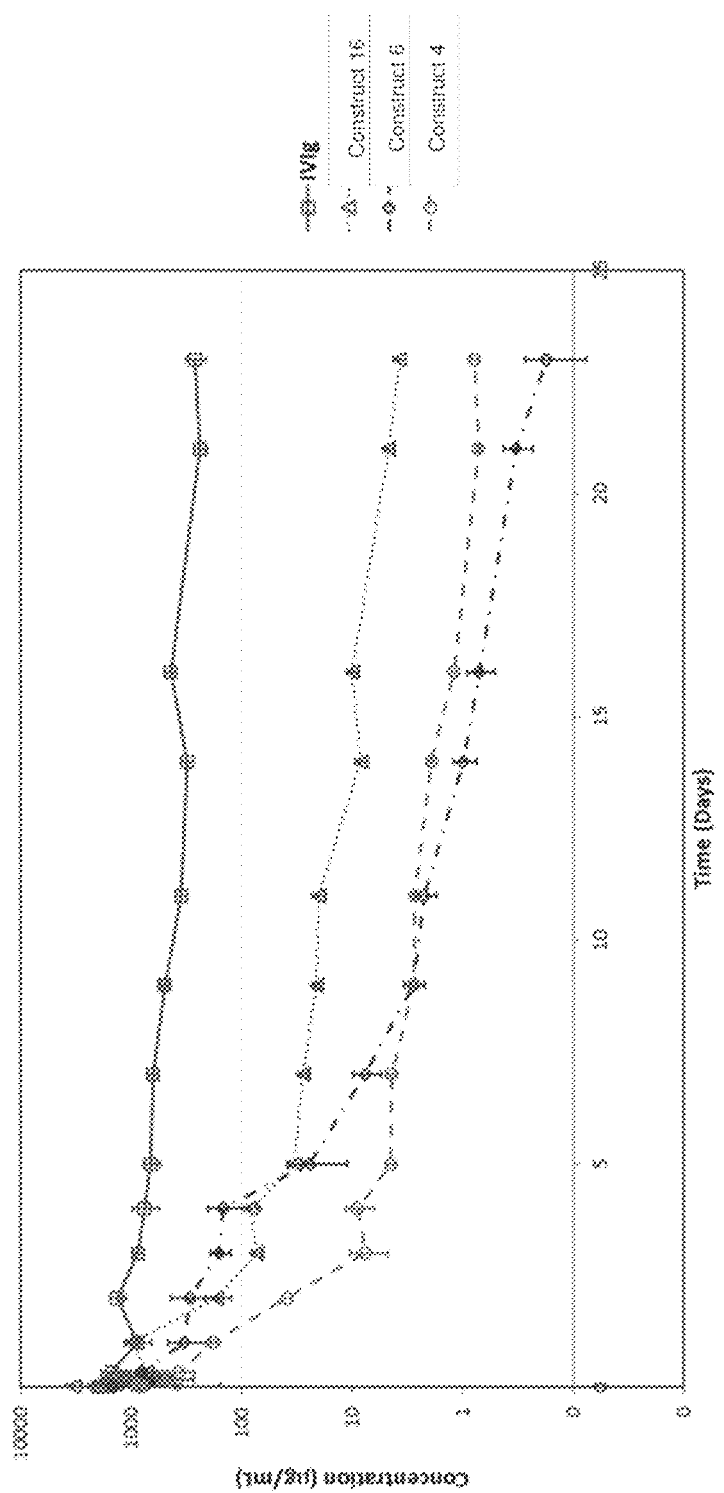
FIG. 21 is a graph comparing the pharmacokinetics of construct 4, construct 6, construct 16, and IVIg in mice.

Example 11. Evaluation of I253A and R292P Amino Acid Modifications on Fc Receptor Pharmacokinetics in Mice The impact of binding-related mutations on pharmacokinetics was initially assessed by comparing construct 4, construct 16, which has reduced FcγRIIb binding in all three Fc domains, and construct 6, which has reduced FcRn binding in two Fc domains. IVIg was included as a comparator showing typical IgG behavior. Female C57BL/6 mice (n=12, 8-10 weeks old), were dosed intravenously (i.v.) with 0.1 g/kg each of construct 4, construct 6, construct 16, or IVIg. Blood samples (50 μL) were collected from saphenous veins of four mice per time point at alternating times 15 min, 30 min, 1 hour, 2 hour, 4 hour, 6 hour, 8 hour, 1 day, 2 days, 3 days, 4 days, and 5 days. All mice were bled at 7, 9, 11, 14, 16, 21, and 23 days. Fc construct and IVIg serum concentrations were determined by human IgG1 Fc-specific ELISA. As demonstrated in FIG. 21, both Fc construct 6 and construct 16 had longer persistence in vivo and resulted in 1.2- to 1.5-fold enhancements in mean residence time (MRT) (previously, enhancements (e.g., three- to four-fold) were measured by area under the curve (AUC)).

Figure 22:
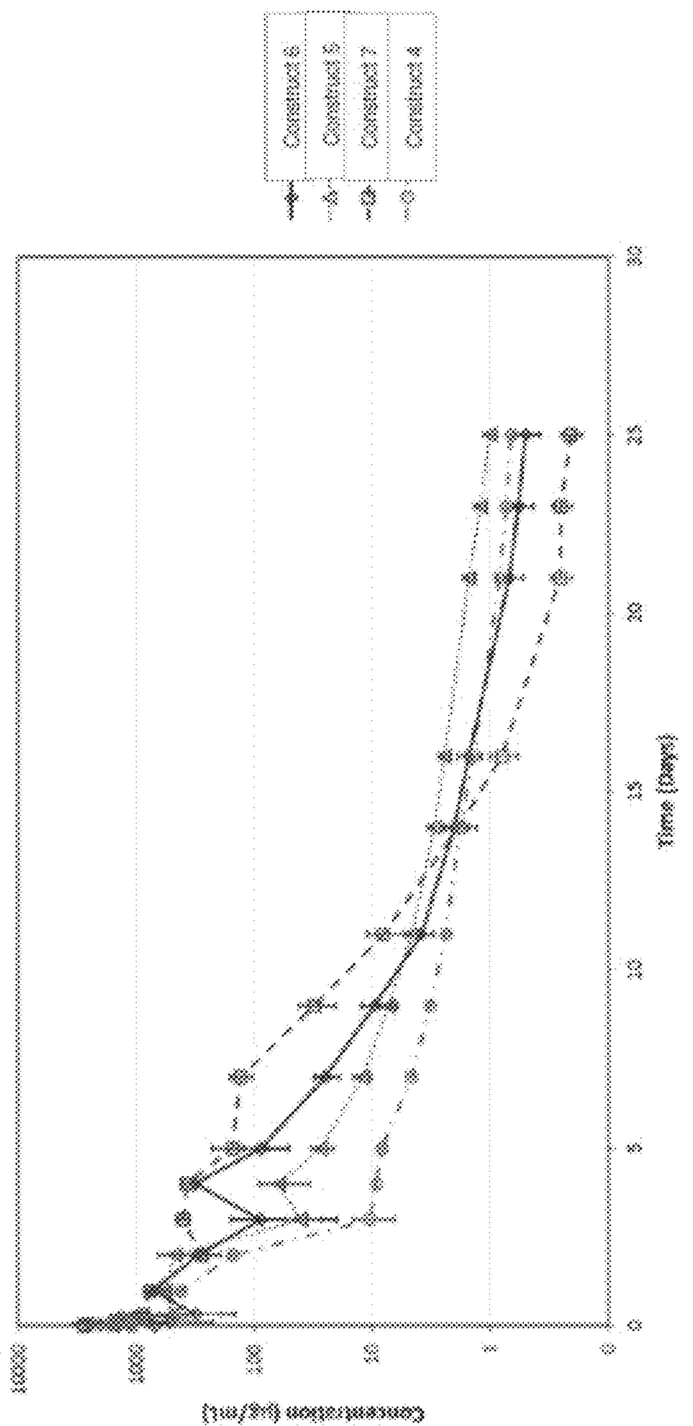
FIG. 22 is a graph comparing the pharmacokinetics of constructs 4, construct 5, construct 6, and construct 7 to evaluate the impact of the number of domains having reduced FcRn binding, e.g., I253A mutations, on pharmacokinetics in mice.

To further explore the impact of I253A amino acid modification valency towards FcRn on the pharmacokinetics, three compounds with one, two, or three domains with reduced affinity to FcRn were compared as described above. As seen in FIG. 22, all of the mutants persisted longer than the parent compound. The mean residence time (MRT) systematically increased with each Fc domain modified for decreased affinity to FcRn. The drug exposure can also be measured by AUC.

Figure 23:
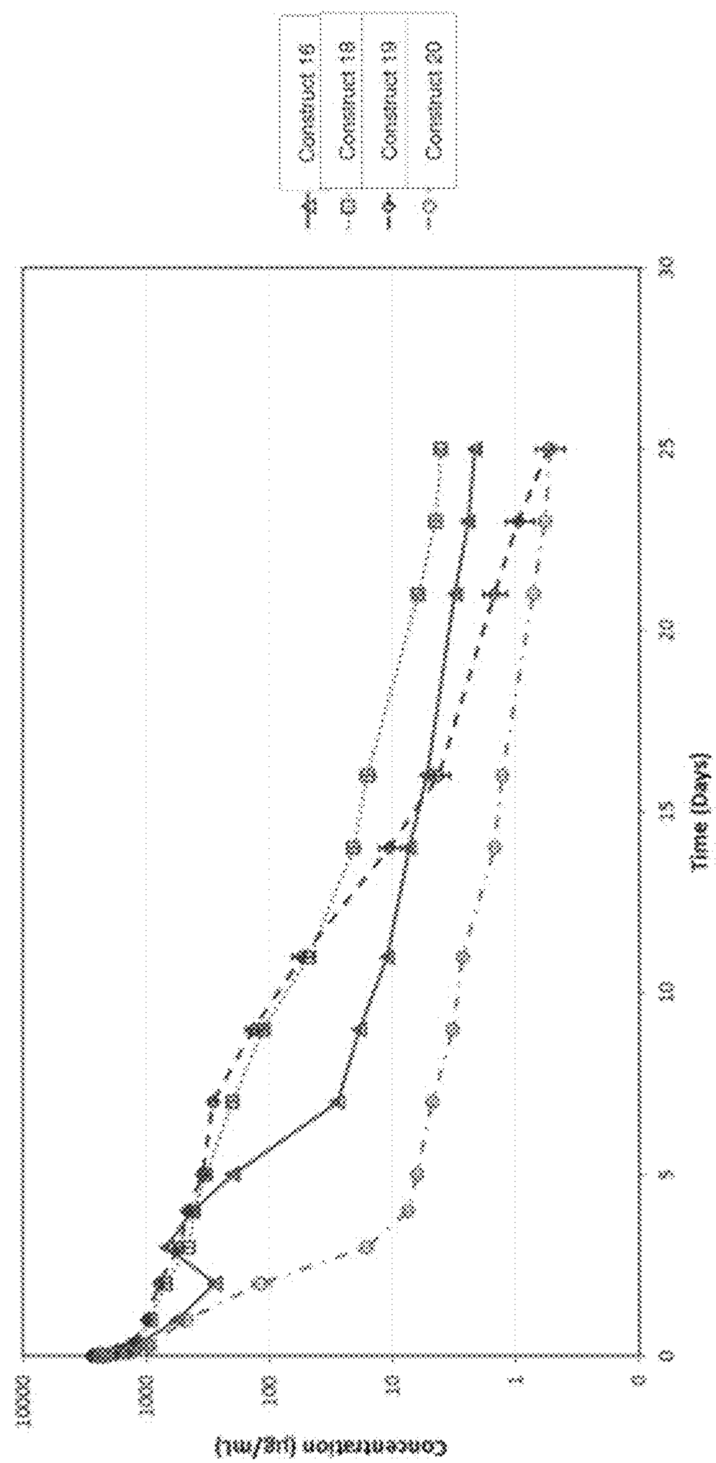
FIG. 23 is a graph comparing the pharmacokinetics of construct 20 (construct 4), construct 16, construct 18, and construct 19 in mice.

The effect of combining the mutations was also explored (FIG. 23). Incorporating mutations to both receptors enhanced the MRT three-fold, compared to the two-fold enhancement achieved in this study by reducing binding to FcγRIIb. The drug exposure can also be measured by AUC, e.g., a six-fold enhancement.

Figure 24:
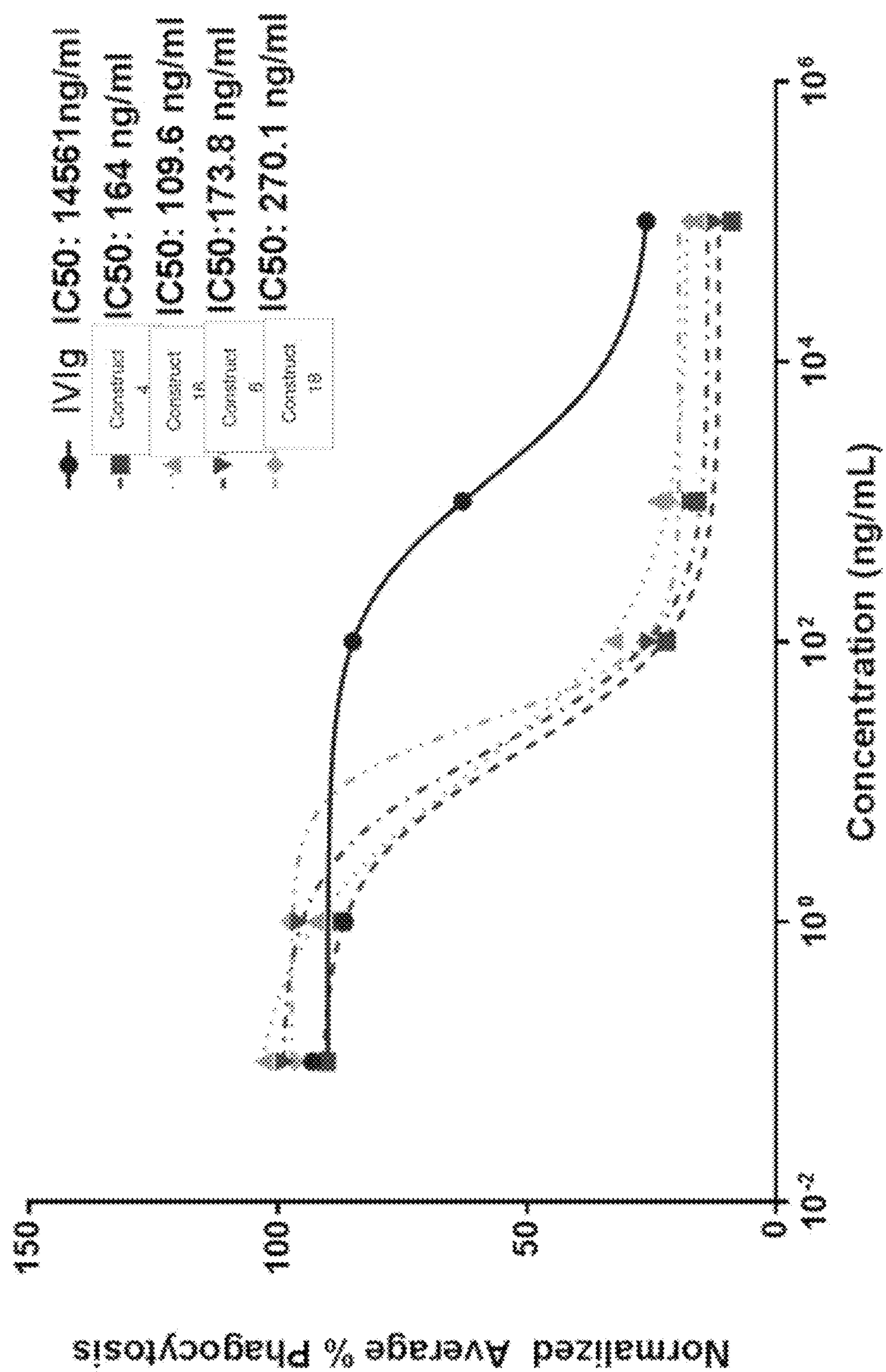
FIG. 24 is a graph comparing the inhibition of phagocytosis in THP-1 cells induced by IVIg, construct 4, construct 6, construct 16, and construct 18.

Example 12. Evaluation of I253A and R292P Amino Acid Modifications on In Vitro Efficacy The impact of the binding mutations on efficacy in vitro was assessed using assays previously shown to be sensitive to valency towards Fc gamma receptors. Inhibition of phagocytosis in THP-1 cells was comparable between all Fc constructs (FIG. 24). THP-1 cells were plated in 96-well plates. Fc constructs were 10-fold serially diluted and added to cells. Incubation proceeded for 15 min at 37° C.; FITC-labeled rabbit-IgG coated latex beads (Cayman Chemical) were then added to the cells. Incubation proceeded for 3 h at 37° C. Cells were washed twice and resuspended in 100 μL of FACS buffer (PBS/2% FBS); Trypan blue was added to quench the cell surface FITC signal, and samples were read on a BD Canto flow cytometer. Data are reported as the percentage of FITC-positive cells compared to the total cell population in the absence of inhibitor (100% phagocytosis).

Figure 25:
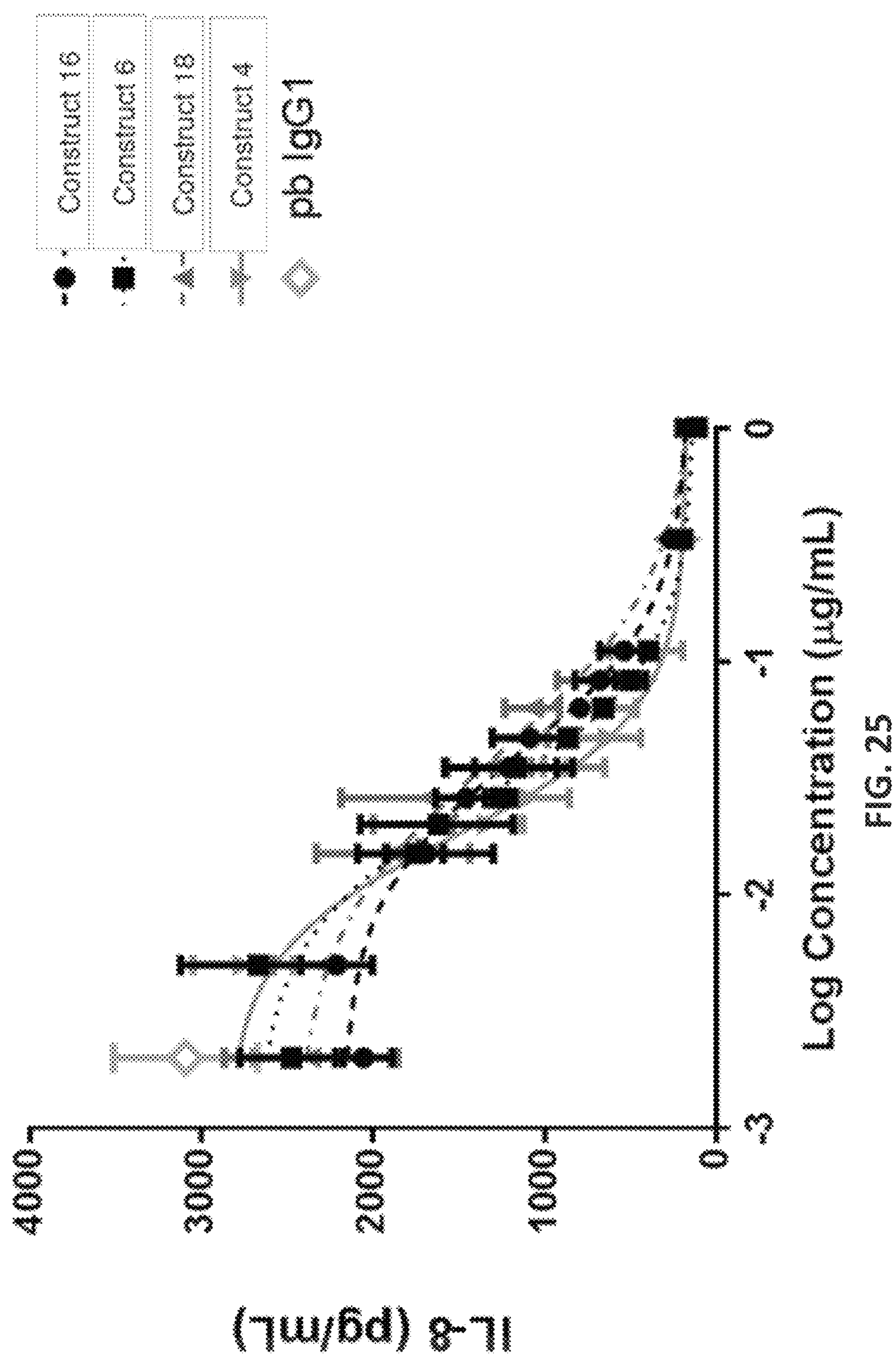
FIG. 25 is a graph comparing the inhibition of IL-8 release in monocytes induced by pacific-blue labeled IgG1, construct 4, construct 6, construct 16, and construct 18.

IL-8 release by plate-bound IgG-stimulated monocytes was comparably inhibited by all Fc constructs (FIG. 25). PBMCs were isolated from buffy coats of healthy human donors (Research Blood Components) by density gradient centrifugation on Ficoll-Paque Plus (GE Healthcare Life Sciences). Monocytes were isolated by negative selection using the Human Monocyte Enrichment Kit without CD16 Depletion (StemCell Technologies). FcγR-mediated cytokine production was stimulated using 96-well plates coated overnight with 50 μl of 100 μg/mL human IgG1 (SouthernBiotech). IVIg or each Fc construct was serially diluted in the culture plate at twice the final concentration in the assay. Purified monocytes (1.5×105 cells/well) were added, incubated for 24 h, and the culture supernatants analyzed for IL-8 concentration (Custom Human Cytokine kit for high abundance IL-8, Meso Scale Discovery).

Figure 26:
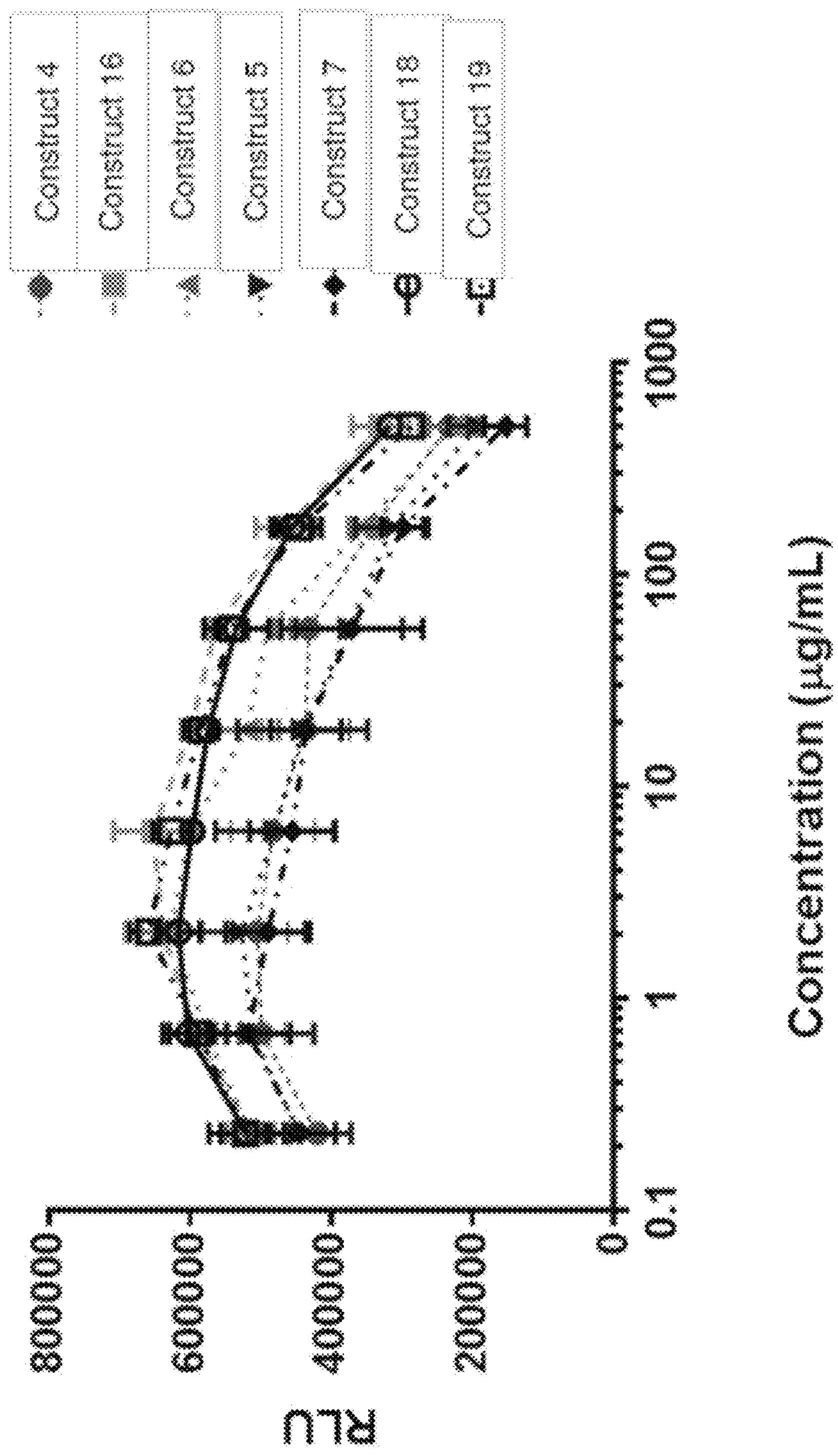
FIG. 26 is a graph comparing the inhibition of antibody-dependent cell-mediated cytotoxicity (ADCC) induced by construct 4, construct 5, construct 6, construct 7, construct 16, construct 18, and construct 19.

Likewise, the inhibition of ADCC was comparable across all Fc constructs (FIG. 26). NK cells (Hemacare) were thawed and rested overnight in LGM-3 media (Lonza). Cultured Raji cells were incubated in the presence of different concentrations of each test compound and rituximab (2 ug/mL) for 30 minutes before the NK cells were added at an effector:target cell ratio of 50K:10K. NK and Raji cells were also plated in the presence of the probes alone. The cells were incubated for 6 hours. Cytotox-Glo was used as readouts.

In all assays, the mutations caused negligible reductions on efficacy.

Example 13. Evaluation of I253A and R292P Amino Acid Modifications on In Vivo Efficacy To further assess the impact of the receptor binding mutations on activity, the Fc constructs were tested in vivo using the collagen antibody-induced arthritis (CAIA) model. Male C57BL/6 mice were injected i.p. with an arthritogenic monoclonal antibody cocktail of four antibodies to collagen II (ArthritoMab, MDBiosciences; 8 mg). On Day 4, animals were injected i.p. with lipopolysaccharide (100 μg). For therapeutic dosing, animals were randomized based on disease severity into study groups on Day 6, excluding animals with poor disease induction (score of 0 on day of randomization), and dosed i.v. with vehicle or test compound. For prophylactic dosing, animals were dosed i.v. with vehicle or test compound on a single day ranging from Day 1 to Day −14 (days were numbered omitting zero). Clinical scoring parameters were as follows: 0=normal, no swelling, redness, or distortion; complete joint flexibility. 1=mild arthritis: mild swelling and/or distortion; complete joint flexibility. 2=moderate arthritis: moderate swelling and/or distortion; reduced joint flexibility or grip strength. 3=severe arthritis: severe swelling and/or distortion; severely reduced joint flexibility or grip strength. 4=ankylosed joints; no joint flexibility and severely impaired movement; moribund. Animals were sacrificed after 12 days.

Figure 27:
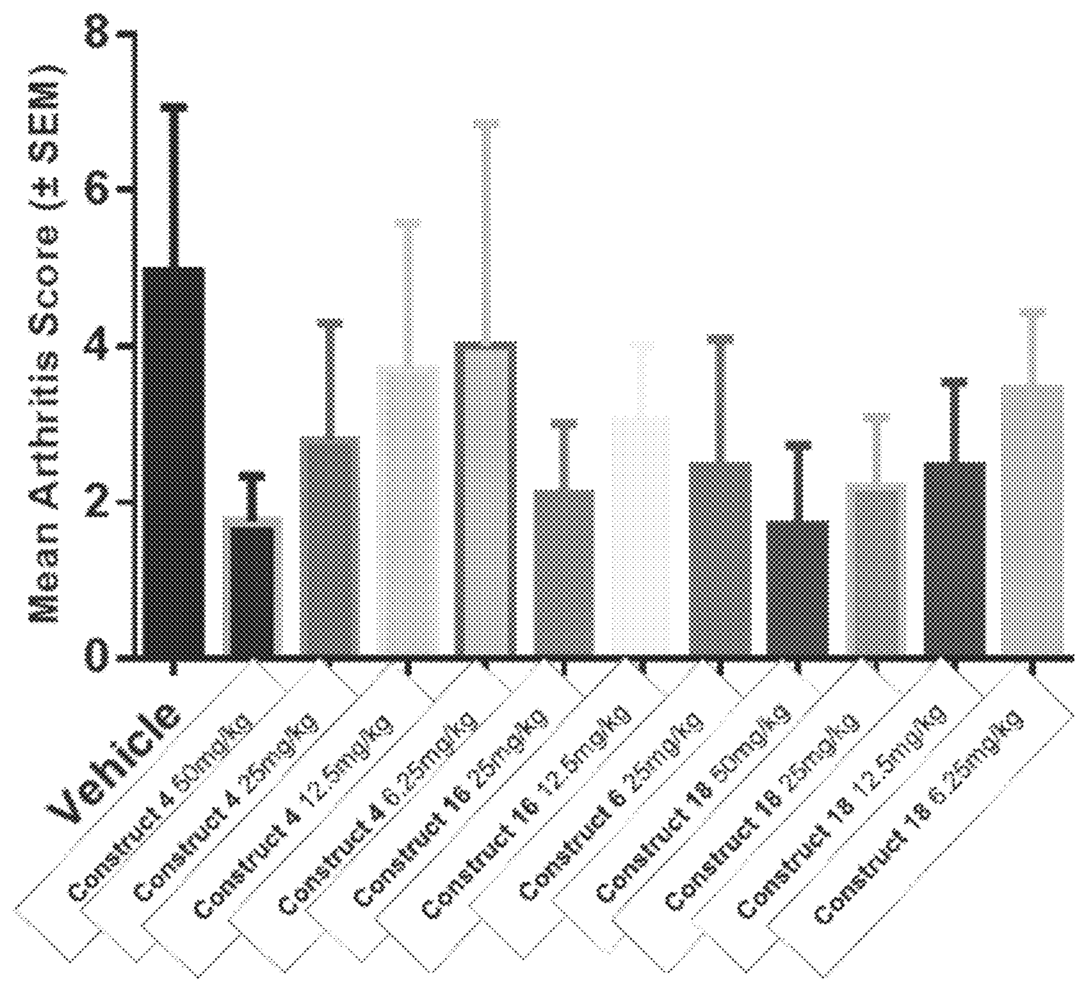
FIG. 27 is a graph comparing the efficacy of construct 4, construct 6, construct 16, and construct 18 at various concentrations in a collagen antibody-induced arthritis (CAIA) model as measured by Day 12 clinical scores.

As shown in FIG. 27, reducing binding to FcγRIIb (construct 16), FcRn (construct 6), or both (construct 18) had minimal effect on efficacy relative to the parent molecule (construct 4).

Figure 28:
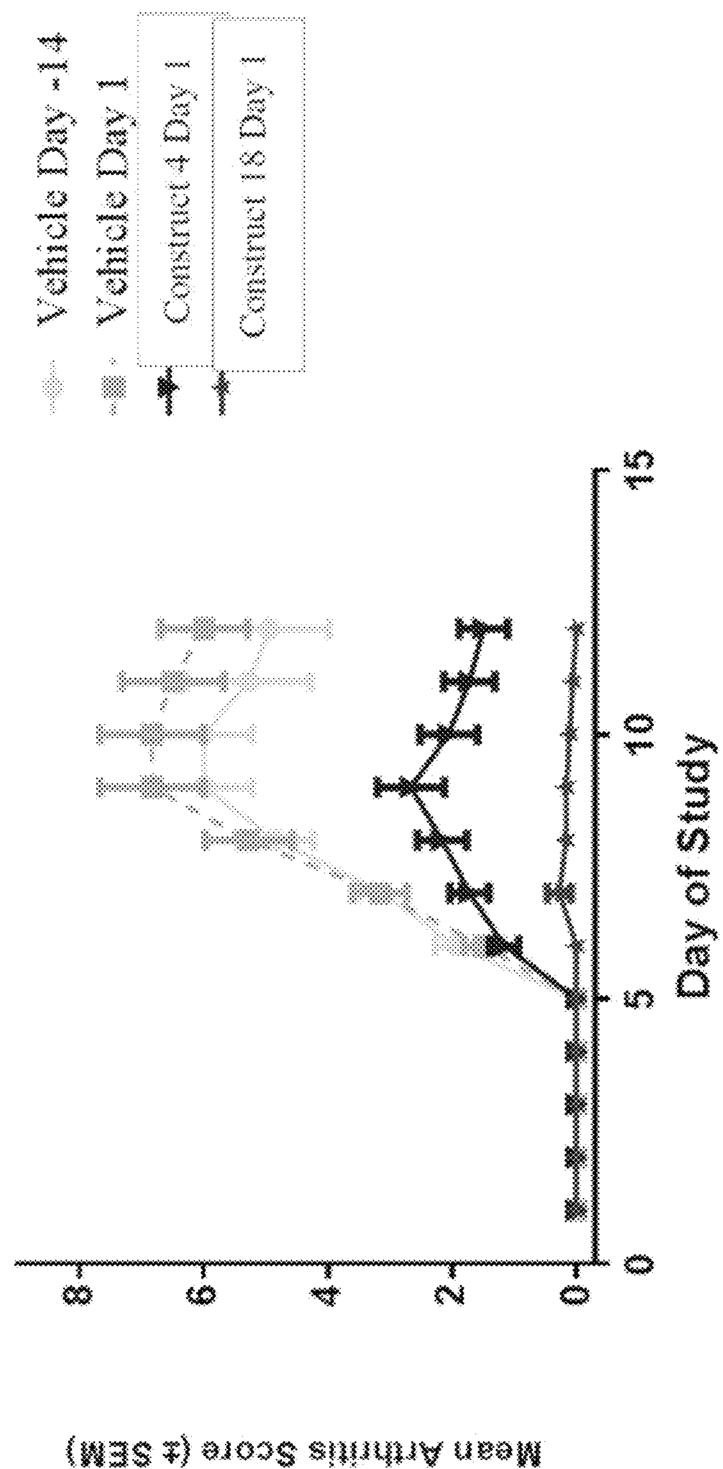
FIG. 28 is a graph comparing the efficacy of construct 4 and construct 18 in the CAIA model dosed prophylactically at Day 1 as measured by clinical scores.
Figure 29:
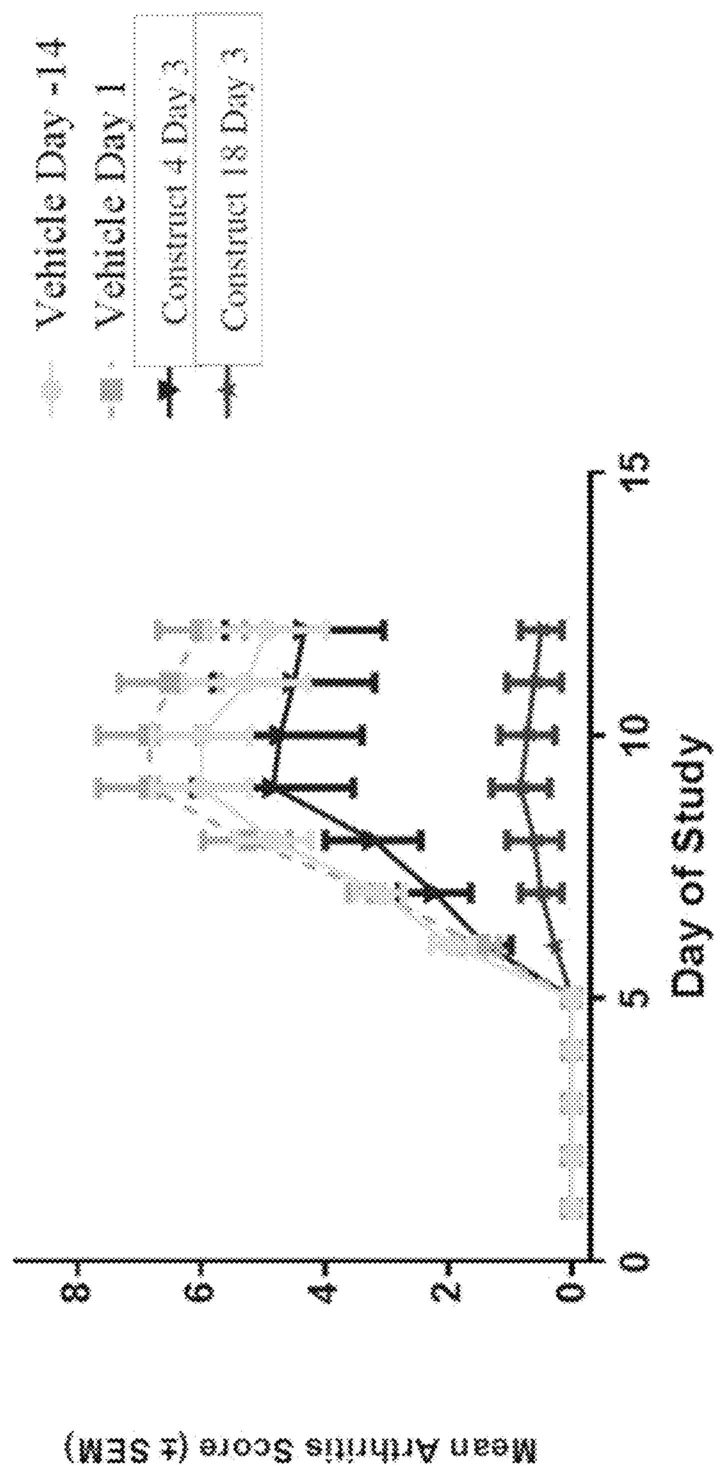
FIG. 29 is a graph comparing the efficacy of construct 4 and construct 18 in the CAIA model dosed prophylactically at Day −3 as measured by clinical scores.
Figure 30:
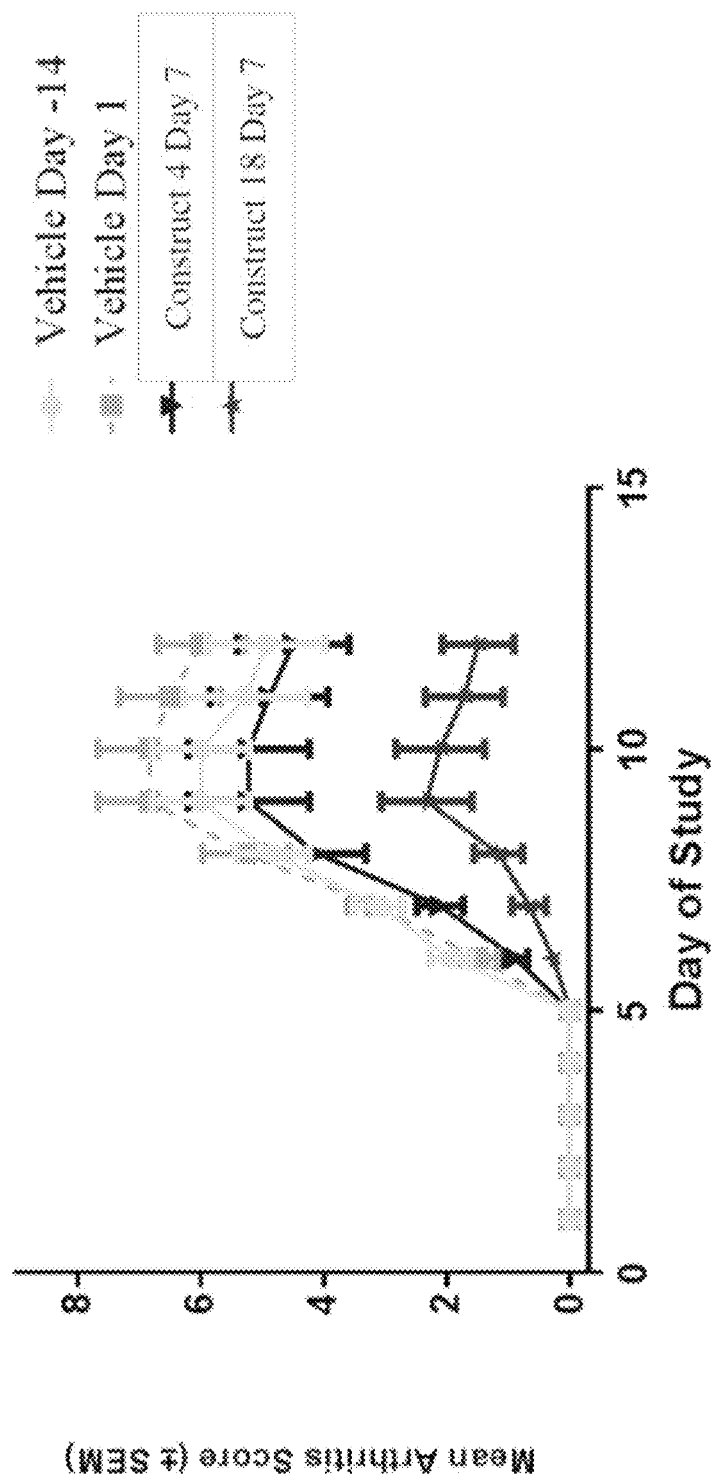
FIG. 30 is a graph comparing the efficacy of construct 4 and construct 18 in the CAIA model dosed prophylactically at Day −7 as measured by clinical scores.
Figure 31:
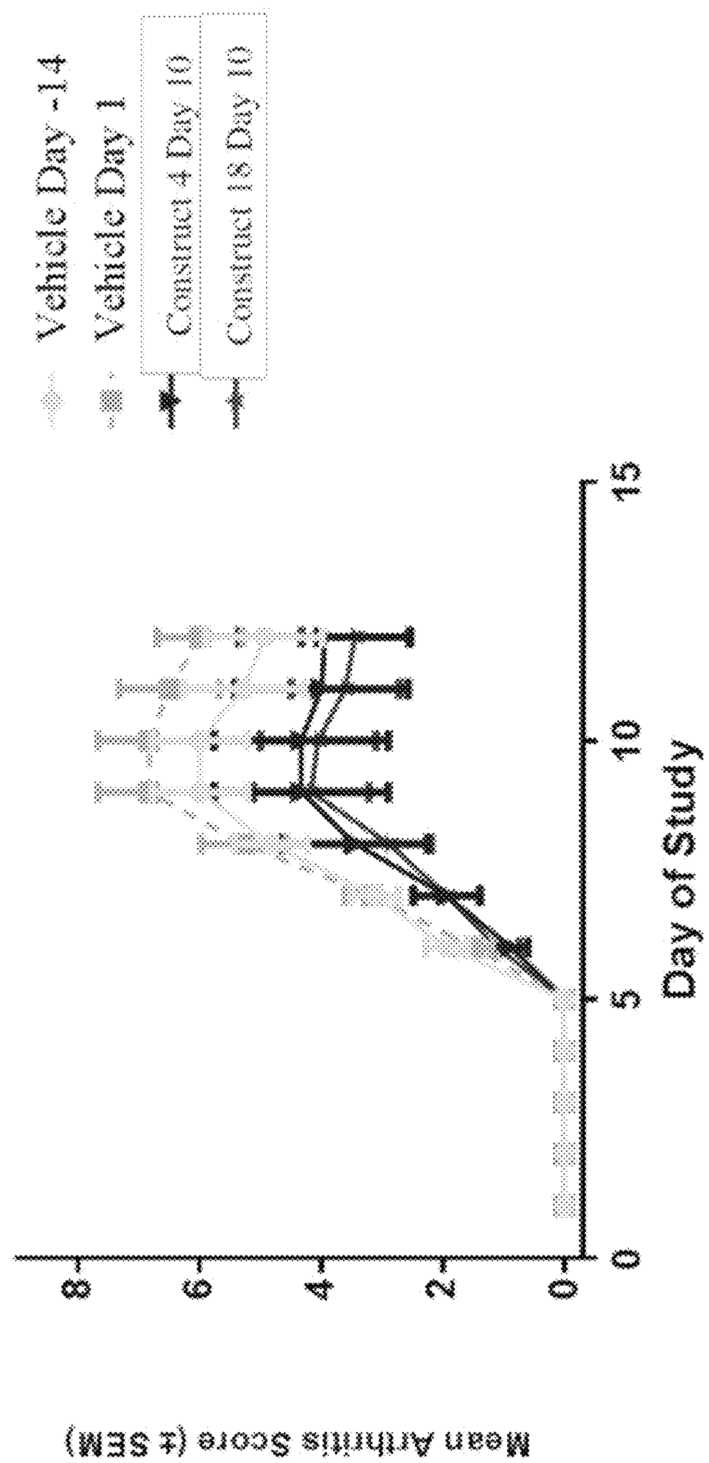
FIG. 31 is a graph comparing the efficacy of construct 4 and construct 18 in the CAIA model dosed prophylactically at Day −10 as measured by clinical scores.

Example 14. Evaluation of I253A and R292P Amino Acid Modifications on In Vivo Durability of Response Mice in the CAIA model were treated prophylactically up to 14 days prior to injection with the arthritogenic antibodies. As seen in FIG. 28, prophylactic treatment at Day 1 was more effective with the slower-clearing Q1 (Construct 18) than with construct 4, presumably due to the greater drug exposure throughout the multi-day disease induction. The construct 4 compound lost effectiveness when dosed 3 days prior to disease induction (FIG. 29), while Q1 (Construct 18) provided protection even when dosed up to 7 days prior to disease induction (FIG. 30). Both constructs were ineffective when dosed 10 days prior to disease induction (FIG. 31). These results demonstrate that the longer pharmacokinetic profile of construct 18 compared to construct 4 translated into a greater durability of response.

Figure 34:
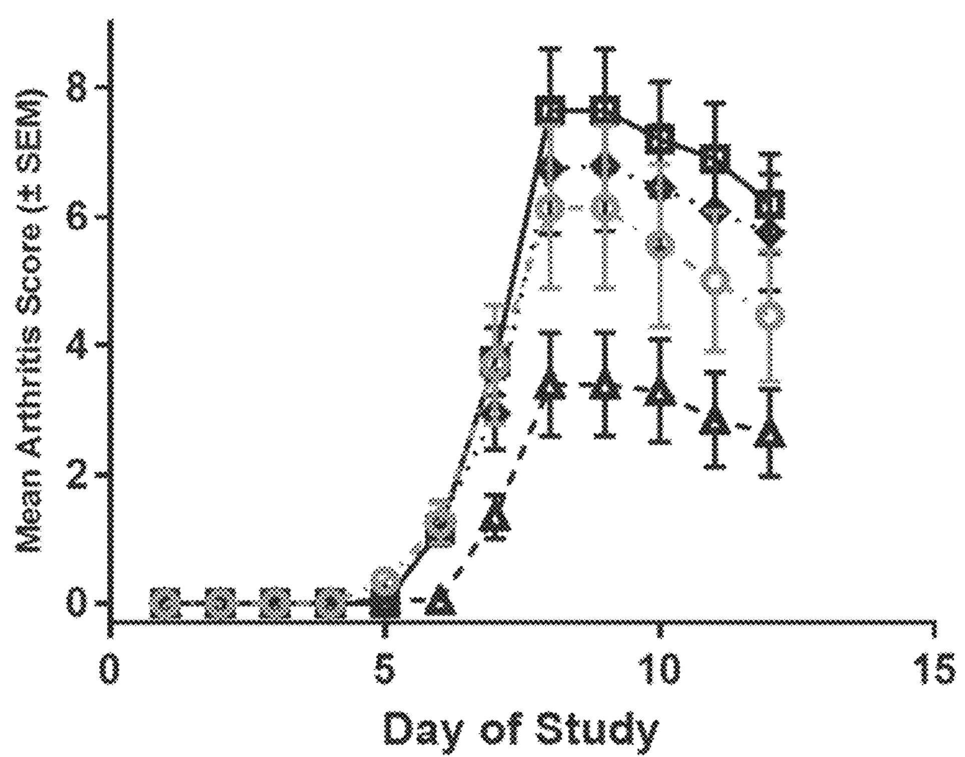
FIG. 34 is a graph comparing the efficacy of construct 4 (AA: black squares, solid line), construct 18 (Q1: black triangles, dashed line), or construct 19 (Q2: black diamonds, dotted line) dosed at 100 mg/kg on day −7 in a collagen antibody-induced arthritis (CAIA) model. An equivalent volume of saline (gray circles, dash-dot line) was dosed on day 1. Mean and standard error of the mean are shown for each time point.
Figure 35:
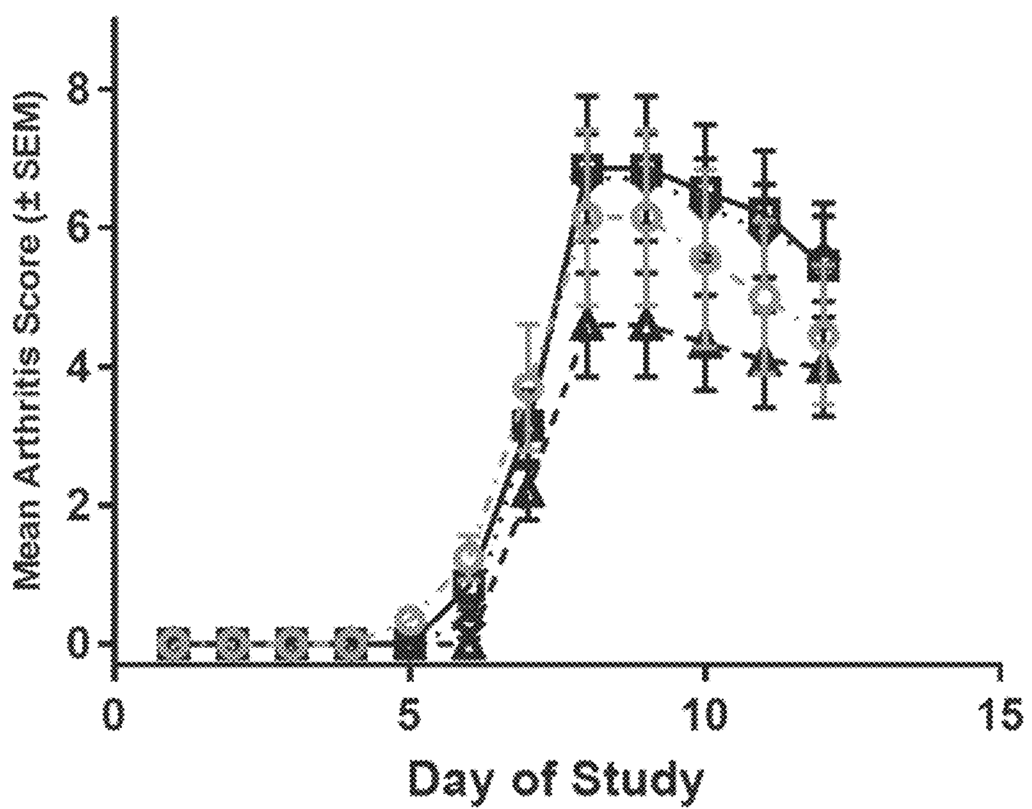
FIG. 35 is a graph comparing the efficacy of construct 4 (AA: black squares, solid line), construct 18 (Q1: black triangles, dashed line), or construct 19 (Q2: black diamonds, dotted line) dosed at 100 mg/kg on day −10 in a collagen antibody-induced arthritis (CAIA) model. An equivalent volume of saline (gray circles, dash-dot line) was dosed on day 1. Mean and standard error of the mean are shown for each time point.

Prophylactic dosing in the CAIA model was performed with 100 mg/kg of construct 4 (parent molecule), construct 18 (I253A in two domains and R292P in three domains) (Q1), or construct 19 (I253A and R292P in all three domains)(Q2) on Day 1 (FIG. 32), Day −3 (FIG. 33), Day −7 (FIG. 34), or Day −10 (FIG. 35). The vehicle control (saline) was dosed only on Day 1.

Figure 32:
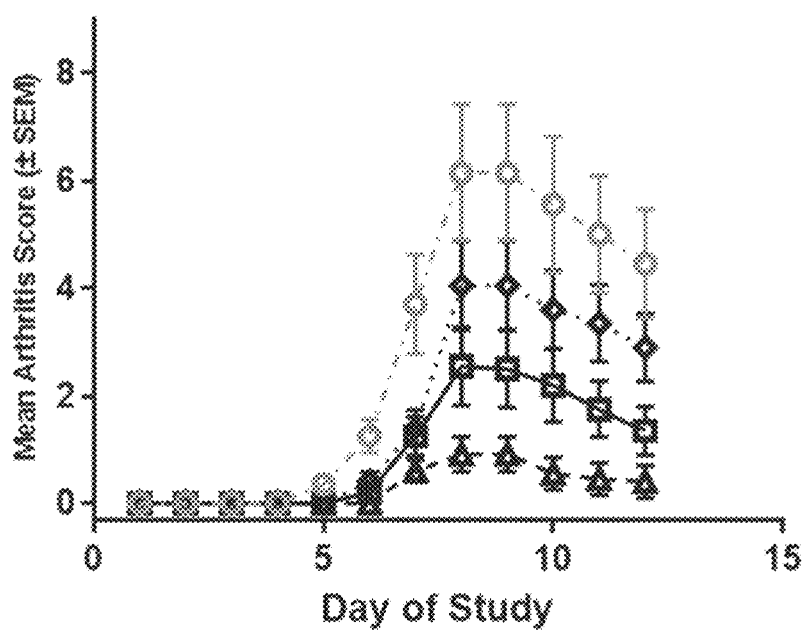
FIG. 32 is a graph comparing the efficacy of construct 4 (AA: black squares, solid line), construct 18 (Q1: black triangles, dashed line), construct 19 (Q2: black diamonds, dotted line), or saline (gray circles, dash-dot line) dosed at 100 mg/kg on day 1 in a collagen antibody-induced arthritis (CAIA) model. An equivalent volume of saline (gray circles, dash-dot line) was dosed on day 1. Mean and standard error of the mean are shown for each time point.
Figure 33:
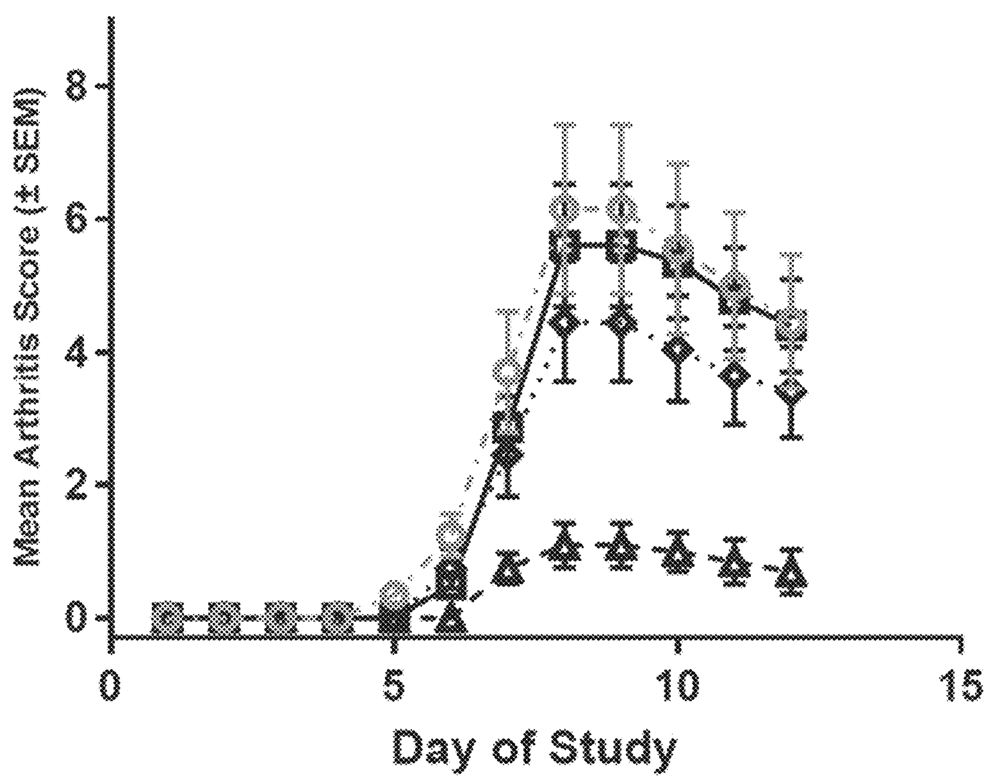
FIG. 33 is a graph comparing the efficacy of construct 4 (AA: black squares, solid line), construct 18 (Q1: black triangles, dashed line), or construct 19 (Q2: black diamonds, dotted line) dosed at 100 mg/kg on day −3 in a collagen antibody-induced arthritis (CAIA) model. An equivalent volume of saline (gray circles, dash-dot line) was dosed on day 1. Mean and standard error of the mean are shown for each time point.

FIG. 32 is a graph comparing the efficacy of construct 4 (AA: black squares, solid line), construct 18 (Q1: black triangles, dashed line), construct 19 (Q2: black diamonds, dotted line), or saline (gray circles, dash-dot line) dosed at 100 mg/kg on day 1 in a collagen antibody-induced arthritis (CAIA) model. FIG. 33 is a graph comparing construct 4 (AA: black squares, solid line), construct 18 (Q1: black triangles, dashed line), or construct 19 (Q2: black diamonds, dotted line) dosed at 100 mg/kg on day −3. FIG. 34 is a graph comparing construct 4 (AA: black squares, solid line), construct 18 (Q1: black triangles, dashed line), or construct 19 (Q2: black diamonds, dotted line) dosed at 100 mg/kg on day −7. FIG. 35 is a graph comparing construct 4 (AA: black squares, solid line), construct 18 (Q1: black triangles, dashed line), or construct 19 (Q2: black diamonds, dotted line) dosed at 100 mg/kg on day −10. For each, an equivalent volume of saline (gray circles, dash-dot line) was dosed on day 1. Mean and standard error of the mean are shown for each time point.

Example 15. Evaluation of I253A and R292P Amino Acid Modifications on Fc Multimers Fc multimers were generated as described in (Strome et al, US 2010/0239633 A1; Jain et al, Arthritis Res. Ther. 14, R192 (2012)). Specifically, IgG1 Fc was fused at the C-terminus to an IgG2 hinge sequence. DNA constructs were generated using wildtype IgG1 Fc sequence (construct X1) and using the I253A/R292P double mutant (construct X2). DNA plasmid constructs were transfected via liposomes into HEK293 cells. Following seven days in culture, cells were cleared by centrifugation.

The expressed proteins were purified from the cell culture supernatant by Protein A-based affinity column chromatography, using a Poros MabCapture A column. Captured constructs were washed with phosphate buffered saline (low-salt wash) and eluted with 100 mM glycine, pH 3. The eluate was quickly neutralized by the addition of 1 M TRIS pH 7.4 and sterile filtered through a 0.2 μm filter.

The proteins were further fractionated by ion exchange chromatography using Poros XS resin. The column was pre-equilibrated with 50 mM MES, pH 6 (buffer A), and the sample was diluted in the equilibration buffer before loading. The sample was eluted using a multi-step gradient with 50 mM MES, 400 mM sodium chloride, pH 6 (buffer B) as the elution buffer. The gradient steps included 0-40% B for 2 column volumes (CV) to remove low molecular weight species, a step hold at 40% B (4 CV), followed by 40-80% B (4 CV) to isolate the target species and then increased linearly to 100% B. All protein-containing fractions were screened by analytical size exclusion chromatography and components quantified by absorbance at 280 nm. Fractions with more than 8% total content of Fc (approximately 50 kDa) plus Fc dimer (approximately 100 kDa) were excluded. For Construct X1, all remaining fractions were combined. Due to a shift in the molecular weight distribution between Constructs X1 and X2, fractions of Construct X2 were selected to mimic the molecular weight distribution of Construct X1.

After ion-exchange, the target fraction was buffer exchanged into PBS buffer using a 30 kDa cutoff polyether sulfone (PES) membrane cartridge on a tangential flow filtration system. The samples were concentrated to approximately 30 mg/mL and sterile filtered through a 0.2 μm filter.

Figure 36:
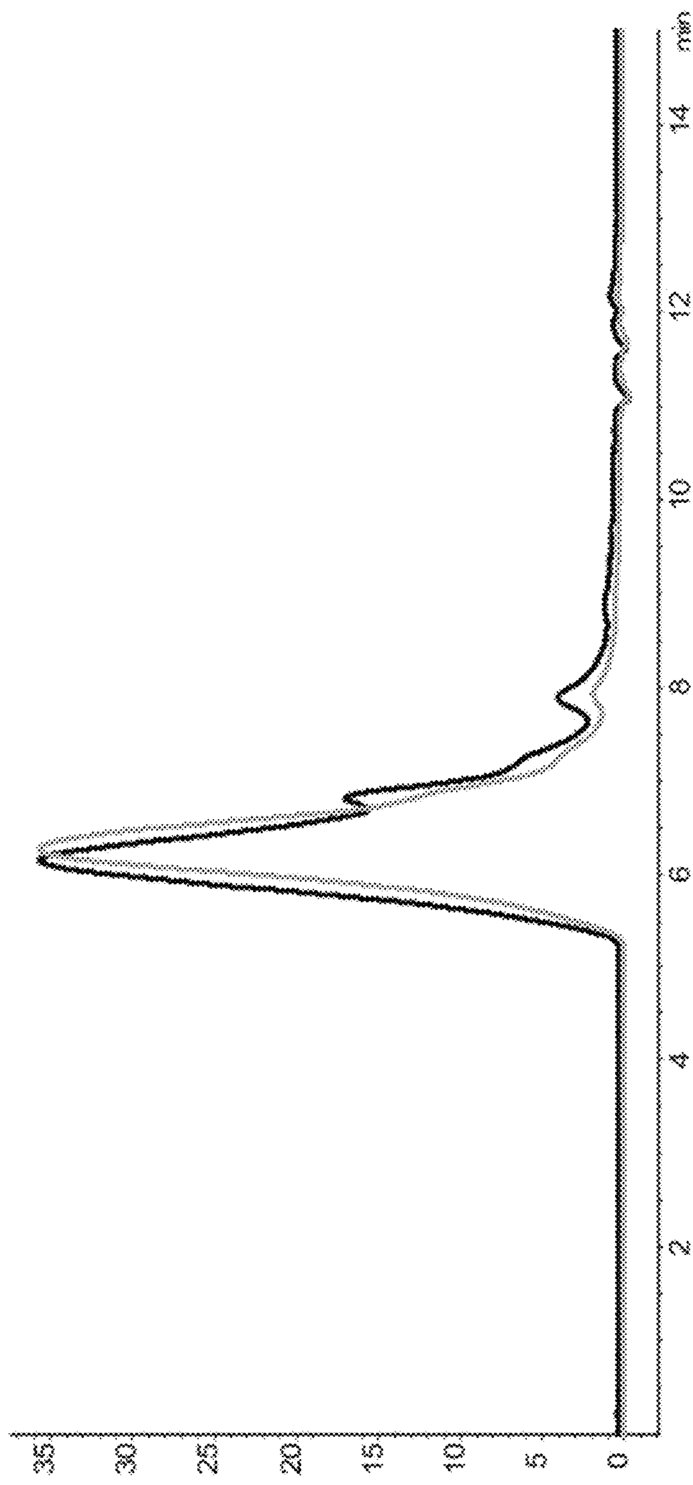
FIG. 36 is a graph comparing the size exclusion chromatography profile of purified constructs X1 (gray) and X2 (black), normalized to the peak maxima.
Figure 37:
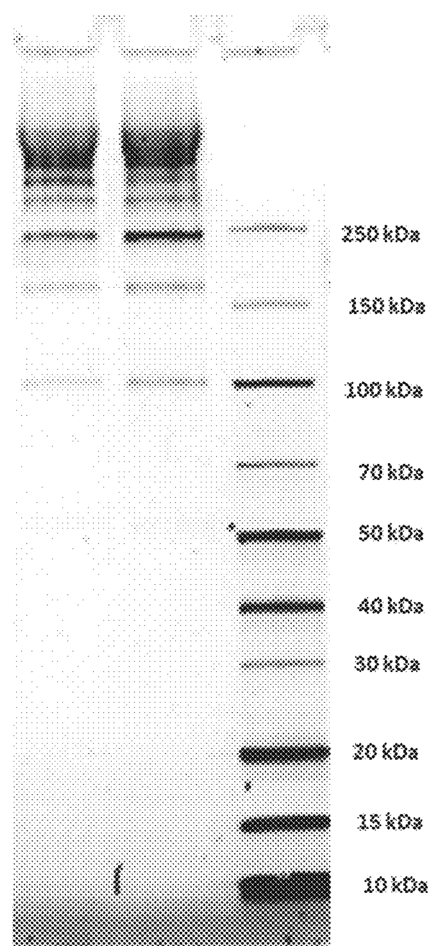
FIG. 37 is an image of the non-reduced sodium dodecyl sulfate polyacrylamide gel electrophoresis result for the purified Construct X1 (right), purified Construct X2 (middle), and molecular weight standards (right). Equal masses of the two constructs were loaded.

The molecular weight distributions of Construct 4 and Construct X1 were compared by analytical size exclusion chromatography (FIG. 36)(purified constructs X1 (gray) and X2 (black), normalized to the peak maxima) and sodium dodecyl sulfate-polyacrylamide gel electrophoresis (FIG. 37)(purified Construct X1 (right), purified Construct X2 (middle), and molecular weight standards (right). Equal masses of the two constructs were loaded). Constructs X1 and X2 are comprised of multiple species ranging from ~100 kDa (two Fc domains) with numerous bands above 250 kDa and with no single component in the majority. The size distribution of Construct X2 is similar to Construct X1, but slightly wider with more of both the highest and lowest molecular weight components.

Female C57BL/6 mice (n=15, 8 weeks old), were dosed intravenously (i.v.) with 0.1 g/kg each of construct X1 or construct 4. Blood (25 μL) was collected from the submandibular vein and was processed for serum. Five mice per group were bled at alternating time points through day 5, while for all remaining time points all fifteen mice were bled in each group. Time points collected included 15 and 30 min; 1, 2, 4, 6, 8, 24 h; 2 days. Fc multimer serum concentrations were determined by an anti-human IgG ELISA with an Fc specific detection antibody.

Figure 38:
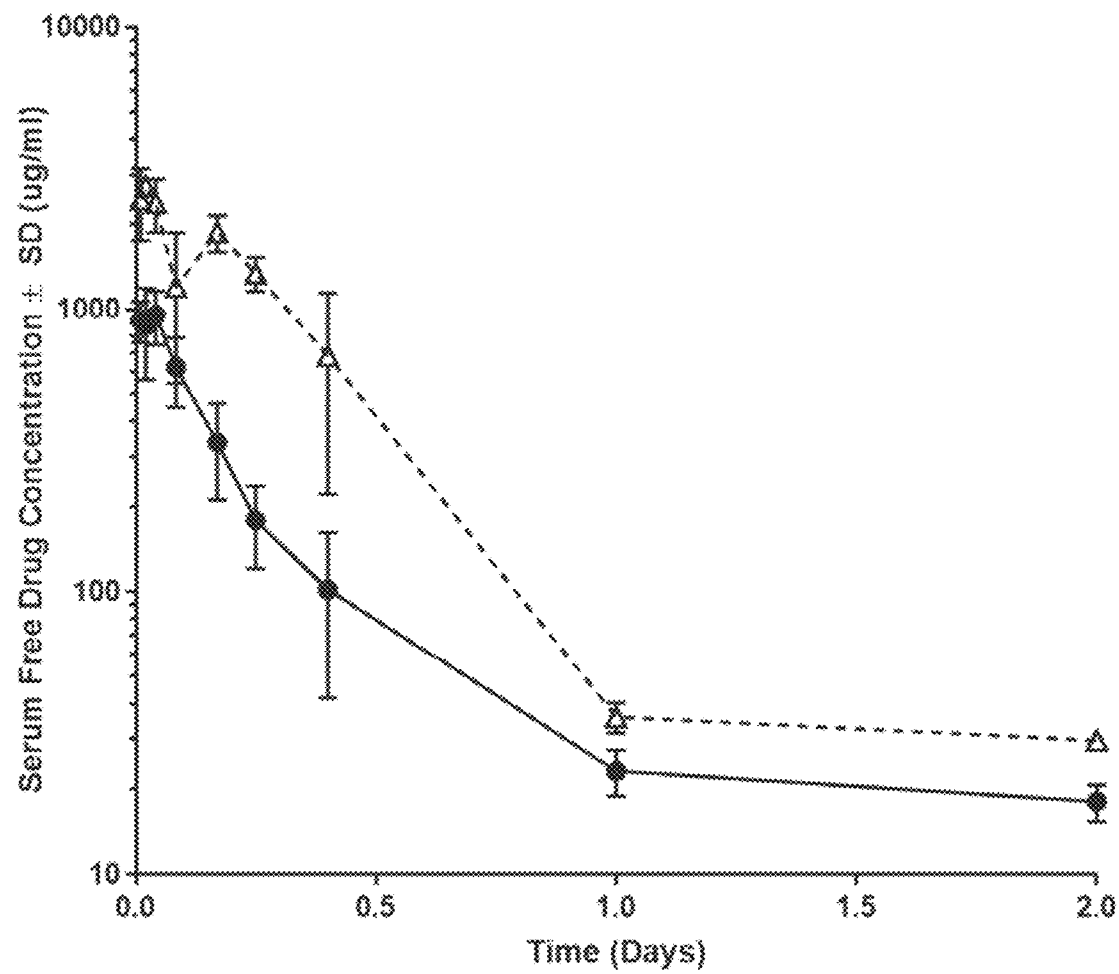
FIG. 38 is a graph comparing the pharmacokinetics of construct X1 (wild type Fc multimer)(black circles, solid line) and construct X2 (Fc multimer with I253A/R292P mutations)(triangles, dashed line) to evaluate the impact of reducing FcRn and FcγRIIb binding on pharmacokinetics. Mean and standard deviation are shown for each time point.

As demonstrated in FIG. 38, the serum levels of construct X1 are lower than those of construct X2 at each time point. Introduction of the I253A and R292P mutations into construct X2 delayed the clearance of the Fc multimer compared to the corresponding wild type material (construct X1).

Example 16. Evaluation of I253A and R292P Amino Acid Modifications on Fc Receptor Pharmacokinetics in Cynomolgus Monkeys The impact of binding-related mutations on pharmacokinetics in cynomolgus monkeys was assessed by comparing constructs 6, 16, and 18. Historical data for construct 4 came from a study in cynomolgus monkeys performed at different dose levels than the study comparing constructs 6, 16, and 18. Male cynomolgus monkeys (N=3) were dosed i.v. with 10 or 30 mg/kg each of constructs 6, 16, and 18. Blood samples were collected over the course of 44 days. Fc construct concentrations were determined by an ELISA using antibodies specific for human IgG1 Fc constructs, including constructs 4, 6, 16, and 18.

Figure 39:
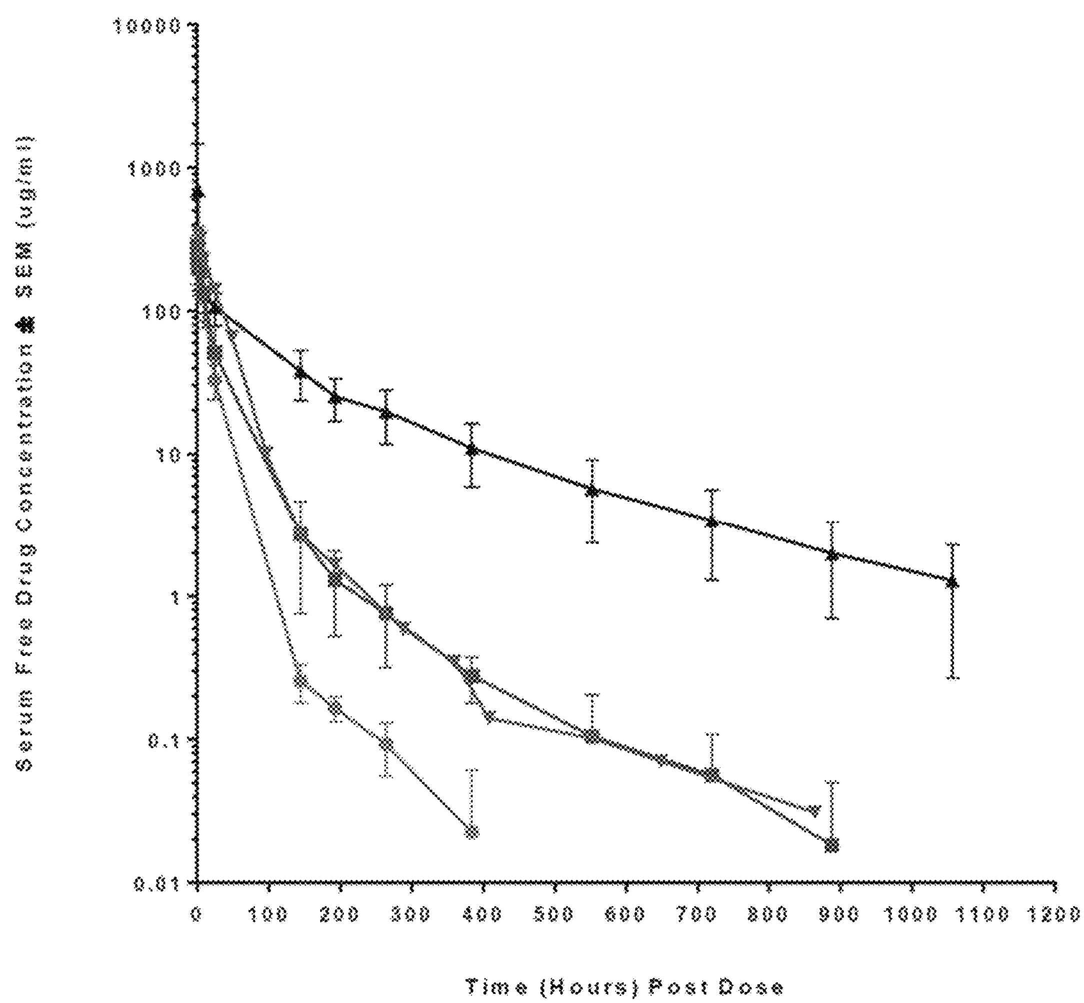
FIG. 39 is a graph showing the pharmacokinetics of constructs 6 (circles; SEQ ID NOs: 64 and 63), 16 (triangles; SEQ ID NOs:76/70), and 18 (squares; SEQ ID Nos: 78 and 73) dosed at 10 mg/kg in cynomolgus monkeys. Construct 4 (inverted triangles; SEQ ID Nos: 49 and 48) was dosed at 20 mg/kg in cynomolgus monkeys.

As demonstrated in FIG. 39, construct 16 dosed at 10 mg/kg persists longer in vivo than construct 4 dosed at 20 mg/kg. Construct 18 dosed at 10 mg/kg has similar persistence in vivo to construct 4 dosed at 20 mg/kg. Construct 6 dosed at 10 mg/kg does not persist as long in vivo as construct 4 dosed at 20 mg/kg.

Figure 40:
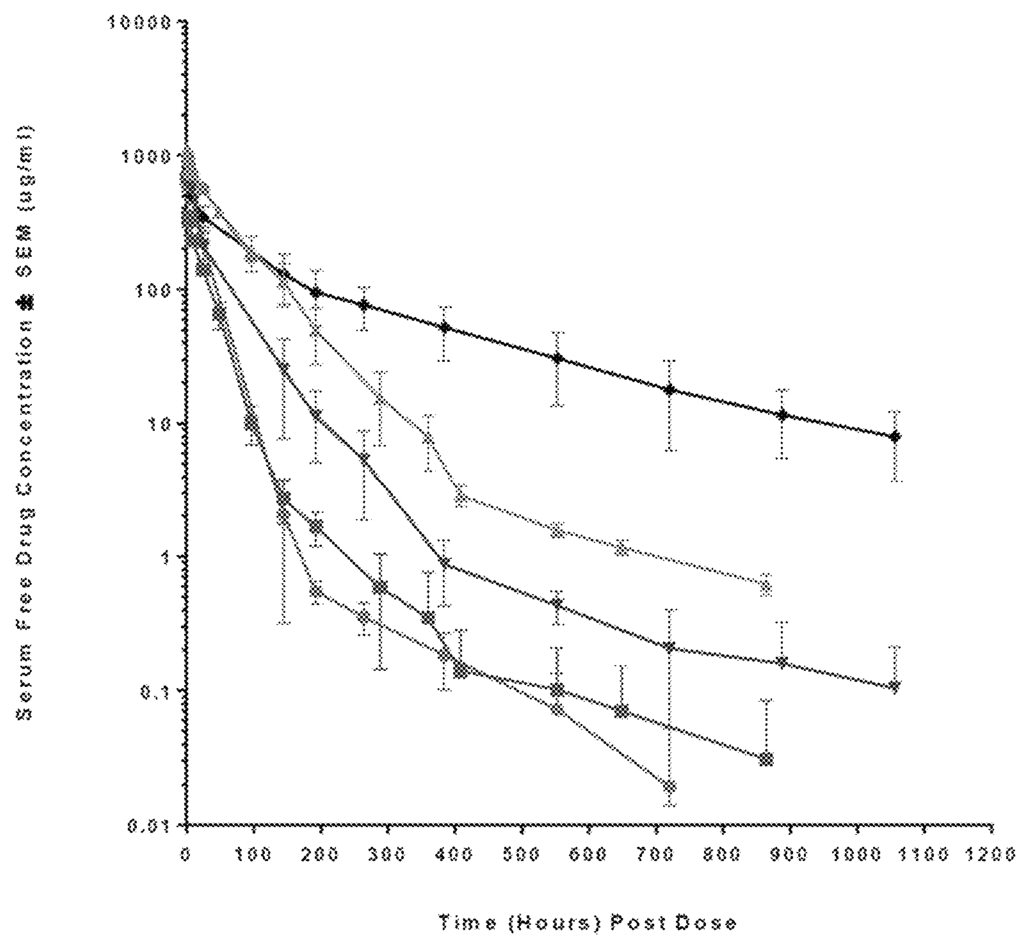
FIG. 40 is a graph showing the pharmacokinetics of constructs 6 (gray circles; SEQ ID NOs: 64 and 63), 16 (diamonds; SEQ ID NOs:76 and 70), and 18 (inverted triangles; SEQ ID Nos: 78 and 73) dosed at 30 mg/kg in cynomolgus monkeys. Construct 4 (SEQ ID Nos: 49 and 48) was dosed at 20 mg/kg (squares), 30 mg/kg (circles) and 50 mg/kg (triangles) in cynomolgus monkeys.

As demonstrated in FIG. 40, construct 16 dosed at 30 mg/kg persists longer in vivo than construct 4 dosed at either 20 or 50 mg/kg. The persistence of construct 18 dosed at 30 mg/kg is intermediate between that of construct 4 dosed at 20 or 50 mg/kg. Construct 6 dosed at 30 mg/kg does not persist as long in vivo as construct 4 dosed at 20 or 50 mg/kg.

It is noteworthy that the pharmacokinetic behavior in cynomolgus monkeys differs from that in mice. In mice, both the reduction of FcRn and Fc gamma RIIb binding each resulted in increased persistence, and the combination of both resulted in further increases in persistence. In cynomolgus monkeys, the reduction of FcRn decreased persistence, the reduction of Fc gamma RIIb binding increased persistence, and the combination had little net change in persistence compared to the parent molecule (construct 4).

OTHER EMBODIMENTS

All publications, patents, and patent applications mentioned in this specification are incorporated herein by reference to the same extent as if each independent publication or patent application was specifically and individually indicated to be incorporated by reference.

While the disclosure has been described in connection with specific embodiments thereof, it will be understood that it is capable of further modifications and this application is intended to cover any variations, uses, or adaptations of the disclosure following, in general, the principles of the disclosure and including such departures from the disclosure that come within known or customary practice within the art to which the disclosure pertains and may be applied to the essential features hereinbefore set forth, and follows in the scope of the claims.

Other embodiments are within the claims.

The invention claimed is:

1. An Fc construct comprising:

a) a first polypeptide comprising i). a first Fc domain monomer;

ii). a second Fc domain monomer; and iii). a linker joining the first Fc domain monomer to the second Fc domain monomer;

b). a second polypeptide comprising i). a third Fc domain monomer;

ii). a fourth Fc domain monomer; and iii). a linker joining the third Fc domain monomer to the fourth Fc domain monomer;

c). a third polypeptide comprises a fifth Fc domain monomer; and d). a fourth polypeptide comprises a sixth Fc domain monomer;

wherein the first Fc domain monomer and fifth Fc domain monomer combine to form a first Fc domain; the second Fc domain monomer and fourth Fc domain monomer combine to form a second Fc domain; and the third Fc domain monomer and sixth Fc domain monomer combine to form a third Fc domain; each of the first and second polypeptides comprises the sequence of SEQ ID NO: 78; and each of the third and fourth polypeptides comprises the sequence of SEQ ID NO: 73.

2. A pharmaceutical composition comprising the construct of claim 1 and one or more pharmaceutically acceptable carriers or excipients.

3. A method of reducing immune cell activation of the immune response in a subject, the method comprising administering to the subject an Fc construct of claim 1.

4. The method of claim 3, wherein the subject has an autoimmune disease.

5. A method of treating inflammation in a subject, the method comprising administering to the subject the Fc construct of claim 1.

6. A method of promoting clearance of autoantibodies and/or suppressing antigen presentation in a subject, the method comprising administering to the subject the Fc construct of claim 1.

7. A composition comprising a polypeptide comprising or consisting of the sequence:

```
                                                  (SEQ ID NO: 78)
DKTHTCPPCPAPELLGGPSVFLEPPKPKDTLMASRTPEVTCVVVDVSHE

DPEVKFNWYVDGVEVHNAKTKPPEEQYNSTYRVVSVLTVLHQDWLNGKE

YKCKVSNKALPAPIEKTISKAKGQPREPQVYTLPPCRDKLTKNQVSLWC

LVKGFYPSDIAVEWESNGQPENNYKTTPPVLDSDGSFFLYSKLTVDKSR

WQQGNVFSCSVMHEALHNHYTQKSLSLSPGKGGGGGGGGGGGGGGGGGG

GGDKTHTCPPCPAPELLGGPSVFLEPPKPKDTLMISRTPEVTCVVVDVS

HEDPEVKFNWYVDGVEVHNAKTKPPEEQYNSTYRVVSVLTVLHQDWLNG

KEYKCKVSNKALPAPIEKTISKAKGQPREPQVYTLPPSRDELTKNQVSL

TCLVKGFYPSDIAVEWESNGQPENNYKTTPPVLKSDGSFFLYSDLTVDK

SRWQQGNVFSCSVMHEALHNHYTQKSLSLSPG,
```

and a polypeptide comprising or consisting of the sequence:

```
                                                  (SEQ ID NO: 73)
DKTHTCPPCPAPELLGGPSVFLFPPKPKDTLMASRTPEVTCVVVDVSHE

DPEVKFNWYVDGVEVHNAKTKPPEEQYNSTYRVVSVLTVLHQDWLNGKE

YKCKVSNKALPAPIEKTISKAKGQPREPQVCTLPPSRDELTKNQVSLSC

AVDGFYPSDIAVEWESNGQPENNYKTTPPVLDSDGSFFLVSKLTVDKSR

WQQGNVFSCSVMHEALHNHYTQKSLSLSPG.
```

8. A method for treating an inflammatory or autoimmune disease in a subject in need thereof, comprising administering a therapeutically effective amount of the Fc construct of claim 1.

9. The method of claim 8, wherein the inflammatory or autoimmune disease is selected from the group consisting of: rheumatoid arthritis (RA); systemic lupus erythematosus (SLE); ANCA-associated vasculitis; antiphospholipid antibody syndrome; autoimmune hemolytic anemia; chronic inflammatory demyelinating neuropathy; graft versus host disease; dermatomyositis; Goodpasture's Syndrome; Guillain Barre syndrome; ulcerative colitis; idiopathic thrombocytopenia purpura; Myasthenia Gravis; Kawasaki Disease; inclusion body myositis; systemic sclerosis; IgA nephropathy; Graves disease; autoimmune inner ear disease (AIED); antiphospholipid syndrome (APS); pemphigus vulgaris; pemphigus follaceus; pemphigus gestationis; paraneoplastic pemphigus; syndrome; synovitis; glomerulitis; and vasculitis.

* * * * *